(12) United States Patent
Banyai et al.

(10) Patent No.: US 9,981,239 B2
(45) Date of Patent: May 29, 2018

(54) DEVICES AND METHODS FOR OLIGONUCLEIC ACID LIBRARY SYNTHESIS

(71) Applicant: TWIST BIOSCIENCE CORPORATION, San Francisco, CA (US)

(72) Inventors: William Banyai, San Francisco, CA (US); Bill James Peck, Santa Clara, CA (US); Andres Fernandez, San Francisco, CA (US); Siyuan Chen, San Mateo, CA (US); Pierre Indermuhle, Berkeley, CA (US); Eugene P. Marsh, El Granada, CA (US)

(73) Assignee: TWIST BIOSCIENCE CORPORATION, San Francisco, CA (US)

( * ) Notice: Subject to any disclaimer, the term of this patent is extended or adjusted under 35 U.S.C. 154(b) by 12 days.

(21) Appl. No.: 15/135,434

(22) Filed: Apr. 21, 2016

(65) Prior Publication Data

US 2016/0310927 A1 Oct. 27, 2016

Related U.S. Application Data

(60) Provisional application No. 62/150,795, filed on Apr. 21, 2015, provisional application No. 62/220,856, filed on Sep. 18, 2015.

(51) Int. Cl.
*B01J 19/00* (2006.01)
*B01L 3/00* (2006.01)

(52) U.S. Cl.
CPC .. *B01J 19/0046* (2013.01); *B01J 2219/00317* (2013.01); *B01J 2219/00497* (2013.01); *B01J 2219/00511* (2013.01); *B01J 2219/00522* (2013.01); *B01J 2219/00585* (2013.01); *B01J 2219/00596* (2013.01); *B01J 2219/00635* (2013.01); *B01J 2219/00637* (2013.01); *B01J 2219/00662* (2013.01); *B01J 2219/00722* (2013.01); *B01L 3/50857* (2013.01)

(58) Field of Classification Search
CPC . C12M 1/00; C12Q 1/68; C07H 21/04; B01L 3/50857
See application file for complete search history.

(56) References Cited

U.S. PATENT DOCUMENTS

| | | |
|---|---|---|
| 3,549,368 A | 12/1970 | Robert et al. |
| 3,920,714 A | 11/1975 | Streck |
| 4,123,661 A | 10/1978 | Wolf et al. |
| 4,415,732 A | 11/1983 | Caruthers et al. |
| 4,613,398 A | 9/1986 | Chiong et al. |
| 4,726,877 A | 2/1988 | Fryd et al. |
| 4,808,511 A | 2/1989 | Holmes |
| 4,837,401 A | 6/1989 | Hirose et al. |
| 4,863,557 A | 9/1989 | Kokaku et al. |
| 4,981,797 A | 1/1991 | Jessee et al. |
| 4,988,617 A | 1/1991 | Landegren et al. |
| 5,102,797 A | 4/1992 | Tucker et al. |
| 5,137,814 A | 8/1992 | Rashtchian et al. |
| 5,143,854 A | 9/1992 | Pirrung et al. |
| 5,242,794 A | 9/1993 | Whiteley et al. |
| 5,242,974 A | 9/1993 | Holmes |
| 5,288,514 A | 2/1994 | Ellman |
| 5,299,491 A | 4/1994 | Kawada |
| 5,384,261 A | 1/1995 | Winkler et al. |
| 5,387,541 A | 2/1995 | Hodge et al. |
| 5,395,753 A | 3/1995 | Prakash |
| 5,431,720 A | 7/1995 | Nagai et al. |
| 5,445,934 A | 8/1995 | Fodor et al. |
| 5,449,754 A | 9/1995 | Nishioka |
| 5,459,039 A | 10/1995 | Modrich et al. |
| 5,474,796 A | 12/1995 | Brennan |
| 5,476,930 A | 12/1995 | Letsinger et al. |
| 5,487,993 A | 1/1996 | Herrnstadt et al. |
| 5,494,810 A | 2/1996 | Barany et al. |
| 5,501,893 A | 3/1996 | Laermer et al. |
| 5,508,169 A | 4/1996 | Deugau et al. |
| 5,510,270 A | 4/1996 | Fodor et al. |
| 5,514,789 A | 5/1996 | Kempe |
| 5,527,681 A | 6/1996 | Holmes |
| 5,530,516 A | 6/1996 | Sheets |
| 5,556,750 A | 9/1996 | Modrich et al. |
| 5,586,211 A | 12/1996 | Dumitrou et al. |
| 5,641,658 A | 6/1997 | Adams et al. |
| 5,677,195 A | 10/1997 | Winkler et al. |

(Continued)

FOREIGN PATENT DOCUMENTS

| EP | 0090789 A1 | 10/1983 |
|---|---|---|
| EP | 0126621 B1 | 8/1990 |

(Continued)

OTHER PUBLICATIONS

ATDBio, "Nucleic Acid Structure," Nucleic Acids Book, 9 pages, published on Jan. 22, 2005. from: http://www.atdbio.com/content/5/Nucleic-acid-structure.
ATDBio, "Solid-Phase Oligonucleotide Synthesis," Nucleic Acids Book, 20 pages, Published on Jul. 31, 2011. from: http://www.atdbio.com/content/17/Solid-phase-oligonucleotide-synthesis.
Barton et al., A desk electrohydrodynamic jet printing system. Mechatronics, 20:611-616, 2010.
Blanchard, et al., "High-Density Oligonucleotide Arrays," Biosensors & Bioelectronics, 11(6/7):687-690, 1996.
Brunet, Aims and methods of biosteganography. Journal of Biotechnology, 226:56-64, 2016.
Buermans et al., "Next Generation sequencing technology: Advances and applications," Biochimica et Biophysica Acta (BBA)—Molecular Basis of Disease, 1842:1931-1941, 2014.
Church et al., Next-generation digital information storage in DNA. Science, 337:6102, 1628-1629, 2012.
Cleary et al., "Production of complex nucleic acid libraries using highly parallel in situ oligonucleotide synthesis," Nature Methods, 1(13):241-248, 2004.

(Continued)

*Primary Examiner* — Narayan Bhat
(74) *Attorney, Agent, or Firm* — Wilson Sonsini Goodrich & Rosati

(57) ABSTRACT

Devices and methods for de novo synthesis of large and highly accurate libraries of oligonucleic acids are provided herein. Devices include structures having a main channel and microchannels, where the microchannels have a high surface area to volume ratio. Devices disclosed herein provide for de novo synthesis of oligonucleic acids having a low error rate.

28 Claims, 33 Drawing Sheets

(56) References Cited

U.S. PATENT DOCUMENTS

| | | |
|---|---|---|
| 5,679,522 A | 10/1997 | Modrich et al. |
| 5,700,637 A | 12/1997 | Southern |
| 5,700,642 A | 12/1997 | Monforte et al. |
| 5,702,894 A | 12/1997 | Modrich et al. |
| 5,707,806 A | 1/1998 | Shuber |
| 5,712,124 A | 1/1998 | Walker |
| 5,739,386 A | 4/1998 | Holmes |
| 5,750,672 A | 5/1998 | Kempe |
| 5,780,613 A | 7/1998 | Letsinger et al. |
| 5,830,655 A | 11/1998 | Monforte et al. |
| 5,830,662 A | 11/1998 | Soares et al. |
| 5,834,252 A | 11/1998 | Stemmer et al. |
| 5,843,767 A | 12/1998 | Beattie |
| 5,858,754 A | 1/1999 | Modrich et al. |
| 5,861,482 A | 1/1999 | Modrich et al. |
| 5,869,245 A | 2/1999 | Yeung |
| 5,877,280 A | 3/1999 | Wetmur |
| 5,882,496 A | 3/1999 | Northrup et al. |
| 5,922,539 A | 7/1999 | Modrich et al. |
| 5,922,593 A | 7/1999 | Livingston |
| 5,928,907 A | 7/1999 | Woudenberg et al. |
| 5,976,846 A | 11/1999 | Passmore et al. |
| 6,008,031 A | 12/1999 | Modrich et al. |
| 6,013,440 A | 1/2000 | Lipshutz et al. |
| 6,015,674 A | 1/2000 | Woudenberg et al. |
| 6,027,898 A | 2/2000 | Gjerde et al. |
| 6,028,189 A | 2/2000 | Blanchard |
| 6,028,198 A | 2/2000 | Liu et al. |
| 6,040,138 A | 3/2000 | Lockhart et al. |
| 6,077,674 A | 6/2000 | Schleifer et al. |
| 6,103,474 A | 8/2000 | Dellinger et al. |
| 6,107,038 A | 8/2000 | Choudhary et al. |
| 6,110,682 A | 8/2000 | Dellinger et al. |
| 6,114,115 A | 9/2000 | Wagner, Jr. |
| 6,132,997 A | 10/2000 | Shannon |
| 6,136,568 A | 10/2000 | Hiatt et al. |
| 6,171,797 B1 | 1/2001 | Perbost |
| 6,180,351 B1 | 1/2001 | Cattell |
| 6,201,112 B1 | 3/2001 | Ach |
| 6,218,118 B1 | 4/2001 | Sampson et al. |
| 6,221,653 B1 | 4/2001 | Caren et al. |
| 6,222,030 B1 | 4/2001 | Dellinger et al. |
| 6,232,072 B1 | 5/2001 | Fisher |
| 6,235,483 B1 | 5/2001 | Wolber et al. |
| 6,242,266 B1 | 6/2001 | Schleifer et al. |
| 6,251,588 B1 | 6/2001 | Shannon et al. |
| 6,251,595 B1 | 6/2001 | Gordon et al. |
| 6,251,685 B1 | 6/2001 | Dorsel et al. |
| 6,258,454 B1 | 7/2001 | Lefkowitz et al. |
| 6,262,490 B1 | 7/2001 | Hsu et al. |
| 6,274,725 B1 | 8/2001 | Sanghvi et al. |
| 6,284,465 B1 | 9/2001 | Wolber |
| 6,287,776 B1 | 9/2001 | Hefti |
| 6,297,017 B1 | 10/2001 | Schmidt et al. |
| 6,300,137 B1 | 10/2001 | Earhart et al. |
| 6,306,599 B1 | 10/2001 | Perbost |
| 6,309,822 B1 | 10/2001 | Fodor et al. |
| 6,309,828 B1 | 10/2001 | Schleifer et al. |
| 6,319,674 B1 | 11/2001 | Fulcrand et al. |
| 6,323,043 B1 | 11/2001 | Caren et al. |
| 6,329,210 B1 | 12/2001 | Schleifer |
| 6,346,423 B1 | 2/2002 | Schembri |
| 6,365,355 B1 | 4/2002 | McCutchen-Maloney |
| 6,372,483 B2 | 4/2002 | Schleifer et al. |
| 6,375,903 B1 | 4/2002 | Cerrina et al. |
| 6,376,285 B1 | 4/2002 | Joyner et al. |
| 6,384,210 B1 | 5/2002 | Blanchard |
| 6,387,636 B1 | 5/2002 | Perbost et al. |
| 6,399,394 B1 | 6/2002 | Dahm et al. |
| 6,399,516 B1 | 6/2002 | Ayon |
| 6,403,314 B1 | 6/2002 | Lange et al. |
| 6,406,849 B1 | 6/2002 | Dorsel et al. |
| 6,406,851 B1 | 6/2002 | Bass |
| 6,419,883 B1 | 7/2002 | Blanchard |
| 6,428,957 B1 | 8/2002 | Delenstarr |
| 6,440,669 B1 | 8/2002 | Bass et al. |
| 6,444,268 B2 | 9/2002 | Lefkowitz et al. |
| 6,446,642 B1 | 9/2002 | Caren et al. |
| 6,446,682 B1 | 9/2002 | Viken |
| 6,451,998 B1 | 9/2002 | Perbost |
| 6,458,526 B1 | 10/2002 | Schembri et al. |
| 6,458,583 B1 | 10/2002 | Bruhn et al. |
| 6,461,812 B2 | 10/2002 | Barth et al. |
| 6,461,816 B1 | 10/2002 | Wolber et al. |
| 6,469,156 B1 | 10/2002 | Schafer et al. |
| 6,492,107 B1 | 12/2002 | Kauffman et al. |
| 6,518,056 B2 | 2/2003 | Schembri et al. |
| 6,521,427 B1 | 2/2003 | Evans |
| 6,521,453 B1 | 2/2003 | Crameri et al. |
| 6,558,908 B2 | 5/2003 | Wolber et al. |
| 6,566,495 B1 | 5/2003 | Fodor et al. |
| 6,582,908 B2 | 6/2003 | Fodor et al. |
| 6,582,938 B1 | 6/2003 | Su et al. |
| 6,586,211 B1 | 7/2003 | Staehler et al. |
| 6,587,579 B1 | 7/2003 | Bass |
| 6,589,739 B2 | 7/2003 | Fisher |
| 6,599,693 B1 | 7/2003 | Webb |
| 6,602,472 B1 | 8/2003 | Zimmermann et al. |
| 6,610,978 B2 | 8/2003 | Yin et al. |
| 6,613,513 B1 | 9/2003 | Parce et al. |
| 6,613,523 B2 | 9/2003 | Fischer |
| 6,613,560 B1 | 9/2003 | Tso et al. |
| 6,613,893 B1 | 9/2003 | Webb |
| 6,621,076 B1 | 9/2003 | Van et al. |
| 6,630,581 B2 | 10/2003 | Dellinger et al. |
| 6,632,641 B1 | 10/2003 | Brennan et al. |
| 6,635,226 B1 | 10/2003 | Tso et al. |
| 6,642,373 B2 | 11/2003 | Manoharan et al. |
| 6,649,348 B2 | 11/2003 | Bass et al. |
| 6,660,338 B1 | 12/2003 | Hargreaves |
| 6,664,112 B2 | 12/2003 | Mulligan et al. |
| 6,670,127 B2 | 12/2003 | Evans |
| 6,670,461 B1 | 12/2003 | Wengel et al. |
| 6,673,552 B2 | 1/2004 | Frey |
| 6,682,702 B2 | 1/2004 | Barth et al. |
| 6,689,319 B1 | 2/2004 | Fisher et al. |
| 6,702,256 B2 | 3/2004 | Killeen et al. |
| 6,706,875 B1 | 3/2004 | Goldberg et al. |
| 6,709,852 B1 | 3/2004 | Bloom et al. |
| 6,709,854 B2 | 3/2004 | Donahue et al. |
| 6,713,262 B2 | 3/2004 | Gillibolian et al. |
| 6,716,629 B2 | 4/2004 | Hess et al. |
| 6,716,634 B1 | 4/2004 | Myerson |
| 6,723,509 B2 | 4/2004 | Ach |
| 6,743,585 B2 | 6/2004 | Dellinger et al. |
| 6,753,145 B2 | 6/2004 | Holcomb et al. |
| 6,768,005 B2 | 7/2004 | Mellor et al. |
| 6,770,748 B2 | 8/2004 | Imanishi et al. |
| 6,770,892 B2 | 8/2004 | Corson et al. |
| 6,773,676 B2 | 8/2004 | Schembri |
| 6,773,888 B2 | 8/2004 | Li et al. |
| 6,787,308 B2 | 9/2004 | Balasubramanian et al. |
| 6,789,965 B2 | 9/2004 | Barth et al. |
| 6,790,620 B2 | 9/2004 | Bass et al. |
| 6,794,499 B2 | 9/2004 | Wengel et al. |
| 6,796,634 B2 | 9/2004 | Caren et al. |
| 6,800,439 B1 | 10/2004 | McGall et al. |
| 6,814,846 B1 | 11/2004 | Berndt |
| 6,815,218 B1 | 11/2004 | Jacobson et al. |
| 6,824,866 B1 | 11/2004 | Glazer et al. |
| 6,830,890 B2 | 12/2004 | Lockhart et al. |
| 6,833,246 B2 | 12/2004 | Balasubramanian |
| 6,833,450 B1 | 12/2004 | McGall et al. |
| 6,835,938 B2 | 12/2004 | Ghosh et al. |
| 6,838,888 B2 | 1/2005 | Peck |
| 6,841,131 B2 | 1/2005 | Zimmermann et al. |
| 6,845,968 B2 | 1/2005 | Killeen et al. |
| 6,846,454 B2 | 1/2005 | Peck |
| 6,846,922 B1 | 1/2005 | Manoharan et al. |
| 6,852,850 B2 | 2/2005 | Myerson et al. |
| 6,858,720 B2 | 2/2005 | Myerson et al. |
| 6,879,915 B2 | 4/2005 | Cattell |
| 6,880,576 B2 | 4/2005 | Karp et al. |
| 6,884,580 B2 | 4/2005 | Caren et al. |

(56) References Cited

U.S. PATENT DOCUMENTS

| | | |
|---|---|---|
| 6,887,715 B2 | 5/2005 | Schembri |
| 6,890,723 B2 | 5/2005 | Perbost et al. |
| 6,890,760 B1 | 5/2005 | Webb |
| 6,893,816 B1 | 5/2005 | Beattie |
| 6,897,023 B2 | 5/2005 | Fu et al. |
| 6,900,047 B2 | 5/2005 | Bass |
| 6,900,048 B2 | 5/2005 | Perbost |
| 6,911,611 B2 | 6/2005 | Wong et al. |
| 6,914,229 B2 | 7/2005 | Corson et al. |
| 6,916,113 B2 | 7/2005 | De et al. |
| 6,916,633 B1 | 7/2005 | Shannon |
| 6,919,181 B2 | 7/2005 | Hargreaves |
| 6,927,029 B2 | 8/2005 | Lefkowitz et al. |
| 6,929,951 B2 | 8/2005 | Corson et al. |
| 6,936,472 B2 | 8/2005 | Earhart et al. |
| 6,938,476 B2 | 9/2005 | Chesk |
| 6,939,673 B2 | 9/2005 | Bass et al. |
| 6,943,036 B2 | 9/2005 | Bass |
| 6,946,285 B2 | 9/2005 | Bass |
| 6,950,756 B2 | 9/2005 | Kincaid |
| 6,958,119 B2 | 10/2005 | Yin et al. |
| 6,960,464 B2 | 11/2005 | Jessee et al. |
| 6,969,488 B2 | 11/2005 | Bridgham et al. |
| 6,976,384 B2 | 12/2005 | Hobbs et al. |
| 6,977,223 B2 | 12/2005 | George et al. |
| 6,987,263 B2 | 1/2006 | Hobbs et al. |
| 6,989,267 B2 | 1/2006 | Kim et al. |
| 7,008,037 B2 | 3/2006 | Caren et al. |
| 7,025,324 B1 | 4/2006 | Slocum et al. |
| 7,026,124 B2 | 4/2006 | Barth et al. |
| 7,027,930 B2 | 4/2006 | Cattell |
| 7,028,536 B2 | 4/2006 | Karp et al. |
| 7,029,854 B2 | 4/2006 | Collins et al. |
| 7,034,290 B2 | 4/2006 | Lu et al. |
| 7,051,574 B2 | 5/2006 | Peck |
| 7,052,841 B2 | 5/2006 | Delenstarr |
| 7,062,385 B2 | 6/2006 | White et al. |
| 7,064,197 B1 | 6/2006 | Rabbani et al. |
| 7,070,932 B2 | 7/2006 | Leproust et al. |
| 7,075,161 B2 | 7/2006 | Barth |
| 7,078,167 B2 | 7/2006 | Delenstarr et al. |
| 7,078,505 B2 | 7/2006 | Bass et al. |
| 7,094,537 B2 | 8/2006 | Leproust et al. |
| 7,097,974 B1 | 8/2006 | Staehler et al. |
| 7,101,508 B2 | 9/2006 | Thompson et al. |
| 7,101,986 B2 | 9/2006 | Dellinger et al. |
| 7,105,295 B2 | 9/2006 | Bass et al. |
| 7,115,423 B1 | 10/2006 | Mitchell |
| 7,122,303 B2 | 10/2006 | Delenstarr et al. |
| 7,125,488 B2 | 10/2006 | Li |
| 7,125,523 B2 | 10/2006 | Sillman |
| 7,128,876 B2 | 10/2006 | Yin et al. |
| 7,129,075 B2 | 10/2006 | Gerard et al. |
| 7,135,565 B2 | 11/2006 | Dellinger et al. |
| 7,138,062 B2 | 11/2006 | Yin et al. |
| 7,141,368 B2 | 11/2006 | Fisher et al. |
| 7,141,807 B2 | 11/2006 | Joyce et al. |
| 7,147,362 B2 | 12/2006 | Caren et al. |
| 7,153,689 B2 | 12/2006 | Tolosko et al. |
| 7,163,660 B2 | 1/2007 | Lehmann |
| 7,166,258 B2 | 1/2007 | Bass et al. |
| 7,179,659 B2 | 2/2007 | Stolowitz et al. |
| 7,183,406 B2 | 2/2007 | Belshaw et al. |
| 7,192,710 B2 | 3/2007 | Gellibolian et al. |
| 7,193,077 B2 | 3/2007 | Dellinger et al. |
| 7,198,939 B2 | 4/2007 | Dorsel et al. |
| 7,202,264 B2 | 4/2007 | Ravikumar et al. |
| 7,202,358 B2 | 4/2007 | Hargreaves |
| 7,205,128 B2 | 4/2007 | Ilsley et al. |
| 7,205,400 B2 | 4/2007 | Webb |
| 7,206,439 B2 | 4/2007 | Zhou et al. |
| 7,208,322 B2 | 4/2007 | Stolowitz et al. |
| 7,217,522 B2 | 5/2007 | Brenner |
| 7,220,573 B2 | 5/2007 | Shea et al. |
| 7,221,785 B2 | 5/2007 | Curry et al. |
| 7,226,862 B2 | 6/2007 | Staehler et al. |
| 7,227,017 B2 | 6/2007 | Mellor et al. |
| 7,229,497 B2 | 6/2007 | Stott et al. |
| 7,247,337 B1 | 7/2007 | Leproust et al. |
| 7,247,497 B2 | 7/2007 | Dahm et al. |
| 7,252,938 B2 | 8/2007 | Leproust et al. |
| 7,269,518 B2 | 9/2007 | Corson |
| 7,271,258 B2 | 9/2007 | Dellinger et al. |
| 7,276,336 B1 | 10/2007 | Webb et al. |
| 7,276,378 B2 | 10/2007 | Myerson |
| 7,276,599 B2 | 10/2007 | Moore et al. |
| 7,282,183 B2 | 10/2007 | Peck |
| 7,282,332 B2 | 10/2007 | Caren et al. |
| 7,282,705 B2 | 10/2007 | Brennen |
| 7,291,471 B2 | 11/2007 | Sampson et al. |
| 7,302,348 B2 | 11/2007 | Ghosh et al. |
| 7,314,599 B2 | 1/2008 | Roitman et al. |
| 7,323,320 B2 | 1/2008 | Oleinikov |
| 7,344,831 B2 | 3/2008 | Wolber et al. |
| 7,348,144 B2 | 3/2008 | Minor |
| 7,351,379 B2 | 4/2008 | Schleifer |
| 7,353,116 B2 | 4/2008 | Webb et al. |
| 7,361,906 B2 | 4/2008 | Ghosh et al. |
| 7,364,896 B2 | 4/2008 | Schembri |
| 7,368,550 B2 | 5/2008 | Dellinger et al. |
| 7,371,348 B2 | 5/2008 | Schleifer et al. |
| 7,371,519 B2 | 5/2008 | Wolber et al. |
| 7,371,580 B2 | 5/2008 | Yakhini et al. |
| 7,372,982 B2 | 5/2008 | Le |
| 7,385,050 B2 | 6/2008 | Dellinger et al. |
| 7,390,457 B2 | 6/2008 | Schembri |
| 7,393,665 B2 | 7/2008 | Brenner |
| 7,396,676 B2 | 7/2008 | Robotti et al. |
| 7,399,844 B2 | 7/2008 | Sampson et al. |
| 7,402,279 B2 | 7/2008 | Schembri |
| 7,411,061 B2 | 8/2008 | Myerson et al. |
| 7,413,709 B2 | 8/2008 | Roitman et al. |
| 7,417,139 B2 | 8/2008 | Dellinger et al. |
| 7,422,911 B2 | 9/2008 | Schembri |
| 7,427,679 B2 | 9/2008 | Dellinger et al. |
| 7,435,810 B2 | 10/2008 | Myerson et al. |
| 7,439,272 B2 | 10/2008 | Xu |
| 7,476,709 B2 | 1/2009 | Moody et al. |
| 7,488,607 B2 | 2/2009 | Tom-Moy et al. |
| 7,504,213 B2 | 3/2009 | Sana et al. |
| 7,514,369 B2 | 4/2009 | Li et al. |
| 7,517,979 B2 | 4/2009 | Wolber |
| 7,524,942 B2 | 4/2009 | Wang et al. |
| 7,524,950 B2 | 4/2009 | Dellinger et al. |
| 7,531,303 B2 | 5/2009 | Dorsel et al. |
| 7,534,561 B2 | 5/2009 | Sana et al. |
| 7,534,563 B2 | 5/2009 | Hargreaves |
| 7,537,936 B2 | 5/2009 | Dahm et al. |
| 7,563,600 B2 | 7/2009 | Oleinikov |
| 7,572,585 B2 | 8/2009 | Wang |
| 7,572,907 B2 | 8/2009 | Dellinger et al. |
| 7,572,908 B2 | 8/2009 | Dellinger et al. |
| 7,585,970 B2 | 9/2009 | Dellinger et al. |
| 7,588,889 B2 | 9/2009 | Wolber et al. |
| 7,595,350 B2 | 9/2009 | Xu |
| 7,604,941 B2 | 10/2009 | Jacobson |
| 7,608,396 B2 | 10/2009 | Delenstarr |
| 7,618,777 B2 | 11/2009 | Myerson et al. |
| 7,629,120 B2 | 12/2009 | Bennett et al. |
| 7,635,772 B2 | 12/2009 | McCormac |
| 7,648,832 B2 | 1/2010 | Jessee et al. |
| 7,651,762 B2 | 1/2010 | Xu et al. |
| 7,659,069 B2 | 2/2010 | Belyaev et al. |
| 7,682,809 B2 | 3/2010 | Sampson |
| 7,709,197 B2 | 5/2010 | Drmanac |
| 7,718,365 B2 | 5/2010 | Wang |
| 7,737,088 B1 | 6/2010 | Staehler et al. |
| 7,737,089 B2 | 6/2010 | Guimil et al. |
| 7,749,701 B2 | 7/2010 | Leproust et al. |
| 7,759,471 B2 | 7/2010 | Dellinger et al. |
| 7,776,021 B2 | 8/2010 | Borenstein et al. |
| 7,790,369 B2 | 9/2010 | Stahler et al. |
| 7,790,387 B2 | 9/2010 | Dellinger et al. |
| 7,807,356 B2 | 10/2010 | Sampson et al. |

(56) References Cited

U.S. PATENT DOCUMENTS

| | | |
|---|---|---|
| 7,811,753 B2 | 10/2010 | Eshoo |
| 7,816,079 B2 | 10/2010 | Fischer |
| 7,855,281 B2 | 12/2010 | Dellinger et al. |
| 7,867,782 B2 | 1/2011 | Barth |
| 7,875,463 B2 | 1/2011 | Adaskin et al. |
| 7,879,541 B2 | 2/2011 | Kincaid |
| 7,879,580 B2 | 2/2011 | Carr et al. |
| 7,894,998 B2 | 2/2011 | Kincaid |
| 7,919,239 B2 | 4/2011 | Wang |
| 7,919,308 B2 | 4/2011 | Schleifer |
| 7,927,797 B2 | 4/2011 | Nobile et al. |
| 7,927,838 B2 | 4/2011 | Shannon |
| 7,932,025 B2 | 4/2011 | Carr et al. |
| 7,932,070 B2 | 4/2011 | Hogrefe et al. |
| 7,939,645 B2 | 5/2011 | Borns |
| 7,943,046 B2 | 5/2011 | Martosella et al. |
| 7,943,358 B2 | 5/2011 | Hogrefe et al. |
| 7,960,157 B2 | 6/2011 | Borns |
| 7,977,119 B2 | 7/2011 | Kronick et al. |
| 7,979,215 B2 | 7/2011 | Sampas |
| 7,998,437 B2 | 8/2011 | Berndt et al. |
| 7,999,087 B2 | 8/2011 | Dellinger et al. |
| 8,021,844 B2 | 9/2011 | Wang |
| 8,048,664 B2 | 11/2011 | Guan et al. |
| 8,053,191 B2 | 11/2011 | Blake |
| 8,058,001 B2 | 11/2011 | Crameri et al. |
| 8,058,004 B2 | 11/2011 | Oleinikov |
| 8,058,055 B2 | 11/2011 | Barrett et al. |
| 8,067,556 B2 | 11/2011 | Hogrefe et al. |
| 8,073,626 B2 | 12/2011 | Troup et al. |
| 8,076,064 B2 | 12/2011 | Wang |
| 8,076,152 B2 | 12/2011 | Robotti |
| 8,097,711 B2 | 1/2012 | Timar et al. |
| 8,148,068 B2 | 4/2012 | Brenner |
| 8,154,729 B2 | 4/2012 | Baldo et al. |
| 8,168,385 B2 | 5/2012 | Brenner |
| 8,168,388 B2 | 5/2012 | Gormley et al. |
| 8,173,368 B2 | 5/2012 | Staehler et al. |
| 8,194,244 B2 | 6/2012 | Wang et al. |
| 8,198,071 B2 | 6/2012 | Goshoo et al. |
| 8,202,983 B2 | 6/2012 | Dellinger et al. |
| 8,202,985 B2 | 6/2012 | Dellinger et al. |
| 8,206,952 B2 | 6/2012 | Carr et al. |
| 8,213,015 B2 | 7/2012 | Kraiczek et al. |
| 8,242,258 B2 | 8/2012 | Dellinger et al. |
| 8,247,221 B2 | 8/2012 | Fawcett |
| 8,263,335 B2 | 9/2012 | Carr et al. |
| 8,268,605 B2 | 9/2012 | Sorge et al. |
| 8,283,148 B2 | 10/2012 | Sorge et al. |
| 8,298,767 B2 | 10/2012 | Brenner et al. |
| 8,304,273 B2 | 11/2012 | Stellacci et al. |
| 8,309,307 B2 | 11/2012 | Barrett et al. |
| 8,309,706 B2 | 11/2012 | Dellinger et al. |
| 8,309,710 B2 | 11/2012 | Sierzchala et al. |
| 8,314,220 B2 | 11/2012 | Mullinax et al. |
| 8,318,433 B2 | 11/2012 | Brenner |
| 8,318,479 B2 | 11/2012 | Domansky et al. |
| 8,357,489 B2 | 1/2013 | Chua et al. |
| 8,357,490 B2 | 1/2013 | Froehlich et al. |
| 8,367,016 B2 | 2/2013 | Quan et al. |
| 8,367,335 B2 | 2/2013 | Staehler et al. |
| 8,380,441 B2 | 2/2013 | Webb et al. |
| 8,415,138 B2 | 4/2013 | Leproust |
| 8,435,736 B2 | 5/2013 | Gibson et al. |
| 8,470,996 B2 | 6/2013 | Brenner |
| 8,476,018 B2 | 7/2013 | Brenner |
| 8,476,598 B1 | 7/2013 | Pralle et al. |
| 8,481,292 B2 | 7/2013 | Casbon et al. |
| 8,481,309 B2 | 7/2013 | Zhang et al. |
| 8,491,561 B2 | 7/2013 | Borenstein et al. |
| 8,507,226 B2 | 8/2013 | Carr et al. |
| 8,507,239 B2 | 8/2013 | Lubys et al. |
| 8,507,272 B2 | 8/2013 | Zhang et al. |
| 8,530,197 B2 | 9/2013 | Li et al. |
| 8,552,174 B2 | 10/2013 | Dellinger et al. |
| 8,569,046 B2 | 10/2013 | Love et al. |
| 8,577,621 B2 | 11/2013 | Troup et al. |
| 8,614,092 B2 | 12/2013 | Zhang et al. |
| 8,642,755 B2 | 2/2014 | Sierzchala et al. |
| 8,664,164 B2 | 3/2014 | Ericsson et al. |
| 8,679,756 B1 | 3/2014 | Brenner et al. |
| 8,685,642 B2 | 4/2014 | Sampas |
| 8,685,676 B2 | 4/2014 | Hogrefe et al. |
| 8,685,678 B2 | 4/2014 | Casbon et al. |
| 8,715,933 B2 | 5/2014 | Oliver |
| 8,715,967 B2 | 5/2014 | Casbon et al. |
| 8,716,467 B2 | 5/2014 | Jacobson |
| 8,722,368 B2 | 5/2014 | Casbon et al. |
| 8,722,585 B2 | 5/2014 | Wang |
| 8,728,766 B2 | 5/2014 | Casbon et al. |
| 8,741,606 B2 | 6/2014 | Casbon et al. |
| 8,808,896 B2 | 8/2014 | Choo et al. |
| 8,808,986 B2 | 8/2014 | Jacobson et al. |
| 8,889,851 B2 | 11/2014 | Leproust et al. |
| 9,018,365 B2 | 4/2015 | Brenner |
| 9,023,601 B2 | 5/2015 | Oleinikov |
| 9,051,666 B2 | 6/2015 | Oleinikov |
| 9,073,962 B2 | 7/2015 | Fracchia et al. |
| 9,074,204 B2 | 7/2015 | Anderson et al. |
| 9,085,797 B2 | 7/2015 | Gebeyehu et al. |
| 9,133,510 B2 | 9/2015 | Andersen et al. |
| 9,139,874 B2 | 9/2015 | Myers et al. |
| 9,150,853 B2 | 10/2015 | Hudson et al. |
| 9,187,777 B2 | 11/2015 | Jacobson et al. |
| 9,194,001 B2 | 11/2015 | Brenner |
| 9,216,414 B2 | 12/2015 | Chu |
| 9,217,144 B2 | 12/2015 | Jacobson et al. |
| 9,279,149 B2 | 3/2016 | Efcavitch et al. |
| 9,286,439 B2 | 3/2016 | Shapiro et al. |
| 9,295,965 B2 | 3/2016 | Jacobson et al. |
| 9,315,861 B2 | 4/2016 | Hendricks et al. |
| 9,375,748 B2 | 6/2016 | Harumoto et al. |
| 9,376,677 B2 | 6/2016 | Mir |
| 9,388,407 B2 | 7/2016 | Jacobson |
| 9,394,333 B2 | 7/2016 | Wada et al. |
| 9,403,141 B2 | 8/2016 | Banyai et al. |
| 9,409,139 B2 | 8/2016 | Banyai et al. |
| 9,410,149 B2 | 8/2016 | Brenner et al. |
| 9,422,600 B2 | 8/2016 | Ramu et al. |
| 9,555,388 B2 | 1/2017 | Banyai et al. |
| 9,670,529 B2 | 6/2017 | Osborne et al. |
| 9,670,536 B2 | 6/2017 | Casbon et al. |
| 9,677,067 B2 | 6/2017 | Toro et al. |
| 9,695,211 B2 | 7/2017 | Wada et al. |
| 9,745,619 B2 | 8/2017 | Rabbani et al. |
| 9,765,387 B2 | 9/2017 | Rabbani et al. |
| 9,833,761 B2 | 12/2017 | Banyai et al. |
| 9,839,894 B2 | 12/2017 | Banyai et al. |
| 2001/0018512 A1 | 8/2001 | Blanchard |
| 2001/0039014 A1 | 11/2001 | Bass et al. |
| 2001/0055761 A1 | 12/2001 | Kanemoto et al. |
| 2002/0012930 A1 | 1/2002 | Rothberg et al. |
| 2002/0076716 A1 | 6/2002 | Sabanayagam et al. |
| 2002/0081582 A1 | 6/2002 | Gao et al. |
| 2002/0094533 A1 | 7/2002 | Hess et al. |
| 2002/0095073 A1 | 7/2002 | Jacobs et al. |
| 2002/0119459 A1 | 8/2002 | Griffiths et al. |
| 2002/0132308 A1 | 9/2002 | Liu et al. |
| 2002/0155439 A1 | 10/2002 | Rodriguez et al. |
| 2002/0160536 A1 | 10/2002 | Regnier et al. |
| 2002/0164824 A1 | 11/2002 | Xiao et al. |
| 2003/0008411 A1 | 1/2003 | Van et al. |
| 2003/0022207 A1 | 1/2003 | Balasubramanian et al. |
| 2003/0022317 A1 | 1/2003 | Jack et al. |
| 2003/0044781 A1 | 3/2003 | Korlach et al. |
| 2003/0058629 A1 | 3/2003 | Hirai et al. |
| 2003/0064398 A1 | 4/2003 | Barnes |
| 2003/0068633 A1 | 4/2003 | Belshaw et al. |
| 2003/0100102 A1 | 5/2003 | Rothberg et al. |
| 2003/0108903 A1 | 6/2003 | Wang et al. |
| 2003/0120035 A1 | 6/2003 | Gao et al. |
| 2003/0138782 A1 | 7/2003 | Evans |
| 2003/0143605 A1 | 7/2003 | Lok et al. |
| 2003/0148291 A1 | 8/2003 | Robotti |

(56) References Cited

U.S. PATENT DOCUMENTS

| | | |
|---|---|---|
| 2003/0148344 A1 | 8/2003 | Rothberg et al. |
| 2003/0171325 A1 | 9/2003 | Gascoyne et al. |
| 2003/0186226 A1 | 10/2003 | Brennan et al. |
| 2003/0228602 A1 | 12/2003 | Parker et al. |
| 2003/0228620 A1 | 12/2003 | Du |
| 2004/0043509 A1 | 3/2004 | Stahler et al. |
| 2004/0053362 A1 | 3/2004 | De et al. |
| 2004/0086892 A1 | 5/2004 | Crothers et al. |
| 2004/0087008 A1 | 5/2004 | Schembri |
| 2004/0106130 A1 | 6/2004 | Besemer et al. |
| 2004/0106728 A1 | 6/2004 | McGall et al. |
| 2004/0110133 A1 | 6/2004 | Xu et al. |
| 2004/0175710 A1 | 9/2004 | Haushalter |
| 2004/0175734 A1 | 9/2004 | Stahler et al. |
| 2004/0191810 A1 | 9/2004 | Yamamoto |
| 2004/0236027 A1 | 11/2004 | Maeji et al. |
| 2004/0248161 A1 | 12/2004 | Rothberg et al. |
| 2005/0022895 A1 | 2/2005 | Barth et al. |
| 2005/0049796 A1 | 3/2005 | Webb et al. |
| 2005/0053968 A1 | 3/2005 | Bharadwaj et al. |
| 2005/0079510 A1 | 4/2005 | Berka et al. |
| 2005/0100932 A1 | 5/2005 | Lapidus et al. |
| 2005/0112608 A1 | 5/2005 | Grossman et al. |
| 2005/0124022 A1 | 6/2005 | Srinivasan et al. |
| 2005/0227235 A1 | 10/2005 | Carr et al. |
| 2005/0255477 A1 | 11/2005 | Carr et al. |
| 2005/0266045 A1 | 12/2005 | Canham et al. |
| 2005/0277125 A1 | 12/2005 | Benn et al. |
| 2005/0282158 A1 | 12/2005 | Landegren |
| 2006/0003381 A1 | 1/2006 | Gilmore et al. |
| 2006/0012784 A1 | 1/2006 | Ulmer |
| 2006/0012793 A1 | 1/2006 | Harris |
| 2006/0019084 A1 | 1/2006 | Pearson |
| 2006/0024678 A1 | 2/2006 | Buzby |
| 2006/0024711 A1 | 2/2006 | Lapidus et al. |
| 2006/0024721 A1 | 2/2006 | Pedersen |
| 2006/0076482 A1 | 4/2006 | Hobbs et al. |
| 2006/0078909 A1 | 4/2006 | Srinivasan et al. |
| 2006/0078927 A1 | 4/2006 | Peck et al. |
| 2006/0078937 A1 | 4/2006 | Korlach et al. |
| 2006/0127920 A1 | 6/2006 | Church et al. |
| 2006/0134638 A1 | 6/2006 | Mulligan et al. |
| 2006/0171855 A1 | 8/2006 | Yin et al. |
| 2006/0202330 A1 | 9/2006 | Reinhardt et al. |
| 2006/0203236 A1 | 9/2006 | Ji et al. |
| 2006/0203237 A1 | 9/2006 | Ji et al. |
| 2006/0207923 A1 | 9/2006 | Li |
| 2006/0219637 A1 | 10/2006 | Killeen et al. |
| 2007/0031857 A1 | 2/2007 | Makarov et al. |
| 2007/0031877 A1 | 2/2007 | Stahler et al. |
| 2007/0054127 A1 | 3/2007 | Hergenrother et al. |
| 2007/0059692 A1 | 3/2007 | Gao et al. |
| 2007/0087349 A1 | 4/2007 | Staehler et al. |
| 2007/0099208 A1 | 5/2007 | Drmanac et al. |
| 2007/0196854 A1 | 8/2007 | Stahler et al. |
| 2007/0207482 A1 | 9/2007 | Church et al. |
| 2007/0207487 A1 | 9/2007 | Emig et al. |
| 2007/0231800 A1 | 10/2007 | Roberts et al. |
| 2007/0238104 A1 | 10/2007 | Barrett et al. |
| 2007/0238106 A1 | 10/2007 | Barrett et al. |
| 2007/0238108 A1 | 10/2007 | Barrett et al. |
| 2007/0259344 A1 | 11/2007 | Leproust et al. |
| 2007/0259345 A1 | 11/2007 | Sampas |
| 2007/0259346 A1 | 11/2007 | Gordon et al. |
| 2007/0259347 A1 | 11/2007 | Gordon et al. |
| 2007/0269870 A1 | 11/2007 | Church et al. |
| 2008/0085514 A1 | 4/2008 | Peck et al. |
| 2008/0087545 A1 | 4/2008 | Jensen et al. |
| 2008/0161200 A1 | 7/2008 | Yu et al. |
| 2008/0182296 A1 | 7/2008 | Chanda et al. |
| 2008/0214412 A1 | 9/2008 | Stahler et al. |
| 2008/0227160 A1 | 9/2008 | Kool |
| 2008/0233616 A1 | 9/2008 | Liss |
| 2008/0287320 A1 | 11/2008 | Baynes et al. |
| 2008/0308884 A1 | 12/2008 | Kalvesten |
| 2009/0036664 A1 | 2/2009 | Peter |
| 2009/0053704 A1 | 2/2009 | Novoradovskaya et al. |
| 2009/0062129 A1 | 3/2009 | McKernan et al. |
| 2009/0087840 A1 | 4/2009 | Baynes et al. |
| 2009/0088679 A1 | 4/2009 | Wood et al. |
| 2009/0170802 A1 | 7/2009 | Stahler et al. |
| 2009/0176280 A1 | 7/2009 | Hutchison, III et al. |
| 2009/0181861 A1 | 7/2009 | Li et al. |
| 2009/0194483 A1 | 8/2009 | Robotti et al. |
| 2009/0230044 A1 | 9/2009 | Bek |
| 2009/0238722 A1 | 9/2009 | Mora-Fillat et al. |
| 2009/0239759 A1 | 9/2009 | Balch |
| 2009/0263802 A1 | 10/2009 | Drmanac |
| 2010/0004143 A1 | 1/2010 | Shibahara |
| 2010/0047805 A1 | 2/2010 | Wang |
| 2010/0051967 A1 | 3/2010 | Bradley et al. |
| 2010/0069250 A1 | 3/2010 | White, III et al. |
| 2010/0090341 A1 | 4/2010 | Wan et al. |
| 2010/0160463 A1 | 6/2010 | Wang et al. |
| 2010/0167950 A1 | 7/2010 | Juang et al. |
| 2010/0173364 A1 | 7/2010 | Evans, Jr. et al. |
| 2010/0216648 A1 | 8/2010 | Staehler et al. |
| 2010/0256017 A1 | 10/2010 | Larman et al. |
| 2010/0258487 A1 | 10/2010 | Zelechonok et al. |
| 2010/0286290 A1 | 11/2010 | Lohmann et al. |
| 2010/0292102 A1 | 11/2010 | Nouri |
| 2010/0300882 A1 | 12/2010 | Zhang et al. |
| 2011/0009607 A1 | 1/2011 | Komiyama et al. |
| 2011/0114244 A1 | 5/2011 | Yoo et al. |
| 2011/0114549 A1 | 5/2011 | Yin et al. |
| 2011/0124049 A1 | 5/2011 | Li et al. |
| 2011/0124055 A1 | 5/2011 | Carr et al. |
| 2011/0126929 A1 | 6/2011 | Velasquez-Garcia et al. |
| 2011/0171651 A1 | 7/2011 | Richmond |
| 2011/0172127 A1 | 7/2011 | Jacobson et al. |
| 2011/0201057 A1 | 8/2011 | Carr et al. |
| 2011/0217738 A1 | 9/2011 | Jacobson |
| 2011/0230653 A1 | 9/2011 | Novoradovskaya et al. |
| 2011/0254107 A1 | 10/2011 | Bulovic et al. |
| 2011/0287435 A1 | 11/2011 | Grunenwald et al. |
| 2012/0003713 A1 | 1/2012 | Hansen et al. |
| 2012/0021932 A1 | 1/2012 | Mershin et al. |
| 2012/0027786 A1 | 2/2012 | Gupta et al. |
| 2012/0028843 A1 | 2/2012 | Ramu et al. |
| 2012/0050411 A1 | 3/2012 | Mabritto et al. |
| 2012/0094847 A1 | 4/2012 | Warthmann et al. |
| 2012/0129704 A1 | 5/2012 | Gunderson et al. |
| 2012/0149602 A1 | 6/2012 | Friend et al. |
| 2012/0164691 A1 | 6/2012 | Eshoo et al. |
| 2012/0184724 A1 | 7/2012 | Sierzchala et al. |
| 2012/0220497 A1 | 8/2012 | Jacobson et al. |
| 2012/0231968 A1 | 9/2012 | Bruhn et al. |
| 2012/0238737 A1 | 9/2012 | Dellinger et al. |
| 2012/0258487 A1 | 10/2012 | Chang et al. |
| 2012/0264653 A1 | 10/2012 | Carr et al. |
| 2012/0270750 A1 | 10/2012 | Oleinikov |
| 2012/0270754 A1 | 10/2012 | Blake |
| 2012/0283140 A1 | 11/2012 | Chu |
| 2012/0288476 A1 | 11/2012 | Hartmann et al. |
| 2012/0289691 A1 | 11/2012 | Dellinger et al. |
| 2012/0315670 A1 | 12/2012 | Jacobson et al. |
| 2012/0322681 A1 | 12/2012 | Kung et al. |
| 2013/0005612 A1 | 1/2013 | Carr et al. |
| 2013/0017642 A1 | 1/2013 | Milgrew et al. |
| 2013/0017977 A1 | 1/2013 | Oleinikov |
| 2013/0017978 A1 | 1/2013 | Kavanagh et al. |
| 2013/0035261 A1 | 2/2013 | Sierzchala et al. |
| 2013/0045483 A1 | 2/2013 | Treusch et al. |
| 2013/0053252 A1 | 2/2013 | Xie et al. |
| 2013/0059296 A1 | 3/2013 | Jacobson et al. |
| 2013/0059761 A1 | 3/2013 | Jacobson et al. |
| 2013/0065017 A1 | 3/2013 | Sieber |
| 2013/0109595 A1 | 5/2013 | Routenberg |
| 2013/0109596 A1 | 5/2013 | Peterson et al. |
| 2013/0123129 A1 | 5/2013 | Zeiner et al. |
| 2013/0130321 A1 | 5/2013 | Staehler et al. |
| 2013/0137161 A1 | 5/2013 | Zhang et al. |
| 2013/0137173 A1 | 5/2013 | Zhang et al. |
| 2013/0137174 A1 | 5/2013 | Zhang et al. |

(56) References Cited

U.S. PATENT DOCUMENTS

| | | |
|---|---|---|
| 2013/0137861 A1 | 5/2013 | Leproust et al. |
| 2013/0225421 A1 | 8/2013 | Li et al. |
| 2013/0244884 A1 | 9/2013 | Jacobson et al. |
| 2013/0252849 A1 | 9/2013 | Hudson et al. |
| 2013/0281308 A1 | 10/2013 | Kung et al. |
| 2013/0296192 A1 | 11/2013 | Jacobson et al. |
| 2013/0296194 A1 | 11/2013 | Jacobson et al. |
| 2013/0309725 A1 | 11/2013 | Jacobson et al. |
| 2013/0323722 A1 | 12/2013 | Carr et al. |
| 2013/0323725 A1 | 12/2013 | Peter et al. |
| 2013/0330778 A1 | 12/2013 | Zeiner et al. |
| 2014/0011226 A1 | 1/2014 | Bernick et al. |
| 2014/0018441 A1 | 1/2014 | Fracchia et al. |
| 2014/0038240 A1 | 2/2014 | Temme et al. |
| 2014/0106394 A1 | 4/2014 | Ko et al. |
| 2014/0141982 A1 | 5/2014 | Jacobson et al. |
| 2014/0170665 A1 | 6/2014 | Hiddessen et al. |
| 2014/0178992 A1 | 6/2014 | Nakashima et al. |
| 2014/0274729 A1 | 9/2014 | Kurn et al. |
| 2014/0274741 A1 | 9/2014 | Hunter et al. |
| 2014/0303000 A1 | 10/2014 | Armour et al. |
| 2014/0309119 A1 | 10/2014 | Jacobson et al. |
| 2014/0309142 A1 | 10/2014 | Tian |
| 2015/0010953 A1 | 1/2015 | Lindstrom et al. |
| 2015/0012723 A1 | 1/2015 | Park et al. |
| 2015/0031089 A1 | 1/2015 | Lindstrom |
| 2015/0038373 A1 | 2/2015 | Banyai et al. |
| 2015/0057625 A1 | 2/2015 | Coulthard |
| 2015/0065393 A1 | 3/2015 | Jacobson |
| 2015/0120265 A1 | 4/2015 | Amirav-Drory et al. |
| 2015/0159152 A1 | 6/2015 | Allen et al. |
| 2015/0183853 A1 | 7/2015 | Sharma et al. |
| 2015/0191719 A1 | 7/2015 | Hudson et al. |
| 2015/0196917 A1 | 7/2015 | Kay et al. |
| 2015/0203839 A1 | 7/2015 | Jacobson et al. |
| 2015/0211047 A1 | 7/2015 | Borns |
| 2015/0225782 A1 | 8/2015 | Walder et al. |
| 2015/0240232 A1 | 8/2015 | Zamore et al. |
| 2015/0261664 A1 | 9/2015 | Goldman et al. |
| 2015/0321191 A1 | 11/2015 | Kendall et al. |
| 2015/0322504 A1 | 11/2015 | Lao et al. |
| 2015/0344927 A1 | 12/2015 | Sampson et al. |
| 2015/0353921 A9 | 12/2015 | Tian |
| 2015/0353994 A1 | 12/2015 | Myers et al. |
| 2015/0361420 A1 | 12/2015 | Hudson et al. |
| 2015/0361422 A1 | 12/2015 | Sampson et al. |
| 2015/0361423 A1 | 12/2015 | Sampson et al. |
| 2015/0368687 A1 | 12/2015 | Saaem et al. |
| 2015/0376602 A1 | 12/2015 | Jacobson et al. |
| 2016/0001247 A1 | 1/2016 | Oleinikov |
| 2016/0002621 A1 | 1/2016 | Nelson et al. |
| 2016/0002622 A1 | 1/2016 | Nelson et al. |
| 2016/0010045 A1 | 1/2016 | Cohen et al. |
| 2016/0017394 A1 | 1/2016 | Liang et al. |
| 2016/0017425 A1 | 1/2016 | Ruvolo et al. |
| 2016/0024138 A1 | 1/2016 | Gebeyehu et al. |
| 2016/0024576 A1 | 1/2016 | Chee |
| 2016/0026753 A1 | 1/2016 | Krishnaswami et al. |
| 2016/0026758 A1 | 1/2016 | Jabara et al. |
| 2016/0046973 A1 | 2/2016 | Efcavitch et al. |
| 2016/0046974 A1 | 2/2016 | Efcavitch et al. |
| 2016/0082472 A1 | 3/2016 | Perego et al. |
| 2016/0097051 A1 | 4/2016 | Jacobson et al. |
| 2016/0102322 A1 | 4/2016 | Ravinder et al. |
| 2016/0108466 A1 | 4/2016 | Nazarenko et al. |
| 2016/0122755 A1 | 5/2016 | Hall et al. |
| 2016/0168611 A1 | 6/2016 | Efcavitch et al. |
| 2016/0184788 A1 | 6/2016 | Hall et al. |
| 2016/0200759 A1 | 7/2016 | Srivastava et al. |
| 2016/0229884 A1 | 8/2016 | Indermuhle et al. |
| 2016/0230175 A1 | 8/2016 | Carstens |
| 2016/0251651 A1 | 9/2016 | Banyai et al. |
| 2016/0264958 A1 | 9/2016 | Toro et al. |
| 2016/0289839 A1 | 10/2016 | Harumoto et al. |
| 2016/0303535 A1 | 10/2016 | Banyai et al. |
| 2016/0310426 A1 | 10/2016 | Wu |
| 2016/0310927 A1 | 10/2016 | Banyai et al. |
| 2016/0333340 A1 | 11/2016 | Wu |
| 2016/0339409 A1 | 11/2016 | Banyai et al. |
| 2016/0340672 A1 | 11/2016 | Banyai et al. |
| 2016/0354752 A1 | 12/2016 | Banyai et al. |
| 2017/0017436 A1 | 1/2017 | Church |
| 2017/0081660 A1 | 3/2017 | Cox et al. |
| 2017/0081716 A1 | 3/2017 | Peck |
| 2017/0095785 A1 | 4/2017 | Banyai et al. |
| 2017/0141793 A1 | 5/2017 | Strauss et al. |
| 2017/0151546 A1 | 6/2017 | Peck et al. |
| 2017/0159044 A1 | 6/2017 | Toro et al. |
| 2017/0327819 A1 | 11/2017 | Banyai et al. |
| 2017/0357752 A1 | 12/2017 | Diggans |

FOREIGN PATENT DOCUMENTS

| | | |
|---|---|---|
| EP | 0753057 A1 | 1/1997 |
| EP | 1314783 A1 | 5/2003 |
| EP | 1546387 A2 | 6/2005 |
| EP | 1153127 B1 | 7/2006 |
| EP | 1728860 A1 | 12/2006 |
| EP | 1072010 B1 | 4/2010 |
| EP | 2175021 A2 | 4/2010 |
| EP | 2330216 A1 | 6/2011 |
| EP | 1343802 B1 | 5/2012 |
| EP | 2504449 A1 | 10/2012 |
| EP | 2928500 A1 | 10/2015 |
| EP | 2971034 A1 | 1/2016 |
| EP | 3030682 A2 | 6/2016 |
| EP | 3044228 A4 | 4/2017 |
| EP | 2994509 B1 | 6/2017 |
| WO | WO-9015070 A1 | 12/1990 |
| WO | WO-9210092 A1 | 6/1992 |
| WO | WO-9210588 A1 | 6/1992 |
| WO | WO-9309668 A1 | 5/1993 |
| WO | WO-9525116 A1 | 9/1995 |
| WO | WO-9526397 A1 | 10/1995 |
| WO | WO-9615861 A1 | 5/1996 |
| WO | WO-9710365 A1 | 3/1997 |
| WO | WO-9822541 A2 | 5/1998 |
| WO | WO-9841531 A2 | 9/1998 |
| WO | WO-9942813 A1 | 8/1999 |
| WO | WO-0013017 A2 | 3/2000 |
| WO | WO-0018957 A1 | 4/2000 |
| WO | WO-0042559 A1 | 7/2000 |
| WO | WO-0042560 A2 | 7/2000 |
| WO | WO-0042561 A2 | 7/2000 |
| WO | WO-0049142 A1 | 8/2000 |
| WO | WO-0210443 A1 | 2/2002 |
| WO | WO-0220537 A2 | 3/2002 |
| WO | WO-0224597 A2 | 3/2002 |
| WO | WO-0233669 A1 | 4/2002 |
| WO | WO-03040410 A1 | 5/2003 |
| WO | WO-03046223 A1 | 6/2003 |
| WO | WO-03054232 A2 | 7/2003 |
| WO | WO-03064026 A1 | 8/2003 |
| WO | WO-03064027 A2 | 8/2003 |
| WO | WO-03064699 A2 | 8/2003 |
| WO | WO-03065038 A2 | 8/2003 |
| WO | WO-03066212 A2 | 8/2003 |
| WO | WO-03089605 A2 | 10/2003 |
| WO | WO-03100012 A2 | 12/2003 |
| WO | WO-2004024886 A2 | 3/2004 |
| WO | WO-2004029220 A2 | 4/2004 |
| WO | WO-2004029586 A1 | 4/2004 |
| WO | WO-2004031351 A2 | 4/2004 |
| WO | WO-2004031399 A2 | 4/2004 |
| WO | WO-2005051970 A2 | 6/2005 |
| WO | WO-2006076679 A1 | 7/2006 |
| WO | WO-2006116476 A1 | 11/2006 |
| WO | WO-2007120627 A2 | 10/2007 |
| WO | WO-2007137242 A2 | 11/2007 |
| WO | WO-2008006078 A2 | 1/2008 |
| WO | WO-2008027558 A2 | 3/2008 |
| WO | WO-2008054543 A2 | 5/2008 |
| WO | WO-2008063135 A1 | 5/2008 |
| WO | WO-2008109176 A2 | 9/2008 |

(56) References Cited

FOREIGN PATENT DOCUMENTS

| | | |
|---|---|---|
| WO | WO-2010025310 A2 | 3/2010 |
| WO | WO-2010025566 A1 | 3/2010 |
| WO | WO-2010027512 A2 | 3/2010 |
| WO | WO-2011053957 A2 | 5/2011 |
| WO | WO-2011056872 A2 | 5/2011 |
| WO | WO-2011066185 A1 | 6/2011 |
| WO | WO-2011066186 A1 | 6/2011 |
| WO | WO-2011085075 A2 | 7/2011 |
| WO | WO-2011103468 A2 | 8/2011 |
| WO | WO-2011143556 A1 | 11/2011 |
| WO | WO-2011150168 A1 | 12/2011 |
| WO | WO-2011161413 A2 | 12/2011 |
| WO | WO-2012061832 A1 | 5/2012 |
| WO | WO-2012078312 A2 | 6/2012 |
| WO | WO-2012149171 A1 | 11/2012 |
| WO | WO-2012154201 A1 | 11/2012 |
| WO | WO-2013032850 A2 | 3/2013 |
| WO | WO-2013036668 A1 | 3/2013 |
| WO | WO-2013101896 A1 | 7/2013 |
| WO | WO-2013177220 A1 | 11/2013 |
| WO | WO-2014004393 A1 | 1/2014 |
| WO | WO-2014035693 A2 | 3/2014 |
| WO | WO-2014088693 A1 | 6/2014 |
| WO | WO-2014089160 | 6/2014 |
| WO | WO-2014089160 A1 | 6/2014 |
| WO | WO-2014093694 A1 | 6/2014 |
| WO | WO-2014151696 A1 | 9/2014 |
| WO | WO-2014160004 A1 | 10/2014 |
| WO | WO-2014160059 A1 | 10/2014 |
| WO | WO-2015017527 A2 | 2/2015 |
| WO | WO-2015021080 A2 | 2/2015 |
| WO | WO-2015021280 A1 | 2/2015 |
| WO | WO-2015040075 A1 | 3/2015 |
| WO | WO-2015054292 A1 | 4/2015 |
| WO | WO-2015081114 A2 | 6/2015 |
| WO | WO-2015090879 A1 | 6/2015 |
| WO | WO-2015120403 A1 | 8/2015 |
| WO | WO-2015160004 A1 | 10/2015 |
| WO | WO-2015175832 A1 | 11/2015 |
| WO | WO-2016007604 A1 | 1/2016 |
| WO | WO-2016011080 A2 | 1/2016 |
| WO | WO-2016022557 A1 | 2/2016 |
| WO | WO-2016053883 A1 | 4/2016 |
| WO | WO-2016065056 A1 | 4/2016 |
| WO | WO-2016126882 A1 | 8/2016 |
| WO | WO-2016126987 A1 | 8/2016 |
| WO | WO-2016130868 A2 | 8/2016 |
| WO | WO-2016172377 A1 | 10/2016 |
| WO | WO-2016183100 A1 | 11/2016 |
| WO | WO-2017049231 A1 | 3/2017 |
| WO | WO-2017053450 A1 | 3/2017 |
| WO | WO-2017095958 A1 | 6/2017 |

OTHER PUBLICATIONS

Cohen et al., Human population: The next half century. Science, 302:1172-1175, 2003.
Elsik et al., The Genome sequence of taurine cattle: A window of ruminant biology and evolution. Science, 324:522-528, 2009.
Fodor et al. "Light-Directed, Spatially Addressable Parallel Chemical Synthesis," Science, 251(4995):767-773, 1991.
Gu et al., Depletion of abundant sequences by hybridization (DASH): using Cas9 to remove unwanted high-abundance species in sequencing libraries and molecular counting applications. Genome Biology, 17:41, 13 pages, 2016.
Kim et al., High-resolution patterns of quantum dots formed by electrohydrodynamic jet printing for light-emitting diodes. Nano Letters, 15:969-973, 2015.
Kosuri and Church, "Large-scale de novo DNA synthesis: technologies and applications," Nature Methods, 11:499-507, 2014. Available at: http://www.nature.com/nmeth/journal/v11/n5/full/nmeth.2918.html.
Krayden, Inc., A Guide to Silane Solutions. Silane coupling agents. 7 pages. Published on May 31, 2005 at: http://krayden.com/pdf/xia_silane_chemistry.pdf.
Lausted et al., "POSaM: a fast, flexible, open-source, inkjet oligonucleotide synthesizer and microarrayer," Genome Biology, 5:R58, 17 pages, 2004. available at https://www.ncbi.nlm.nih.gov/pmc/articles/PMC507883/.
Leproust et al., "Synthesis of high-quality libraries of long (150mer) oligonucleotides by a novel depurination controlled process," Nucleic Acids Research, 35(8):2522-2540, 2010.
Lewontin and Harti, Population genetics in forensic DNA typing. Science, 254:1745-1750, 1991.
McBride & Caruthers, "An investigation of several deoxynucleoside phosphoramidites useful for synthesizing deoxyoligonucleotides." Tetrahedron Lett. 24: 245-248, 1983.
Milo and Phillips, Numbers here reflect the number of protein coding genes and excludes tRNA and non-coding RNA. Cell Biology by the Numbers, p. 286, 2015.
PCT Patent Application No. PCT/US2016/052336 International Search Report and Written Opinion dated Dec. 7, 2016.
PCT Patent Application No. PCT/US2016/052916 International Search Report and Written Opinion dated Dec. 30, 2016.
Pray. "Discovery of DNA Structure and Function: Watson and Crick," Nature Education, 2008, 6 pages. available at: http://www.nature.com/scitable/topicpage/discovery-of-dna-structure-and-function-watson-397.
Quan et al., "Parallel on-chip gene synthesis and application to optimization of protein expression," Nature Biotechnology, 29(5):449-452, 2011.
Rafalski and Morgante, Corn and humans: recombination and linkage disequilibrium in two genomes of similar size. Trends in Genetics, 20(2):103-111, 2004.
Raje and Murma, A Review of electrohydrodynamic-inkjet printing technology. International Journal of Emerging Technology and Advanced Engineering, 4(5):174-183, 2014.
Sargolzaei et al., Extent of linkage disequilibrium in Holstein cattle in North America. J.Dairy Science, 91:2106-2117, 2007.
The Hood Laboratory, "Beta Group." Assembly Manual for the POSaM: The ISB Piezoelelctric Oligonucleotide Synthesizer and Microarrayer, Inkjet Microarrayer Manual Version 1.2, 50 pages, May 28, 2004.
U.S. Appl. No. 14/885,962 Office Action dated Dec. 16, 2016.
U.S. Appl. No. 14/885,965 Office Action dated Feb. 10, 2017.
U.S. Appl. No. 15/154,879 Notice of Allowance dated Feb. 1, 2017.
U.S. Appl. No. 15/187,721 Notice of Allowance dated Dec. 7, 2016.
U.S. Appl. No. 15/187,721 Office Action dated Oct. 14, 2016.
U.S. Appl. No. 15/233,835 Office Action dated Feb. 8, 2017.
U.S. Appl. No. 15/233,835 Restriction Requirement dated Nov. 4, 2016.
U.S. Appl. No. 15/245,054 Office Action dated Oct. 19, 2016.
Van Tassell et al., SNP discovery and allele frequency estimation by deep sequencing of reduced representation libraries. Nature Methods, 5:247-252, 2008.
Wijshoff, Herman. Structure and fluid-dynamics in Piezo inkjet printheads. Thesis. Venio, The Netherlands, published 2008, p. 1-185.
Xiong et al., Chemical gene synthesis: Strategies, softwares, error corrections, and applications. FEMS Microbiol. Rev., 32:522-540, 2008.
Abudayyeh et al., C2c2 is a single-component programmable RNA-guided RNA-targeting CRISPR effector. Science, available on line, Jun. 13, 2016, at: http://zlab.mit.edu/assets/reprints/Abudayyeh_OO_Science_2016.pdf , 17 pages.
Crick. On protein synthesis. Symp Soc Exp Biol12:138-163,1958.
Doudna et al. Genome editing. The new frontier of genome engineering with CRISPR-Cas9. Science 346(6213):1258096-1-1258096-9, 2014.
Genomics 101. An Introduction to the Genomic Workflow. 2016 edition, 64 pages. Available at: http://www.frontlinegenomics.com/magazine/6757/genomics-101/.
Hughes et al. Principles of early drug discovery. Br J Pharmacol 162(2):1239-1249, 2011.
Liu et al., Comparison of Next-Generation Sequencing Systems. Journal of Biomedicine and Biotechnology, 11 pages, 2012.
PCT Patent Application No. PCT/US2016/028699 International Search Report and Written Opinion dated Jul. 29, 2016.

(56) References Cited

OTHER PUBLICATIONS

PCT Patent Application No. PCT/US2016/031674 International Search Report and Written Opinion dated Aug. 11, 2016.
Pirrung. How to make a DNA chip. Angew. Chem. Int. Ed., 41:1276-1289, 2002.
Poster. Reimagine Genome Scale Research. 2016, 1 page. Available at http://www2.twistbioscience.com/Oligo_Pools_CRISPR_poster.
Powers et al. Optimal strategies for the chemical and enzymatic synthesis of bihelical deoxyribonucleic acids. J Am Chem Soc., 97(4):875-884, 1975.
Taylor et al., Impact of surface chemistry and blocking strategies on DNA microarrays. Nucleic Acids Research, 31(16):e87, 19 pages, 2003.
U.S. Appl. No. 14/885,965 Office Action dated Jul. 7, 2016.
U.S. Appl. No. 14/452,429 Notice of Allowance dated Jun. 7, 2016.
U.S. Appl. No. 14/885,962 Office Action dated Sep. 8, 2016.
U.S. Appl. No. 14/885,963 Notice of Allowance dated May 24, 2016.
Andoni and Indyk, Near-Optimal Hashing Algorithms for Approximate Nearest Neighbor in High Dimensions, Communications of the ACM, 51(1):117-122, 2008.
Bethge et al., "Reverse synthesis and 3'-modification of RNA." Jan. 1, 2011, pp. 64-64, XP055353420, Retrieved from the Internet: URL: http://www.is3na.org/assets/events/Category%202-Medicinal%20Chemistry%20of%20Oligonucleotides%20%2864-108%29.pdf.
Blawat et al., Forward error correction for DNA data storage. Procedia Computer Science, 80:1011-1022, 2016.
Bornholt et al., A DNA-Based Archival Storage System, in International Conference on Architectural Support for Programming Languages and Operating Systems (ASPLOS), Apr. 2-6, 2016, Atlanta, GA, 2016, 637-649.
Cardelli, Two-Domain DNA Strand Displacement, Electron. Proc. Theor. Comput. Sci., 26:47-61, 2010.
Carlson, "Time for New DNA Synthesis and Sequencing Cost Curves," 2014. [Online]. Available: http://www.synthesis.cc/synthesis/2014/02/time_for_new_cost_curves_2014., 10 pages.
Caruthers, The Chemical Synthesis of DNA/RNA: Our Gift to Science. J. Biol. Chem., 288(2):1420-1427, 2013.
Chen et al., Programmable chemical controllers made from DNA, Nat. Nanotechnol., 8(10):755-762, 2013.
Erlich and Zielinski, DNA fountain enables a robust and efficient storage architecture. Science, 355(6328):950-054, 2017.
European Patent Application No. 14834665.3 extended European Search Report dated Apr. 28, 2017.
Finger et al., The wonders of Flap Endonucleases: Structure, function, mechanism and regulation. Subcell Biochem., 62:301-326, 2012.
Fogg et al., Structural basis for uracil recognition by archaeal family B DNA polymerases. Nature Structural Biology, 9(12):922-927, 2002.
GeneArt Seamless Cloning and Assembly Kits. Life Technologies Synthetic Biology. 8 pages, available online Jun. 15, 2012.
Gibson Assembly. Product Listing. Application Overview. 2 pages, available online Dec. 16, 2014.
Goldman et al., Towards practical, high-capacity, low-maintenance information storage in synthesized DNA, Nature, 494(7435):77-80, 2013.
Grass, et al., Robust chemical preservation of digital information on DNA in silica with error-correcting codes, Angew. Chemie—Int. Ed., 54(8):2552-2555, 2015.
Greagg et al., A read-ahead function in archaeal DNA polymerases detects promutagenic template-strand uracil. Proc. Nat. Acad. Sci. USA, 96:9045-9050, 1999.
In-Fusion Cloning: Accuracy, Not Background. Cloning & Competent Cells, ClonTech Laboratories, 3 pages, available online Jul. 6, 2014.
Jinek et al., A Programmable dual-RNA-guided DNA endonuclease in adaptive bacterial immunity. Science, 337:816-821, 2012.
Limbachiya et al., Natural data storage: A review on sending information from now to then via Nature. ACM Journal on Emerging Technologies in Computing Systems, V(N):Article A, May 19, 2015, 17 pages.
Link Technologies. "Product Guide 2010." Nov. 27, 2009 (Nov. 27, 2009), XP055353191, 136 pages. Retrieved from the Internet: URL: http://www.linktech.co.uk/documents/517/517.pdf.
Liu et al., Rational design of CXCR4 specific antibodies with elongated CDRs. JACS, 136:10557-10560, 2014.
Morin et al., Profiling the HeLa S3 transcriptome using randomly primed cDNA and massively parallel short-read sequencing. Biotechniques, 45:81-94, 2008.
Neiman M.S,. Negentropy principle in information processing systems. Radiotekhnika, 1966, NΦ11, p. 2-9.
Neiman M.S., On the bases of the theory of information retrieval. Radiotekhnika, 1967, NΦ 5, p. 2-10.
Neiman M.S., On the molecular memory systems and the directed mutations. Radiotekhnika, 1965, No. 6, pp. 1-8.
Neiman M.S., On the relationships between the reliability, performance and degree of microminiaturization at the molecular-atomic level. Radiotekhnika, 1965, No. 1, pp. 1-9.
Neiman M.S., Some fundamental issues of microminiaturization. Radiotekhnika, 1964, No. 1, pp. 3-12.
Organick et al., Scaling up DNA data storage and random access retrieval, bioRxiv, preprint first posted online Mar. 7, 2017, 14 pages.
PCT/US2015/043605 International Preliminary Report on Patentability dated Feb. 16, 2017.
PCT/US2016/016459 International Preliminary Report on Patentability dated Aug. 17, 2017.
PCT/US2016/016636 International Preliminary Report on Patentability dated Aug. 17, 2017.
PCT/US2016/064270 International Search Report and Written Opinion dated Apr. 28, 2017.
PCT/US2017/026232 International Search Report and Written Opinion dated Aug. 28, 2017.
PCT/US2017/036868 International Search Report and Written Opinion dated Aug. 11, 2017.
Qian and Winfree, Scaling up digital circuit computation with DNA strand displacement cascades. Science, 332(6034):196-1201, 2011.
Qian, et al., Neural network computation with DNA strand displacement cascades, Nature, 475(7356):368-372, 2011.
Rastegari, et al., XNOR-Net: ImageNet Classification Using Binary Convolutional Neural Networks, in ECCV 2016, Part IV, LNCS 9908, p. 525-542, 2016.
Seelig, et al., Enzyme-Free Nucleic Acid Logic Circuits, Science 314(5805):1585-1588, 2006.
Simonyan and Zisserman, Very Deep Convolutional Networks for Large-Scale Image Recognition, Published as a conference paper at Int. Conf. Learn. Represent., pp. 1-14, 2015.
Srivannavit et al., Design and fabrication of microwell array chips for a solution-based, photogenerated acid-catalyzed parallel oligonuclotide DNA synthesis. Sensors and Actuators A, 116:150-160, 2004.
Srivastava et al., "RNA synthesis: phosphoramidites for RNA synthesis in the reverse direction. Highly efficient synthesis and application to convenient introduction of ligands, chromophores and modifications of synthetic RNA at the 3'-end", Nucleic Acids Symposium Series, 52(1):103-104, 2008. (Abstract only).
The SLIC, Gibson, CPEC and SLiCE assembly methods (and GeneArt Seamless, In-Fusion Cloning). 5 pages, available online, Sep. 2, 2010.
U.S. Appl. No. 14/241,874 Office Action dated Feb. 27, 2017.
U.S. Appl. No. 14/885,965 Office Action dated Aug. 30, 2017.
U.S. Appl. No. 15/135,434 Restriction Requirement dated Jul. 12, 2017.
U.S. Appl. No. 15/233,835 Office Action dated Jul. 26, 2017.
U.S. Appl. No. 15/245,054 Office Action dated Mar. 21, 2017.
U.S. Appl. No. 15/377,547 Office Action dated Mar. 24, 2017.
Wagner et al., "Nucleotides, Part LXV, Synthesis of 2'-Deoxyribonucleoside 5'-Phosphoramidites: New Building Blocks for the Inverse (5'-3')-Oligonucleotide Approach." Helvetica Chimica Acta, 83(8):2023-2035, 2000.

(56) References Cited

OTHER PUBLICATIONS

Wan et al., Deep Learning for Content-Based Image Retrieval: A comprehensive study. in Proceedings of the 22nd ACM International Conference on Multimedia—Nov. 3-7, 2014, Orlando, FL, p. 157-166, 2014.
Wright and Church, An open-source oligomicroarray standard for human and mouse. Nature Biotechnology, 20:1082-1083, 2002.
Xu et al., Design of 240,000 orthogonal 25mer DNA barcode probes. PNAS, 106(7):2289-2294, 2009.
Yazdi, et al., A Rewritable, Random-Access DNA-Based Storage System, Scientific Reports, 5, Article No. 14138, 27 pages, 2015.
Zhang and Seelig, Dynamic DNA nanotechnology using strand-displacement reactions, Nat. Chem., 3(2):103-113, 2011.
Zhirnov et al., Nucleic acid memory. Nature Materials, 15:366, 2016.
Adessi, et al. Solid phase DNA amplification: characterisation of primer attachment and amplification mechanisms. Nucleic Acids Res. Oct. 15, 2000;28(20):E87.
Alexeyev, Mikhail F. et al., "Gene synthesis, bacterial expression and purification of the Rickettsia prowazekii ATP/ADP translocase", Biochimica et Biophysics Acta, vol. 1419, 299-306 (1999).
Al-Housseiny et al., Control of interfacial instabilities using flow geometry Nature Physics, 8:747-750 (2012); Published online at: DOI:10.1038/NPHYS2396.
Amblard, Francois et al., "A magnetic manipulator for studying local rheology and micromechanical properties of biological systems", Rev. Sci. Instrum., vol. 67, No. 3, 818-827, Mar. 1996.
Arkles, et al. The Role of Polarity in the Structure of Silanes Employed in Surface Modification. Silanes and Other Coupling Agents. 2009; 5:51-64.
Arkles, Hydrophobicity, Hydrophilicity Reprinted with permission from the Oct. 2006 issue of Paint & Coatings Industry magazine, Retrieved on Mar. 19, 2016, 10 pages.
Assi, Fabiano et al., "Massive-parallel adhesion and reactivity-measurements using simple and inexpensive magnetic tweezers", J. Appl. Phys., vol. 92, No. 9, 5584-5586, Nov. 1, 2002.
Au, Lo-Chun et al. "Gene synthesis by a LCR-based approach: high level production of Leptin-L54 using synthetic gene in *Escherichia coli*", Biochemical and Biophysical Research Communications, vol. 248, 200-203 (1998).
Baedeker, Mathias et al., Overexpression of a designed 2.2kb gene of eukaryotic phenylalanine ammonialyase in *Escherichia coli*. FEBS Letters, vol. 457, 57-60 (1999).
Barbee, et al. Magnetic Assembly of High-Density DNA Arrays for Genomic Analyses. Anal Chem. Mar. 15, 2008; 80(6): 2149-2154.
Beaucage, et al. Advances in the synthesis of oligonucleotides by the phosphoramidite approach. Tetrahedron. 1992; 48:2223-2311.
Beaucage, et al. Deoxynucleoside phosphoramidites—A new class of key intermediates for deoxypolynucleotide synthesis. Tetrahedron Lett. 1981; 22(20):1859-1862.
Beaulieu, Martin et al., "PCR candidate region mismatch scanning adaptation to quantitative, high throughput genotyping", Nucleic Acids Research, vol. 29, No. 5, 1114-1124 (2001).
Beigelman, et al. Base-modified phosphoramidite analogs of pyrimidine ribonucleosides for RNA structure-activity studies. Methods Enzymol. 2000;317:39-65.
Biswas, Indranil et al., "Identification and characterization of a thermostable MutS homolog from Thennus aquaticus", The Journal of Biological Chemistry, vol. 271, No. 9, 5040-5048 (Mar. 1, 1996).
Biswas, Indranil et al., "Interaction of MutS/protein with the major and minor grooves of a heteroduplex DNA", The Journal of Biological Chemistry, vol. 272, No. 20, 13355-13364 (May 1, 1997).
Bjornson, Keith P. et al., "Differential and simultaneous adenosine Di- and Tri~hosphate binding by MutS", The Journal of Biological Chemistry, vol. 278, No. 20, 18557-18562 (May 16, 2003).
Blanchard, et al. High-Density Oligonucleotide Arrays. Biosens. & Bioelectronics. 1996; 11:687-690.
Blanchard, in: Genetic Engineering, Principles and Methods, vol. 20, Ed. J. Sedlow, New York: Plenum Press, p. 111-124, 1979.
Butler, et al. In situ synthesis of oligonucleotide arrays by using surface tension. J Am Chem Soc. Sep. 19, 2001;123(37):8887-94.
Calvert, Lithographically patterned self-assembled films. In: Organic Thin Films and Surfaces: Directions for the Nineties, vol. 20, p. 109, ed. by Abraham Ulman, San Diego: Academic Press, 1995.
Carr, et al. Protein-mediated error correction for de novo DNA synthesis. Nucleic Acids Res. Nov. 23, 2004;32(20):e162.
Caruthers, Chemical synthesis of deoxyoligonucleotides by the phosphoramidite method. In Methods in Enzymology, Chapter 15, 154:287-313 (1987).
Caruthers. Gene synthesis machines: DNA chemistry and its uses. Science. Oct. 18, 1985;230(4723):281-5.
Casmiro, Danilo R. et al., "PCR-based gene synthesis and protein NMR spectroscopy", Structure, vol. 5, •No. 11, 1407-1412 (1997).
Cello, et al. Chemical synthesis of poliovirus cDNA: generation of infectious virus in the absence of natural template. Science. Aug. 9, 2002;297(5583):1016-8. Epub Jul. 11, 2002.
Chalmers, et al. Scaling up the ligase chain reaction-based approach to gene synthesis. Biotechnigues. Feb. 2001;30(2):249-52.
Chan, et al. Natural and engineered nicking endonucleases—from cleavage mechanism to engineering of strand-specificity. Nucleic Acids Res. Jan. 2011; 39(1): 1-18.
Chen, et al. Chemical modification of gene silencing oligonucleotides for drug discovery and development. Drug Discov Today. Apr. 15, 2005;10(8):587-93.
Cheng, et al. High throughput parallel synthesis of oligonucleotides with 1536 channel synthesizer. Nucleic Acids Res. Sep. 15, 2002;30(18):e93.
Cho, et al. Capillary passive valve in microfluidic systems. NSTI-Nanotech. 2004; 1:263-266.
Chrisey et al., Fabrication of patterned DNA surfaces Nucleic Acids Research, 24(15):3040-3047 (1996).
Chung et al., One-step preparation of competent *Escherichia coli*:transformation and storage of bacterial cells in the same solution. Proc Natl Acad Sci U S A. Apr. 1989;86(7):2172-2175.
Cleary, et al. Production of complex nucleic acid libraries using highly parallel in situ oligonucleotide synthesis. Nat Methods. Dec. 2004;1(3):241-8. Epub Nov. 18, 2004.
Cutler, David J. et al., "High-throughput variation detection and genotyping using microarrays", Genome Research, vol. 11, 1913-19 (2001 ).
Dahl, et al. Circle-to-circle amplification for precise and sensitive DNA analysis. Proc Natl Acad Sci U S A. Mar. 30, 2004;101(13):4548-53. Epub Mar. 15, 2004.
De Mesmaeker, et al. Backbone modifications in oligonucleotides and peptide nucleic acid systems. Curr Opin Struct Biol. Jun. 1995;5(3):343-55.
Deamer, David W. et al., "Characterization of nucleic acids by nanopore analysis", Ace. Cham. Res., vol. 35, No. 10, 817-825 (2002).
Deaven, The Human Genome Project: Recombinant clones for mapping and sequencing DNA. Los Alamos Science, 20:218-249, 1992.
Deng et al., Targeted bisulfite sequencing reveals changes in DNA methylation associated with nuclear reprogramming Nature Biotechnology, 27:352-360 (2009).
Dietrich, Rudiger.et al., "Gene assembly based on blunt-ended double-stranded DNA-modules", Biotechnology Techniques, vol. 12, No. 1, 49-54 (Jan. 1998).
Dower et al., High efficiency transformation of *E.coli* by high voltage electroporation. Nucleic Acids Res. 16(13):6127-45 (1988).
Dressman, et al. Transforming single DNA molecules into fluorescent magnetic particles for detection and enumeration of genetic variations. Proc Natl Acad Sci U S A. Jul. 22, 2003;100(15):8817-22. Epub Jul. 11, 2003.
Drmanac, et al. Human genome sequencing using unchained base reads on self-assembling DNA nanoarrays. Science. Jan. 1, 2010;327(5961):78-81. doi: 10.1126/science.1181498. Epub Nov. 5, 2009.

(56) References Cited

OTHER PUBLICATIONS

Droege and Hill, The Genome Sequencer FLXTM System-Longer reads, more applications, straight forward bioinformatics and more complete data sets Journal of Biotechnology, 136:3-10, 2008.
Duffy, et al. Rapid Prototyping of Microfluidic Systems in Poly(dimethylsiloxane). Anal Chem. Dec. 1, 1998;70(23):4974-84. doi: 10.1021/ac980656z.
Duggan, et al. Expression profiling using cDNA microarrays. Nat Genet. Jan. 1999;21(1 Suppl):10-4.
Eadie, et al. Guanine modification during chemical DNA synthesis. Nucleic Acids Res. Oct. 26, 1987;15(20):8333-49.
Eisen, Jonathan A., "A phylogenomic study of the MutS family of proteins", Nucleic Acids Research, vol. 26, No. 18, 4291-4300 (1998).
Ellis, et al. DNA assembly for synthetic biology: from parts to pathways and beyond. Integr Biol (Camb). Feb. 2011;3(2):109-18. doi: 10.1039/c0ib00070a. Epub Jan. 19, 2011.
El-Sagheer, et al. Biocompatible artificial DNA linker that is read through by DNA polymerases and is functional in *Escherichia coli*. Proc Natl Acad Sci U S A. Jul. 12, 2011;108(28):11338-43. doi: 10.1073/pnas.1101519108. Epub Jun. 27, 2011.
Elsner et al., 172 nm excimer VUV-triggered photodegradation and micropatterning of aminosilane films, Thin Solid Films, 517:6772-6776 (2009).
Engler, et al. A one pot, one step, precision cloning method with high throughput capability. PLoS One. 2008;3(11):e3647. doi: 10.1371/journal.pone.0003647. Epub Nov. 5, 2008.
Engler, et al. Golden gate shuffling: a one-pot DNA shuffling method based on type IIs restriction enzymes. PLoS One. 2009;4(5):e5553. doi: 10.1371/journal.pone.0005553. Epub May 14, 2009.
Evans et al., DNA Repair Enzymes. Current Protocols in Molecular Biology 84:III:3.9:3.9.1-3.9.12 http://www.ncbi.nlm.nih.gov/pubmed/18972391 (Published online Oct. 1, 2008 Abstract only provided.
Fahy, et al. Self-sustained sequence replication (3SR): an isothermal transcription-based amplification system alternative to PCR. PCR Methods Appl. Aug. 1991;1(1):25-33.
Fedoryak, Olesya D. et al., "Brominated hydroxyquinoline as a photolabile protecting group with sensitivity to multiphoton excitation", Org. Lett., vol. 4, No. 2 , 3419-3422 (2002).
Ferretti et al., Total synthesis of a gene for bovine rhodopsin. PNAS, 83:599-603 (1986).
Fodor, et al. Light-directed, spatially addressable parallel chemical synthesis. Science. Feb. 15, 1991;251(4995):767-73.
Foldesi, et al. The synthesis of deuterionucleosides. Nucleosides Nucleotides Nucleic Acids. Oct.-Dec. 2000;19(10-12):1615-56.
Frandsen, et al. Efficient four fragment cloning for the construction of vectors for targeted gene replacement in filamentous fungi. BMC Molecular Biology 2008, 9:70.
Frandsen. Experimental setup. Dec. 7, 2010, 3 pages. http://www.rasmusfrandsen.dk/experimental_setup.htm.
Frandsen. The USER Friendly technology. USER cloning. Oct. 7, 2010, 2 pages. http://www.rasmusfrandsen.dk/user_cloning.htm.
Fullwood et al., Next-generation DNA sequencing of paired-end tags [PET] for transcriptome and genome analysis Genome Research, 19:521-532, 2009.
Galneder. et al., Microelectrophoresis of a bilayer-coated silica bead in an optical trap: application to enzymology. Biophysical Journal, vol. 80, No. 5, 2298-2309 (May 2001).
Gao, et al. A flexible light-directed DNA chip synthesis gated by deprotection using solution photogenerated acids. Nucleic Acids Res. Nov. 15, 2001;29(22):4744-50.
Gao, et al. Thermodynamically balanced inside-out (TBIO) PCR-based gene synthesis: a novel method of primer design for high-fidelity assembly of longer gene sequences. Nucleic Acids Res. Nov. 15, 2003;31(22):e143.
Garaj, et al. Graphene as a subnanometre trans-electrode membrane. Nature. Sep. 9, 2010;467(7312):190-3. doi: 10.1038/nature09379.
Garbow, Norbert et al., "Optical tweezing electroghoresis of isolated, highly charged colloidal spheres", Colloids and Surfaces A: Physiochem. Eng. Aspects, vol. 195, 227-241 (2001).
Geu-Flores, et al. USER fusion: a rapid and efficient method for simultaneous fusion and cloning of multiple PCR products. Nucleic Acids Res. 2007;35(7):e55. Epub Mar. 27, 2007.
Gibson, et al. Complete chemical synthesis, assembly, and cloning of a Mycoplasma genitalium genome. Science. Feb. 29, 2008;319(5867):1215-20. doi: 10.1126/science.1151721. Epub Jan. 24, 2008.
Gosse, Charlie et al. "Magnetic tweezers: micromanipulation and force measurement at the molecular level", Biophysical Journal, vol. 8, 3314-3329 (Jun. 2002).
Grovenor. Microelectronic materials. Graduate Student Series in Materials Science and Engineering. Bristol, England: Adam Hilger, 1989; p. 113-123.
Haber, Charbel et al., Magnetic tweezers for DNA micromanipulation, Rev. Sci. Instrum., vol. 71, No. 12, 4561-4570 (Dec. 2000).
Hanahan and Cold Spring Harbor Laboratory, Studies on transformation of *Escherichia coli* with plasmids J. Mol. Biol. 166:557-580 (1983).
Hanahan et al., Plasmid transformation of *Escherichia coli* and other bacteria. Methods Enzymol, vol. 204, p. 63-113 (1991).
Harada, et al. Unexpected substrate specificity of T4 DNA ligase revealed by in vitro selection. Nucleic Acids Res. May 25, 1993;21(10):2287-91.
Heckers Karl H. et al., "Error analysis of chemically synthesized polynucleotides", BioTechniques, vol. 24, No. 2, 256-260 (1998).
Herzer et al.: Fabrication of patterned silane based self-assembled monolayers by photolithography and surface reactions on silicon-oxide substrates Chem. Commun., 46:5634-5652 (2010).
Hoover et al., "DNAWorks: an automated method for designing oligonucleotides for PCR-based gene synthesis", Nucleic Acids Research, vol. 30, No. 10, e43, 7 pages (2002).
Hosu, Basarab G. et al., Magnetic tweezers for intracellular applications*, Rev. Sci. Instrum., vol. 74, No. 9, 4158-4163 (Sep. 2003).
Huang, Hayden et al., "Three-dimensional cellular deformation analysis with a two-photon magnetic manipulator workstation", Biophysical Journal, vol. 82, No. 4, 2211-2223 (Apr. 2002).
Hughes, et al. Expression profiling using microarrays fabricated by an ink-jet oligonucleotide synthesizer. Nat Biotechnol. Apr. 2001;19(4):342-7.
Hutchison, et al. Cell-free cloning using phi29 DNA polymerase. Proc Natl Acad Sci U S A. Nov. 29, 2005;102(48):17332-6. Epub Nov. 14, 2005.
Jackson, Brian A. et al., "Recognition of DNA base mismatches by a rhodium intercalator", J. Am. Chem. Soc., vol. 19, 12986-12987 (1997).
Jacobs and Schar, DNA glycosylases: In DNA repair and beyond Chromosome, 121:1-20 (2012)—http://www.ncbi.nlm.nih.gov/pmc/articles/PMC3260424/.
Karagiannis and El-Osta, RNA interference and potential therapeutic applications of short interfering RNAs Cancer Gene Therapy, 12:787-795, 2005.
Ke, Song-Hua et al., "Influence of neighboring base pairs on the stability of single base bulges and base pairs in a DNA fragment", Biochemistry, Vo. 34, 4593-4600 (1995).
Kelley, Shana, et al. Single-base mismatch detection based on charge transduction through DNA, Nucleic Acids Research, vol. 27, No. 24, 4830-4837 (1999).
Kim, Yang-Gyun et al., "Chimeric restriction endonuclease", Proc. Natl. Acad. Sci. USA, vol. 91, 883-887 (Feb. 1994).
Kim, Yang-Gyun, "The interaction between Z-ONA and the Zab domain of double-stranded RNA adenosine deaminase characterized using fusion nucleases", The Journal of Biological Chemistry, vol. 274, No. 27, 19081-19086 (1999).
Kim, Yan-Gyun et al., "Site specific cleavage of DNA-RNA hybrids by zinc finger/Fok I cleavage domain fusions" Gene, vol. 203, 43-49 (1997).
Kinde et al., Detection and quantification of rare mutations with massively parallel sequencing PNAS, 108(23):9530-9535, 2011.

(56) References Cited

OTHER PUBLICATIONS

Kodumal, et al. Total synthesis of long DNA sequences: synthesis of a contiguous 32-kb polyketide synthase gene cluster. Proc Natl Acad Sci U S A. Nov. 2, 2004;101(44):15573-8. Epub Oct. 20, 2004.
Kong et al., Parallel gene synthesis in a microfluidic device. Nucleic Acids Res., 35(8):e61 (2007).
Kong. Microfluidic Gene Synthesis. MIT Thesis. Submitted to the program in Media Arts and Sciences, School of Architecture and Planning, in partial fulfillment of the requirements for the degree of Doctor of Philosophy in Media Arts and Sciences at the Massachusetts Institute of Technology. 143 pages Jun. 2008.
Kopp, Martin U. et al., "Chemical amplification: continuous-flow PCR on a chip", Science, vol. 280, 1046-1048 (May 15, 1998).
Kosuri et al., A scalable gene synthesis platform using high-fidelity DNA microchips Nat.Biotechnol., 28(12):1295-1299, 2010.
Lagally, E.T. et al., "Single-molecule DNA amplification and analysis in an integrated microfluidic device" Anal. Chem., vol. 73, No. 565-570 (Feb. 1, 2001).
Lahue, R.S. et al., "DNA mismatch correction in a defined system", Science, vol. 425; No. 4914, 160-164 (Jul. 14, 1989).
Lambrinakos, A. et al., "Reactivity of potassium permanganate and tetraethylammonium chloride with mismatched bases and a simple mutation detection protocol." ,Nucleic Acids Research, vol. 27, No. 8, 1866-1874 (1999).
Landegren, et al. A ligase-mediated gene detection technique. Science. Aug. 26, 1988;241(4869):1077-80.
Lang, Matthew J. et al., "An automated two-dimensional optical force clamp for single molecule studies", Biophysical Journal, vol. 83, 491-501 (Jul. 2002).
Lashkari, et al. An automated multiplex oligonucleotide synthesizer: development of high-throughput, low-cost DNA synthesis. Proc Natl Acad Sci U S A. Aug. 15, 1995;92(17):7912-5.
Leamon, et al. A massively parallel PicoTiterPlate based platform for discrete picoliter-scale polymerase chain reactions. Electrophoresis. Nov. 2003;24(21):3769-77.
Lee, Covalent end-immobilization of oligonucleotides onto solid surfaces. Thesis submitted to the Department of Chemical Engineering in Partial Fulfillment of the Requirements for the Degree of Doctor of Philosophy in Chemical Engineering at the Massachusetts Institute of Technology. Aug. 2001, 315 pages.
Lee, C.S. et al., "Microelectromagnets for the control of magnetic nanoparticles", Appl. Phys. Lett., vol. 79, No. 20, 3308-3310 (Nov. 12, 2001).
Lee, et al. A microfluidic oligonucleotide synthesizer. Nucleic Acids Research 2010 vol. 38(8):2514-2521. DOI: 10.1093/nar/gkq092.
Leproust, et al. Agilent's Microarray Platform: How High-Fidelity DNA Synthesis Maximizes the Dynamic Range of Gene Expression Measurements. 2008; 1-12. http://www.miltenyibiotec.com/~/media/Files/Navigation/Genomic%20Services/Agilent_DNA_Microarray_Platform.ashx.
Leproust, et al. Synthesis of high-quality libraries of long (150mer) oligonucleotides by a novel depurination controlled process. Nucleic Acids Research. 2010; 38(8):2522-2540.
Lesnikowski, et al. Nucleic acids and nucleosides containing carboranes. J. Organometallic Chem. 1999; 581:156-169.
Leumann. DNA analogues: from supramolecular principles to biological properties. Bioorg Med Chem. Apr. 2002;10(4):841-54.
Levene, et al. Zero-mode waveguides for single-molecule analysis at high concentrations. Science. Jan. 31, 2003;299(5607):682-6.
Lipshutz, Robert J. et al., "High density synthetic oligonucleotide arrays", Nature Genetics Supplement, vol. 21, 20-24 (Jan. 1999).
Lishanski, Alia et al., "Mutation detection by mismatch binding protein, MutS, in amplified DNA: application to the cystic fibrosis gene", Proc. Natl. Acad. Sci. USA, vol. 91, 2674-2678 (Mar. 1994).
Liu, et al. Enhanced Signals and Fast Nucleic Acid Hybridization by Microfluidic Chaotic Mixing. Angew. Chem. Int. Ed. 2006; 45:3618-3623.
Lizardi, et al. Mutation detection and single-molecule counting using isothermal rolling-circle amplification. Nat Genet. Jul. 1998;19(3):225-32.
Li, Lin et al., "Functional domains in Fok I restriction endonuclease", Proc. Natl. Acad. Sci. USA, vol. 89, 4275-4279 (May 1992).
Lu, A.-Lien et al., "Methyl-directed repair of DNA base-pair mismatches in vitro", Proc. Natl. Acad. Sci. USA, vol. 80, 4639-4643 (Aug. 1983).
Lund, et al. A validated system for ligation-free uracilexcision based assembly of expression vectors for mammalian cell engineering. DTU Systems of Biology. 2011. 1 page. http://www.lepublicsystemepco.com/files/modules/gestion_rubriques/REF-B036-Lund_Anne%20Mathilde.pdf.
Ma, et al. DNA synthesis, assembly and application in synthetic biology. Current Opinion in Chemical Biology. 2012; 16:260-267.
Ma et al., Versatile surface functionalization of cyclic olefin copolymer (COC) with sputtered SiO2 thin film for potential BioMEMS applications. Journal of Materials Chemistry, DOI: 10.1039/b904663a, 11 pages (2009).
Mahato et al., Modulation of gene expression by antisense and antigene oligodeoxynucleotides and small interfering RNA Expert Opin. Drug Delivery, 2(1):3-28, 2005.
Margulies, et al. Genome sequencing in open microfabricated high-density picolitre reactors. Nature. Sep. 15, 2005;437(7057):376-80. Epub Jul. 31, 2005.
Matteucci, et al. Synthesis of deoxyoligonucleotides on a polymer support. J. Am. Chem. Soc. 1981; 103(11):3185-3191.
Matzas et al., Next generation gene synthesis by targeted retrieval of bead-immobilized, sequence verified DNA clones from a high throughput pyrosequencing device. Nat. Biotechnol., 28(12):1291-1294, 2010.
McGall, et al. Light-directed synthesis of high-density oligonucleotide arrays using semiconductor photoresists. Proc Natl Acad Sci U S A. Nov. 26, 1996;93(24):13555-60.
McGall, et al. The Efficiency of Light-Directed Synthesis of DNA Arrays on Glass Substrates. J. Am. Chem. Soc. 1997; 119(22):5081-5090.
Mei et al., Cell-free protein synthesis in microfluidic array devices Biotechnol. Prog., 23(6):1305-1311, 2007.
Mendel-Hartvig. Padlock probes and rolling circle amplification. New possibilities for sensitive gene detection. Comprehensive Summaries of Uppsala Dissertations from the Faculty of Medicine 1175. Uppsala University. 2002, 39 pages. http://www.diva-porta.org/smash/get/diva2:161926/FULLTEXT01.pdf.
Meyers and Friedland, Knowledge-based simulation of genetic regulation in bacteriophage lambda. Nucl. Acids Research, 12(1):1-16, 1984.
Mitra, et al. In situ localized amplification and contact replication of many individual DNA molecules. Nucleic Acids Res. Dec. 15, 1999;27(24):e34.
Muller, Caroline et al. "Protection and labelling of thymidine by a fluorescent photolabile group", Helvetica Chimica Acta, vol. 84, 3735-3741 (2001).
Nakatani, Kazuhiko et al., "Recognition of a single guanine bulge by 2-Acylamino-1 ,8-naphthyridine", J. Am. Chem. Soc., vol. 122, 2172-2177 (2000).
Nishikura, A short primer on RNAi: RNA-directed RNA polymerase acts as a key catalyst Cell, 107:415-418, 2001.
Nour-Eldin, et al. USER Cloning and USER Fusion: The Ideal Cloning Techniques for Small and Big Laboratories. Plant Secondary Metabolism Engineering. Methods in Molecular Biology vol. 643, 2010, pp. 185-200.
Ochman, et al. Genetic applications of an inverse polymerase chain reaction. Genetics. Nov. 1988;120(3):621-3.
Pan, et al. An approach for global scanning of single nucleotide variations. Proc Natl Acad Sci USA. Jul. 9, 2002;99(14):9346-51.
Pankiewicz. Fluorinated nucleosides. Carbohydr Res. Jul. 10, 2000;327(1-2):87-105.
PCT Patent Application No. PCT/US14/049834 International Preliminary Report on Patentability dated Feb. 18, 2016.
PCT Patent Application No. PCT/US2015/043605 International Search Report and Written Opinion dated Jan. 6, 2016.

(56) References Cited

OTHER PUBLICATIONS

PCT Patent Application No. PCT/US2015/043605 Invitation to Pay Additional Fees dated Oct. 28, 2015.
PCT Patent Application No. PCT/US2016/016459 International Search Report and Written Opinion dated Apr. 13, 2016.
PCT Patent Application No. PCT/US2016/016636 International Search Report and Written Opinion dated May 2, 2016.
PCT/US2014/049834 International Search Report and Written Opinion dated Mar. 19, 2015.
PCT/US2014/049834, "Invitation to Pay Additional Fees and, where applicable, protest fee," dated Jan. 5, 2015.
Pease, et al. Light-generated oligonucleotide arrays for rapid DNA sequence analysis. Proc Natl Acad Sci U S A. May 24, 1994;91(11):5022-6.
Peisajovich, et al. BBF RFC 28: A method for combinatorial multi-part assembly based on the type-IIs restriction enzyme aarI. Sep. 16, 2009, 7 pages.
Pellois, et al. "Individually addressable parallel peptide synthesis on microchips", Nature Biotechnology, vol. 20 , 922-926 (Sep. 2002).
Petersen, et al. LNA: a versatile tool for therapeutics and genomics. Trends Biotechnol. Feb. 2003;21(2):74-81.
Pierce, et al. Linear-after-the-exponential polymerase chain reaction and allied technologies. Real-time detection strategies for rapid, reliable diagnosis from single cells. Methods Mol Med. 2007;132:65-85.
Pon. Solid-phase supports for oligonucleotide synthesis. Methods Mol Biol. 1993;20:465-96.
Prodromou, et al. Recursive PCR: a novel technique for total gene synthesis. Protein Eng. Dec. 1992;5(8):827-9.
Quan, et al. Parallel on-chip gene synthesis and application to optimization of protein expression. Nature Biotechnology. 2011; 29:449-452.
Reimagine SequenceSpace, Reimagine Research, Twist Bioscience, Product Brochure, Published Apr. 6, 2016 online at: www2.twistbioscience.com/TB_Product_Brochure_04.2016, 8 pages.
RF Electric discharge type excimer lamp. Products Catalog. Excimer lamp light source "flat excimer," 16 pages dated Jan. 2016. From: http://www.hamamatsu.com/jp/en/product/category/1001/3026/index.html.
Richmond, et al. Amplification and assembly of chip-eluted DNA (AACED): a method for high-throughput gene synthesis. Nucleic Acids Res. Sep. 24, 2004;32(17):5011-8. Print 2004.
Roche. Restriction Enzymes from Roche Applied Science—A Tradition of Premium Quality and Scientific Support. FAQS and Ordering Guide. Roche Applied Science. Accessed Jan. 12, 2015, 37 pages.
Ruminy, et al., "Long-range identification of hepatocyte nuclear factor-3 (FoxA) high and low-affinity binding Sites with a chimeric nuclease", J. Mol. Bioi., vol. 310, 523-535 (2001).
Saaem et al., In situ synthesis of DNA microarray on functionalized cyclic olefin copolymer substrate ACS Applied Materials & Interfaces, 2(2):491-497, 2010.
Saboulard, et al. High-throughput site-directed mutagenesis using oligonucleotides synthesized on DNA chips. Biotechniques. Sep. 2005;39(3):363-8.
Sacconi, L. et al., Three-dimensional magneto-optic trap for microobject manipulation, Optics Letters, vol. 26, No. 17, 1359-1361 (Sep. 1, 2001).
Saiki et al. Analysis of enzymatically amplified beta-globin and HLA-DQ alpha DNA with allele-specific oligonucleotide probes Nature 324:163-166 (1986).
Sandhu, et al. Dual asymmetric PCR: one-step construction of synthetic genes. Biotechniques. Jan. 1992;12(1):14-6.
Schaller, et al. Studies on Polynucleotides. XXV.1 The Stepwise Synthesis of Specific Deoxyribopolynucleotides (5). Further Studies on the Synthesis of Internucleotide Bond by the Carbodiimide Method. The Synthesis of Suitably Protected Dinucleotides as Intermediates in the Synthesis of Higher Oligonucleotides. J. Am. Chem. Soc. 1963; 85(23):3828-3835.
Schmalzing, Dieter et al., "Microchip electrophoresis: a method for high-speed SNP detection", Nucleic Acids Research, vol. 28, No. 9, i-vi (2000).
Smith, et al. Generating a synthetic genome by whole genome assembly: phiX174 bacteriophage from synthetic oligonucleotides. Proc Natl Acad Sci U S A. Dec. 23, 2003;100(26):15440-5. Epub Dec. 2, 2003.
Smith, et al. Generation of cohesive ends on PCR products by UDG-mediated excision of dU, and application for cloning into restriction digest-linearized vectors. PCR Methods Appl. May 1993;2(4):328-32.
Smith, Jane et al., "Mutation detection with MutH, MutL, and MutS mismatch repair proteins", Proc. Natl. Acad. Sci. USA, vol. 93, 4374-4379 (Apr. 1996).
Smith Jane et al., "Removal of Polymerase-Produced mutant sequences from PCR products", Proc. Natl. Acad. Sci. USA, vol. 94, 6847-6850 (Jun. 1997).
Smith, Steven B. et al., "Direct mechanical measurements of the elasticity of single DNA molecules using magnetic beads", Science, vol. 258, 1122-1126 (Nov. 13, 1992).
Soni, et al. Progress toward ultrafast DNA sequencing using solid-state nanopores. Clin Chem. Nov. 2007;53(11):1996-2001. Epub Sep. 21, 2007.
Southern, et al. Analyzing and comparing nucleic acid sequences by hybridization to arrays of oligonucleotides: evaluation using experimental models. Genomics. Aug. 1992;13(4):1008-17.
Sproat, et al. An efficient method for the isolation and purification of oligoribonucleotides. Nucleosides & Nucleotides. 1995; 14(1 &2):255-273.
Steel, The Flow-Thru Chip A Three-dimensional biochip platform. In: Schena, Microarray Biochip Technology, Chapter 5, Natick, MA: Eaton Publishing, 2000, 33 pages.
Stemmer, et al. Single-step assembly of a gene and entire plasmid from large numbers of oligodeoxyribonucleotides. Gene. Oct. 16, 1995;164(1):49-53.
Stryer. DNA Probes and genes can be synthesized by automated solid-phase methods. Biochemistry, 3rd edition, New York: W.H. Freeman and Company, 1988; 123-125.
Stutz, et al. Novel fluoride-labile nucleobase-protecting groups for the synthesis of 3'(2')-O-amino-acylated RNA sequences. Helv. Chim. Acta. 2000; 83(9):2477-2503.
Takahashi, Cell-free cloning using multiply-primed rolling circle amplification with modified RNA primers. Biotechniques. Jul. 2009;47(1):609-15. doi: 10.2144/000113155.
Tanase, M. et al., "Magnetic trapping of multicomponent nanowires", The Johns Hopkins University, Baltimore, Maryland, p. 1-3 (Jun. 25, 2001).
Tian, et al. Accurate multiplex gene synthesis from programmable DNA microchips. Nature. Dec. 23, 2004;432(7020):1050-4.
Tsai et al., Dimeric CRISPR RNA-guided FokI nucleases for highly specific genome editing Nat.Biotechnol., 32(6):569-576, 2014.
Unger, et al. Monolithic microfabricated valves and pumps by multilayer soft lithography. Science. Apr. 7, 2000;288(5463):113-6.
U.S. Appl. No. 14/452,429 Office Action dated Apr. 9, 2015.
U.S. Appl. No. 14/452,429 Office Action dated Oct. 21, 2015.
U.S. Appl. No. 14/452,429 Restriction Requirement dated Dec. 12, 2014.
U.S. Appl. No. 14/885,962 Restriction Requirment dated Mar. 1, 2016.
U.S. Appl. No. 14/885,965 Office Action dated Feb. 18, 2016.
Vaijayanthi, et al. Recent advances in oligonucleotide synthesis and their applications. Indian J Biochem Biophys. Dec. 2003;40(6):377-91.
Van Den Brulle, et al. A novel solid phase technology for high-throughput gene synthesis. Biotechniques. 2008; 45(3):340-343.
Vargeese, et al. Efficient activation of nucleoside phosphoramidites with 4,5-dicyanoimidazole during oligonucleotide synthesis. Nucleic Acids Res. Feb. 15, 1998;26(4):1046-50.
Verma, et al. Modified oligonucleotides: synthesis and strategy for users. Annu Rev Biochem. 1998;67:99-134.
Vincent, et al. Helicase-dependent isothermal DNA amplification. EMBO Rep. Aug. 2004;5(8):795-800.

(56) References Cited

OTHER PUBLICATIONS

Visscher et al., "Construction of multiple-beam optical traps with nanometer-resolution position sensing", IEEE Journal of Selected Topics in Quantum Electronics, vol. 2, No. 4, 1066-1076 (Dec. 1996).
Voldmans Joel et al., "Holding forces of single-particle dielectrophoretic traps." Biophysical Journal, vol. 80, No. 1, 531-541 (Jan. 2001).
Vos, et al. AFLP:A new technique for DNA fingerprinting. Nucleic Acids Res. Nov. 11, 1995;23(21):4407-14.
Wah, David A. et al., "Structure of Fok I has implications for DNA cleavage", Proc. Natl. Acad. Sci. USA, vol. 95, 10564-10569 (Sep. 1998).
Wah, David A. et al., "Structure of the multimodular endonuclease Fok I bound to DNA", Nature, vol. 388, 97-100 (Jul. 1997).
Walker, et al. Strand displacement amplification—an isothermal, in vitro DNA amplification technique. Nucleic Acids Res. Apr. 11, 1992;20(7):1691-6.
Weber, et al. A modular cloning system for standardized assembly of multigene constructs. PLoS One. Feb. 18, 2011;6(2):e16765. doi: 10.1371/journal.pone.0016765.
Welz, et al. 5-(Benzylmercapto)-1H-tetrazole as activator for 2'-O-TBDMS phosphoramidite building blocks in RNA synthesis. Tetrahedron Lett. 2002; 43(5):795-797.
Westin et al., Anchored multiplex amplification on a microelectronic chip array Nature Biotechnology, 18:199-202 (2000) (abstract only).
Whitehouse, Adrian et al. "Analysis of the mismatch and insertion/deletion binding properties of Thermus thermophilus, HB8, MutS", Biochemical and Biophysical Research Communications, vol. 233, 834-837 (1997).
Wirtz, Denis, "Direct measurement of the transport properties of a single DNA molecule", Physical Review Letters, vol. 75, No. 12, 2436-2439 (Sep. 18, 1995).
Withers-Martinez, Chrislaine et al., "PCR-based gene synthesis as an efficient approach for expression of the A+ T-rich malaria genome", Protein Engineering, vol. 12, No. 12, 1113-1120 (1999).
Wood, Richard D. et al., "Human DNA repair genes", Science, vol. 291, 1284-1289 (Feb. 16, 2001).
Wosnick, et al. Rapid construction of large synthetic genes: total chemical synthesis of two different versions of the bovine prochymosin gene. Gene. 1987;60(1):115-27.
Wu, et al. RNA-mediated gene assembly from DNA arrays. Angew Chem Int Ed Engl. May 7, 2012;51(19):4628-32. doi: 10.1002/anie.201109058.
Wu, et al. Specificity of the nick-closing activity of bacteriophage T4 DNA ligase. Gene. 1989;76(2):245-54.
Wu, Xing-Zheng et al., "An improvement of the on-line electrophoretic concentration method for capillary electrophoresis of proteins an experimental factors affecting he concentration effect", Analytical Sciences, vol. 16, 329-331 (Mar. 2000).
Xiong, et al. A simple, rapid, high-fidelity and cost-effective PCR-based two-step DNA synthesis method for long gene sequences. Nucleic Acids Res. Jul. 7, 2004;32(12):e98.
Xiong, et al. Non-polymerase-cycling-assembly-based chemical gene synthesis: Strategies, methods, and progress. Biotechnology Advances. 2008; 26(2):121-134.
Yang, et al "Purification, cloning, and characterization of the CEL I nuclease", Biochemistry, vol. 39, No. 13, 3533-351 (2000).
Yehezkel et al., De novo DNA synthesis using single molecule PCR Nucleic Acids Research, 36(17):e107, 2008.
Youil, Rima et al., "Detection of 81 of 81 known mouse Beta-Globin promoter mutations with T4 Endonuclease VII—The EMC Method", Genomics, vol. 32, 431-435 (1996).
Young, et al. Two-step total gene synthesis method. Nucleic Acids Res. Apr. 15, 2004;32(7):e59.
Zheleznaya, et al. Nicking endonucleases. Biochemistry (Mosc). Dec. 2009;74(13):1457-66.
Zhou et al., Microfluidic PicoArray synthesis of oligodeoxynucleotides and simultaneous assembling of multiple DNA sequences Nucleic Acids Research, 32(18):5409-5417, 2004.
Binkowski et al., Correcting errors in synthetic DNA through consensus shuffling. Nucleic Acids Research, 33(6):e55, 8 pages, 2005.
Bonini and Mondino, Adoptive T-cell therapy for cancer: The era of engineered T cells. European Journal of Immunology, 45:2457-2469, 2015.
Borovkov et al., High-quality gene assembly directly from unpurified mixtures of microassay-synthesized oligonucleotides. Nucleic Acid Research, 38(19):e180, 10 pages, 2010.
Dormitzer et al., Synthetic generation of influenza vaccine viruses for rapid response to pandemics. Sci Translational Medicine, 5(185):185ra68, 14 pages, 2013.
Morris and Stauss, Optimizing T-cell receptor gene therapy for hematologic malignancies. Blood, 127(26):3305-3311, 2016.
PCT/US2016/028699 International Preliminary Report on Patentability dated Nov. 2, 2017.
PCT/US2016/031674 International Preliminary Report on Patentability dated Nov. 23, 2017.
PCT/US2017/045105 International Search Report and Written Opinion dated Oct. 20, 2017.
Rogozin et al., Origin and evolution of spliceosomal introns. Biology Direct, 7:11, 2012.
Schmitt et al., New strategies in engineering T-cell receptor gene-modified T cells to more effectively target malignancies. Clinical Cancer Research, 21(23):5191-5197, 2015.
Sharpe and Mount, Genetically modified T cells in cancer therapy: opportunities and challenges. Disease Models and Mechanisms, 8:337-350, 2015.
U.S. Appl. No. 14/885,962 Notice of Allowance dated Nov. 8, 2017 and Sep. 29, 2017.
U.S. Appl. No. 15/233,835 Notice of Allowance dated Oct. 4, 2017.
U.S. Appl. No. 15/377,547 Office Action dated Nov. 30, 2017.
U.S. Appl. No. 15/602,991 Notice of Allowance dated Oct. 25, 2017.
U.S. Appl. No. 15/602,991 Office Action dated Sep. 21, 2017.
U.S. Appl. No. 15/603,013 Office Action dated Oct. 20, 2017.
U.S. Appl. No. 15/682,100 Restriction Requirement dated Nov. 8, 2017.

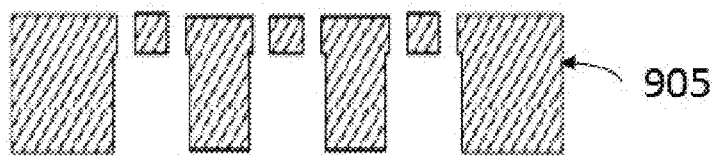
*FIG. 9A*
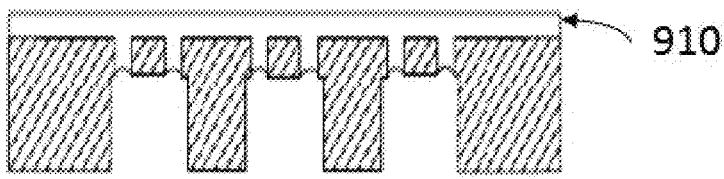
*FIG. 9B*
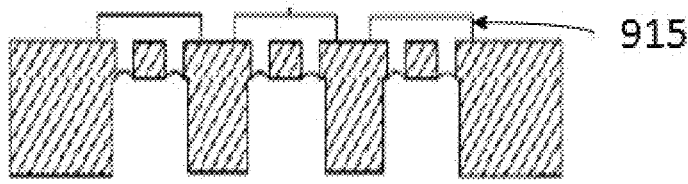
*FIG. 9C*
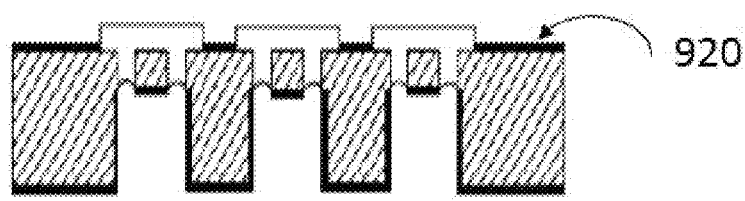
*FIG. 9D*
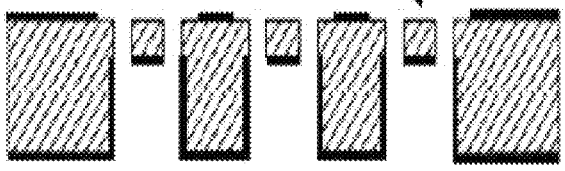
*FIG. 9E*
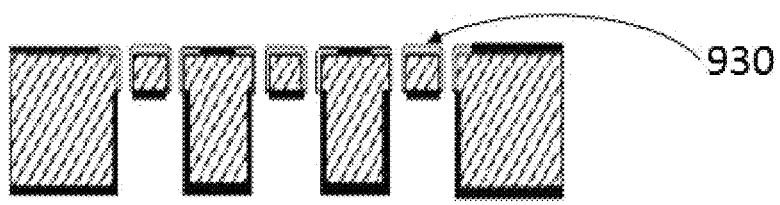
*FIG. 9F*
FIGS. 9A-9F

SEQUENCE LISTING

```
<160> NUMBER OF SEQ ID NOS: 73

<210> SEQ ID NO 1
<211> LENGTH: 112
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (101)..(102)
<223> OTHER INFORMATION: Thymidine-succinyl hexamide CED phosphoramidite

<400> SEQUENCE: 1
cgggatcctt atcgtcatcg tcgtacagat cccgacccat ttgctgtcca ccagtcatgc      60
tagccatacc atgatgatga tgatgatgag aacccgcat ttttttttt tt                112

<210> SEQ ID NO 2
<211> LENGTH: 62
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
atgaccatga ttacggattc actggccgtc gttttacaac gtcgtgactg ggaaaaccct      60
```

<210> SEQ ID NO 3
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
gccagctggc gaaaggggga tgtgctgcaa ggcgattaag ttgggtaacg ccagggtttt      60
cccagtcacg ac                                                          72

<210> SEQ ID NO 4
<211> LENGTH: 70
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4 cccccttcg ccagctggcg taatagcgaa gaggcccgca ccgatcgccc ttcccaacag       60
ttgcgcagcc                                                             70

<210> SEQ ID NO 5
<211> LENGTH: 69
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5
cggcaccgct tctggtgccg gaaaccaggc aaagcgccat tcgccattca ggctgcgcaa      60
ctgttggga                                                              69

<210> SEQ ID NO 6
<211> LENGTH: 70
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 6
caccagaagc ggtgccggaa agctggctgg agtgcgatct tcctgaggcc gatactgtcg      60
tcgtcccctc                                                             70

<210> SEQ ID NO 7
<211> LENGTH: 75
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 7
gataggtcac gttggtgtag atgggcgcat cgtaaccgtg catctgccag tttgagggga      60
cgacgacagt atcgg                                                       75

<210> SEQ ID NO 8

```
<211> LENGTH: 74
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 8
cccatctaca ccaacgtgac ctatcccatt acggtcaatc cgccgtttgt tcccacggag      60
aatccgacgg gttg                                                        74

<210> SEQ ID NO 9
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 9
gtctggcctt cctgtagcca gctttcatca acattaaatg tgagcgagta acaacccgtc      60
ggattctccg tg                                                          72

<210> SEQ ID NO 10
<211> LENGTH: 73
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 10
gctggctaca ggaaggccag acgcgaatta tttttgatgg cgttaactcg gcgtttcatc      60
tgtggtgcaa cgg                                                         73

<210> SEQ ID NO 11
<211> LENGTH: 74
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 11
caggtcaaat tcagacggca aacgactgtc ctggccgtaa ccgacccagc gcccgttgca      60
ccacagatga aacg                                                        74

<210> SEQ ID NO 12
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 12
cgtttgccgt ctgaatttga cctgagcgca ttttacgcg ccggagaaaa ccgcctcgcg       60
gtgatggtgc tg                                                          72

<210> SEQ ID NO 13
<211> LENGTH: 72
<212> TYPE: DNA
<213> ORGANISM: Artificial Sequence
<220> FEATURE:
```

<223> OTHER INFORMATION: Description of Artificial Sequence: Synthetic
      oligonucleotide

<400> SEQUENCE: 13
gccgctcatc cgccacatat cctgatcttc cagataactg ccgtcactcc agcgcagcac    60
catcaccgcg ag    72

<210> SEQ ID NO 14
<211> LENGTH: 77
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 14
aggatatgtg gcggatgagc ggcattttcc gtgacgtctc gttgctgcat aaaccgacta    60
cacaaatcag cgatttc    77

<210> SEQ ID NO 15
<211> LENGTH: 78
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 15
ctccagtaca gcgcggctga aatcatcatt aaagcgagtg gcaacatgga aatcgctgat    60
ttgtgtagtc ggtttatg    78

<210> SEQ ID NO 16
<211> LENGTH: 75
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 16
atttcagccg cgctgtactg gaggctgaag ttcagatgtg cggcgagttg cgtgactacc    60
tacgggtaac agttt    75

<210> SEQ ID NO 17
<211> LENGTH: 71
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 17
aaaggcgcgg tgccgctggc gacctgcgtt tcaccctgcc ataaagaaac tgttacccgt    60
aggtagtcac g    71

<210> SEQ ID NO 18
<211> LENGTH: 70
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 18

```
gcggcaccgc gcctttcggc ggtgaaatta tcgatgagcg tggtggttat gccgatcgcg    60
tcacactacg                                                           70
```

<210> SEQ ID NO 19
<211> LENGTH: 74
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 19

```
gatagagatt cgggatttcg gcgctccaca gtttcgggtt ttcgacgttc agacgtagtg    60
tgacgcgatc ggca                                                      74
```

<210> SEQ ID NO 20
<211> LENGTH: 74
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 20

```
gagcgccgaa atcccgaatc tctatcgtgc ggtggttgaa ctgcacaccg ccgacggcac    60
gctgattgaa gcag                                                      74
```

<210> SEQ ID NO 21
<211> LENGTH: 73
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 21

```
cagcagcaga ccattttcaa tccgcacctc gcggaaaccg acatcgcagg cttctgcttc    60
aatcagcgtg ccg                                                       73
```

<210> SEQ ID NO 22
<211> LENGTH: 74
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 22

```
cggattgaaa atggtctgct gctgctgaac ggcaagccgt tgctgattcg aggcgttaac    60
cgtcacgagc atca                                                      74
```

<210> SEQ ID NO 23
<211> LENGTH: 75
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 23

```
gcaggatatc ctgcaccatc gtctgctcat ccatgacctg accatgcaga ggatgatgct    60
cgtgacggtt aacgc                                                     75
```

<210> SEQ ID NO 24
<211> LENGTH: 75
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 24
cagacgatgg tgcaggatat cctgctgatg aagcagaaca actttaacgc cgtgcgctgt    60
tcgcattatc cgaac                                                    75

<210> SEQ ID NO 25
<211> LENGTH: 74
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 25
tccaccacat acaggccgta gcggtcgcac agcgtgtacc acagcggatg gttcggataa    60
tgcgaacagc gcac                                                     74

<210> SEQ ID NO 26
<211> LENGTH: 75
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 26
gctacggcct gtatgtggtg gatgaagcca atattgaaac ccacggcatg gtgccaatga    60
atcgtctgac cgatg                                                    75

<210> SEQ ID NO 27
<211> LENGTH: 73
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 27
gcaccattcg cgttacgcgt tcgctcatcg ccggtagcca gcgcggatca tcggtcagac    60
gattcattgg cac                                                      73

<210> SEQ ID NO 28
<211> LENGTH: 73
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 28
cgcgtaacgc gaatggtgca gcgcgatcgt aatcacccga gtgtgatcat ctggtcgctg    60
gggaatgaat cag                                                      73

<210> SEQ ID NO 29
<211> LENGTH: 78

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 29
ggatcgacag atttgatcca gcgatacagc gcgtcgtgat tagcgccgtg gcctgattca    60
ttccccagcg accagatg                                                  78

<210> SEQ ID NO 30
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 30
gtatcgctgg atcaaatctg tcgatccttc ccgcccggtg cagtatgaag gcggcggagc    60
cgacaccacg gc                                                        72

<210> SEQ ID NO 31
<211> LENGTH: 71
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 31
cgggaagggc tggtcttcat ccacgcgcgc gtacatcggg caaataatat cggtggccgt    60
ggtgtcggct c                                                         71

<210> SEQ ID NO 32
<211> LENGTH: 73
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 32
tggatgaaga ccagcccttc ccggctgtgc cgaaatggtc catcaaaaaa tggctttcgc    60
tacctggaga gac                                                       73

<210> SEQ ID NO 33
<211> LENGTH: 73
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 33
ccaagactgt tacccatcgc gtgggcgtat tcgcaaagga tcagcgggcg cgtctctcca    60
ggtagcgaaa gcc                                                       73

<210> SEQ ID NO 34
<211> LENGTH: 73
<212> TYPE: DNA
<213> ORGANISM: Artificial Sequence
<220> FEATURE:
<223> OTHER INFORMATION: Description of Artificial Sequence: Synthetic
``` oligonucleotide

<400> SEQUENCE: 34
cgcgatgggt aacagtcttg gcggtttcgc taaatactgg caggcgtttc gtcagtatcc    60
ccgtttacag ggc                                                      73

<210> SEQ ID NO 35
<211> LENGTH: 78
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 35
gccgttttca tcatatttaa tcagcgactg atccacccag tcccagacga agccgccctg    60
taaacgggga tactgacg                                                 78

<210> SEQ ID NO 36
<211> LENGTH: 76
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 36
cagtcgctga ttaaatatga tgaaaacggc aacccgtggt cggcttacgg cggtgatttt    60
ggcgatacgc cgaacg                                                   76

<210> SEQ ID NO 37
<211> LENGTH: 67
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 37
gcggcgtgcg gtcggcaaag accagaccgt tcatacagaa ctggcgatcg ttcggcgtat    60
cgccaaa                                                             67

<210> SEQ ID NO 38
<211> LENGTH: 71
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 38
cgaccgcacg ccgcatccag cgctgacgga agcaaaacac cagcagcagt ttttccagtt    60
ccgtttatcc g                                                        71

<210> SEQ ID NO 39
<211> LENGTH: 79
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 39

```
ctcgttatcg ctatgacgga acaggtattc gctggtcact tcgatggttt gcccggataa    60
acggaactgg aaaaactgc                                                  79
```

<210> SEQ ID NO 40
<211> LENGTH: 75
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 40

```
aatacctgtt ccgtcatagc gataacgagc tcctgcactg gatggtggcg ctggatggta    60
agccgctggc aagcg                                                      75
```

<210> SEQ ID NO 41
<211> LENGTH: 76
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 41

```
gttcaggcag ttcaatcaac tgtttacctt gtggagcgac atccagaggc acttcaccgc    60
ttgccagcgg cttacc                                                     76
```

<210> SEQ ID NO 42
<211> LENGTH: 78
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 42

```
caaggtaaac agttgattga actgcctgaa ctaccgcagc cggagagcgc cgggcaactc    60
tggctcacag tacgcgta                                                   78
```

<210> SEQ ID NO 43
<211> LENGTH: 71
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 43

```
gcgctgatgt gcccggcttc tgaccatgcg gtcgcgttcg gttgcactac gcgtactgtg    60
agccagagtt g                                                          71
```

<210> SEQ ID NO 44
<211> LENGTH: 67
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 44

```
ccgggcacat cagcgcctgg cagcagtggc gtctggcgga aaacctcagt gtgacgctcc    60
ccgccgc                                                               67
```

<210> SEQ ID NO 45
<211> LENGTH: 71
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 45
ccagctcgat gcaaaaatcc atttcgctgg tggtcagatg cgggatggcg tgggacgcgg    60
cggggagcgt c                                                         71

<210> SEQ ID NO 46
<211> LENGTH: 78
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 46
cgaaatggat ttttgcatcg agctgggtaa taagcgttgg caatttaacc gccagtcagg    60
ctttctttca cagatgtg                                                  78

<210> SEQ ID NO 47
<211> LENGTH: 74
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 47
tgaactgatc gcgcagcggc gtcagcagtt gttttttatc gccaatccac atctgtgaaa    60
gaaagcctga ctgg                                                      74

<210> SEQ ID NO 48
<211> LENGTH: 73
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 48
gccgctgcgc gatcagttca cccgtgcacc gctggataac gacattggcg taagtgaagc    60
gacccgcatt gac                                                       73

<210> SEQ ID NO 49
<211> LENGTH: 71
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 49
ggcctggtaa tggcccgccg ccttccagcg ttcgacccag gcgttagggt caatgcgggt    60
cgcttcactt a                                                         71

<210> SEQ ID NO 50
<211> LENGTH: 70
<212> TYPE: DNA

<213> ORGANISM: Artificial Sequence
<220> FEATURE:
<223> OTHER INFORMATION: Description of Artificial Sequence: Synthetic
      oligonucleotide

<400> SEQUENCE: 50
cgggccatta ccaggccgaa gcagcgttgt tgcagtgcac ggcagataca cttgctgatg    60
cggtgctgat                                                          70

<210> SEQ ID NO 51
<211> LENGTH: 75
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 51
tccggctgat aaataaggtt ttcccctgat gctgccacgc gtgagcggtc gtaatcagca    60
ccgcatcagc aagtg                                                    75

<210> SEQ ID NO 52
<211> LENGTH: 78
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 52
ggggaaaacc ttatttatca gccggaaaac ctaccggatt gatggtagtg gtcaaatggc    60
gattaccgtt gatgttga                                                 78

<210> SEQ ID NO 53
<211> LENGTH: 75
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 53
ggcagttcag gccaatccgc gccggatgcg gtgtatcgct cgccacttca acatcaacgg    60
taatcgccat ttgac                                                    75

<210> SEQ ID NO 54
<211> LENGTH: 71
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 54
gcggattggc ctgaactgcc agctggcgca ggtagcagag cgggtaaact ggctcggatt    60
agggccgcaa g                                                        71

<210> SEQ ID NO 55
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 55
ggcagatccc agcggtcaaa acaggcggca gtaaggcggt cgggatagtt ttcttgcggc    60
cctaatccga gc    72

<210> SEQ ID NO 56
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 56
gttttgaccg ctgggatctg ccattgtcag acatgtatac cccgtacgtc ttcccgagcg    60
aaaacggtct gc    72

<210> SEQ ID NO 57
<211> LENGTH: 69
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 57
gtcgccgcgc cactggtgtg ggccataatt caattcgcgc gtcccgcagc gcagaccgtt    60
ttcgctcgg    69

<210> SEQ ID NO 58
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 58
accagtggcg cggcgacttc cagttcaaca tcagccgcta cagtcaacag caactgatgg    60
aaaccagcca tc    72

<210> SEQ ID NO 59
<211> LENGTH: 75
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 59
gaaaccgtcg atattcagcc atgtgccttc ttccgcgtgc agcagatggc gatggctggt    60
ttccatcagt tgctg    75

<210> SEQ ID NO 60
<211> LENGTH: 71
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 60
catggctgaa tatcgacggt ttccatatgg ggattggtgg cgacgactcc tggagcccgt    60

```
cagtatcggc g                                                          71

<210> SEQ ID NO 61
<211> LENGTH: 74
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 61 ttattttga caccagacca actggtaatg gtagcgaccg gcgctcagct ggaattccgc       60
cgatactgac gggc                                                       74

<210> SEQ ID NO 62
<211> LENGTH: 3075
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 62
atgaccatga ttacggattc actggccgtc gttttacaac gtcgtgactg ggaaaaccct     60
ggcgttaccc aacttaatcg ccttgcagca catccccctt tcgccagctg gcgtaatagc    120
gaagaggccc gcaccgatcg cccttcccaa cagttgcgca gcctgaatgg cgaatggcgc    180
tttgcctggt ttccggcacc agaagcggtg ccggaaagct ggctggagtg cgatcttcct    240
gaggccgata ctgtcgtcgt cccctcaaac tggcagatgc acggttacga tgcgcccatc    300
tacaccaacg tgacctatcc cattacggtc aatccgccgt ttgttcccac ggagaatccg    360
acgggttgtt actcgctcac atttaatgtt gatgaaagct ggctacagga aggccagacg    420
cgaattattt ttgatggcgt taactcggcg tttcatctgt ggtgcaacgg gcgctgggtc    480
ggttacggcc aggacagtcg tttgccgtct gaatttgacc tgagcgcatt tttacgcgcc    540
ggagaaaacc gcctcgcggt gatggtgctg cgctggagtg acggcagtta tctggaagat    600
caggatatgt ggcggatgag cggcattttc cgtgacgtct cgttgctgca taaaccgact    660
acacaaatca gcgatttcca tgttgccact cgctttaatg atgatttcag ccgcgctgta    720
ctggaggctg aagttcagat gtgcggcgag ttgcgtgact acctacgggt aacagtttct    780
ttatggcagg gtgaaacgca ggtcgccagc ggcaccgcgc ctttcggcgg tgaaattatc    840
gatgagcgtg gtggttatgc cgatcgcgtc acactacgtc tgaacgtcga aaacccgaaa    900
ctgtggagcg ccgaaatccc gaatctctat cgtgcggtgg ttgaactgca caccgccgac    960
ggcacgctga ttgaagcaga agcctgcgat gtcggtttcc gcgaggtgcg gattgaaaat   1020
ggtctgctgc tgctgaacgg caagccgttg ctgattcgag gcgttaaccg tcacgagcat   1080
catcctctgc atggtcaggt catggatgag cagacgatgg tgcaggatat cctgctgatg   1140
aagcagaaca actttaacgc cgtgcgctgt tcgcattatc gaaccatccg ctgtggtac    1200 acgctgtgcg accgctacgg cctgtatgtg gtggatgaag ccaatattga aacccacggc   1260
atggtgccaa tgaatcgtct gaccgatgat ccgcgctggc taccggcgat gagcgaacgc   1320
gtaacgcgaa tggtgcagcg cgatcgtaat cacccgagtg tgatcatctg gtcgctgggg   1380
aatgaatcag gccacggcgc taatcacgac gcgctgtatc gctggatcaa atctgtcgat   1440
ccttcccgcc cggtgcagta tgaaggcggc ggagccgaca ccacggccac cgatattatt   1500
```

```
tgcccgatgt acgcgcgcgt ggatgaagac cagcccttcc cggctgtgcc gaaatggtcc      1560
atcaaaaaat ggctttcgct acctggagag acgcgcccgc tgatcctttg cgaatacgcc      1620
cacgcgatgg gtaacagtct tggcggtttc gctaaatact ggcaggcgtt tcgtcagtat      1680
ccccgtttac agggcggctt cgtctgggac tgggtggatc agtcgctgat taaatatgat      1740
gaaaacggca acccgtggtc ggcttacggc ggtgattttg gcgatacgcc gaacgatcgc      1800
cagttctgta tgaacggtct ggtctttgcc gaccgcacgc cgcatccagc gctgacggaa      1860
gcaaaacacc agcagcagtt tttccagttc cgtttatccg gcaaaccat cgaagtgacc       1920 agcgaatacc tgttccgtca tagcgataac gagctcctgc actggatggt ggcgctggat      1980
ggtaagccgc tggcaagcgg tgaagtgcct ctggatgtcg ctccacaagg taaacagttg      2040
attgaactgc ctgaactacc gcagccggag agcgccgggc aactctggct cacagtacgc      2100
gtagtgcaac cgaacgcgac cgcatggtca gaagccgggc acatcagcgc ctggcagcag      2160
tggcgtctgg cggaaaaacct cagtgtgacg ctccccgccg cgtccacgc catcccgcat       2220 ctgaccacca gcgaaatgga ttttgcatc gagctgggta ataagcgttg gcaatttaac       2280
cgccagtcag gctttctttc acagatgtgg attggcgata aaaacaact gctgacgccg        2340 ctgcgcgatc agttcacccg tgcaccgctg ataacgaca ttggcgtaag tgaagcgacc       2400
cgcattgacc ctaacgcctg ggtcgaacgc tggaaggcgg cgggccatta ccaggccgaa      2460
gcagcgttgt tgcagtgcac ggcagataca cttgctgatg cggtgctgat tacgaccgct     2520
cacgcgtggc agcatcaggg gaaaaccta tttatcagcc ggaaaaccta ccggattgat        2580
ggtagtggtc aaatggcgat taccgttgat gttgaagtgg cgagcgatac accgcatccg      2640
gcgcggattg gcctgaactg ccagctggcg caggtagcag agcgggtaaa ctggctcgga      2700
ttagggccgc aagaaaacta tcccgaccgc cttactgccg cctgttttga ccgctgggat      2760
ctgccattgt cagacatgta tacccgtac gtcttcccga gcgaaaacgg tctgcgctgc        2820
gggacgcgcg aattgaatta tggcccacac cagtggcgcg cgacttcca gttcaacatc        2880 agccgctaca gtcaacagca actgatggaa accagccatc gccatctgct gcacgcggaa      2940
gaaggcacat ggctgaatat cgacggtttc catatgggga ttggtggcga cgactcctgg      3000
agcccgtcag tatcggcgga attccagctg agcgccggtc gctaccatta ccagttggtc      3060
tggtgtcaaa aataa                                                                                  3075
```

```
<210> SEQ ID NO 63
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 63
atgaccatga ttacggattc actggcc                                                27

<210> SEQ ID NO 64
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 64 ttattttga caccagacca actggtaatg g                                            31
```

<210> SEQ ID NO 65
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 65
atgaccatga ttacggattc actggcc                                         27

<210> SEQ ID NO 66
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 66
gatagagatt cgggatttcg gcgctcc                                         27

<210> SEQ ID NO 67
<211> LENGTH: 931
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 67
atgaccatga ttacggattc actggccgtc gttttacaac gtcgtgactg ggaaaaccct     60
ggcgttaccc aacttaatcg ccttgcagca catcccccct tcgccagctg gcgtaatagc    120
gaagaggccc gcaccgatcg cccttcccaa cagttgcgca gcctgaatgg cgaatggcgc    180
tttgcctggt ttccggcacc agaagcggtg ccggaaagct ggctggagtg cgatcttcct    240
gaggccgata ctgtcgtcgt cccctcaaac tggcagatgc acggttacga tgcgcccatc    300
tacaccaacg tgacctatcc cattacggtc aatccgccgt ttgttcccac ggagaatccg    360
acgggttgtt actcgctcac atttaatgtt gatgaaagct ggctacagga aggccagacg    420
cgaattattt ttgatggcgt taactcggcg tttcatctgt ggtgcaacgg gcgctgggtc    480
ggttacggcc aggacagtcg tttgccgtct gaatttgacc tgagcgcatt tttacgcgcc    540
ggagaaaacc gcctcgcggt gatggtgctg cgctggagtg acggcagtta tctggaagat    600
caggatatgt ggcggatgag cggcattttc cgtgacgtct cgttgctgca taaaccgact    660
acacaaatca gcgatttcca tgttgccact cgctttaatg atgatttcag ccgcgctgta    720
ctggaggctg aagttcagat gtgcggcgag ttgcgtgact acctacgggt aacagtttct    780
ttatggcagg gtgaaacgca ggtcgccagc ggcaccgcgc ctttcggcgg tgaaattatc    840
gatgagcgtg gtggttatgc cgatcgcgtc acactacgtc tgaacgtcga aaacccgaaa    900
ctgtggagcg ccgaaatccc gaatctctat c                                  931

<210> SEQ ID NO 68
<211> LENGTH: 163
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 68

```
atgaccatga ttacggattc actggccgtc gttttacaac gtcgtgactg ggaaaacct      60 ggcgttaccc aacttaatcg ccttgcagca catccccctt tcgccagctg gcgtaatagc    120
gaagaggccc gcaccgatcg cccttcccaa cagttgcgca gcc                      163
```

<210> SEQ ID NO 69
<211> LENGTH: 175
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 69

```
gataggtcac gttggtgtag atgggcgcat cgtaaccgtg catctgccag tttgagggga      60
cgacgacagt atcggcctca ggaagatcgc actccagcca gctttccggc accgcttctg    120
gtgccggaaa ccaggcaaag cgccattcgc cattcaggct gcgcaactgt tggga         175
```

<210> SEQ ID NO 70
<211> LENGTH: 176
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 70

```
cccatctaca ccaacgtgac ctatcccatt acggtcaatc cgccgtttgt tcccacggag      60
aatccgacgg gttgttactc gctcacattt aatgttgatg aaagctggct acaggaaggc    120
cagacgcgaa ttattttttga tggcgttaac tcggcgtttc atctgtggtg caacgg        176
```

<210> SEQ ID NO 71
<211> LENGTH: 176
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 71

```
gccgctcatc cgcccacatat cctgatcttc cagataactg ccgtcactcc agcgcagcac     60
catcaccgcg aggcggtttt ctccggcgcg taaaaatgcg ctcaggtcaa attcagacgg    120
caaacgactg tcctggccgt aaccgaccca gcgcccgttg caccacagat gaaacg        176
```

<210> SEQ ID NO 72
<211> LENGTH: 177
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 72

```
aggatatgtg gcggatgagc ggcatttttcc gtgacgtctc gttgctgcat aaaccgacta     60
cacaaatcag cgatttccat gttgccactc gctttaatga tgatttcagc cgcgctgtac    120
tggaggctga agttcagatg tgcggcgagt tgcgtgacta cctacgggta acagttt       177
```

<210> SEQ ID NO 73
<211> LENGTH: 178

```
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 73
gatagagatt cgggatttcg gcgctccaca gtttcgggtt ttcgacgttc agacgtagtg        60
tgacgcgatc ggcataacca ccacgctcat cgataatttc accgccgaaa ggcgcggtgc       120
cgctggcgac ctgcgtttca ccctgccata aagaaactgt tacccgtagg tagtcacg        178
```

DEVICES AND METHODS FOR OLIGONUCLEIC ACID LIBRARY SYNTHESIS

CROSS REFERENCE

This application claims the benefit of U.S. Provisional Application No. 62/150,795 filed Apr. 21, 2015, and U.S. Provisional Application No. 62/220,856 filed Sep. 18, 2015, both of which are herein incorporated by reference in their entirety.

SEQUENCE LISTING

The instant application contains a Sequence Listing which has been submitted electronically in ASCII format and is hereby incorporated by reference in its entirety. Said ASCII copy, created on Apr. 15, 2016, is named 44854_713_201_SL.txt and is 28,372 bytes in size.

BACKGROUND

Highly efficient chemical gene synthesis with high fidelity and low cost has a central role in biotechnology and medicine, and in basic biomedical research. De novo gene synthesis is a powerful tool for basic biological research and biotechnology applications. While various methods are known for the synthesis of relatively short fragments in a small scale, these techniques often suffer from scalability, automation, speed, accuracy, and cost.

BRIEF SUMMARY

Provided herein are devices for synthesizing oligonucleic acids, comprising: a plate; a main channel, wherein the main channel extends vertically into the plate from an opening on a top side of the plate, and wherein the main channel has a width of 0.5 to 2 mm; and a plurality of microchannels connected to the main channel, wherein each microchannel of the plurality of microchannels extends vertically from an opening on a bottom side of the plate into the main channel, and wherein each microchannel of the plurality of microchannels has a surface area to volume ratio of greater than 0.2 (1/um). Devices are further provided wherein the surface area to volume ratio provides for rapid exchange of chemical exposure during de novo synthesis of oligonucleic acids. Devices are further provided wherein the surface area to volume ratio is about 0.4 (1/um). Devices are further provided wherein the surface area to volume ratio is greater than 0.4 (1/um). Devices are further provided wherein the surface area to volume ratio is 0.41 (1/um). Devices are further provided wherein each microchannel of the plurality of microchannels has a surface area greater than 10,000 $um^2$. Devices are further provided wherein each microchannel of the plurality of microchannels has a surface area greater than 12,000 $um^2$. Devices are further provided wherein each microchannel of the plurality of microchannels has a surface area of about 13,000 $um^2$. Devices are further provided wherein the plurality of microchannels comprises 50 to 500 microchannels. Devices are further provided wherein the plurality of microchannels comprises 100 to 150 microchannels. Devices are further provided wherein a ratio of width to depth of a narrowest segment of each microchannel is from 0.5 to 0.01. Devices are further provided wherein a ratio of width to depth of a narrowest segment of each microchannel is about 0.05, 0.1, or 0.2. Devices are further provided wherein each microchannel of the plurality of microchannels has a total width of 30 um to 100 um. Devices are further provided wherein each microchannel of the plurality of microchannels has a total width of about 60 um. Devices are further provided wherein each microchannel of the plurality of microchannels has a depth of 10 to 500 um. Devices are further provided wherein each microchannel of the plurality of microchannels has a depth of about 30 um. Devices are further provided wherein the main channel has a width from 0.5 to 1.5 mm. Devices are further provided wherein the main channel has a width of about 1.2 mm. Devices are further provided wherein the main channel has a width of 1.15 mm. Devices are further provided wherein the device comprises more than 250 main channels. Devices are further provided wherein the device comprises more than 10,000 main channels. Devices are further provided that further comprising a first molecule, wherein the first molecule is bound to an interior surface of the plurality of microchannels and comprises a reactive group that binds to a nucleoside phosphoramidite. Devices are further provided wherein the first molecule is a silane. Devices are further provided wherein the first molecule is an aminosilane. Devices are further provided wherein the first molecule is 11-acetoxyundecyltriethoxysilane, n-decyltriethoxysilane, (3-aminopropyl)trimethoxysilane, (3-aminopropyl)triethoxysilane, glycidyloxypropyl/trimethoxysilane or N-(3-triethoxysilylpropyl)-4-hydroxybutyramide. Devices are further provided further comprising a second molecule, wherein the second molecule is bound to an interior surface of the main channel and lacks a reactive group that binds to a nucleoside phosphoramidite. Devices are further provided wherein the second molecule is a fluorosilane. Devices are further provided wherein the fluorosilane is (tridecafluorotetrahydrooctyl)-triethoxysilane. Devices are further provided wherein the first molecule has a higher surface energy than the second molecule, and wherein the first molecule has a greater hydrophobicity than the second molecule. Devices are further provided wherein the plate is a silicon plate. Devices are further provided wherein the device comprises at least 30,000 microchannels. Devices are further provided wherein the device comprises at least 700,000 microchannels.

Provided herein are devices for synthesizing oligonucleic acids, comprising: a plate; a main channel, wherein the main channel extends vertically into the silicon plate from an opening on a top side of the plate, and wherein the main channel has a width of 0.5 to 2 mm; and a plurality of microchannels connected to the main channel, wherein each microchannel of the plurality of microchannels extends vertically from an opening on a bottom side of the plate into the main channel, and wherein each microchannel of the plurality of microchannels comprises a total width that is less than 100 um, a microchannel surface area greater than 10,000 um, and a maximum width for the narrowest segment of the microchannel of 10 um. Devices are further provided wherein each microchannel of the plurality of microchannels has a surface area greater than 12,000 $um^2$. Devices are further provided wherein each microchannel of the plurality of microchannels has a surface area of about 13,000 $um^2$. Devices are further provided wherein the plurality of microchannels comprises 50 to 500 microchannels. Devices are further provided wherein the plurality of microchannels comprises 100 to 150 microchannels. Devices are further provided wherein a ratio of width to depth of a narrowest segment of each microchannel is from 0.5 to 0.01. Devices are further provided wherein a ratio of width to depth of a narrowest segment of each microchannel is about 0.05, 0.1, or 0.2. Devices are further provided wherein each microchannel of the plurality of microchannels has a total width of 30 um to 100 um. Devices are further provided wherein each microchannel of the plurality of microchannels has a total width of about 60 um. Devices are further provided wherein each microchannel of the plurality of microchannels has a depth of 10 to 500 um. Devices are further provided wherein each microchannel of the plurality of microchannels has a depth of about 30 um. Devices are further provided wherein the main channel has a width from 0.5 to 1.5 mm. Devices are further provided wherein the main channel has a width of about 1.2 mm. Devices are further provided wherein the main channel has a width of 1.15 mm. Devices are further provided wherein the device comprises more than 250 main channels. Devices are further provided wherein the device comprises more than 10,000 main channels. Devices are further provided further comprising a first molecule, wherein the first molecule is bound to an interior surface of the plurality of microchannels and comprises a reactive group that binds to a nucleoside phosphoramidite. Devices are further provided wherein the first molecule is a silane. Devices are further provided wherein the first molecule is an aminosilane. Devices are further provided wherein the first molecule is 11-acetoxyundecyltriethoxysilane, n-decyltriethoxysilane, (3-aminopropyl)trimethoxysilane, (3-aminopropyl)triethoxysilane, glycidyloxypropyl/trimethoxysilane or N-(3-triethoxysilylpropyl)-4-hydroxybutyramide. Devices are further provided further comprising a second molecule, wherein the second molecule is bound to an interior surface of the main channel and lacks a reactive group that binds to a nucleoside phosphoramidite. Devices are further provided wherein the second molecule is a fluorosilane. Devices are further provided wherein the fluorosilane is (tridecafluorotetrahydrooctyl)-triethoxysilane. Devices are further provided wherein the first molecule has a higher surface energy than the second molecule, and wherein the first molecule has a greater hydrophobicity than the second molecule. Devices are further provided wherein the plate is a silicon plate. Devices are further provided wherein the device comprises at least 30,000 microchannels. Devices are further provided wherein the device comprises at least 700,000 microchannels.

Provided herein are methods for de novo oligonucleic acid synthesis, comprising: providing predetermined sequences for a plurality of non-identical oligonucleic acids; providing a device described herein; adding a droplet of fluid comprising an extension reaction reagent specific to a microchannel; allowing sufficient time for an extension reaction step to occur; and repeating steps (c) and (d) until the plurality of non-identical oligonucleic acids are synthesized, wherein each oligonucleic acid at least 10 bases in length and attached to an inside region of the microchannel, and wherein the synthesized non-identical oligonucleic acids encode sequences with an aggregate error rate of less than 1 in 2000 bases compared to the predetermined sequences. Methods are further provided wherein the synthesized non-identical oligonucleic acids encode sequences with an aggregate error rate of less than 1 in 3000 bases compared to the predetermined sequences. Methods are further provided wherein the synthesized non-identical oligonucleic acids encode sequences with an insertion error rate of less than 1 in 5000 bases compared to the predetermined sequences. Methods are further provided wherein the synthesized non-identical oligonucleic acids encode sequences with a deletion error rate of less than 1 in 2000 bases compared to the predetermined sequences. Methods are further provided that further comprising washing the surface with a washing reagent, and wherein washing removes greater than 95% of unincorporated extension reaction reagent. Methods are further provided wherein washing removes greater than 99% of unincorporated extension reaction reagent. Methods are further provided wherein the droplet of fluid is less than about 32 pL in volume. Methods are further provided wherein the method is completed in less than 24 hours. Methods are further provided wherein the synthesized plurality of non-identical oligonucleic acids are fluidically connected to a single main channel and collectively encode for a single gene. Methods are further provided wherein the oligonucleic acids collectively encode for at least 200 genes at least 1 kb in length. Methods are further provided further comprising: releasing the plurality of non-identical oligonucleic acids from the surface; and subjecting the plurality of non-identical oligonucleic acids to a polymerase chain assembly reaction to assemble at least 200 genes. Methods are further provided wherein the at least 200 genes have an aggregate error rate of less than 1 in 2000 bases compared to the predetermined sequences without correcting errors. Methods are further provided wherein the at least 200 genes have an aggregate error rate of less than 1 in 3000 bases compared to the predetermined sequences without correcting errors. Methods are further provided wherein each oligonucleic acid has a tether region 12 to 25 bases in length. Methods are further provided wherein the tether region is homopolymeric. Methods are further provided wherein each oligonucleic acid is at least 30 bases in length. Methods are further provided wherein each oligonucleic acid 50 to 500 bases in length.

Provided herein are devices for synthesizing oligonucleic acids, comprising a silicon plate; a main channel, wherein the main channel extends vertically into the silicon plate from an opening on a top side of the silicon plate, and wherein the main channel has a width of 0.5 to 2 mm; and 50 to 500 microchannels connected to the main channel, wherein each of the 50 to 500 microchannels extends vertically from an opening on a bottom side of the silicon plate into the main channel, and wherein each microchannel of the 50 to 500 microchannels has a surface area to volume ratio of greater than about 0.4 (1/um), and a ratio of width to depth of a narrowest segment of each microchannel is from 0.5 to 0.01.

INCORPORATION BY REFERENCE

All publications, patents, and patent applications disclosed herein are incorporated by reference to the same extent as if each individual publication, patent, or patent application was specifically and individually indicated to be incorporated by reference. In the event of a conflict between a term disclosed herein and a term in an incorporated reference, the term herein controls.

BRIEF DESCRIPTION OF THE DRAWINGS

FIGS. 9A-9F illustrate a workflow for the passive and active functionalization of an etched substrate.

DETAILED DESCRIPTION

Figure 1:
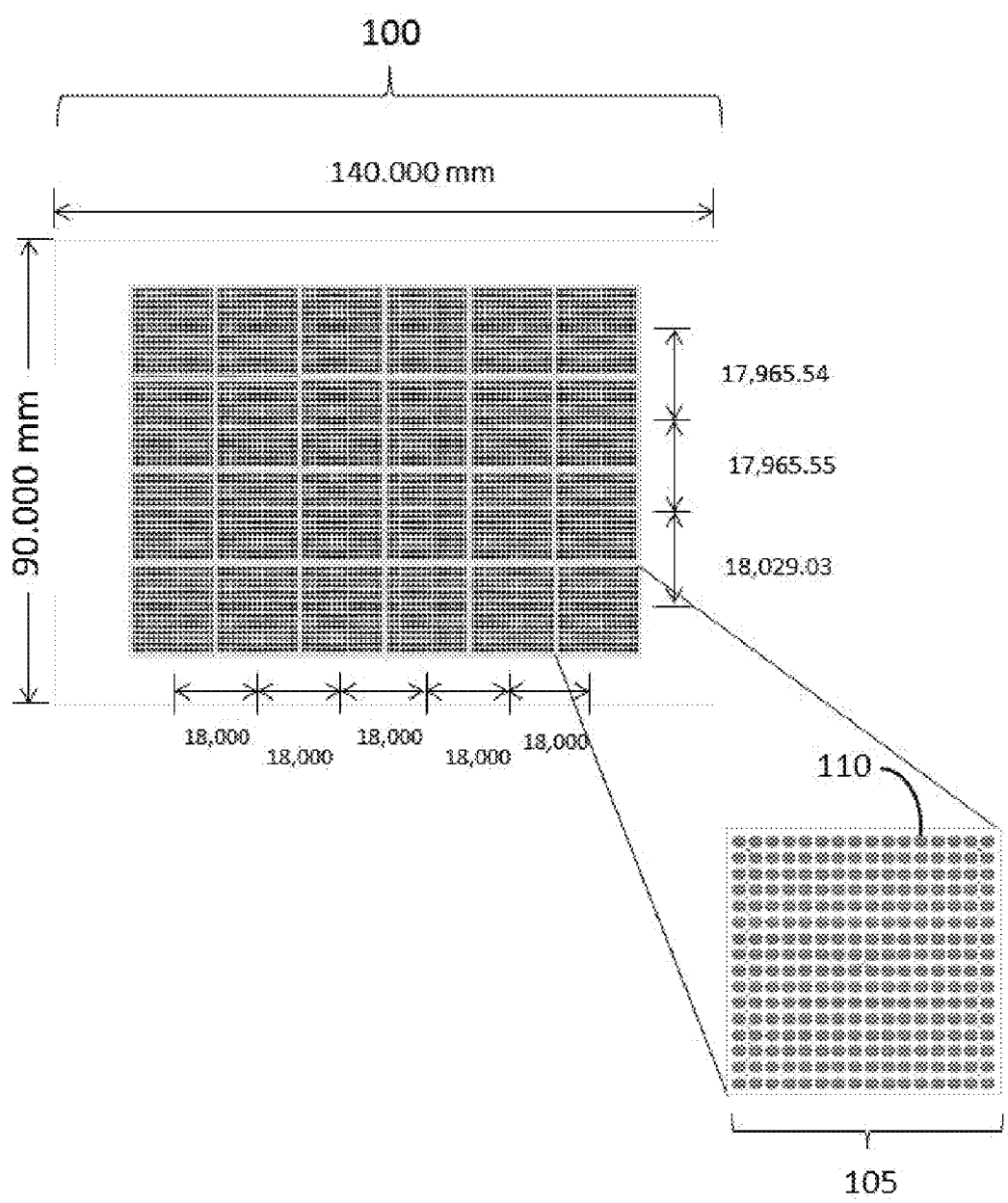
FIG. 1 illustrates a plate configured for oligonucleic acid synthesis comprising 24 regions, or sub-fields, each having an array of 256 clusters.

The present disclosure provides compositions, devices, methods and systems for the de novo synthesis of a library of oligonucleic acids with low error rates. The oligonucleic acids are useful components, such as for the generation of larger nucleic acids, such as genes as part of gene libraries.

Described herein are devices having structural features that control the flow of fluid through small channels ("microchannels") which also serve as locations for oligonucleic acid extension. Factors that can impact the flow of fluid throw the surface include, without limitation, the number of microchannels, microchannel size, the shape of the microchannels, the width of a main channel which a group of microchannels collectively connect, and the chemical properties of surfaces involved (e.g., hydrophobicity and surface energy). During oligonucleic acid synthesis, it is desirable to have channels to have enough width to support the extension of multiple oligonucleic acids, while at the same time be narrow enough to support rapid fluid transfer. Rapid fluid transfer is desirable to provide for efficient chemical exchange during various steps of the de novo nucleic acid synthesis process, and reduce unwanted side reactions that may lead to increased error rates. Devices described herein increase fluid transfer rate through a substrate and also increase the amount of surface available for nucleic acid extension is by having microchannels with a high surface area to volume ratio. Such devices also provide for synthesis of oligonucleic acids with low error rates.

In some cases, oligonucleic acids synthesized within a cluster of extension locations ("loci") comprise specific predetermined sequences that are configured to be assembled to generate a larger nucleic acid. In this manner, the parallel generation of genes is done on a single substrate. The average error rates for oligonucleic acids synthesized within a library using the systems and methods provided are often less than 1 in 1000, and are preferably less than about 1 in 2000, 1 in 5000 or less often.

Definitions

The present disclosure employs, unless otherwise indicated, conventional molecular biology techniques, which are within the skill of the art. Unless defined otherwise, all technical and scientific terms used herein have the same meaning as is commonly understood by one of ordinary skill in the art to which these inventions belong.

Throughout this disclosure, various instances are presented in a range format. It should be understood that the description in range format is merely for convenience and brevity and should not be construed as an inflexible limitation on the scope of any instances. Accordingly, the description of a range should be considered to have specifically described all the possible subranges as well as individual numerical values within that range to the tenth of the unit of the lower limit unless the context clearly dictates otherwise. For example, description of a range such as from 1 to 6 should be considered to have specifically described subranges such as from 1 to 3, from 1 to 4, from 1 to 5, from 2 to 4, from 2 to 6, from 3 to 6 etc., as well as individual values within that range, for example, 1.1, 2, 2.3, 5, and 5.9. This applies regardless of the breadth of the range. The upper and lower limits of these intervening ranges may independently be included in the smaller ranges, and are also encompassed within the invention, subject to any specifically excluded limit in the stated range. Where the stated range includes one or both of the limits, ranges excluding either or both of those included limits are also included in the invention, unless the context clearly dictates otherwise.

Unless specifically stated or obvious from context, as used herein, the term "about" in reference to a number or range of numbers is understood to mean the stated number and numbers +/−10% thereof, or 10% below the lower listed limit and 10% above the higher listed limit for the values listed for a range.

The terminology used herein is for the purpose of describing particular instances only and is not intended to be limiting of any embodiment. As used herein, the singular forms "a," "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items.

As used herein, the term "comprising" is inclusive or open-ended and does not exclude additional unrecited elements, device features, compositional components, or method steps.

The term "locus" as used herein refers to a discrete region on a structure which provides support for extension of an oligonucleic acid.

As used herein, the terms "preselected sequence," "predefined sequence" or "predetermined sequence" are used interchangeably. The terms refer to sequence of a polymer that is known and chosen before synthesis or assembly of the polymer. In particular, various aspects of the invention are described herein primarily with regard to the preparation of nucleic acid molecules, the sequence of the oligonucleotide or polynucleotide being known and chosen before the synthesis or assembly of the nucleic acid molecules.

Substrates, Sub-Fields, Clusters and Loci

Figure 2:
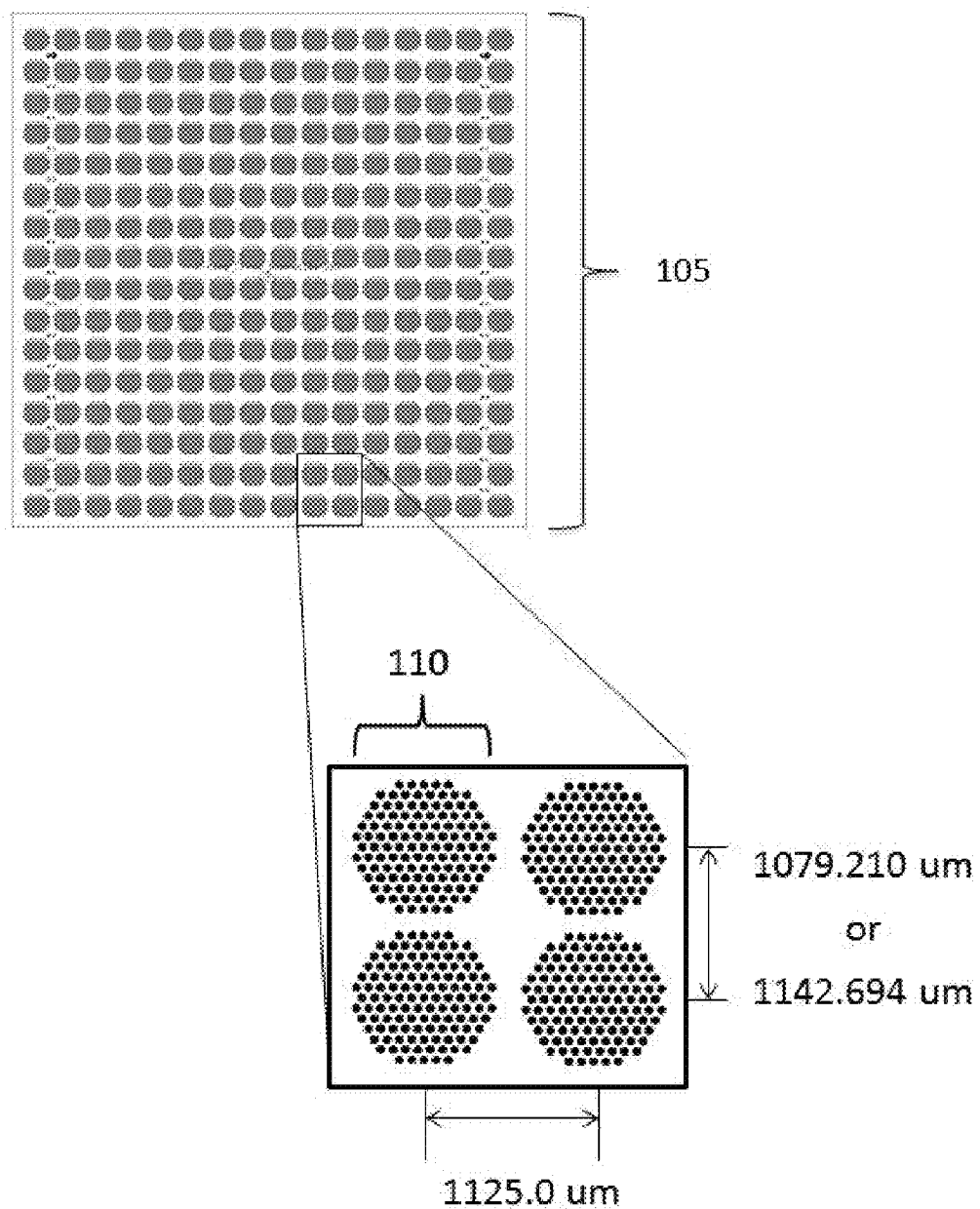
FIG. 2 illustrates a closer view of the sub-field in FIG. 1 having 16×16 of clusters, each cluster having 121 individual loci.
Figure 3:
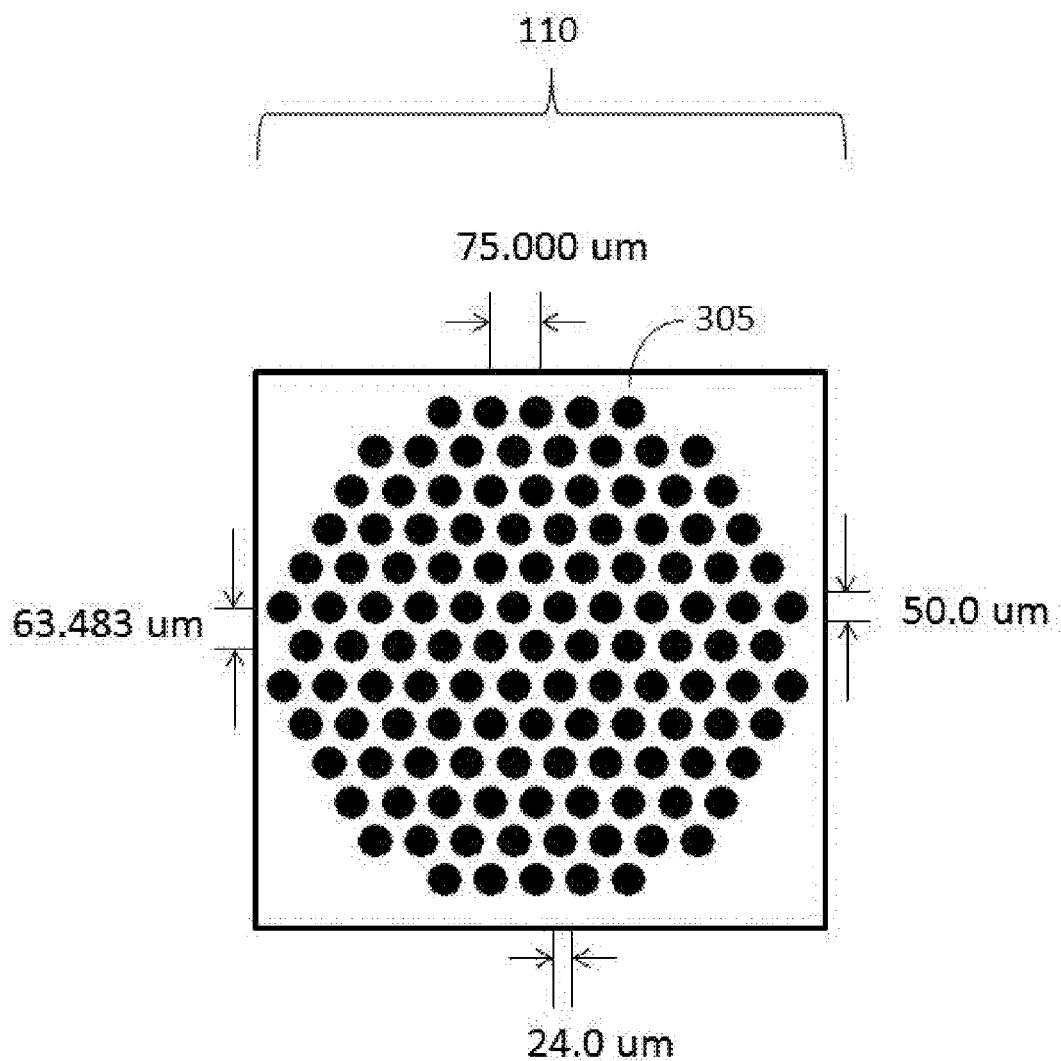
FIG. 3 illustrates a detailed view of the cluster in FIG. 2, where the cluster has 121 loci.

Provided herein are devices having a substrate (e.g., a plate) for the generation of a library of oligonucleic acids. An exemplary substrate 100 is illustrated in FIG. 1, wherein the substrate 100 has about the same size dimensions as a standard 96 well plate: 140 mm by 90 mm. The substrate 100 comprises clusters grouped in 24 regions or sub-fields 105, each sub-field 105 comprising an array of 256 clusters 110. An expanded view of an exemplary sub-field 105 is shown in FIG. 2. In the expanded view of four clusters (FIG. 2), a single cluster 110, has a Y axis cluster pitch (distance from center to center of adjacent clusters) of 1079.210 um or 1142.694 um, and an X axis cluster pitch of 1125 um. An illustrative cluster 110 is depicted in FIG. 3, where the Y axis loci pitch (distance from center to center of adjacent loci) is 63.483 um, and an X axis loci pitch is 75 um. The locus width at the longest part, e.g., diameter for a circular loci, is 50 um and the distance between loci is 24 um. The number of loci 305 in the exemplary cluster in FIG. 3 is 121.

Fluid Conditioning

Figure 4A:
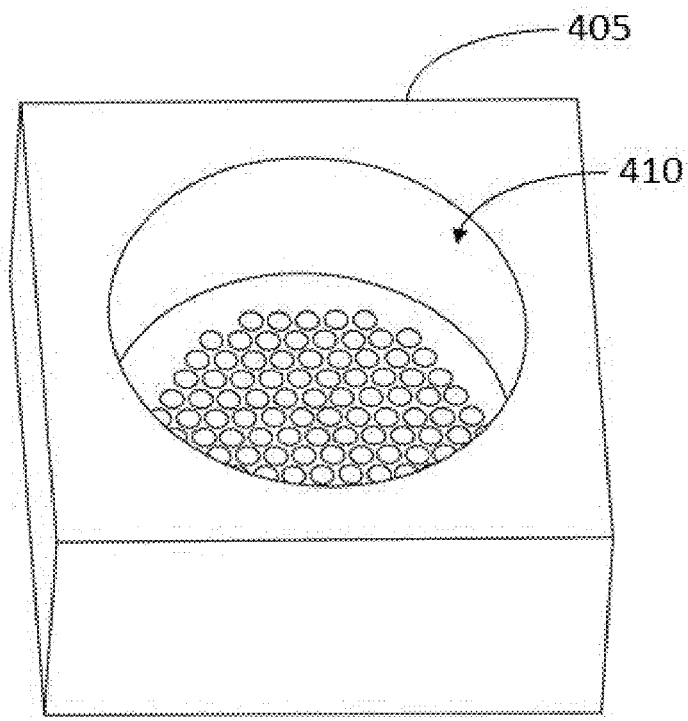
FIG. 4A illustrates a front view of a plate with a plurality of microchannels.
Figure 4B:
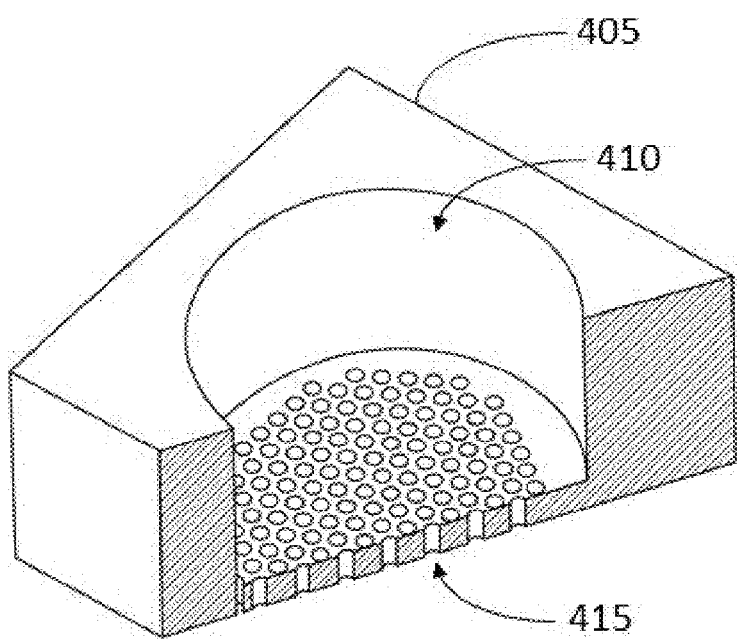
FIG. 4B illustrates a sectional view of plate with a plurality of microchannels.

Provided herein are substrates comprising features which are segregated to allow for efficient chemical exchange of reagents during de novo oligonucleic acid synthesis. An exemplary arrangement is illustrated in FIGS. 4A-4B where a plate 405 is illustrated comprising a main channel 410 and a plurality of microchannels 415 connected to the main channel 410. The connection between the main channel 410 and the plurality of microchannels 415 provides for a fluid communication for flow paths from the main channel 410 to the each of the plurality of microchannels 415. A plate 405 described herein can comprise multiple main channels 410. The plurality of microchannels 415 collectively forms a cluster within the main channel 410. In some cases, a library of oligonucleic acids is synthesized in a plurality of loci where the loci are collectively a plurality of microchannels 415 of a cluster where the cluster is within a main channel 410, followed by the assembly of the oligonucleic acids into a large nucleic acid such as gene, wherein the assembly of the large nucleic acid optionally occurs within a main channel of the cluster, e.g., by using PCA. In further cases, a different oligonucleic acid is grown in each of the microchannels 415 with a main channel 410, and the oligonucleic acids collectively encode for a single gene.

The structure is configured to allow for controlled flow for de novo oligonucleic acid synthesis by providing for rapid exchange of chemical exposure during de novo synthesis of oligonucleic acids. For example, in some cases, configuration described herein provide for the controlled and even distribution of mass transfer paths, chemical exposure times, and/or wash efficiency during oligonucleic acid synthesis. In some instances, the configuration of a substrate allows for increased sweep efficiency, for example by providing sufficient volume for a growing an oligonucleic acid such that the excluded volume by the growing oligonucleic acid does not take up more than 50, 45, 40, 35, 30, 25, 20, 15, 14, 13, 12, 11, 10, 9, 8, 7, 6, 5, 4, 3, 2, 1%, or less of the initially available volume that is available or suitable for growing the oligonucleic acid.

In addition to the physical segregation between each of the microchannels 415 of the plurality of microchannels, chemical coatings also provide and additional means for segregating oligonucleic acid species situated within a microchannel. Segregation can be achieved by differential functionalization of the surface, for example by having active and passive regions for oligonucleic acid synthesis coated on the surface. Differential functionalization can also be achieved by alternating the hydrophobicity across the substrate surface, thereby creating water contact angle effects that may cause beading or wetting of the deposited reagents. Employing larger structures can decrease splashing and cross-contamination of distinct oligonucleic acid synthesis locations with reagents of the neighboring spots. A device, such as an oligonucleic acid synthesizer, may be used to deposit reagents to distinct oligonucleic acid synthesis locations.

Microchannels: Structural Features

Microchannels described herein provide chemical properties, dimensions (width, height/depth, or length) de novo synthesized oligonucleic acids having a low error rate. While the plurality of microchannels 415 in FIG. 4 are circular, various shapes can be used to enhance flow rates through the channel, e.g., microchannels with curves or combs. A microchannel having a shape providing an increased surface area to volume ratio may be desirable for several reasons. First, an increase in surface area provides an increase in area that is suitable for oligonucleic acid attachment and synthesis. Second, a locus in the shape of a microchannel with increased surface area to volume ratio requires less fluid for efficient flow through the channel, thereby allowing less reagent volume per reaction. Third, without wishing to be bound by theory, the efficient flow through a locus in the shape of a microchannel with increased surface area to volume ratio minimizes residual occupation of reagents during flow through the microchannel and enhances wash efficiency, thereby minimizing or essentially eliminating undesirable secondary reactions during the chemical steps involved in the oligonucleotide extension process. Minimizing undesirable secondary reactions is another factor for keeping error rate down during oligonucleic acid synthesis.

Figure 5:
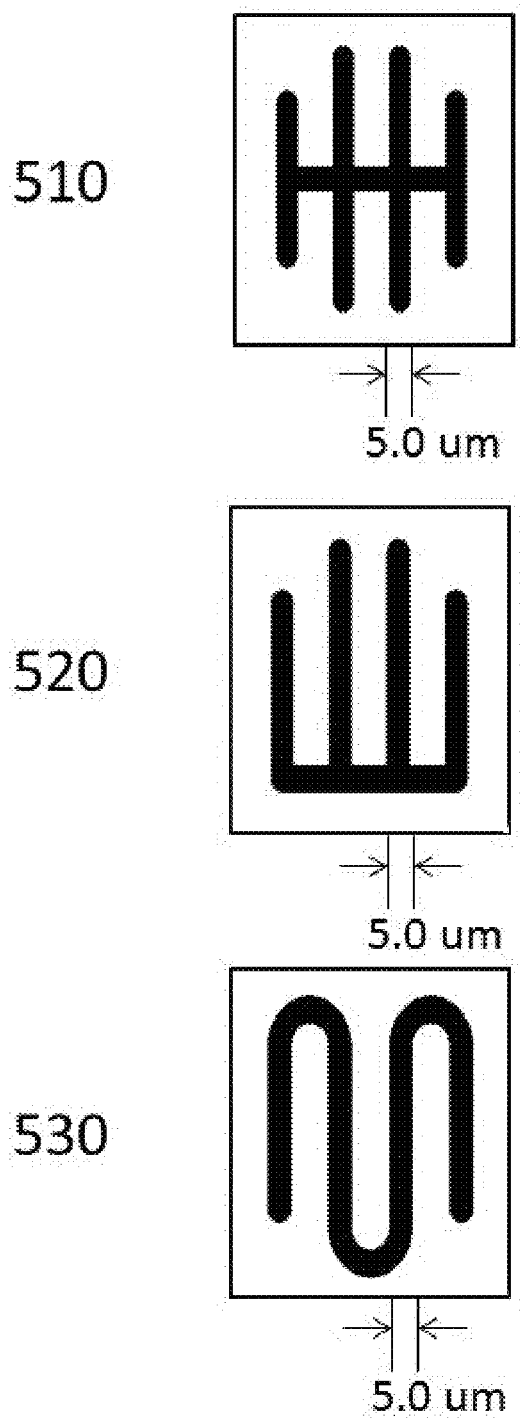
FIG. 5 illustrates three-dimensional arrangements for microchannels.

Exemplary microchannels are illustrated in FIG. 5 which shows a top view of a double comb 510, single comb 520 or serpentine microchannel shape 530. In each exemplary microchannel in FIG. 5, the width of the microchannel at the narrowest segment is 5 um, and each of the microchannel comprises at least one turn greater than 90 degrees in total. In some cases, the microchannel comprises 1 to 10 or more turns greater than 90 degrees in total. In some cases, the turns are curved and the microchannel comprises 1 to 10 or more turns in total. In the case of the single comb 520 and double comb 510, the turns are 90 degrees, i.e. perpendicular fluid paths from a top view. In the case of the serpentine comb 530, the turns are curved and 180 degrees, i.e. a U turn is viewed from top view. In some cases, a turn in a microchannel fluid path is 45 to 180 degrees in total, when viewed from a top view.

Figure 6:
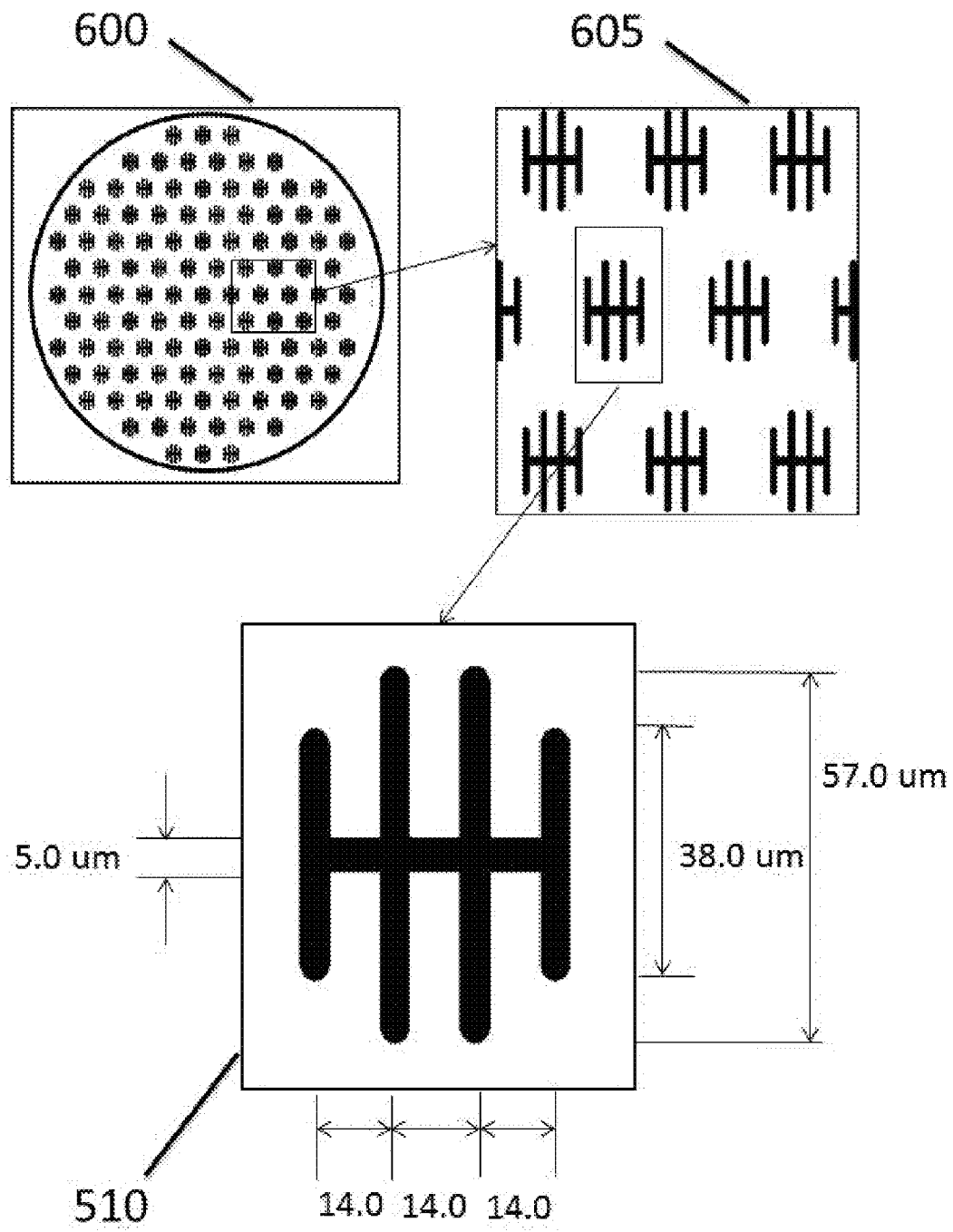
FIG. 6 illustrates a cluster having a plurality of loci with double comb shapes.
Figure 7:
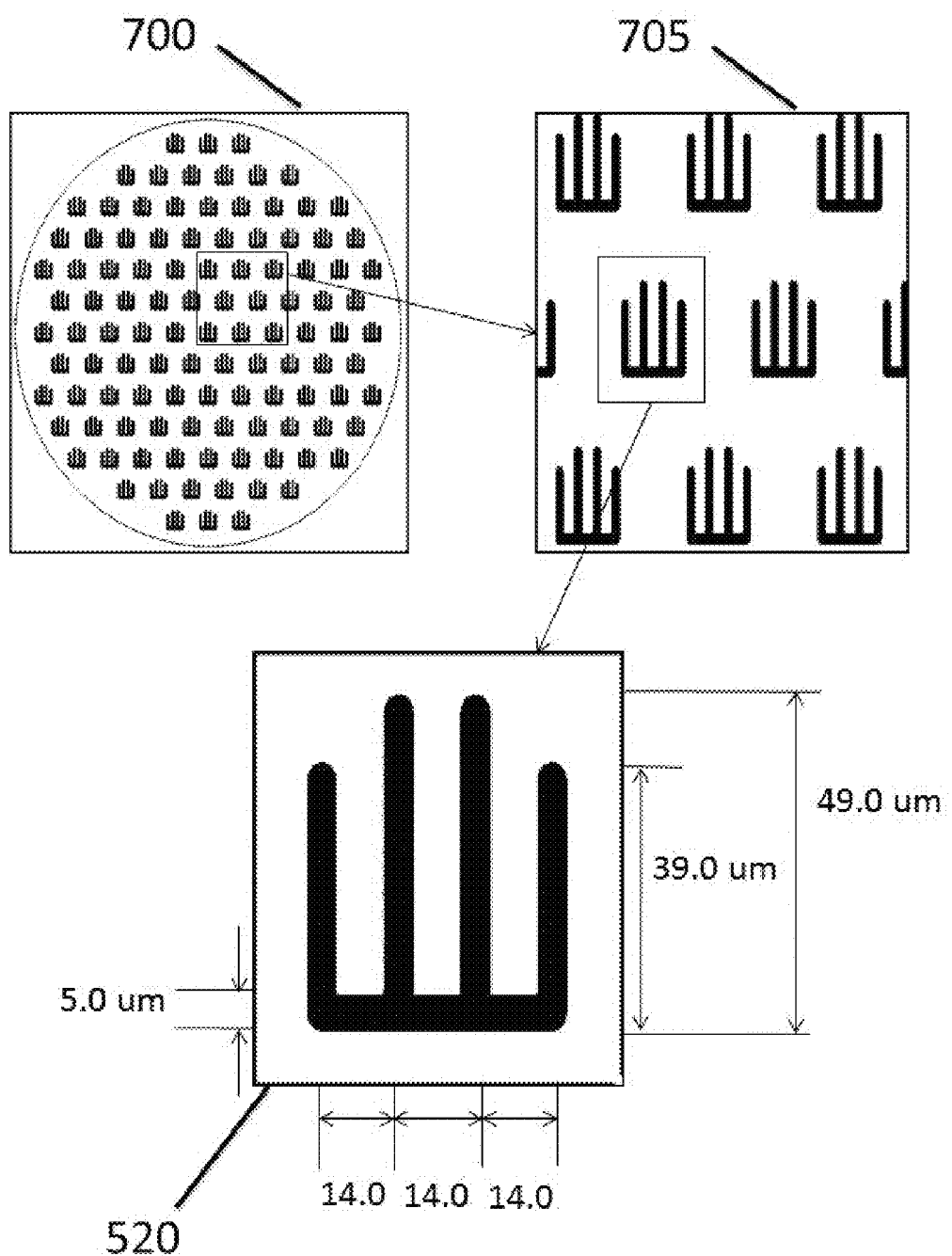
FIG. 7 illustrates a cluster having a plurality of loci with single comb shapes.

In a first example, a main channel 600 comprises a cluster of double comb channels, where each double comb channel 510 has a total width of 57 um, the width of the microchannel at the narrowest segment is 5 um, and each stick of the "comb" is 14 um apart from the center of another stick (FIG. 6). In a second example, a main channel 700 comprises a cluster of single comb channels, where each single comb channel 520 has a total width of 49 um, the width of the microchannel at the narrowest segment is 5 um, and each stick of the "comb" is 14 um apart from the center of another stick (FIG. 7). In a third example, a main channel 800 comprises a cluster of serpentine shaped channels, where each serpentine shaped channel 530 has a total width of 54 um, the width of the microchannel at the narrowest segment is 5 um, and each turn of the shape results in a parallel region 14 um apart from another region (FIG. 7). In some instances, the microchannel extends vertically into the substrate, e.g., a plate.

In some instances, a total surface area for a locus (e.g., a microchannel) in a device described herein is greater than about 9000, 10000, 11000, 12000, 12500, 12600, 12700, 12800, 12900 or 13000 um$^2$. In some instances, the total surface area for a locus in a device described herein is about 10000 to about 15000 um$^2$. In some instances, the total surface area for a locus in a device described herein is about 12000 to about 13000 um$^2$. In some instances, the total surface area to volume ratio (1/um) for a locus in a device described herein is about 0.2 to 0.5. In some instances, the total surface area to volume ratio (1/um) for a locus in a device described herein is greater than 0.20. In some instances, the total surface area to volume ratio (1/um) for a locus in a device described herein is greater than about 0.40. In some instances, the total surface area to volume ratio (1/um) for a locus in a device described herein is about 0.40. In some instances, the total surface area to volume ratio (1/um) for a locus in a device described herein is 0.41.

In some instances, a microchannel described herein has a width to depth (or height) ratio of 1 to 0.01, wherein the width is a measurement of the width at the narrowest segment of the microchannel. In some instances, a microchannel described herein has a width to depth (or height) ratio of 0.5 to 0.01, wherein the width is a measurement of the width at the narrowest segment of the microchannel. In some instances, a microchannel described herein has a width to depth (or height) ratio of about 0.01, 0.05, 0.1, 0.15, 0.16, 0.2, 0.5, or 1.

In some instances, a substrate is provided comprises a plurality of microchannels corresponding to a plurality of loci within a cluster, wherein the height or depth of the microchannel is from about 5 um to about 500 um, from about 5 um to about 400 um, from about 5 um to about 300 um, from about 5 um to about 200 um, from about 5 um to about 100 um, from about 5 um to about 50 um, or from about 10 um to about 50 um. In some cases, the height of a microchannel is less than 100 um, less than 80 um, less than 60 um, less than 40 um or less than 20 um. In some cases, microchannel height is about 10, 20, 30, 40, 50, 60, 70, 80, 90, 100, 200, 300, 400, 500 um or more.

In some instances, the width of a locus (e.g., microchannel or microwell) is from about 0.5 um to about 500 um, from about 1 um to about 200 um, from about 1 um to about 100 um, from about 5 um to about 100 um, or from about 0.1 um to about 100 um, for example, about 90 um, 80 um, 70 um, 60 um, 50 um, 40 um, 30 um, 20 um, 10 um, 5 um, 1 um or 0.5 um. In some instances, the width of a locus (e.g., microchannel) is less than about 100 um, 90 um, 80 um, 70 um, 60 um, 50 um, 40 um, 30 um, 20 um or 10 um. In some instances, the distance between the center of two adjacent loci is from about 1 um to about 500 um, from about 1 um to about 200 um, from about 1 um to about 100 um, from about 5 um to about 200 um, from about 5 um to about 100 um, from about 5 um to about 50 um, or from about 5 um to about 30 um, for example, about 20 um. In some instances, the total width of a microchannel is about 10 um, 20 um, 30 um, 40 um, 50 um, 60 um, 70 um, 80 um, 90 um, or 100 um. In some instances, the total width of a microchannel is about 10 um to 100 um, 30 um to 100 um, or 50 um to 70 um.

In some cases, each locus supports the synthesis of a population of oligonucleic acids having a different sequence than a population of oligonucleic acids grown on another locus. Provided herein are surfaces which comprise at least 10, 100, 256, 500, 1000, 2000, 3000, 4000, 5000, 6000, 7000, 8000, 9000, 10000, 11000, 12000, 13000, 14000, 15000, 20000, 30000, 40000, 50000 or more clusters. Provided herein are surfaces which comprise more than 2,000; 5,000; 10,000; 20,000; 30,000; 50,000; 100,000; 200,000; 300,000; 400,000; 500,000; 600,000; 700,000; 800,000; 900,000; 1,000,000; 5,000,000; or 10,000,000 or more distinct loci (e.g., microchannels). In some cases, each cluster includes 1, 2, 3, 4, 5, 6, 7, 8, 9, 10, 20, 30, 40, 50, 60, 70, 80, 90, 100, 120, 130, 150, 200, 500 or more loci. In some cases, each cluster includes 50 to 500, 50 to 200, 50 to 150, or 100 to 150 loci. In some cases, each cluster includes 100 to 150 loci. In exemplary arrangements, each cluster includes 109, 121, 130 or 137 loci.

Provided herein are structures wherein the distance between the centers of two adjacent loci within a cluster is from about 1 um to about 500 um, from about 5 um to about 200 um, or from about 0.5 um to about 100 um. Provided herein are structures wherein the distance between two centers of adjacent loci is about 0.5 um, 20 um, 25 um, 30 um, 40 um, 50 um, 60 um, 70 um, 80 um, 90 um, or 100 um.

Provided herein are loci having a width at the longest segment of 5 to 100 um. In some cases, the loci have a width at the longest segment of about 30, 35, 40, 45, 50, 55 or 60 um. In some cases, the loci are microchannels having multiple segments, wherein each segment has a center to center distance apart of 5 to 50 um. In some cases, the center to center distance apart for each segment is about 5, 10, 15, 20 or 25 um.

Main Channels: Structural Features

Main channels described herein extend from a top surface of a substrate, e.g., a plate, into the plate until reaching an interface with a plurality of microchannels, each microchannel connecting to a bottom surface of the substrate. In some instances, the main channel extends vertically. Main channels, e.g., main channel 410, can be in circular, rectangular, tapered, or rounded shapes.

In some instances, a width (a diameter in the case of a circle) of a cluster or the width of a main channel comprising a cluster, or both, is between about 0.05 mm to about 50 mm, between about 0.05 mm to about 10 mm, between about 0.05 mm and about 5 mm, between about 0.05 mm and about 4 mm, between about 0.05 mm and about 3 mm, between about 0.05 mm and about 2 mm, between about 0.05 mm and about 1 mm, between about 0.05 mm and about 0.5 mm, between about 0.05 mm and about 0.1 mm, between about 0.1 mm and 10 mm, between about 0.2 mm and 10 mm, between about 0.3 mm and about 10 mm, between about 0.4 mm and about 10 mm, between about 0.5 mm and 10 mm, between about 0.5 mm and about 5 mm, between about 0.5 mm and about 1.5 mm, or between about 0.5 mm and about 2 mm. In some instances, the width of a cluster or main channel or both is less than or about 5 mm, 4 mm, 3 mm, 2 mm, 1.5 mm, 1.2 mm, 1.15 mm, 1 mm, 0.5 mm, 0.1 mm, 0.09 mm, 0.08 mm, 0.07 mm, 0.06 mm or 0.05 mm. In some instances, the width of a cluster or main channel is between about 1.0 and about 1.3 mm. In some instances, the width of a cluster or main channel, or both is about 1.150 mm. In some instances, the width of a cluster or main channel, or both is about 0.08 mm.

In some instances, the height (depth) of a main channel is from about 20 um to about 1000 um, from about 50 um to about 1000 um, from about 100 um to about 1000 um, from about 200 um to about 1000 um, from about 300 um to about 1000 um, from about 400 um to about 1000 um, or from about 500 um to about 1000 um. In some cases, the height of a main channel is less than about 1000 um, less than about 900 um, less than about 800 um, less than about 700 um, or less than about 600 um. In some cases, the height of a main channel is about 500 um. In some cases, the height of a main channel is about 450 um.

In some instances, the number of distinct nucleic acids or genes assembled from a plurality of oligonucleic acids synthesized on a substrate is dependent on the number of clusters available in the substrate. In some instances, the density of clusters within a substrate is at least or about 1 cluster per 100 mm$^2$, 1 cluster per 10 mm$^2$, 1 cluster per 5 mm$^2$, 1 cluster per 4 mm$^2$, 1 cluster per 3 mm$^2$, 1 cluster per 2 mm$^2$, 1 cluster per 1 mm$^2$, 2 clusters per 1 mm$^2$, 3 clusters per 1 mm$^2$, 4 clusters per 1 mm$^2$, 5 clusters per 1 mm$^2$, 10 clusters per 1 mm$^2$, 50 clusters per 1 mm$^2$ or more. In some instances, a substrate comprises from about 1 cluster per 10 mm$^2$ to about 10 clusters per 1 mm$^2$. In some instances, the distance between the centers of two adjacent clusters is less than about 50 um, 100 um, 200 um, 500 um, 1000 um, or 2000 um or 5000 um. In some cases, the distance between the centers of two adjacent clusters is between about 50 um and about 100 um, between about 50 um and about 200 um, between about 50 um and about 300 um, between about 50 um and about 500 um, and between about 100 um to about 2000 um. In some cases, the distance between the centers of two adjacent clusters is between about 0.05 mm to about 50 mm, between about 0.05 mm to about 10 mm, between about 0.05 mm and about 5 mm, between about 0.05 mm and about 4 mm, between about 0.05 mm and about 3 mm, between about 0.05 mm and about 2 mm, between about 0.1 mm and 10 mm, between about 0.2 mm and 10 mm, between about 0.3 mm and about 10 mm, between about 0.4 mm and about 10 mm, between about 0.5 mm and 10 mm, between about 0.5 mm and about 5 mm, or between about 0.5 mm and about 2 mm.

In some instances, the number of distinct oligonucleic acids synthesized on a substrate is dependent on the number of distinct loci available in the substrate. In some instances, the density of loci within a cluster of a substrate is at least or about 1 locus per mm$^2$, 10 loci per mm$^2$, 25 loci per mm$^2$, 50 loci per mm$^2$, 65 loci per mm$^2$, 75 loci per mm$^2$, 100 loci per mm$^2$, 130 loci per mm$^2$, 150 loci per mm$^2$, 175 loci per mm$^2$, 200 loci per mm$^2$, 300 loci per mm$^2$, 400 loci per mm$^2$, 500 loci per mm$^2$, 1,000 loci per mm$^2$ or more. In some cases, a substrate comprises from about 10 loci per mm$^2$ to about 500 mm$^2$, from about 25 loci per mm$^2$ to about 400 mm$^2$, from about 50 loci per mm$^2$ to about 500 mm$^2$, from about 100 loci per mm$^2$ to about 500 mm$^2$, from about 150 loci per mm$^2$ to about 500 mm$^2$, from about 10 loci per mm$^2$ to about 250 mm$^2$, from about 50 loci per mm$^2$ to about 250 mm$^2$, from about 10 loci per mm$^2$ to about 200 mm$^2$, or about 50 loci per mm$^2$ to about 200 mm$^2$. In some instances, the distance between the centers of two adjacent loci within a cluster is from about 10 um to about 500 um, from about 10 um to about 200 um, or from about 10 um to about 100 um. In some cases, the distance between two centers of adjacent loci is greater than about 10 um, 20 um, 30 um, 40 um, 50 um, 60 um, 70 um, 80 um, 90 um or 100 um. In some cases, the distance between the centers of two adjacent loci is less than about 200 um, 150 um, 100 um, 80 um, 70 um, 60 um, 50 um, 40 um, 30 um, 20 um or 10 um.

A device described herein may comprise multiple main channels. In some cases, a device described herein comprises 1 to 250, 2 to 250, 1 to 500 or more main channels. In some cases, a device described herein comprises about 2, 10, 50, 100, 150, 200, 250, 256, 500, 512, 1000, 2500, 3000, 4000, 5000, 6000, 6144, 10000 or more main channels. In some cases, a plate described herein comprises about 2, 10, 50, 100, 150, 200, 250, 256, 500, 512, 1000, 2500, 3000, 4000, 5000, 6000, 6144, 10000 or more main channels. In some cases, the plate is a silicon plate or a silicon on insulator (SOI) plate.

In some instances, a substrate comprises a surface that supports the synthesis of a plurality of oligonucleic acids having different predetermined sequences at addressable locations on a common support. In some instances, a substrate described herein provides support for the synthesis of more than 2,000; 5,000; 10,000; 20,000; 30,000; 50,000; 100,000; 200,000; 300,000; 400,000; 500,000; 600,000; 700,000; 800,000; 900,000; 1,000,000; 1,200,000; 1,400,000; 1,600,000; 1,800,000; 2,000,000; 2,500,000; 3,000,000; 3,500,000; 4,000,000; 4,500,000; 5,000,000; 10,000,000 or more non-identical oligonucleic acids. In some cases, the substrate provides support for the synthesis of more than 2,000; 5,000; 10,000; 20,000; 50,000; 100,000; 200,000; 300,000; 400,000; 500,000; 600,000; 700,000; 800,000; 900,000; 1,000,000; 1,200,000; 1,400,000; 1,600,000; 1,800,000; 2,000,000; 2,500,000; 3,000,000; 3,500,000; 4,000,000; 4,500,000; 5,000,000; 10,000,000 or more oligonucleic acids encoding for distinct sequences. In some instances, at least a portion of the oligonucleic acids have an identical sequence or are configured to be synthesized with an identical sequence. In some instances, the substrate provides a surface environment for the growth of oligonucleic acids having at least about 50, 60, 70, 75, 80, 85, 90, 95, 100, 110, 120, 130, 140, 150, 160, 175, 200, 225, 250, 275, 300, 325, 350, 375, 400, 425, 450, 475, 500 bases or more.

In some instances, oligonucleic acids are synthesized on distinct loci of a substrate, wherein each locus supports the synthesis of a population of oligonucleic acids. In some cases, each locus supports the synthesis of a population of oligonucleic acids having a different sequence than a population of oligonucleic acids grown on another locus. In some instances, the loci of a substrate are located within a plurality of clusters. In some instances, a substrate comprises at least 10, 500, 1000, 2000, 3000, 4000, 5000, 6000, 7000, 8000, 9000, 10000, 11000, 12000, 13000, 14000, 15000, 20000, 30000, 40000, 50000 or more clusters. In some instances, a substrate comprises more than 2,000; 5,000; 10,000; 100,000; 200,000; 300,000; 400,000; 500,000; 600,000; 700,000; 800,000; 900,000; 1,000,000; 1,100,000; 1,200,000; 1,300,000; 1,400,000; 1,500,000; 1,600,000; 1,700,000; 1,800,000; 1,900,000; 2,000,000; 300,000; 400,000; 500,000; 600,000; 700,000; 800,000; 900,000; 1,000,000; 1,200,000; 1,400,000; 1,600,000; 1,800,000; 2,000,000; 2,500,000; 3,000,000; 3,500,000; 4,000,000; 4,500,000; 5,000,000; or 10,000,000 or more distinct loci. In some cases, each cluster includes 1, 2, 3, 4, 5, 6, 7, 8, 9, 10, 20, 30, 40, 50, 60, 70, 80, 90, 100, 120, 130, 150 or more loci. In some instances, each cluster includes 50 to 500, 100 to 150, or 100 to 200 loci. In some instances, each cluster includes 109, 121, 130 or 137 loci. In some instances, each cluster includes 5, 6, 7, 8, 9, 10, 11 or 12 loci.

In some instances, oligonucleic acids from distinct loci within one cluster have sequences that, when assembled, encode for a contiguous longer oligonucleic acid of a predetermined sequence, for example, a gene. In some cases, a substrate comprising more than 20,000 loci (e.g., microchannels) is used for the synthesis of up to 200 distinct genes of predetermined sequence. In some cases, a substrate comprising more than 29,000 loci (e.g., microchannels) is used for the synthesis of about 240 distinct genes of predetermined sequence. In some cases, a substrate comprising more than 700,000 loci is used for the synthesis of about 6,000 distinct genes of predetermined sequence.

Substrate: Materials

Substrates provided may be fabricated from a variety of materials suitable for the methods and compositions described herein. In certain instances, substrate materials are fabricated to exhibit a low level of nucleotide binding. In some cases, substrate materials are modified to generate distinct surfaces that exhibit a high level of nucleotide binding. In some instances, substrate materials are transparent to visible and/or UV light. In some instances, substrate materials are sufficiently conductive, e.g., are able to form uniform electric fields across all or a portion of a substrate. In some instances, conductive materials may be connected to an electric ground. In some cases, the substrate is heat conductive or insulated. In some cases, the materials are chemical resistant and heat resistant to support chemical or biochemical reactions, for example oligonucleic acid synthesis reaction processes. In some instances, a substrate comprises flexible materials. Flexible materials include, without limitation, modified nylon, unmodified nylon, nitrocellulose, polypropylene, and the like. In some instances, a substrate comprises rigid materials. Rigid materials include, without limitation, glass, fuse silica, silicon, silicon dioxide, silicon nitride, plastics (for example, polytetraflouroethylene, polypropylene, polystyrene, polycarbonate, and blends thereof, and the like), and metals (for example, gold, platinum, and the like). In some instances, a substrate is fabricated from a material comprising silicon, polystyrene, agarose, dextran, cellulosic polymers, polyacrylamides, polydimethylsiloxane (PDMS), glass, or any combination thereof. The substrates may be manufactured with a combination of materials listed herein or any other suitable material known in the art. In some instances, substrates described herein are in the shape of a plate, film or tape.

Substrate: Structural Features

In some instances, a substrate is about the size of a standard 96 well plate, for example between about 100 and 200 mm by between about 50 and 150 mm. In some instances, a substrate has a diameter less than or equal to about 1000 mm, 500 mm, 450 mm, 400 mm, 300 mm, 250 nm, 200 mm, 150 mm, 100 mm or 50 mm. In some instances, the diameter of a substrate is between about 25 mm and 1000 mm, between about 25 mm and about 800 mm, between about 25 mm and about 600 mm, between about 25 mm and about 500 mm, between about 25 mm and about 400 mm, between about 25 mm and about 300 mm, or between about 25 mm and about 200. Non-limiting examples of substrate size include about 300 mm, 200 mm, 150 mm, 130 mm, 100 mm, 76 mm, 51 mm and 25 mm. In some instances, a substrate has a planar surface area of at least about 100 mm$^2$; 200 mm$^2$; 500 mm$^2$; 1,000 mm$^2$; 2,000 mm$^2$; 5,000 mm$^2$; 10,000 mm$^2$; 12,000 mm$^2$; 15,000 mm$^2$; 20,000 mm$^2$; 30,000 mm$^2$; 40,000 mm$^2$; 50,000 mm$^2$ or more. In some instances, the thickness of a substrate is between about 50 mm and about 2000 mm, between about 50 mm and about 1000 mm, between about 100 mm and about 1000 mm, between about 200 mm and about 1000 mm, or between about 250 mm and about 1000 mm. Non-limiting examples of substrate thickness include 275 mm, 375 mm, 525 mm, 625 mm, 675 mm, 725 mm, 775 mm and 925 mm. In some cases, the thickness of a substrate varies with diameter and depends on the composition of the substrate. For example, a substrate comprising materials other than silicon may have a different thickness than a silicon substrate of the same diameter. Substrate thickness may be determined by the mechanical strength of the material used and the substrate must be thick enough to support its own weight without cracking during handling.

In some instances, a substrate described herein comprises a plurality of smaller regions, for example, at least about 2, 4, 6, 8, 10, 16, 24, 39, 50, 100 or more regions, wherein each region may be used independently from another region. In some cases, regions of a substrate are sub-fields or chips of a substrate. In some instances, reference to a substrate includes a region of a substrate.

Active and Passive Functionalization

Selective deposition or selective functionalization refers to a process that produces two or more distinct areas on a structure, wherein at least one area has a different surface or chemical property that another area of the same structure. Such properties include, without limitation, surface energy, chemical termination, surface concentration of a chemical moiety, and the like. In some cases, active functionalization refers to a method comprising the functionalization of a surface that will be utilized for oligonucleic acid synthesis. In some cases, passive functionalization refers to a method comprising the functionalization of a surface that will render these areas ineffective for oligonucleic acid synthesis. Any suitable process that changes the chemical properties of the surface described herein or known in the art may be used to functionalize the surface, for example chemical vapor deposition of an organosilane. Typically, this results in the deposition of a self-assembled monolayer (SAM) of the functionalization species.

In some instances, a method for functionalizing a surface of a substrate for oligonucleic acid synthesis comprises a resist or photoresist coat. Photoresist, in many cases, refers to a light-sensitive material useful in photolithography to form patterned coatings. It can be applied as a liquid to solidify on a substrate as volatile solvents in the mixture evaporate. In some instances, the resist is applied in a spin coating process as a thin film, e.g., 1 um to 100 um. In some cases, the coated resist is patterned by exposing it to light through a mask or reticle, changing its dissolution rate in a developer. In some cases, the resist cost is used as a sacrificial layer that serves as a blocking layer for subsequent steps that modify the underlying surface, e.g., etching, and then is removed by resist stripping. In some instances, the flow of resist throughout various features of the structure is controlled by the design of the structure. In some instances, a surface of a structure is functionalized while areas covered in resist are protected from active or passive functionalization.

In some instances, a substrate suitable for functionalization (e.g., an etched substrate comprising three-dimensional features) is deposited with resist, for example, by an oligonucleic acid synthesizer devices capable of delivering drops of fluid with micrometer accuracy. To resist coat only a small region of the substrate (e.g., lowered features such as a well and/or channel), a droplet of resist may be deposited into the lowered feature where it optionally spreads. In some instances, a portion of the resist is removed, for example, by etching (e.g., oxygen plasma etch) to leave a smooth surface covering only a select area. In some instances, the substrate is passively functionalized with a passive functionalization agent comprising a chemically inert moiety to create a surface having low surface energy. In some instances, the passively functionalized substrate is resist stripped, exposing areas of the substrate that were exposed during front-end processing (etched regions).

Described herein are methods for the synthesis of oligonucleic acids having a low error rate compared to a predetermined sequence using a device configured to regulate the flow of reagents in a microfluidic environment. An exemplary method is illustrated in FIGS. 9A-9F, which depicts a workflow for active functionalization of a microchannels and passive functionalization of surrounding areas, e.g., main channels. An etched substrate 905 is prepared for active functionalization. In FIG. 9A, the substrate is wet cleaned, for example, using a piranha solution. In some instances, the substrate is plasma cleaned, for example, by dry oxygen plasma exposure. In FIG. 9B, the device layer is coated with photoresist 910, optionally after cleaning. In some instances, the photoresist is coated by a process governed by wicking into the device layer channels. In some instances, the photoresist is patterned using photolithography to expose areas that are desired to be passive (i.e., areas where oligonucleic acid synthesis is not designed to take place). Patterning by photolithography may occur by exposing the resist to light through a binary mask that has a pattern of interest. After exposure, the resist in the exposed regions may be removed in developer solution in FIG. 9C, and leaves photoresist at predetermined regions 915. A subsequent step, as shown in FIG. 9D, involves exposure to a passive functionalization agent 920 such as a low surface energy silane (e.g., fluorosilane gas vapor), for example, by chemical vapor deposition (CVD). Exposure to fluorosilane gas results in the deposition of a fluorocarbon on the surfaces without photoresist. In some cases, the substrate is exposed to a hydrocarbon silane. In some instances, passive functionalization comprises exposing a substrate to a passive functionalization agent such as one comprising silane. In some instances, the passively functionalized substrate are unresponsive to additional layers of functionalization agent (e.g., active functionalization agent) creating a monolayer on the surface. A substrate that has been coated with resist, and optionally patterned by photolithography and/or optionally passively functionalized, in many cases, is resist stripped. Resist stripping as shown in FIG. 9E leaves some surfaces passively functionalized while exposing regions of the substrate that was underneath the resist 925. For example, a resist is dissolved in an organic solvent. As another example, resist stripping of a substrate that was passively functionalized with a fluorosilane gas, leaves a surface having some regions of fluorination. In some cases, regions that were underneath the resist comprise silicon or silicon dioxide. In FIG. 9F, the surface is actively functionalized to prepare the surface for oligonucleic acid synthesis. An exemplary active functionalization agent is one that has a higher surface energy than the passive functionalization agent.

An exemplary workflow for the generation of differential functionalization patterns of a substrate is described herein, FIGS. 9A-F. The following workflow is an example process and any step or component may be omitted or changed in accordance with properties desired of the final functionalized substrate. In some cases, additional components and/or process steps are added to the process workflows embodied herein. In some instances, a substrate is first cleaned, for example, using a piranha solution. An example of a cleaning process includes soaking a substrate in a piranha solution (e.g., 90% $H_2SO_4$, 10% $H_2O_2$) at an elevated temperature (e.g., 120° C.) and washing (e.g., water) and drying the substrate (e.g., nitrogen gas). The process optionally includes a post piranha treatment comprising soaking the piranha treated substrate in a basic solution (e.g., $NH_4OH$) followed by an aqueous wash (e.g., water). In some instances, a substrate is plasma cleaned, optionally following the piranha soak and optional post piranha treatment. An example of a plasma cleaning process comprises an oxygen plasma etch. In some instances, the surface is deposited with an active functionalization agent following by vaporization. In some instances, the substrate is actively functionalized prior to cleaning, for example, by piranha treatment and/or plasma cleaning.

The process for substrate functionalization optionally comprises a resist coat and a resist strip. In some instances, following active surface functionalization, the substrate is spin coated with a resist, for example, SPR™ 3612 positive photoresist. The process for substrate functionalization, in various instances, comprises lithography with patterned functionalization. In some instances, photolithography is performed following resist coating. In some instances, after lithography, the substrate is visually inspected for lithography defects. The process for substrate functionalization, in some instances, comprises a cleaning step, whereby residues of the substrate are removed, for example, by plasma cleaning or etching. In some instances, the plasma cleaning step is performed at some step after the lithography step.

In some instances, a substrate coated with a resist is treated to remove the resist, for example, after functionalization and/or after lithography. In some cases, the resist is removed with a solvent, for example, with a stripping solution comprising N-methyl-2-pyrrolidone. In some cases, resist stripping comprises sonication or ultrasonication. In some instances, a resist is coated and stripped, followed by active functionalization of the exposed areas to create a desired differential functionalization pattern.

In various instances, the methods and compositions described herein relate to the application of photoresist for the generation of modified surface properties in selective areas, wherein the application of the photoresist relies on the fluidic properties of the substrates defining the spatial distribution of the photoresist. Without being bound by theory, surface tension effects related to the applied fluid may define the flow of the photoresist. For example, surface tension and/or capillary action effects may facilitate drawing of the photoresist into small structures in a controlled fashion before the resist solvents evaporate. In some instances, resist contact points are pinned by sharp edges, thereby controlling the advance of the fluid. The underlying structures may be designed based on the desired flow patterns that are used to apply photoresist during the manufacturing and functionalization processes. A solid organic layer left behind after solvents evaporate may be used to pursue the subsequent steps of the manufacturing process. Substrates may be designed to control the flow of fluids by facilitating or inhibiting wicking effects into neighboring fluidic paths. For example, a substrate is designed to avoid overlap between top and bottom edges, which facilitates the keeping of the fluid in top structures allowing for a particular disposition of the resist. In an alternative example, the top and bottom edges overlap, leading to the wicking of the applied fluid into bottom structures. Appropriate designs may be selected accordingly, depending on the desired application of the resist.

Figure 10A:
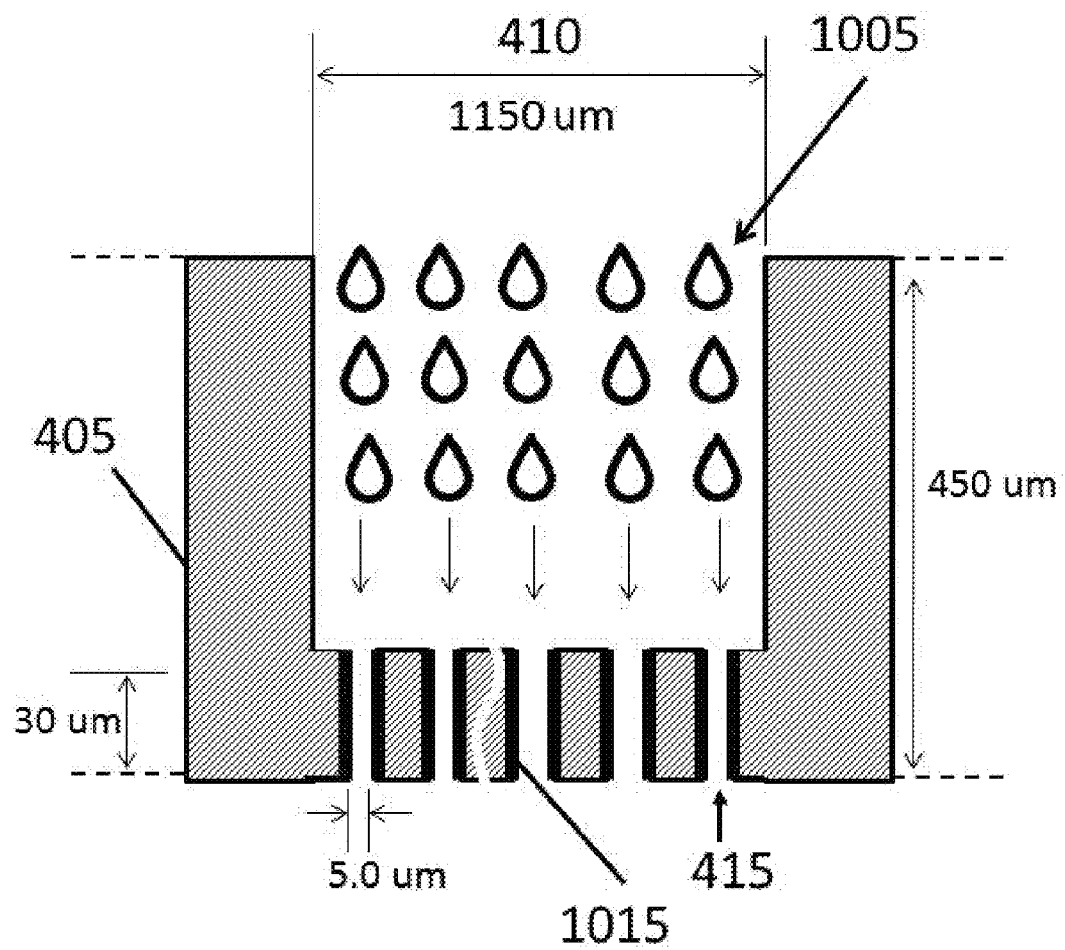
FIGS. 10A-10C illustrate reagent deposition directly into microchannels within a main channel, where: microchannels are actively functionalized (FIG. 10A), main channels are passively functionalized (FIG. 10B); and microchannels are actively functionalized and main channels are passively functionalized (FIG. 10C). The dotted lines indicate that the image depicts one main channel of many in a single substrate (e.g., a plate).
Figure 10B:
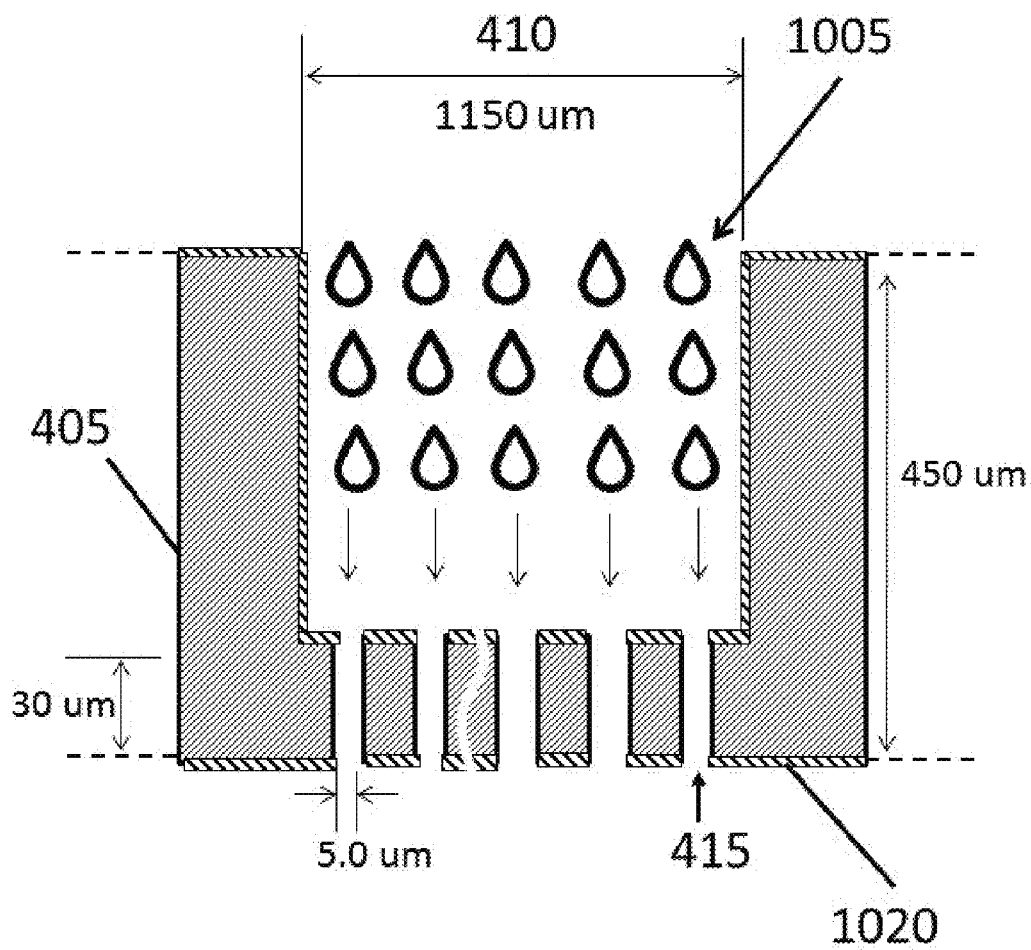
Figure 10C:
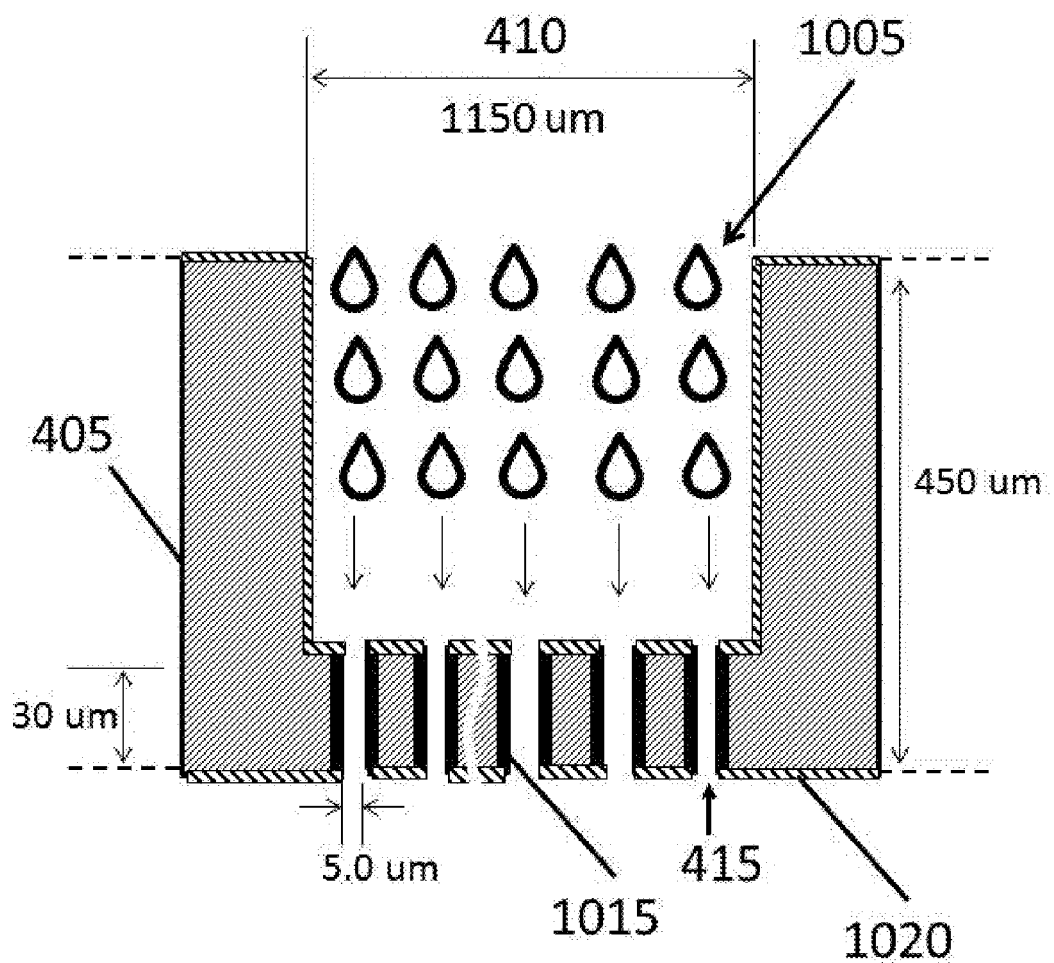
Figure 11A:
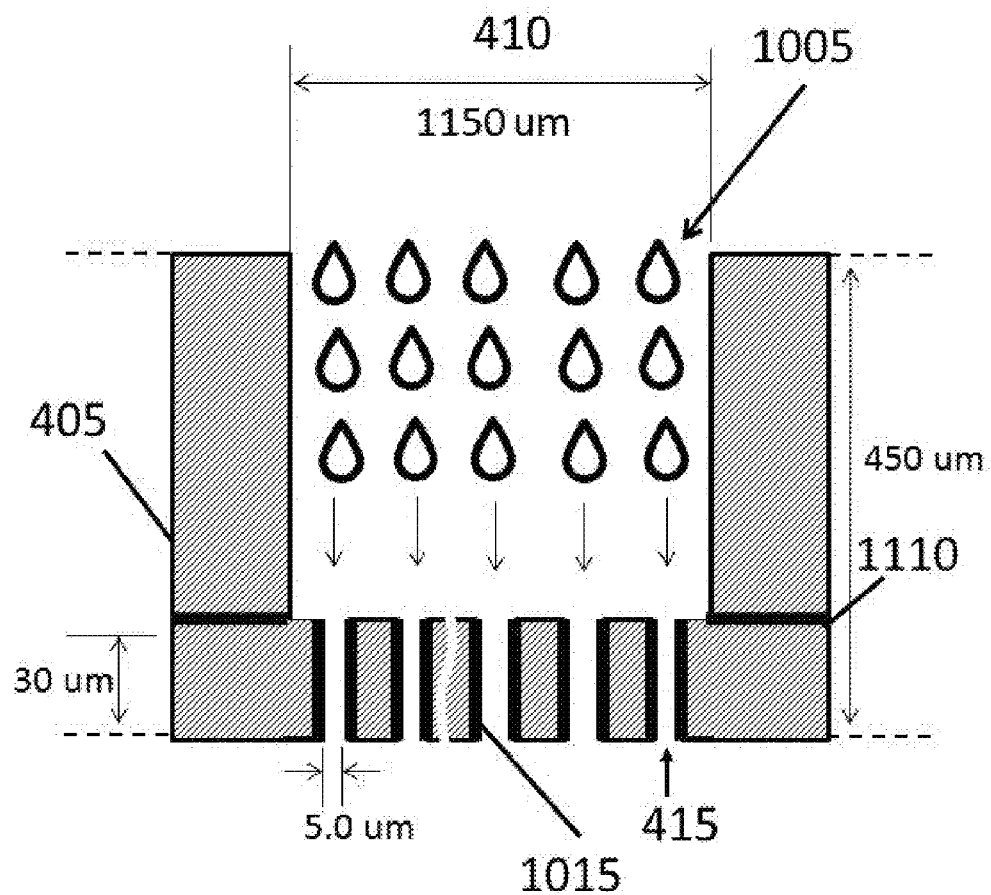
FIGS. 11A-11C illustrate reagent deposition directly into microchannels within a main channel, where a plate contains a silicon oxide later at a boundary between a main channel and a microchannel, where: microchannels are actively functionalized (FIG. 11A), main channels are passively functionalized (FIG. 11B); and microchannels are actively functionalized and main channels are passively functionalized (FIG. 11C). The dotted lines indicate that the image depicts one main channel of many in a single substrate (e.g., a plate).
Figure 11B:
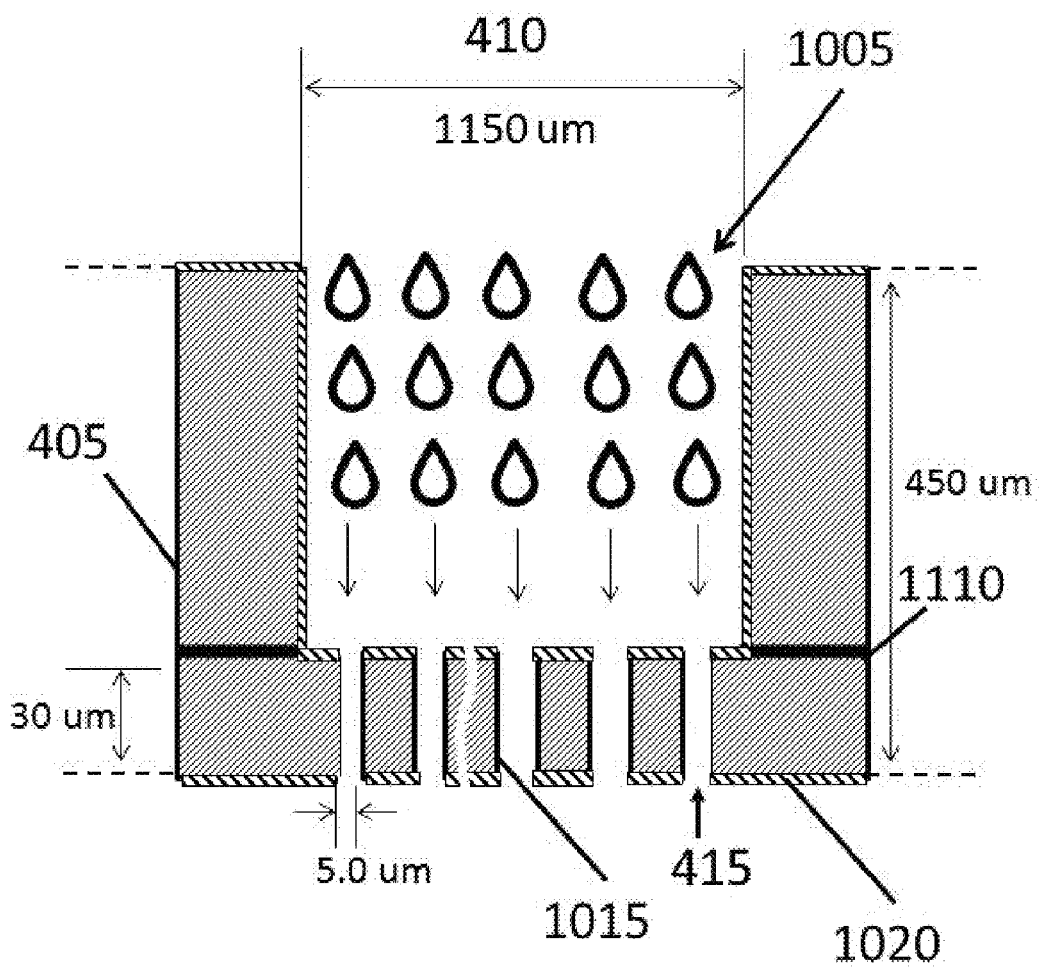
Figure 11C:
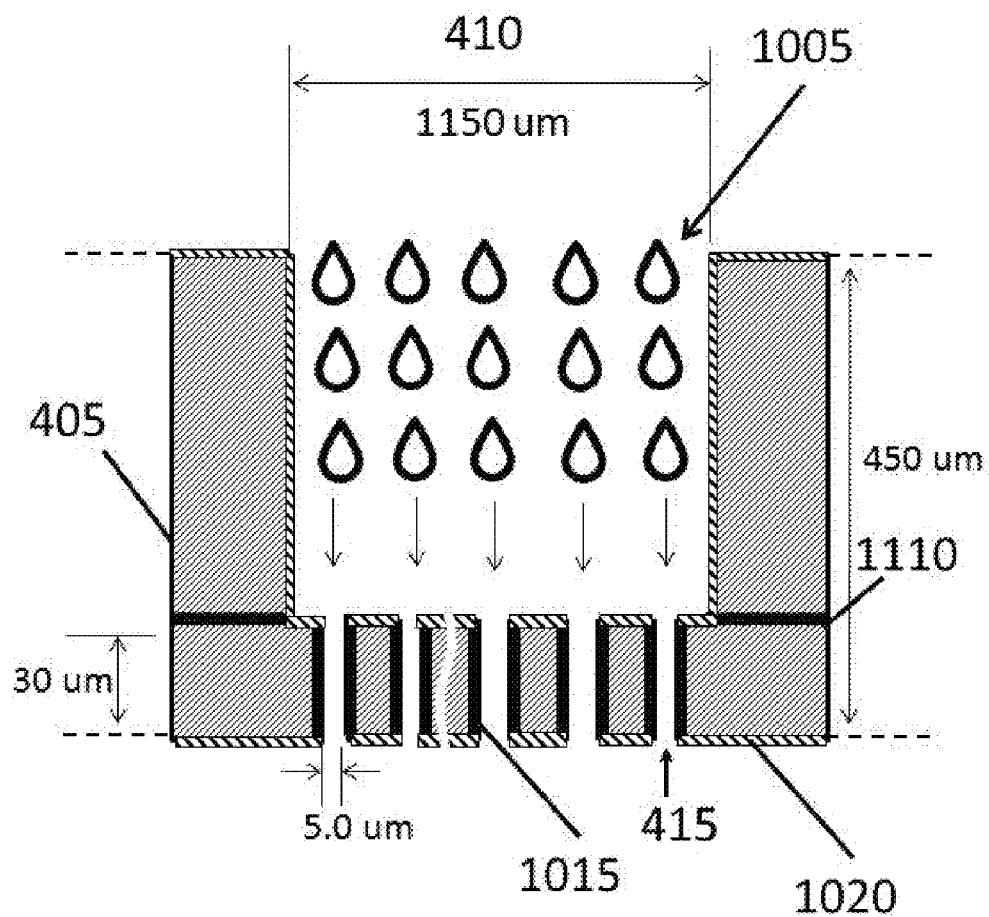

As illustrated in the detailed cross view of FIG. 10A, an exemplary described herein is coated with a layer of material comprising on or more active functionalization agent. FIG. 10A illustrates the deposition of reagents 1005 on a plate 405. The substrate 405 comprises a plurality of microchannels 415 in fluidic connection with a main channel 410. In this exemplary device, a single main channel 410 is depicted, and the dashed lines indicate that this is just one of many main channel 410/plurality of microchannels 415 connections in a single plate 405. Each of the plurality of microchannels 415 is coated with an active functionalization agent 1015. Each microchannel 415 of the plurality of microchannels in the example has a width of 5 um and a depth of 30 um. The main channel 410 has a diameter of 1150 um. The total height of the plate is 450 um. The main channel 410 encircles a cluster of microchannels. In some instances, as illustrated in FIG. 10B, a substrate described herein is coated with a layer of material comprising on or more passive functionalization agents. In this exemplary device, a passive functionalization agent 1020 coats surface of a plate 405. In some instances, as illustrated in FIG. 10C, a substrate described herein is coated with a layer of material comprising on or more passive functionalization agents and the microchannels of the substrate are coated with one or more active functionalization agents. In another exemplary device, the starting substrate is a silicon on insulator plate, where layers of silicon sandwich an insulator layer 1110, typically silicon dioxide. In some instances, the thickness of the insulator layer 1110 is from 1 to 50 um, e.g., 20 um. The remaining feature of this exemplary device, as shown in FIGS. 11A-11C, as the same as those depicted in FIGS. 10A-10C.

In some cases, only loci (i.e., microchannels) in a device described herein are coated with active functionalization agent. An active functionalization agent is a molecule that binds to the surface of the substrate and is also capable of binding to a nucleic acid monomer, thereby supporting a coupling reaction to the surface. Exemplary active functionalization agents are molecules having a hydroxyl group available for coupling with a nucleoside in a coupling reaction. In some cases, only main channels and/or surrounding areas (and not the microchannels) in a device described herein are coated with passive functionalization agent. A passive functionalization agent is a molecule that binds to the surface of the substrate and lacks a moiety available for coupling with a nucleoside in a coupling reaction.

Oligonucleic acids synthesized in the channels may be released for the purposes of generating longer nucleic acids. In some cases, following oligonucleic acid synthesis, oligonucleic acids within one cluster are released from their respective surfaces and pool into the main channel. In some cases, the pooled oligonucleic acids are assembled into a larger nucleic acid, such as a gene, within the main channel, so that the main channel functions as a reactor for nucleic acid assembly. In other cases, following oligonucleic acid synthesis, oligonucleic acids within one cluster are released from their respective surfaces and pool into a nanoreactor in fluidic communication with the microchannels.

In some embodiments, nucleic acid verification (e.g., sequencing of oligonucleic acids and/or assembled genes) is performed within a reactor or well. Nucleic acid assembly includes polymerase cycling assembly (PCA). In some cases, a capping element or other device is placed over open sides of the main channel to create an enclosed reactor. A substrate comprising a main channel that functions as a reactor for each cluster has the advantage that each cluster may have a different environment from another cluster in another reactor. As an example, sealed reactors (e.g., those with capping elements) may experience controlled humidity, pressure or gas content.

In some instances, a substrate is configured for both active and passive functionalization moieties bound to the surface at different areas of the substrate surface, generating distinct regions for oligonucleic acid synthesis to take place. In some instances, both active and passive functionalization agents are mixed within a particular region of the surface. Such a mixture provides a diluted region of active functionalization agent and therefore lowers the density of functionalization agent in a particular region.

Substrates described herein may comprise a high surface energy region at the site of active functionalization agent deposition. In some instances, the high surface energy region is coated with aminosilane. The silane group binds to the surface, while the rest of the molecule provides a distance from the surface and a free group at the end to which incoming bases attach. In some instances, the free group is a hydroxyl group. In some instances the high surface energy region includes an active functionalization reagent, e.g., a chemical that binds the substrate efficiently and also couples efficiently to monomeric nucleic acid molecules. In some cases, such molecules have a hydroxyl group which is available for interacting with a nucleoside in a coupling reaction. In some instances, the amino silane is selected from the group consisting of 11-acetoxyundecyltriethoxysilane, n-decyltriethoxysilane, (3-aminopropyl)trimethoxysilane, (3-aminopropyl)triethoxysilane, glycidyloxypropyl/trimethoxysilane and N-(3-triethoxysilylpropyl)-4-hydroxybutyramide. In some instances the high surface energy region includes a passive functionalization reagent, e.g., a chemical that binds the substrate efficiently but does not couple efficiently to monomeric nucleic acid molecules.

In some instances, described herein are substrates comprising a plurality of clusters, wherein each cluster comprises a plurality of loci that support the attachment and synthesis of oligonucleic acids. In some instances, a locus is on a three-dimensional surface, e.g., a well, microchannel, channel, or post. In some instances, a surface of a locus comprises a material that is actively functionalized to attach to at least one nucleotide for oligonucleic acid synthesis, or preferably, a population of identical nucleotides for synthesis of a population of oligonucleic acids. In some instances, oligonucleic acid refers to a population of oligonucleic acids encoding for the same nucleic acid sequence. In some cases, a surface of a substrate is inclusive of one or a plurality of surfaces of a substrate.

In some cases, the addition of a chemical layer on top of a surface (referred to as adhesion promoter) facilitates structured patterning of loci on a surface of a substrate. Exemplary surfaces which can benefit from adhesion promotion include, without limitation, glass, silicon, silicon dioxide and silicon nitride. In some cases, the adhesion promoter is a chemical with a high surface energy. In some instances, a second chemical layer is deposited on a surface of a substrate. In some cases, the second chemical layer has a low surface energy. The surface energy of a chemical layer coated on a surface can facilitate localization of droplets on the surface. Depending on the patterning arrangement selected, the proximity of loci and/or area of fluid contact at the loci can be altered.

In some instances, a substrate surface, or resolved loci, onto which nucleic acids or other moieties are deposited, e.g., for oligonucleic acid synthesis, are smooth or substantially planar or have raised or lowered features. In some instances, a substrate surface is modified with one or more different layers of compounds. Such modification layers of interest include, without limitation, inorganic and organic layers such as metals, metal oxides, polymers, small organic molecules and the like. Non-limiting polymeric layers include peptides, proteins, nucleic acids or mimetics thereof (e.g., peptide nucleic acids and the like), polysaccharides, phospholipids, polyurethanes, polyesters, polycarbonates, polyureas, polyamides, polyetheyleneamines, polyarylene sulfides, polysiloxanes, polyimides, polyacetates, and any other suitable compounds described herein or otherwise known in the art. In some cases, polymers are heteropolymeric. In some cases, polymers are homopolymeric. In some cases, polymers comprise functional moieties or are conjugated.

In some instances, resolved loci of a substrate are functionalized with one or more moieties that increase and/or decrease surface energy. In some cases, a moiety is chemically inert. In some cases, a moiety is configured to support a desired chemical reaction, for example, one or more processes in an oligonucleic acid synthesis reaction. The surface energy, or hydrophobicity, of a surface is a factor for determining the affinity of a nucleotide to attach onto the surface. In some instances, a method for substrate functionalization comprises: (a) providing a substrate (e.g., a plate); and (b) silanizing the loci (e.g., microchannels) with a suitable silanizing agent described herein or otherwise known in the art, for example, an organofunctional alkoxysilane molecule. In some cases, the organofunctional alkoxysilane molecule comprises dimethylchloro-octodecyl-silane, methyldichloro-octodecyl-silane, trichloro-octodecyl-silane, trimethyl-octodecyl-silane, triethyl-octodecyl-silane, or any combination thereof. In some instances, a substrate surface comprises functionalized with polyethylene/polypropylene (functionalized by gamma irradiation or chromic acid oxidation, and reduction to hydroxyalkyl surface), highly crosslinked polystyrene-divinylbenzene (derivatized by chloromethylation, and aminated to benzylamine functional surface), nylon (the terminal aminohexyl groups are directly reactive), or etched with reduced polytetrafluoroethylene.

In some instances, a substrate surface is functionalized by contact with a derivatizing composition that contains a mixture of silanes, under reaction conditions effective to couple the silanes to the substrate surface, typically via reactive hydrophilic moieties present on the substrate surface. Silanization generally can be used to cover a surface through self-assembly with organofunctional alkoxysilane molecules. A variety of siloxane functionalizing reagents can further be used as currently known in the art, e.g., for lowering or increasing surface energy. The organofunctional alkoxysilanes are classified according to their organic functions. Non-limiting examples of siloxane functionalizing reagents include hydroxyalkyl siloxanes (silylate surface, functionalizing with diborane and oxidizing the alcohol by hydrogen peroxide), diol (dihydroxyalkyl) siloxanes (silylate surface, and hydrolyzing to diol), aminoalkyl siloxanes (amines require no intermediate functionalizing step), glycidoxysilanes (3-glycidoxypropyl-dimethyl-ethoxysilane, glycidoxy-trimethoxysilane), mercaptosilanes (3-mercaptopropyl-trimethoxysilane, 3-4 epoxycyclohexyl-ethyltrimethoxysilane or 3-mercaptopropyl-methyl-dimethoxysilane), bicyclohepthenyl-trichlorosilane, butyl-aldehydrtrimethoxysilane, or dimeric secondary aminoalkyl siloxanes. The hydroxyalkyl siloxanes can include allyl trichlorochlorosilane turning into 3-hydroxypropyl, or 7-oct-1-enyl trichlorochlorosilane turning into 8-hydroxyoctyl. The diol (dihydroxyalkyl) siloxanes include glycidyl trimethoxysilane-derived (2,3-dihydroxypropyloxy)propyl (GOPS). The aminoalkyl siloxanes include 3-aminopropyl trimethoxysilane turning into 3-aminopropyl (3-aminopropyl-triethoxysilane, 3-aminopropyl-diethoxy-methylsilane, 3-aminopropyl-dimethyl-ethoxysilane, or 3-aminopropyl-trimethoxysilane). The dimeric secondary aminoalkyl siloxanes can be bis(3-trimethoxysilylpropyl) amine turning into bis(silyloxylpropyl)amine. In some instances, the functionalizing agent comprises 11-acetoxyundecyltriethoxysilane, n-decyltriethoxysilane, (3-aminopropyl)trimethoxysilane, (3-aminopropyl)triethoxysilane, glycidyloxypropyl/trimethoxysilane and N-(3-triethoxysilylpropyl)-4-hydroxybutyramide.

In some instances, a substrate surface is contacting with a mixture of functionalization groups, e.g., aminosilanes, which can be in any different ratio. In some instances, a mixture comprises at least 2, 3, 4, 5 or more different types of functionalization agents. In some instances, the mixture comprises 1, 2, 3 or more silanes. In cases, the ratio of the at least two types of surface functionalization agents in a mixture is about 1:1, 1:2, 1:3, 1:4, 1:5, 1:6, 1:7, 1:8, 1:9, 1:10, 2:3, 2:5, 2:7, 2:9, 2:11, 2:13, 2:15, 2:17, 2:19, 3:5, 3:7, 3:8, 3:10, 3:11, 3:13, 3:14, 3:16, 3:17, 3:19, 4:5, 4:7, 4:9, 4:11, 4:13, 4:15, 4:17, 4:19, 5:6, 5:8, 5:9, 5:11, 5:12, 5:13, 5:14, 5:16, 5:17, 5:18, 5:19, 6:7, 6:11, 6:13, 6:17, 6:19, 7:8, 7:9, 7:10, 7:11, 7:12, 7:13, 7:15, 7:16, 7:18, 7:19, 8:9, 8:11, 8:13, 8:15, 8:17, 8:19, 9:10, 9:11, 9:13, 9:14, 9:16, 9:17, 9:19, 10:11, 10:13, 10:17, 10:19, 11:12, 11:13, 11:14, 11:15, 11:16, 11:17, 11:18, 11:19, 11:20, 12:13, 12:17, 12:19, 13:14, 13:15, 13:16, 13:17, 13:18, 13:19, 13:20, 14:15, 14:17, 14:19, 15:16, 15:17, 15:19, 16:17, 16:19, 17:18, 17:19, 17:20, 18:19, 19:20, or any other ratio to achieve a desired surface representation of two groups. In some instances, a ratio of silanes is about 1:100, 1:1000, 1:2000 or 1:3000.

In some cases, an active functionalization agent comprises 11-acetoxyundecyltriethoxysilane. In some cases, an active functionalization agent comprises n-decyltriethoxysilane. In some cases, the active functionalization areas comprise one or more different species of silanes, for example, 1, 2, 3, 4, 5, 6, 7, 8, 9, 10 or more silanes. In some cases, one of the one or more silanes is present in the functionalization composition in an amount greater than another silane. For example, a mixed silane solution having two silanes comprises a 99:1, 98:2, 97:3, 96:4, 95:5, 94:6, 93:7, 92:8, 91:9, 90:10, 89:11, 88:12, 87:13, 86:14, 85:15, 84:16, 83:17, 82:18, 81:19, 80:20, 75:25, 70:30, 65:35, 60:40, 55:45 ratio of one silane to another silane. In some instances, an active functionalization agent comprises 11-acetoxyundecyltriethoxysilane and n-decyltriethoxysilane (e.g., in a ratio from about 20:80 to about 1:99, or about 10:90 to about 2:98, or preferably about 5:95). In some cases, an active functionalization agent comprises glycidyloxypropyltriethoxysilane (GOPS). In some instances, the silane is a fluorosilane. In some instances, the silane is a hydrocarbon silane. In some cases, the silane is 3-iodo-propyltrimethoxysilane. In some cases, the silane is octylchlorosilane. In some instances, an active functionalization agent comprises N-(3-triethosysilyl-propyl)-4-hydroxybutyramide. In some cases, the passive functionalization agent comprises a silane. In some cases, the passive functionalization agent comprises a mixture of silanes. In some cases, the passive functionalization agent comprises perfluorooctyltrichlorosilane.

In some instances, desired surface tensions, wettabilities, water contact angles, and/or contact angles for other suitable solvents are achieved by providing a substrate surface with a suitable ratio of functionalization agents. In some cases, the agents in a mixture are chosen from suitable reactive and inert moieties, thus diluting the surface density of reactive groups to a desired level for downstream reactions. In some instances, the density of the fraction of a surface functional group that reacts to form a growing oligonucleotide in an oligonucleotide synthesis reaction is about 0.005, 0.01, 0.05, 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 3.0, 3.5, 4.0, 4.5, 5.0, 7.0, 10.0, 15.0, 20.0, 50.0, 75.0, 100.0 $\mu Mol/m^2$.

In some instances, a surface of a substrate is prepared to have a low surface energy. In some cases, a region of a surface of a substrate described herein is functionalized to enable covalent binding of molecular moieties that can lower the surface energy so that wettability can be reduced. In some instances, a region of surface of a substrate described herein is prepared to have a high surface energy and increased wettability. In some instances, a surface is modified to have a higher surface energy, or become more hydrophilic with a coating where the coating includes molecules having reactive hydrophilic moieties. By altering the surface energy of different parts of a substrate surface, spreading of a deposited reagent liquid (e.g., a reagent deposited during an oligonucleic acid synthesis method) can be adjusted, in some cases facilitated. In some instances, a droplet of reagent is deposited over a predetermined area of a surface with high surface energy. The liquid droplet can spread over and fill a small surface area having a higher surface energy as compared to a nearby surface. In some instances, a substrate surface is modified to comprise reactive hydrophilic moieties such as hydroxyl groups, carboxyl groups, thiol groups, and/or substituted or unsubstituted amino groups. Suitable materials include, but are not limited to, supports that can be used for solid phase chemical synthesis, e.g., cross-linked polymeric materials (e.g., divinylbenzene styrene-based polymers), agarose (e.g., Sepharose®), dextran (e.g., Sephadex®), cellulosic polymers, polyacrylamides, silica, glass (particularly controlled pore glass, or "CPG"), ceramics, and the like. The supports may be obtained commercially and used as is, or they may be treated or coated prior to functionalization.

In some instances, provided herein are methods for the manufacture of a substrate using a multilayer activation process. In some instances, one or more layers deposited during a multilayer activation process comprise one or more silanes. In some instances, a substrate, e.g., a silicon plate, is treated with a first layer of a material that modifies the surface to allow for adhesion of a photoresist. Non-limiting examples of materials for surface modification include 11-acetoxyundecyltriethoxysilane, n-decyltriethoxysilane, (3-aminopropyl)trimethoxysilane, (3-aminopropyl)triethoxysilane, glycidyloxypropyl/trimethoxysilane and N-(3-triethoxysilylpropyl)-4-hydroxybutyramide, and mixtures thereof, and/or other suitable materials described elsewhere herein or known in the art. In some instances, the modified substrate is treated with resist, exposed, developed, and residual resist is removed by plasma cleaning, exemplary details of which are described previously herein. In some instances, the substrate is passively functionalized, for example, with fluorosilane, to generate hydrophobic regions. In some instances, the substrate is stripped to remove remaining resist. In some instances, the first modified layer of the substrate is activated to change one or more functional groups of the surface modification material to a hydroxyl group. In a subsequent step, the hydroxyl surface of the substrate is treated with a second layer of surface modification material to dilute surface functional groups and increase coupling efficiency for nucleotide attachment. In some instances, the second layer is activated to change one or more functional groups to a hydroxyl group to support oligonucleic acid synthesis. In some instances, steps comprising the addition of a surface modification material followed by subsequent activation are repeated for one or more additional cycles (e.g., 1, 2, 3, 4, 5 or more additional cycles) to provide optimal spacing between oligonucleic acids during synthesis. In some instances, second and subsequent layers have purely organic chemistries of the general form A-R1-B and C-R2-D where A reacts with the terminal OH group. The system is then purged and C-R2-D reacts with the B group. R1 and R2 chemistries can be repeated to yield the desired film thickness in a molecular layer deposition process. The terminal groups B and D can be hydroxyl or could be converted to hydroxyl in the final step of the deposition.

In some cases, the substrate may be two-dimensional (e.g., substantially planar) or three-dimension (e.g., comprise wells and/or channels). In some instances, an actively functionalized surface comprises a specific concentration of hydroxyl groups to achieve a pre-determined surface density for oligonucleic acid synthesis. In some instances, active functionalization is achieved by a wet process using a solution comprising an active functionalization agent. In some cases, the active functionalization agent comprises a silane or mixed silanes. In an example, a surface to be actively functionalized is treated with a solution comprising an active functionalization agent (e.g., 1% solution of N-(3-triethoxysilylpropyl-4hydroxybutyramide in ethanol and acetic acid) and the substrate incubated at a high temperature (e.g., 150° C. for 14 hours). In another example, a chemical vapor deposition process is employed wherein an active functionalization agent is delivered to the surface in a gaseous state. In some cases, an active functionalization agent is delivered by CVD with a controlled deposition pressure (e.g., 200 mTor) and temperature (e.g., 150° C.). A CVD process allows for in-situ plasma cleaning and is well suited for producing highly ordered self-assembled monolayers (SAMs).

Hydrophilic and Hydrophobic Surfaces

The surface energy, or hydrophobicity of a surface, can be evaluated or measured by measuring a water contact angle. Water contact angle is the angle between the drop surface and a solid surface where a water droplet meets the solid surface. A surface with a water contact angle of smaller than 90°, the solid surface can be considered hydrophilic or polar. A surface with a water contact angle of greater than 90°, the solid surface can be considered hydrophobic or apolar.

Surface characteristics of coated surfaces can be adjusted in various ways suitable for oligonucleotide synthesis. In some cases, the surface is selected to be inert to the conditions of ordinary oligonucleotide synthesis; e.g. the solid surface may be devoid of free hydroxyl, amino, or carboxyl groups to the bulk solvent interface during monomer addition, depending on the selected chemistry. In some cases, the surface may comprise reactive moieties prior to the start of a first cycle, or first few cycles of an oligonucleotide synthesis process, wherein the reactive moieties can be quickly depleted to unmeasurable densities after one, two, three, four, five, or more cycles of the oligonucleotide synthesis reaction. The surface can further be optimized for well or pore wetting, e.g., by common organic solvents such as acetonitrile and the glycol ethers or aqueous solvents, relative to surrounding surfaces.

Without being bound by theory, the wetting phenomenon is understood to be a measure of the surface tension or attractive forces between molecules at a solid-liquid interface, and is expressed in dynes/cm$^2$. For example, fluorocarbons have very low surface tension, which is typically attributed to the unique polarity (electronegativity) of the carbon-fluorine bond. In tightly structured Langmuir-Blodgett type films, surface tension of a layer can be primarily determined by the percent of fluorine in the terminus of the alkyl chains. For tightly ordered films, a single terminal trifluoromethyl group can render a surface nearly as lipophobic as a perfluoroalkyl layer. When fluorocarbons are covalently attached to an underlying derivatized solid (e.g. a highly crosslinked polymeric) support, the density of reactive sites can be lower than Langmuir-Blodgett and group density. For example, surface tension of a methyltrimethoxysilane surface can be about 22.5 mN/m and aminopropyltriethoxysilane surface can be about 35 mN/m. Briefly, hydrophilic behavior of surfaces is generally considered to occur when critical surface tensions are greater than 45 mN/m. As the critical surface tension increases, the expected decrease in contact angle is accompanied with stronger adsorptive behavior. Hydrophobic behavior of surfaces is generally considered to occur when critical surface tensions are less than 35 mN/m. At first, the decrease in critical surface tension is associated with oleophilic behavior, i.e. the wetting of the surfaces by hydrocarbon oils. As the critical surface tensions decrease below 20 mN/m, the surfaces resist wetting by hydrocarbon oils and are considered both oleophobic as well as hydrophobic. For example, silane surface modification can be used to generate a broad range of critical surface tensions. Accordingly, the methods and compositions of the invention may use surface coatings, e.g. those involving silanes, to achieve surface tensions of less than 5, 6, 7, 8, 9, 10, 12, 15, 20, 25, 30, 35, 40, 45, 50, 60, 70, 80, 90, 100, 110, 115, 120 mN/m, or higher. Further, the methods and compositions of the invention may use surface coatings, e.g. those involving silanes, to achieve surface tensions of more than 115, 110, 100, 90, 80, 70, 60, 50, 45, 40, 35, 30, 25, 20, 15, 12, 10, 9, 8, 7, 6 mN/m or less. The water contact angle and the surface tension of non-limiting examples of surface coatings, e.g., those involving silanes, are described in Table 1 and Table 2 of Arkles et al. (Silanes and Other Coupling Agents, Vol. 5v: The Role of Polarity in the Structure of Silanes Employed in Surface Modification. 2009), which is incorporated herein by reference in its entirety. The tables are replicated below.

TABLE 1

Contact angles of water (degrees) on smooth surfaces

| | |
|---|---|
| Heptadecafluorodecyltrimethoxysilane | 113-115 |
| Poly(tetrafluoroethylene) | 108-112 |
| Polypropylene | 108 |
| Octadecyldimethylchlorosilane | 110 |
| Octadecyltrichlorosilane | 102-109 |
| Tris(trimethylsiloxy)silylethyldimethylchlorosilane | 103-104 |
| Octyldimethylchlorosilane | 104 |
| Butyldimethylchlorosilane | 100 |
| Trimethylchlorosilane | 90-100 |
| Polyethylene | 88-103 |
| Polystyrene | 94 |
| Poly(chlorotrifluoroethylene) | 90 |
| Human skin | 75-90 |
| Diamond | 87 |
| Graphite | 86 |
| Silicon (etched) | 86-88 |
| Talc | 82-90 |
| Chitosan | 80-81 |
| Steel | 70-75 |
| Methoxyethoxyundecyltrichlorosilane | 73-74 |
| Methacryloxypropyltrimethoxysilane | 70 |
| Gold, typical (see gold, clean) | 66 |
| Intestinal mucosa | 50-60 |
| Kaolin | 42-46 |
| Platinum | 40 |
| Silicon nitride | 28-30 |
| Silver iodide | 17 |
| [Methoxy(polyethyleneoxy)propyl]trimethoxysilane | 15-16 |
| Sodalime glass | <15 |
| Gold, clean | <10 |
| Trimethoxysilylpropyl substituted poly(ethyleneimine), hydrochloride | <10 |

TABLE 2

Critical surface tensions (mN/m)

| | |
|---|---|
| Heptadecafluorodecyltrichlorosilane | 12 |
| Poly(tetrafluoroethylene) | 18.5 |
| Octadecyltrichlorosilane | 20-24 |
| Methyltrimethoxysilane | 22.5 |
| Nonafluorohexyltrimethoxysilane | 23 |
| Vinyltriethoxysilane | 25 |
| Paraffin wax | 25.5 |
| Ethyltrimethoxysilane | 27.0 |
| Propyltrimethoxysilane | 28.5 |
| Glass, sodalime (wet) | 30.0 |
| Poly(chlorotrifluoroethylene) | 31.0 |
| Polypropylene | 31.0 |
| Poly(propylene oxide) | 32 |
| Polyethylene | 33.0 |
| Trifluoropropyltrimethoxysilane | 33.5 |
| 3-(2-Aminoethyl)aminopropyltrimethoxysilane | 33.5 |
| Polystyrene | 34 |
| p-Tolyltrimethoxysilane | 34 |
| Cyanoethyltrimethoxysilane | 34 |
| Aminopropyltriethoxysilane | 35 |
| Acetoxypropyltrimethoxysilane | 37.5 |

TABLE 2-continued

| Critical surface tensions (mN/m) | |
|---|---|
| Poly(methyl methacrylate) | 39 |
| Poly(vinyl chloride) | 39 |
| Phenyltrimethoxysilane | 40.0 |
| Chloropropyltrimethoxysilane | 40.5 |
| Mercaptopropyltrimethoxysilane | 41 |
| Glycidoxypropyltrimethoxysilane | 42.5 |
| Poly(ethylene terephthalate) | 43 |
| Copper (dry) | 44 |
| Poly(ethylene oxide) | 43-45 |
| Aluminum (dry) | 45 |
| Nylon 6/6 | 45-46 |
| Iron (dry) | 46 |
| Glass, sodalime (dry) | 47 |
| Titanium oxide (anatase) | 91 |
| Ferric oxide | 107 |
| Tin oxide | 111 |

The surface of the substrate or a portion of the surface of the substrate can be functionalized or modified to be more hydrophilic or hydrophobic as compared to the surface or the portion of the surface prior to the functionalization or modification. In some cases, one or more surfaces can be modified to have a difference in water contact angle of greater than 90°, 85°, 80°, 75°, 70°, 65°, 60°, 55°, 50°, 45°, 40°, 35°, 30°, 25°, 20°, 15° or 10° as measured on one or more uncurved, smooth or planar equivalent surfaces. In some cases, the surface of the microstructures, channels, resolved loci, resolved reactor caps or other parts of the substrate may be modified to have a differential hydrophobicity corresponding to a difference in water contact angle that is greater than 90°, 85°, 80°, 75°, 70°, 65°, 60°, 55°, 50°, 45°, 40°, 35°, 30°, 25°, 20°, 15° or 10° as measured on uncurved, smooth or planar equivalent surfaces of such structures. Unless otherwise stated, water contact angles mentioned herein correspond to measurements that would be taken on uncurved, smooth or planar equivalents of the surfaces in question.

In some cases, hydrophilic resolved loci can be generated by first applying a protectant, or resist, over each loci within the substrate. The unprotected area can be then coated with a hydrophobic agent to yield an unreactive surface. For example, a hydrophobic coating can be created by chemical vapor deposition of (tridecafluorotetrahydrooctyl)-triethoxysilane onto the exposed oxide surrounding the protected channels or wells. Finally, the protectant, or resist, can be removed exposing the loci regions of the substrate for further modification and oligonucleotide synthesis. In some instances, the initial modification of such unprotected regions may resist further modification and retain their surface functionalization, while newly unprotected areas can be subjected to subsequent modification steps.

Substrate Etching

A process for carving features out of a substrate (e.g., a silicon plate) may include providing a substrate having a device layer and a handle layer, wherein the device layer is optionally separated from the handle layer by an electrical insulator layer, e.g., a layer of silicon dioxide—an exemplary substrate is a SOI wafer. In some instances, the provided substrate is oxidized on both surfaces. Photolithography may be applied to the device side of the substrate to create a mask of photoresist. In a subsequent step, a deep reactive-ion etching (DRIE) step may be used to etch vertical side-walls (e.g., until an insulator layer in a substrate comprising an insulator layer) at locations devoid of photoresist. In a following step, the photoresist may be stripped. In some instances, photolithography, DRIE and photoresist strip steps are repeated on the substrate handle side. In cases wherein the substrate comprises an insulator layer such as silicon dioxide, buried oxide (BOX) may be removed using an etching process. Thermal oxidation can then be applied to remove contaminating polymers that may have been deposited on the side walls during the method. In a subsequent step, the thermal oxidation may be stripped using a wet etching process. In some instances, this method is used to generate a substrate having the features of a substrate exemplified in FIGS. 4A-4B. As another example, the process for manufacturing a substrate comprises a front-end process method comprising providing a starting material substrate, oxidizing both the device and handle sides; performing photolithography, DRIE and stripping of photoresist on the handle side; performing photolithography, DRIE and stripping of photoresist on the device side; removal of the oxide layer (e.g., BOX); and oxide growth (e.g., oxide is coated on one or more surfaces of the substrate to create a silicon substrate having a plurality of features).

In some instances, the substrate starting material comprises silicon. In some instances, the substrate is oxidized on one or more surfaces. In some instances, photolithography is applied to the front-side, back-side or both the front and back sides of the substrate, for example, to the back-side, to create a mask of photoresist. As a next step, the substrate is etched at locations devoid of photoresist, in many cases, beyond the oxidized layer, to create wells. As an example, the back-side is etched. In a subsequent step, the photoresist is stripped. In some instances, wherein photolithography was first applied to one side of the substrate, following photoresist stripping, a second side of the substrate is subjected to photolithography. For example, the back-side was first subjected to photolithography followed by photolithography of the front-side of the substrate. In some examples, a deep reactive-ion etching (DRIE) is used to etch vertical side walls to a prescribed depth, for example, about 450 um. In some cases, DRIE is used on the front-side, back-side or both the front and back sides during photolithography. In some instances, only one side of a substrate is etched to create three-dimensional features. In some instances, two sides, e.g., device and handle sides, of a substrate is etched to create three-dimensional features. In some processes, as an alternative or supplement to etching by DRIE, a SOI substrate (silicon on insulator silicon wafer) is used and the handle layer is etched down to the buried oxide, wherein the buried oxide can serve as an etch stop. Following photolithography on a second side of a substrate, the photoresist is stripped to generate a desired pattern. For example, the front-end is resist stripped to generate three dimensional features. In some cases, contaminates of the process (e.g., fluoropolymers) are removed by thermal oxidation followed by stripping of the thermal oxidation by a wet etching process. The substrate processed may comprise a plurality of wells, where the distance from the center of one main channel to the center of another main channel is about 1.69 mm and the total height of the main channel/microchannel is about 450 um.

Fiducial Marks

A substrate described herein may comprise fiducial marks to facilitate alignment with other components of a system. In some cases, substrates have one or more fiducial marks, e.g. 2, 3, 4, 5, 6, 7, 8, 9, 10, or more fiducial marks. A fiducial mark may be located near the origin, where the fiducial mark is closer to the origin than any one cluster. In some instances, a fiducial mark is located near an edge of the substrate portion. The fiducial mark may be located from about 0.1 mm to about 10 mm from the edge of the substrate portion, e.g., about 0.5 mm from the edge. The fiducial mark may be located close to or distant to a cluster. For example, a fiducial is located from about 1 mm to about 10 mm form a cluster, e.g., 1.69 mm. In some instances, a distance from the center of a fiducial mark and a nearest corner of a substrate in one dimension is from about 0.5 mm to about 10 mm, e.g., about 1 mm. In some instances, a length of a fiducial mark in one dimension is from about 0.5 mm to about 5 mm, e.g., about 1 mm. In some instances, the width of a fiducial mark is from about 0.01 mm to about 2 mm, e.g., 0.05 mm. The substrates described herein, in some instances, comprise one or more regions for annotation. In some instances, a substrate may have a label or serial number which is located a distance (e.g., 4 mm) from the edge of the substrate with a length (e.g., 9 mm) and width (e.g., 1.5 mm).

Oligonucleic Acid Synthesis

Figure 12:
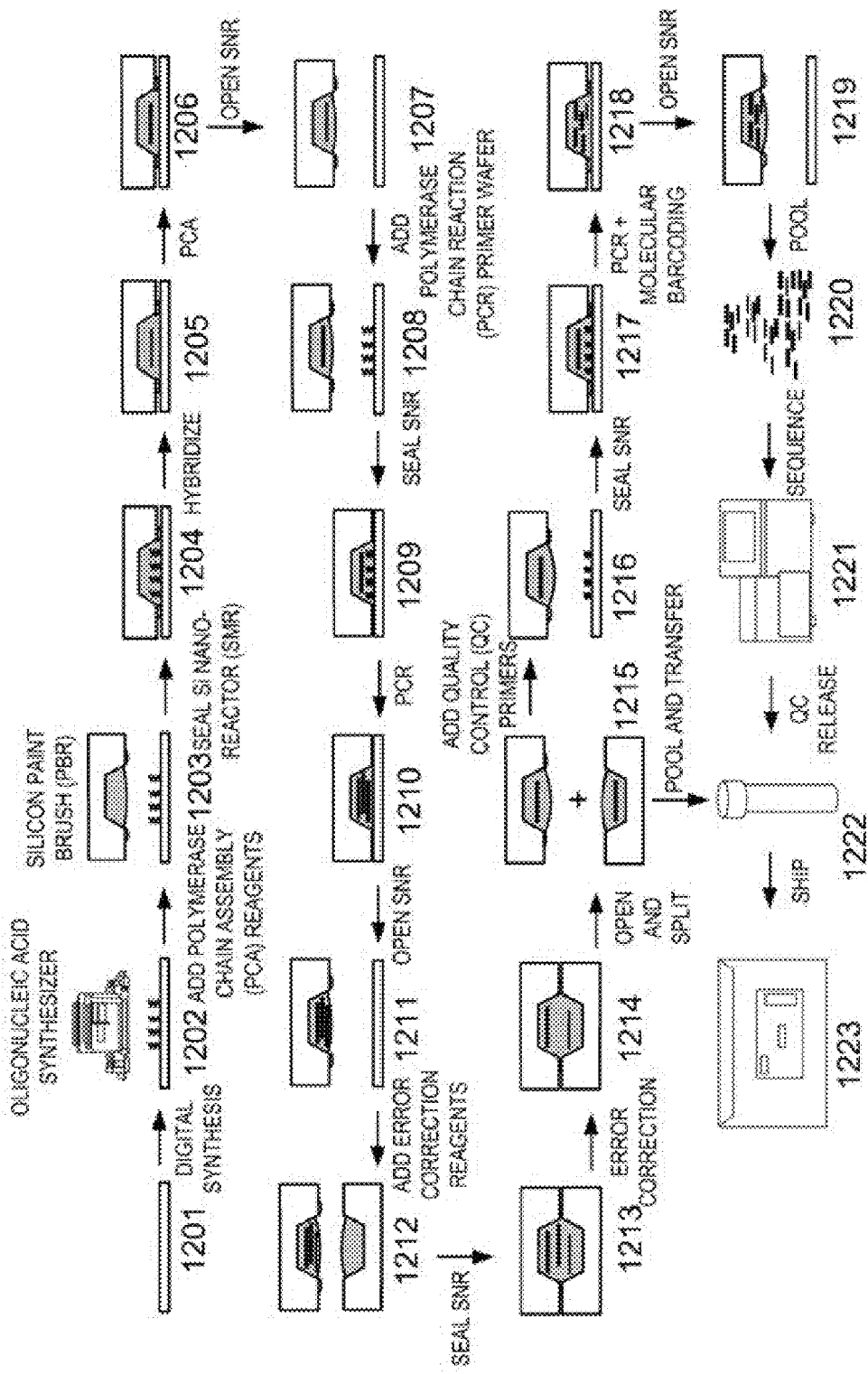
FIG. 12 illustrates a workflow for de novo oligonucleotide synthesis.

Structures having modified surfaces described herein may be used for de novo synthesis processes. An exemplary workflow for one such process is divided generally into phases: (1) de novo synthesis of a single stranded oligonucleic acid library, (2) joining oligonucleic acids to form larger fragments, (3) error correction, (4) quality control, and (5) shipment, FIG. 12. Prior to de novo synthesis, an intended nucleic acid sequence or group of nucleic acid sequences is preselected. For example, a group of genes is preselected for generation.

Once preselected nucleic acids for generation are selected, a predetermined library of oligonucleic acids is designed for de novo synthesis. Various suitable methods are known for generating high density oligonucleic acid arrays. In the workflow example, a surface layer 1201 is provided. In the example, chemistry of the surface is altered in order to improve the oligonucleic acid synthesis process. Areas of low surface energy are generated to repel liquid while areas of high surface energy are generated to attract liquids. The surface itself may be in the form of a planar surface or contain variations in shape, such as protrusions, microwells, or microchannels which increase surface area. In the workflow example, high surface energy molecules selected serve a dual function of supporting DNA chemistry, as described in International Patent Application Publication WO/2015/021280, which is herein incorporated by reference in its entirety.

In situ preparation of oligonucleic acid arrays is generated on a solid support and utilizes single nucleotide extension process to extend multiple oligomers in parallel. A device, such as an oligonucleic acid synthesizer, is designed to release reagents in a step wise fashion such that multiple oligonucleic acids extend, in parallel, one residue at a time to generate oligomers with a predetermined nucleic acid sequence 1202. In some cases, oligonucleic acids are cleaved from the surface at this stage. Cleavage may include gas cleavage, e.g., with ammonia or methylamine.

The generated oligonucleic acid libraries are placed in a reaction chamber. In this exemplary workflow, the reaction chamber (also referred to as "nanoreactor") is a silicon coated main channel, containing PCR reagents and lowered onto the oligonucleic acid library 1203. Prior to or after the sealing 1204 of the oligonucleic acids, a reagent is added to release the oligonucleic acids from the surface. In the exemplary workflow, the oligonucleic acids are released subsequent to sealing of the nanoreactor 1205. Once released, fragments of single stranded oligonucleic acids hybridize in order to span an entire long range sequence of DNA. Partial hybridization 1205 is possible because each synthesized oligonucleic acid is designed to have a small portion overlapping with at least one other oligonucleic acid in the pool.

After hybridization, a PCA reaction is commenced. During the polymerase cycles, the oligonucleic acids anneal to complementary fragments and gaps are filled in by a polymerase. Each cycle increases the length of various fragments randomly depending on which oligonucleic acids find each other. Complementarity amongst the fragments allows for forming a complete large span of double stranded DNA 1206.

After PCA is complete, the nanoreactor is separated from the surface 1207 and positioned for interaction with a polymerase 1208. After sealing, the nanoreactor is subject to PCR 1209 and the larger nucleic acids are formed. After PCR 1210, the nanochamber is opened 1211, error correction reagents are added 1212, the chamber is sealed 1213 and an error correction reaction occurs to remove mismatched base pairs and/or strands with poor complementarity from the double stranded PCR amplification products 1214. The nanoreactor is opened and separated 1215. Error corrected product is next subject to additional processing steps, such as PCR and molecular bar coding, and then packaged 1222 for shipment 1223.

In some cases, quality control measures are taken. After error correction, quality control steps include for example interaction with a wafer having sequencing primers for amplification of the error corrected product 1216, sealing the wafer to a chamber containing error corrected amplification product 1217, and performing an additional round of amplification 1218. The nanoreactor is opened 1219 and the products are pooled 1220 and sequenced 1221. After an acceptable quality control determination is made, the packaged product 1222 is approved for shipment 1223.

Oligonucleic acids may be synthesized on a substrate described herein using a system comprising an oligonucleic acid synthesizer that deposits reagents necessary for synthesis. Reagents for oligonucleic acid synthesis include, for example, reagents for oligonucleic acid extension and wash buffers. As non-limiting examples, the oligonucleic acid synthesizer deposits coupling reagents, capping reagents, oxidizers, de-blocking agents, acetonitrile and gases such as nitrogen gas. In addition, the oligonucleic acid synthesizer optionally deposits reagents for the preparation and/or maintenance of substrate integrity. An oligonucleic acid synthesizer may comprise material deposition devices that can move in the X-Y direction to align with the location of the substrate. The oligonucleic acid synthesizer can also move in the Z direction to seal with the substrate, forming a resolved reactor. In some instances, a substrate having a plurality of clusters is configured to seal with a capping element having a plurality of caps, wherein when the substrate and capping element are sealed, each cluster is separate from another cluster to form separate resolved reactors for each cluster. In some instances, the capping element is not present in the system or is present and stationary. A resolved reactor is configured to allow for the transfer of fluid, including oligonucleic acids and/or reagents, from the substrate to the capping element and/or vice versa. Fluid may pass through either or both the substrate and the capping element and includes, without limitation, coupling reagents, capping reagents, oxidizers, de-blocking agents, acetonitrile and nitrogen gas. The oligonucleic acid synthesizer of an oligonucleic acid synthesis system may comprise a plurality of material deposition devices, for example from about 1 to about 50 material deposition devices. Each material deposition device, in various instances, deposits a reagent component that is different from another material deposition device. In some cases, each material deposition device has a plurality of nozzles, where each nozzle is optionally configured to correspond to a cluster on a substrate. For example, for a substrate having 256 clusters, a material deposition device has 256 nozzles and 100 µm fly height. In some cases, each nozzle deposits a reagent component that is different from another nozzle.

The substrates described herein comprise actively functionalized surfaces configured to support the attachment and synthesis of oligonucleic acids. Synthesized oligonucleic acids include oligonucleic acids comprising modified and/or non-canonical bases and/or modified backbones. In various methods, a library of oligonucleic acids having pre-selected sequences is synthesized on a substrate. In some cases, one or more of the oligonucleic acids has a different sequence and/or length than another oligonucleic acid in the library. In some instances, the stoichiometry of each oligonucleic acid synthesized on a substrate is controlled and tunable by varying one or more features of the substrate (e.g., functionalized surface) and/or oligonucleic acid sequence to be synthesized; one or more methods for substrate functionalization and/or oligonucleic acid synthesis; or a combination thereof. In many instances, controlling the density of a growing oligonucleic acid on a resolved locus of a substrate allows for oligonucleic acids to be synthesized with a low error rate.

An example of a synthesis method that is useful with the substrates provided herein is one based on phosphoramidite chemistry. In some instances, oligonucleic acid synthesis methods comprise coupling a linker to a surface of a substrate, for example, to an actively functionalized surface of a substrate. In some instances, a linker separates a synthesized oligonucleic acid from a surface of the substrate. A linker includes a cleavable linker, such as a photocleavable linker. In some instances, a synthesized oligonucleic acid comprises a cleavable moiety that is introduced during synthesis. In some cases, a synthesized oligonucleic acid does not comprise a linker. For example, the synthesized oligonucleic acid is separated from the linker by one or more cleavable moieties. In some instances, the synthesized oligonucleic acid comprises a primer and/or adapter sequence that connects to a linker.

Without wishing to be bound by theory, the distance between extending oligonucleic acids is a factor correlating to error rate occurrence in synthesis of an oligonucleic acid library. One way to reduce the frequency of error is to minimize chain interaction during extension. Polymer "wobble" is controlled by altering the length of the tethering group at the base of the extending polymeric structure. In some instances, regulating "wobble" reduces error rate of polymer over the course of the synthesis process. In some instances, a linker comprises one or more bases coupled to the surface of a substrate and a cleavable moiety, wherein the cleavable moiety is configured to connect to the synthesized oligonucleic acid. In some cases, a linker is referred to as a tether or a tether region. In some instances, a linker comprises about or at least about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50 or more bases located between a surface of a substrate and a synthesized oligonucleic acid. In some instances, a linker is synthesized and extends 12 to 25 bases from a device surface.

In some instances, a linker comprises a cleavable moiety, wherein the cleavable moiety is a modified or non-canonical base. When a plurality of synthesized oligonucleic acids of a library are connected to a substrate surface by a plurality of linkers having the same cleavable moiety, the cleavable moiety is referred to as a universal moiety. Examples of cleavable moieties include, without limitation, thymidine-succinyl hexamide CED phosphoramidite and DMMA. In some instances, a cleavable moiety is gas cleavable. In some instances, the linker comprises thymidine-succinyl hexamide CED phosphoramidite or DMMA. In some instances, the linker comprises a photocleavable primer. In an example, a photocleavable linker allows for the synthesized oligonucleic acid to be removed from the substrate without cleaving the protecting groups on the nitrogenous functionalities of each base, for example, by irradiation with light at about 350 nm.

Oligonucleic acids synthesized using the methods and/or substrates described herein comprise, in various instances, at least about 50, 60, 70, 75, 80, 90, 100, 120, 150, 200, 300, 400, 500, 600, 700, 800 or more bases. In some instances, a library of oligonucleic acids is synthesized, wherein a population of distinct oligonucleic acids are assembled to generate a larger nucleic acid comprising at least about 500; 1,000; 2,000; 3,000; 4,000; 5,000; 6,000; 7,000; 8,000; 9,000; 10,000; 11,000; 12,000; 13,000; 14,000; 15,000; 16,000; 17,000; 18,000; 19,000; 20,000; 25,000; 30,000; 40,000; or 50,000 bases. In some instances, oligonucleic acid synthesis methods described herein are useful for the generation of an oligonucleic acid library comprising at least 500; 1,000; 5,000; 10,000; 20,000; 50,000; 100,000; 200,000; 300,000; 400,000; 500,000; 600,000; 700,000; 800,000; 900,000; 1,000,000; 1,100,000; 1,200,000; 1,300,000; 1,400,000; 1,500,000; 1,600,000; 1,700,000; 1,800,000; 1,900,000; 2,000,000; 2,200,000; 2,400,000; 2,600,000; 2,800,000; 3,000,000; 3,500,000; 4,00,000; or 5,000,000 distinct oligonucleic acids. In some instances, at least about 1 pmol, 10 pmol, 20 pmol, 30 pmol, 40 pmol, 50 pmol, 60 pmol, 70 pmol, 80 pmol, 90 pmol, 100 pmol, 150 pmol, 200 pmol, 300 pmol, 400 pmol, 500 pmol, 600 pmol, 700 pmol, 800 pmol, 900 pmol, 1 nmol, 5 nmol, 10 nmol, 100 nmol or more of an oligonucleic acid is synthesized within a locus.

Methods for oligonucleic acid synthesis on a surface provided herein allow for synthesis at a fast rate. As an example, at least 3, 4, 5, 6, 7, 8, 9, 10, 11, 12, 13, 14, 15, 16, 17, 18, 19, 20, 21, 22, 23, 24, 25, 26, 27, 28, 29, 30, 35, 40, 45, 50, 55, 60, 70, 80, 90, 100, 125, 150, 175, 200 nucleotides per hour, or more are synthesized. Nucleotides include adenine, guanine, thymine, cytosine, uridine building blocks, or analogs/modified versions thereof. In some instances, libraries of oligonucleic acids are synthesized in parallel on substrate. For example, a substrate comprising about or at least about 100; 1,000; 10,000; 100,000; 1,000,000; 2,000,000; 3,000,000; 4,000,000; or 5,000,000 resolved loci is able to support the synthesis of at least the same number of distinct oligonucleic acids, wherein oligonucleic acid encoding a distinct sequence is synthesized on a resolved locus. In some instances, a library of oligonucleic acids are synthesized on a substrate with low error rates described herein in less than about three months, two months, one month, three weeks, 15, 14, 13, 12, 11, 10, 9, 8, 7, 6, 5, 4, 3, 2 days, 24 hours, 18 hours, 12 hours or less. In some instances, larger nucleic acids assembled from an oligonucleic acid library synthesized with low error rate using the substrates and methods described herein are prepared in less than about three months, two months, one month, three weeks, 15, 14, 13, 12, 11, 10, 9, 8, 7, 6, 5, 4, 3, 2 days, 24 hours, 18 hours, 12 hours or less. In some instances, up to about 800,000 distinct oligonucleic acids having sizes up to about 130 base pairs in length each are synthesized with an error rate below 1:1000, 1:2000, 1:3000 or less on a substrate described herein and using a method described herein in a span of less than about 24 hours.

In some instances, oligonucleic acid error rate is dependent on the efficiency of one or more chemical steps of oligonucleic acid synthesis. In some cases, oligonucleic acid synthesis comprises a phosphoramidite method, wherein a base of a growing oligonucleic acid chain is coupled to phosphoramidite. In some instances, coupling efficiency of the base is related to error rate. For example, higher coupling efficiency correlates to lower error rates. In some cases, the substrates and/or synthesis methods described herein allow for a coupling efficiency greater than 98%, 98.5%, 99%, 99.5%, 99.6%, 99.7%, 99.8%, 99.9%, 99.95%, 99.96%, 99.97%, 99.98%, or 99.99%. In some cases, an oligonucleic acid synthesis method comprises a double coupling process, wherein a base of a growing oligonucleic acid chain is coupled with a phosphoramidite, the oligonucleic acid is washed and dried, and then treated a second time with a phosphoramidite. In some instances, efficiency of deblocking in a phosphoramidite oligonucleic acid synthesis method contributes to error rate. In some cases, the substrates and/or synthesis methods described herein allow for removal of 5'-hydroxyl protecting groups at efficiencies greater than 98%, 98.5%, 99%, 99.5%, 99.6%, 99.7%, 99.8%, 99.9%, 99.95%, 99.96%, 99.97%, 99.98%, or 99.99%. In some instances, error rate is reduced by minimization of depurination side reactions.

Oligonucleic acids synthesized using the methods and/or substrates described herein encode for, in various instances, at least about 50, 60, 70, 75, 80, 90, 100, 120, 150, 200, 240, 300, 400, 500, 600, 700, 800, 900, 1,000, 6000, 6144, 10,000, or more genes. In some instances, a library of oligonucleic acids encode for at least 200 genes. In some instances, a library of oligonucleic acids encode for genes at least 500 bases, 1 kb, 2 kb, 3 kb, 4 kb, 5 kb or more in length.

Methods for oligonucleic acid synthesis, in various instances, include processes involving phosphoramidite chemistry. In some instances, oligonucleic acid synthesis comprises coupling a base with phosphoramidite. In some instances, oligonucleic acid synthesis comprises coupling a base by deposition of phosphoramidite under coupling conditions, wherein the same base is optionally deposited with phosphoramidite more than once, i.e., double coupling. In some instances, oligonucleic acid synthesis comprises capping of unreacted sites. In some cases, capping is optional. In some instances, oligonucleic acid synthesis comprises oxidation. In some instances, oligonucleic acid synthesis comprises deblocking or detritylation. In some instances, oligonucleic acid synthesis comprises sulfurization. In some cases, oligonucleic acid synthesis comprises either oxidation or sulfurization. In some instances, between one or each step during an oligonucleic acid synthesis reaction, the substrate is washed, for example, using tetrazole or acetonitrile. Time frames for any one step in a phosphoramidite synthesis method include less than about 2 min, 1 min, 50 sec, 40 sec, 30 sec, 20 sec and 10 sec.

Oligonucleic acid synthesis using a phosphoramidite method comprises the subsequent addition of a phosphoramidite building block (e.g., nucleoside phosphoramidite) to a growing oligonucleic acid chain for the formation of a phosphite triester linkage. Phosphoramidite oligonucleic acid synthesis proceeds in the 3' to 5' direction. Phosphoramidite oligonucleic acid synthesis allows for the controlled addition of one nucleotide to a growing nucleic acid chain per synthesis cycle. In some instances, each synthesis cycle comprises a coupling step. Phosphoramidite coupling involves the formation of a phosphite triester linkage between an activated nucleoside phosphoramidite and a nucleoside bound to the substrate, for example, via a linker. In some instances, the nucleoside phosphoramidite is provided to the substrate activated. In some instances, the nucleoside phosphoramidite is provided to the substrate with an activator. In some instances, nucleoside phosphoramidites are provided to the substrate in a 1.5, 2, 3, 4, 5, 6, 7, 8, 9, 10, 11, 12, 13, 14, 15, 16, 17, 18, 19, 20, 25, 30, 35, 40, 50, 60, 70, 80, 90, 100-fold excess or more over the substrate-bound nucleosides. In some instances, the addition of nucleoside phosphoramidite is performed in an anhydrous environment, for example, in anhydrous acetonitrile. Following addition of a nucleoside phosphoramidite, the substrate is optionally washed. In some instances, the coupling step is repeated one or more additional times, optionally with a wash step between nucleoside phosphoramidite additions to the substrate. In some instances, an oligonucleic acid synthesis method used herein comprises 1, 2, 3 or more sequential coupling steps. Prior to coupling, in many cases, the nucleoside bound to the substrate is de-protected by removal of a protecting group, where the protecting group functions to prevent polymerization. A common protecting group is 4,4'-dimethoxytrityl (DMT).

Following coupling, phosphoramidite oligonucleic acid synthesis methods optionally comprise a capping step. In a capping step, the growing oligonucleic acid is treated with a capping agent. A capping step is useful to block unreacted substrate-bound 5'-OH groups after coupling from further chain elongation, preventing the formation of oligonucleic acids with internal base deletions. Further, phosphoramidites activated with 1H-tetrazole may react, to a small extent, with the O6 position of guanosine. Without being bound by theory, upon oxidation with $I_2$/water, this side product, possibly via O6-N7 migration, may undergo depurination. The apurinic sites may end up being cleaved in the course of the final deprotection of the oligonucleotide thus reducing the yield of the full-length product. The O6 modifications may be removed by treatment with the capping reagent prior to oxidation with $I_2$/water. In some instances, inclusion of a capping step during oligonucleic acid synthesis decreases the error rate as compared to synthesis without capping. As an example, the capping step comprises treating the substrate-bound oligonucleic acid with a mixture of acetic anhydride and 1-methylimidazole. Following a capping step, the substrate is optionally washed.

In some instances, following addition of a nucleoside phosphoramidite, and optionally after capping and one or more wash steps, the substrate bound growing nucleic acid is oxidized. The oxidation step comprises the phosphite triester is oxidized into a tetracoordinated phosphate triester, a protected precursor of the naturally occurring phosphate diester internucleoside linkage. In some cases, oxidation of the growing oligonucleic acid is achieved by treatment with iodine and water, optionally in the presence of a weak base (e.g., pyridine, lutidine, collidine). Oxidation may be carried out under anhydrous conditions. Oxidation may be carried out using, for example, tert-Butyl hydroperoxide or (1S)-(+)-(10-camphorsulfonyl)-oxaziridine (CSO). In some methods, a capping step is performed following oxidation. A second capping step allows for substrate drying, as residual water from oxidation that may persist can inhibit subsequent coupling. Following oxidation, the substrate and growing oligonucleic acid is optionally washed. In some instances, the step of oxidation is substituted with a sulfurization step to obtain oligonucleotide phosphorothioates, wherein any capping steps can be performed after the sulfurization. Many reagents are capable of the efficient sulfur transfer, including but not limited to, 3-(dimethylaminomethylidene)amino)-3H-1,2,4-dithiazole-3-thione, DDTT, 3H-1,2-benzodithiol-3-one 1,1-dioxide, also known as Beaucage reagent, and N,N,N'N'-tetraethylthiuram disulfide (TETD).

In order for a subsequent cycle of nucleoside incorporation to occur through coupling, the protected 5' end of the substrate bound growing oligonucleic acid must be removed so that the primary hydroxyl group can react with a next nucleoside phosphoramidite. In some instances, the protecting group is DMT and deblocking occurs with trichloroacetic acid in dichloromethane. Conducting detritylation for an extended time or with stronger than recommended solutions of acids may lead to increased depurination of solid support-bound oligonucleotide and thus reduces the yield of the desired full-length product. Methods and compositions of the invention described herein provide for controlled deblocking conditions limiting undesired depurination reactions. In some cases, the substrate bound oligonucleic acid is washed after deblocking. In some cases, efficient washing after deblocking contributes to synthesized oligonucleic acids having a low error rate.

Methods for the synthesis of oligonucleic acids typically involve an iterating sequence of the following steps: application of a protected monomer to an actively functionalized surface (e.g., locus) to link with either the activated surface, a linker or with a previously deprotected monomer; deprotection of the applied monomer so that it can react with a subsequently applied protected monomer; and application of another protected monomer for linking. One or more intermediate steps include oxidation or sulfurization. In some cases, one or more wash steps precede or follow one or all of the steps.

Methods for phosphoramidite based oligonucleic acid synthesis comprise a series of chemical steps. In some instances, one or more steps of a synthesis method involve reagent cycling, where one or more steps of the method comprise application to the substrate of a reagent useful for the step. For example, reagents are cycled by a series of liquid deposition and vacuum drying steps. For substrates comprising three-dimensional features such as wells, microwells, channels, microchannels and the like, reagents are optionally passed through one or more regions of the substrate via the wells and/or channels. In some instances, reagents are passed through the substrate during synthesis. In some cases, reagents are passed horizontally through the substrate. In some cases, reagents are passed vertically through the substrate. In some instances, reagents are passed over a substrate having curved features to enhance flow. In some cases, reagents are delivered to the substrate through the use of photoresist. In some instances, reagents are delivered to the substrate without moving the substrate. For example, reagents are passed over resolved loci within the substrate by flowing them through the substrate from one surface to an opposite surface of the substrate. In some instances, the substrate is moved, for example, to a flow cell, for reagent application, where it is then optionally repositioned. In an example, the substrate is deposited with a nucleoside using an oligonucleic acid synthesizer, moved to a flow cell for treating the substrate to one or more select reagents, and then repositioned back to the oligonucleic acid synthesizer for deposition of a subsequent monomer. Reagent delivery approaches suitable for the synthesis methods of the disclosure include manual and automatic, including use of robotic devices and pulse jets. Reagents include any component of an oligonucleic acid synthesis method, including chemical moieties such as nucleosides, washing solutions, and gases such as nitrogen.

In some instances, one or more reagents applied to the surface of a substrate during oligonucleic acid synthesis comprise a solvent. In some cases, a solvent comprises propylene carbonate. In some cases, a solvent comprises 2-methylglutaronitrile and/or 3-methoxypropionitrile. In some cases, a solvent comprises glutaronitrile. In some cases, a solvent comprises adiponitrile. In some instances, the solvent allows for high surface tension for reagent deposition. In some instances, the solvent allows for low surface tension for reagent deposition.

In some instances, the volume of reagents applied to a surface of substrate during oligonucleic acid synthesis is selected on the size, location and/or density of the surface to which the reagent is applied (e.g., an actively functionalized locus). In some instances, the volume of a drop of reagent applied to a surface during oligonucleic acid synthesis (e.g., deposition of a nucleoside) is less than about 0.5 picoliters (pL), 1 pL, 5 pL, 10 pL, 50 pL, 100 pL, 500 pL, 1000 pL, 5000 pL, 10000 pL, 100000 pL, 1000000 pL or 10000000 pL. In some instances, the reagents are delivered in droplets that have a total volume of about 47 pL or less. In some instances, the reagents are delivered in droplets that have a total volume of about 30 to 50 pL. In some instances, the reagents are delivered in droplets that have a total volume of about 50, 49, 48, 47, 46, 44, 45, 43, 42, 41, 40, 39, 38, 37, 36, 35, 34, 33, 32, 31, 30, 29, 28, 27, 26, or 25 pL. In some instances, the rate at which a drop of reagent is applied is at least about 0.5, 1, 2, 3, 4, 5, 6, 7, 8, 9, 10, 11, 12, 13, 14, 15, 20, 30, 50 or 100 m/sec.

Oligonucleic acid synthesis methods include methods for the application of reagents during one or more steps during synthesis. Controlled application of reagents, such as nucleoside monomers to distinct regions of a substrate is important to achieve low error rates. In some instances, a reagent is deposited directly into a microchannel, with little or no contamination to an adjacent microchannel. In some cases, the volume of a reagent to be deposited within a three-dimensional feature such as a well or channel is adjusted to a small enough size to minimize cross-contamination. In some instances, the reagents are delivered in droplets that have a diameter of less than about 5, 10, 20, 30, 40, 50, 60, 70, 80, 90, 100, 110, 120, 130, 140, 150, 160, 170, 180, 190 or 200 um. A non-limiting method to reduce cross-contamination includes bringing the device that deposits the reagent sufficiently close to the surface such the deposited droplet falls substantially within the selected feature.

In some instances, efficient washing to remove unincorporated nucleosides contributes to low error rate. In some instances, the composition of the wash contributes to low error rate. As described herein, washing during oligonucleic acid synthesis includes one or all wash steps performed during oligonucleic acid synthesis. In some cases, a wash step is performed wherein at least or about 60%, 70, 80, 90, 91, 92, 93, 94, 95, 96, 97, 98, 99 or 100% of unincorporated nucleosides or extension reaction reagent are removed from the surface of the substrate. In some cases, a wash step is performed wherein at least or about 95.0, 95.1, 95.2, 95.3, 95.4, 95.5, 95.6, 95.7, 95.8, 95.9, 96.0, 96.1, 96.2, 96.3, 96.4, 96.5, 96.6, 96.7, 96.8, 96.9, 97.0, 97.1, 97.2, 97.3, 97.4, 97.5, 97.6, 97.7, 97.8, 97.9, 98.0, 98.1, 98.2, 98.3, 98.4, 98.5, 98.6, 98.7, 98.8, 98.9, 99.0, 99.1, 99.2, 99.3, 99.4, 99.5, 99.6, 99.7, 99.8, 99.9, or 100% of unincorporated nucleosides or extension reaction reagent are removed from the surface of the substrate. In some cases, the configuration of a substrate such as one with narrow microchannels, contributes to wash efficiency and error rate. In some cases, substrates having channels are washed by passage of a wash solution through the substrate, minimizing fluid contact of the growing oligonucleic acids. In some cases, the geometry of fluid flow during washing controls interfacial instability. For example, a substrate that is substantial planar, or two-dimensional, may have a curved surface to enhance wash efficiency and therefore error rate. In some instances, optimized wash conditions include those that minimize contact time between the wash reagent and the growing oligonucleic acid. For example, the passage of a wash solution through three-dimensional features allows for the effect washing of all surfaces in a short period of time. A water contact angle for the substrate, in particular, for regions of synthesis and/or surrounding areas, may be chosen in order to reduce depurination and/or speed of synthesis. In some instances, lower amount of depurination may be achieved on surfaces of higher surface energy, i.e. lower contact angle. For example, depurination occurs at a rate less than 0.1%, 0.05%, 0.01%, 0.005%, 0.001%, 0.0005%, or 0.0001%.

In some instances, the surface properties of the substrate change during oligonucleic acid synthesis. Typically, the substrate at the beginning of synthesis can be relatively hydrophobic and while synthesis proceeds, may become increasingly hydrophilic. Oligonucleic acid features can gain substantial surface energy with increasing oligonucleotide length. Generally, these sites or features consisting of protected oligonucleotide acquire enough surface energy to become spontaneously wet to high surface tension organic solvents commonly used in phosphoramidite synthesis, such as acetonitrile or propylene carbonate, after about 10-20 synthesis cycles. The methods and compositions described allow for varying parameters, such as time, flow rate, temperature, volume, viscosity, and/or reagent concentration, during the synthesis of a growing oligonucleic acid as a function of length to account for the changing surface properties on loci of the surface. Such a variation may be applied by changing parameters in constant or varying increments at repeating cycles of the synthesis. Alternatively, parameters may be changed at only selected cycles of the synthesis and can optionally follow a pattern, such as every other cycle, every third, fourth, fifth, sixth, seventh, eighth, ninth, tenth cycle etc.

Oligonucleic acid synthesis methods described herein are suitable for the spatial control of oligonucleic acid synthesis within a small area of a substrate, e.g., a locus. In some instances, oligonucleic acid methods comprise phosphoramidite chemistry. In some instances, spatial control of oligonucleic acid synthesis is achieved using an oligonucleic acid synthesizer. In some instances, spatial control of oligonucleic acid synthesis is achieved using physical masks. In some instances, spatial control of oligonucleic acid synthesis is achieved by modulation of a 5' hydroxyl deblocking during phosphoramidite synthesis. In some instances, spatial control of oligonucleic acid synthesis is achieved by photolithographic deprotection of photolabile monomers. In some instances, spatial control of oligonucleic acid synthesis is achieved by digital activation of photogenerated acids to carry out standard detritylation.

In some instances, the surface of the substrate that provides support for oligonucleic acid synthesis is chemically modified to allow for the synthesized oligonucleic acid chain to be cleaved from the surface. In some cases, the oligonucleic acid chain is cleaved at the same time as the oligonucleic acid is deprotected. In some cases, the oligonucleic acid chain is cleaved after the oligonucleic acid is deprotected. In an exemplary scheme, a trialkoxysilyl amine (e.g., $(CH_3CH_2O)_3Si—(CH_2)_2—NH_2$) is reacted with surface SiOH groups of a substrate, followed by reaction with succinic anhydride with the amine to create and amide linkage and a free OH on which the nucleic acid chain growth is supported.

In some instances, oligonucleic acids are synthesized with photolabile protecting groups, where the hydroxyl groups generated on the surface are blocked by photolabile-protecting groups. When the surface is exposed to UV light, e.g., through a photolithographic mask, a pattern of free hydroxyl groups on the surface may be generated. These hydroxyl groups can react with photoprotected nucleoside phosphoramidites, according to phosphoramidite chemistry. A second photolithographic mask can be applied and the surface can be exposed to UV light to generate second pattern of hydroxyl groups, followed by coupling with 5'-photoprotected nucleoside phosphoramidite. Likewise, patterns can be generated and oligomer chains can be extended. Without being bound by theory, the lability of a photocleavable group depends on the wavelength and polarity of a solvent employed and the rate of photocleavage may be affected by the duration of exposure and the intensity of light. This method can leverage a number of factors, e.g., accuracy in alignment of the masks, efficiency of removal of photoprotecting groups, and the yields of the phosphoramidite coupling step. Further, unintended leakage of light into neighboring sites can be minimized. The density of synthesized oligomer per spot can be monitored by adjusting loading of the leader nucleoside on the surface of synthesis.

Oligonucleotide Libraries with Low Error Rates

The term "error rate" may also be referred to herein as a comparison of the collective sequence encoded by oligonucleic acids generated compared to the aggregate sequence of a predetermined longer nucleic acid, e.g., a gene. Oligonucleic acids are synthesized on a substrate described herein in a process that minimizes the error rate. For example, error rate is less than 1 in 500 bases, 1 in 1000 bases, 1 in 1500 bases, 1 in 2000 bases, 1 in 2500 bases, 1 in 3000, 1 in 5000 bases or less. In some instances, low error rates are achieved for synthesized oligonucleic acid libraries having at least 20,000; 40,000; 60,000; 80,000; 100,000; 200,000; 300,000; 400,000; 500,000; 600,000; 700,000; 800,000; 1,000,000; or 2,000,000 or more oligonucleic acids. In some cases, a subset of oligonucleic acids in the library has the same sequence. In some cases, one or more of the oligonucleic acids in the library comprises a different sequence. Error rates include mismatch error rate, deletion error rate, insertion error rate, indel error rate, and any combination thereof.

In some instances, low overall error rate or low error rates for individual types of errors are achieved. Individual types of error rates include deletions, insertions, or substitutions for an oligonucleic acid library synthesized on the substrate. In some instances, oligonucleic acids synthesized on the substrate have an average error rate of about 1:500, 1:1000, 1:2000, 1:3000, 1:4000, 1:5000, 1:6000, 1:7000, 1:8000, 1:9000, 1:10000, 1:20000, 1:30000, 1:40000, 1:50000 or less. In some instances, these error rates are for at least 50%, 60%, 70%, 80%, 90%, 95%, 98%, 99%, 99.5%, or more of the oligonucleic acids synthesized. In some instances, these error rates are for 100% of the oligonucleic acids synthesized.

In some instances, oligonucleic acids synthesized on the substrate have an average deletion error rate of about 1:500, 1:1000, 1:2000, 1:3000, 1:4000, 1:5000, 1:6000, 1:7000, 1:8000, 1:9000, 1:10000, 1:20000, 1:30000, 1:40000, 1:50000 or less. In some instances, oligonucleic acids synthesized on the substrate have an average insertion error rate of about 1:500, 1:1000, 1:2000, 1:3000, 1:4000, 1:5000, 1:6000, 1:7000, 1:8000, 1:9000, 1:10000, 1:20000, 1:30000, 1:40000, 1:50000 or less. In some instances, oligonucleic acids synthesized on the substrate have an average substitution error rate of about 1:500, 1:1000, 1:2000, 1:3000, 1:4000, 1:5000, 1:6000, 1:7000, 1:8000, 1:9000, 1:10000, 1:20000, 1:30000, 1:40000, 1:50000 or less. In some instances, overall error rate or error rates for individual types of errors such as deletions, insertions, or substitutions for each oligonucleotide synthesized on the substrate, for at least 10%, 20%, 30%, 40%, 50%, 60%, 70%, 80%, 90%, 95%, 98%, 99%, 99.5%, or more of the oligonucleotides synthesized on the substrate, or the substrate average may fall between about 1:500 and 1:50000, 1:500 and 1:40000; 1:500 and 1:30000; 1:500 and 1:20000; 1:500 and 1:10000; 1:500 and 1:9000; 1:500 and 1:8000; 1:500 and 1:7000; 1:500 and 1:6000; or 1:500 and 1:5000.

In some instances, the methods and systems described herein for oligonucleic acid synthesis results in minimal synthesis of truncation products that are less than the full length of the predetermined oligonucleic acid sequence. In some cases, a library of oligonucleic acids are synthesized with less than 1%, 0.5%, 0.1%, 0.05%, 0.01%, 0.005%, 0.001%, or 0.0001% comprising truncation products. In some instances, the methods and systems described herein for oligonucleic acid synthesis result in minimal synthesis of products that are greater than predetermined oligonucleic acid sequence length. In some cases, a library of oligonucleic acids are synthesized with less than 1%, 0.5%, 0.1%, 0.05%, 0.01%, 0.005%, 0.001%, or 0.0001% comprising greater than predetermined sequence length.

The oligonucleic acids synthesized using the systems and methods described herein are optionally evaluated for sequence accuracy prior to subsequent applications, for example, larger nucleic acid assembly. A common method for oligonucleic acid quality control comprises next generation sequencing.

Oligonucleic Acid Release and Assembly

Oligonucleic acids synthesized using the methods and substrates described herein, are optionally released from the surface from which they were synthesized. In some cases, oligonucleic acids are cleaved from the surface at this stage. Cleavage may include gas cleavage, e.g., with ammonia or methylamine. In some instances, all the loci in a single cluster collectively correspond to sequence encoding for a single gene, and optionally, when cleaved, remain on the surface of the loci. In some instances, the application of ammonia gas simultaneous deprotects phosphates groups protected during the synthesis steps, i.e., removal of electron-withdrawing cyano group. In some instances, once released from the surface, oligonucleic acids are assembled into larger nucleic acids. Synthesized oligonucleic acids are useful, for example, as components for gene assembly/synthesis, site-directed mutagenesis, nucleic acid amplification, microarrays, and sequencing libraries.

In some instances, oligonucleic acids of predetermined sequence are designed to collectively span a large region of a target sequence, such as a gene. In some instances, larger oligonucleic acids are generated through ligation reactions to join the synthesized oligonucleic acids. One example of a ligation reaction is polymerase chain assembly (PCA). In some cases, at least of a portion of the oligonucleic acids are designed to include an appended region that is a substrate for universal primer binding. For PCA reactions, the presynthesized oligonucleic acids include overlaps with each other (e.g., 4, 20, 40 or more bases with overlapping sequence).

During the polymerase cycles, the oligonucleic acids anneal to complementary fragments and then are filled in by polymerase. Each cycle thus increases the length of various fragments randomly depending on which oligonucleic acids find each other. Complementarity amongst the fragments allows for forming a complete large span of double stranded DNA. In some cases, after the PCA reaction is complete, an error correction step is conducted using mismatch repair detecting enzymes to remove mismatches in the sequence. Once larger fragments of a target sequence are generated, they can be amplified. For example, in some cases, a target sequence comprising 5' and 3' terminal adaptor sequences is amplified in a polymerase chain reaction (PCR) which includes modified primers, e.g., uracil containing primers the hybridize to the adaptor sequences. The use of modified primers allows for removal of the primers through enzymatic reactions centered on targeting the modified base and/or gaps left by enzymes which cleave the modified base pair from the fragment. What remains is a double stranded amplification product that lacks remnants of adapter sequence. In this way, multiple amplification products can be generated in parallel with the same set of primers to generate different fragments of double stranded DNA.

In some instances, error correction is performed on synthesized oligonucleic acids and/or assembled products. An example strategy for error correction involves site-directed mutagenesis by overlap extension PCR to correct errors, which is optionally coupled with two or more rounds of cloning and sequencing. In certain instances, double-stranded nucleic acids with mismatches, bulges and small loops, chemically altered bases and/or other heteroduplexes are selectively removed from populations of correctly synthesized nucleic acids by affinity purification. In some instances, error correction is performed using proteins/enzymes that recognize and bind to or next to mismatched or unpaired bases within double stranded nucleic acids to create a single or double strand break or to initiate a strand transfer transposition event. Non-limiting examples of proteins/enzymes for error correction include endonucleases (T7 Endonuclease I, E. coli Endonuclease V, T4 Endonuclease VII, mung bean nuclease, Cell, E. coli Endonuclease IV, UVDE), restriction enzymes, glycosylases, ribonucleases, mismatch repair enzymes, resolvases, helicases, ligases, antibodies specific for mismatches, and their variants. Examples of specific error correction enzymes include T4 endonuclease 7, T7 endonuclease 1, S1, mung bean endonuclease, MutY, MutS, MutH, MutL, cleavase, CELI, and HINF1. In some cases, DNA mismatch-binding protein MutS (*Therms aquaticus*) is used to remove failure products from a population of synthesized products. In some instances, error correction is performed using the enzyme Correctase. In some cases, error correction is performed using SURVEYOR endonuclease (Transgenomic), a mismatch-specific DNA endonuclease that scans for known and unknown mutations and polymorphisms for heteroduplex DNA.

In various instances, a synthesized oligonucleic acid as described herein is amplified in an amplification reaction. In various instances, a nucleic acid assembled from an oligonucleic acid synthesized by the methods and systems described herein is amplified in an amplification reaction. As used herein, at least in some instances, an amplification reaction includes any method known in the art to amplify one or more nucleic acids. Provided herein, in various cases, are instances exemplifying polymerase chain reaction (PCR) as an amplification reaction.

In some instances, an amplification reaction, such as PCR, is based on repeated cycles of denaturation, oligonucleic acid primer annealing, and primer extension by thermophilic template dependent polynucleotide polymerase, resulting in the exponential increase in copies of a target nucleic acid sequence flanked by the primers. The two different PCR primers, which anneal to opposite strands of the DNA, are positioned so that the polymerase catalyzed extension product of one primer can serve as a template strand for the other, leading to the accumulation of a discrete double stranded fragment whose length is defined by the distance between the 5' ends of the oligonucleic acid primers.

Systems for Oligonucleic Acid Synthesis

Provided herein are systems for the synthesis of oligonucleic acid libraries on a substrate. In some instances, the system comprises the substrate for synthesis support, as described elsewhere herein. In some instances, the system comprises a device for application of one or more reagents of a synthesis method, for example, an oligonucleic acid synthesizer. In some instances, the system comprises a device for treating the substrate with a fluid, for example, a flow cell. In some instances, the system comprises a device for moving the substrate between the application device and the treatment device.

In one aspect, provided is an automated system for use with an oligonucleic acid synthesis method described herein that is capable of processing one or more substrates, comprising: a material deposition device for spraying a microdroplet comprising a reagent on a substrate; a scanning transport for scanning the substrate adjacent to the material deposition device to selectively deposit the microdroplet at specified sites; a flow cell for treating the substrate on which the microdroplet is deposited by exposing the substrate to one or more selected fluids; an alignment unit for aligning the substrate correctly relative to the material deposition device each time when the substrate is positioned adjacent to the material deposition device for deposition. In some instances, the system optionally comprises a treating transport for moving the substrate between the material deposition device and the flow cell for treatment in the flow cell, where the treating transport and said scanning transport are different elements. In other instances, the system does not comprise a treating transport.

In some instances, a device for application of one or more reagents during a synthesis reagent is an oligonucleic acid synthesizer comprising a plurality of material deposition devices. In some instances, each material deposition device is configured to deposit nucleotide monomers, for example, for phosphoramidite synthesis. In some instances, the oligonucleic acid synthesizer deposits reagents to the resolved loci, wells, and/or microchannels of a substrate. In some cases, the oligonucleic acid synthesizer deposits a drop having a diameter less than about 200 um, 100 um, or 50 um in a volume less than about 1000, 500, 100, 50, or 20 pl. In some cases, the oligonucleic acid synthesizer deposits between about 1 and 10000, 1 and 5000, 100 and 5000, or 1000 and 5000 droplets per second. In some instances, the oligonucleic acid synthesizer uses organic solvents.

In some instances, during oligonucleic acid synthesis, the substrate is positioned within or sealed within a flow cell. In some instances, the flow cell provides continuous or discontinuous flow of liquids such as those comprising reagents necessary for reactions within the substrate, for example, oxidizers and/or solvents. In some instances, the flow cell provides continuous or discontinuous flow of a gas, such as nitrogen, for drying the substrate typically through enhanced evaporation of a volatile substrate. A variety of auxiliary devices are useful to improve drying and reduce residual moisture on the surface of the substrate. Examples of such auxiliary drying devices include, without limitation, a vacuum source, depressurizing pump and a vacuum tank. In some cases, an oligonucleic acid synthesis system comprises one or more flow cells, such as 2, 3, 4, 5, 6, 7, 8, 9, 10, or 20 and one or more substrates, such as 2, 3, 4, 5, 6, 7, 8, 9, 10 or 20. In some cases, a flow cell is configured to hold and provide reagents to the substrate during one or more steps in a synthesis reaction. In some instances, a flowcell comprises a lid that slides over the top of a substrate and can be clamped into place to form a pressure tight seal around the edge of the substrate. An adequate seal, includes, without limitation, a seal that allows for about 1, 2, 3, 4, 5, 6, 7, 8, 9 or 10 atmospheres of pressure. In some cases, the lid of the flow cell is opened to allow for access to an application device such as an oligonucleic acid synthesizer. In some cases, one or more steps of an oligonucleic acid synthesis method are performed on a substrate within a flow cell, without the transport of the substrate.

In some instances, during oligonucleic acid synthesis, a capping element seals with the substrate, to form a resolved reactor. In some instances, a substrate having a plurality of clusters is configured to seal with a capping element having a plurality of caps, wherein when the substrate and capping element are sealed, each cluster is separate from another cluster to form separate resolved reactors for each cluster. In some instances, the capping element is not present in the system or is present and stationary. A resolved reactor is configured to allow for the transfer of fluid, including oligonucleic acids and/or reagents, from the substrate to the capping element and/or vice versa. In some instances, reactors are interconnected or in fluid communication. Fluid communication of reactors allows for washing and perfusion of new reagents for different steps of a synthesis reaction. In some cases, the resolved reactors comprise inlets and/or outlets. In some cases, the inlets and/or outlets are configured for use with a flow cell. As an example, a substrate is sealed within a flow cell where reagents can be introduced and flowed through the substrate, after which the reagents are collected. In some cases, the substrate is drained of fluid and purged with an inert gas such as nitrogen. The flow cell chamber can then be vacuum dried to reduce residual liquids or moisture to less than 1%, 0.1%, 0.01%, 0.001%, 0.0001%, or 0.00001% by volume of the chamber. In some instances, a vacuum chuck is in fluid communication with the substrate for removing gas.

In some instances, an oligonucleic acid synthesis system comprises one or more elements useful for downstream processing of the synthesized oligonucleic acids. As an example, the system comprises a temperature control element such as a thermal cycling device. In some instances, the temperature control element is used with a plurality of resolved reactors to perform nucleic acid assembly such as PCA and/or nucleic acid amplification such as PCR.

Computer Systems

Any of the systems described herein, may be operably linked to a computer and may be automated through a computer either locally or remotely. In various instances, the methods and systems of the invention may further comprise software programs on computer systems and use thereof. Accordingly, computerized control for the synchronization of the dispense/vacuum/refill functions such as orchestrating and synchronizing the material deposition device movement, dispense action and vacuum actuation are within the bounds of the invention. The computer systems may be programmed to interface between the user specified base sequence and the position of a material deposition device to deliver the correct reagents to specified regions of the substrate.

Figure 13:
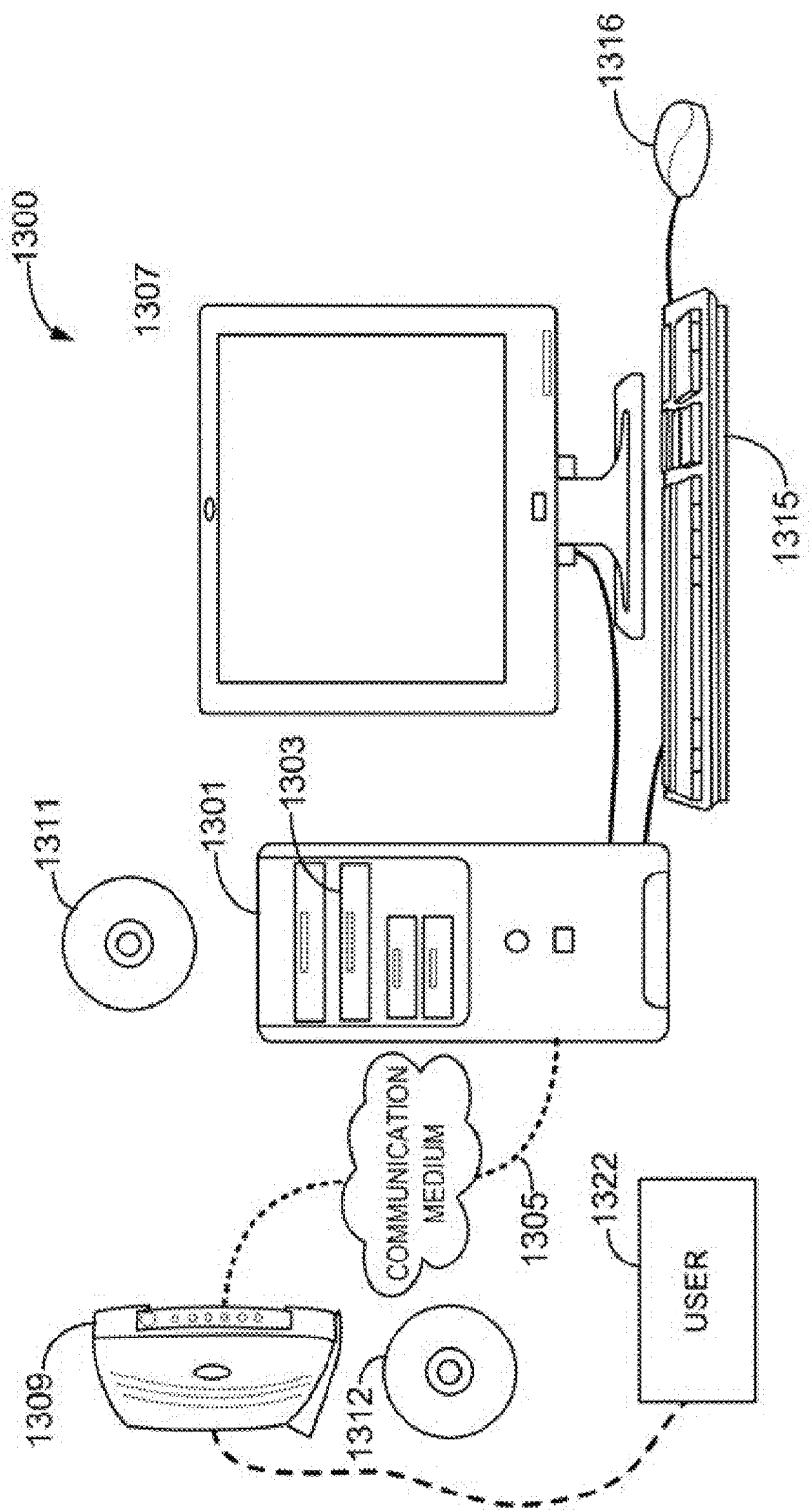
FIG. 13 illustrates a computer system.

The computer system 1300 illustrated in FIG. 13 may be understood as a logical apparatus that can read instructions from media 1311 and/or a network port 1305, which can optionally be connected to server 1309 having fixed media 1312. The system, such as shown in FIG. 13 can include a CPU 1301, disk drives 1303, optional input devices such as keyboard 1315 and/or mouse 1316 and optional monitor 1307. Data communication can be achieved through the indicated communication medium to a server at a local or a remote location. The communication medium can include any means of transmitting and/or receiving data. For example, the communication medium can be a network connection, a wireless connection or an internet connection. Such a connection can provide for communication over the World Wide Web. It is envisioned that data relating to the present disclosure can be transmitted over such networks or connections for reception and/or review by a party 1322 as illustrated in FIG. 13.

Figure 14:
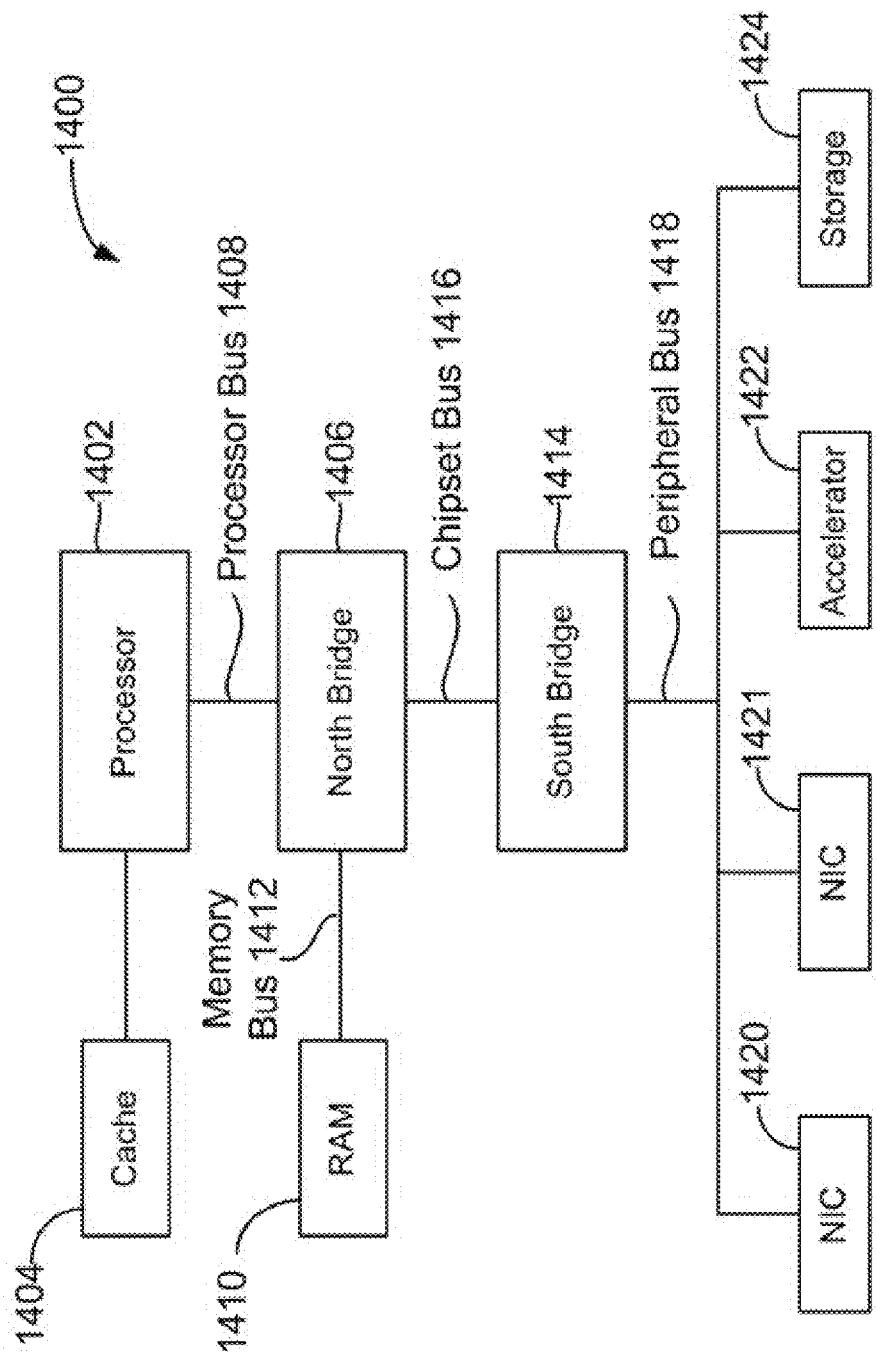
FIG. 14 is a block diagram illustrating architecture of a computer system.

FIG. 14 is a block diagram illustrating a first example architecture of a computer system 1400 that can be used in connection with example instances of the present invention. As depicted in FIG. 14, the example computer system can include a processor 1402 for processing instructions. Non-limiting examples of processors include: Intel Xeon™ processor, AMD Opteron™ processor, Samsung 14-bit RISC ARM 1176JZ(F)-S v1.0™ processor, ARM Cortex-A8 Samsung S5PC100™ processor, ARM Cortex-A8 Apple A4™ processor, Marvell PXA 930™ processor, or a functionally-equivalent processor. Multiple threads of execution can be used for parallel processing. In some instances, multiple processors or processors with multiple cores can also be used, whether in a single computer system, in a cluster, or distributed across systems over a network comprising a plurality of computers, cell phones, and/or personal data assistant devices.

As illustrated in FIG. 14, a high speed cache 1404 can be connected to, or incorporated in, the processor 1402 to provide a high speed memory for instructions or data that have been recently, or are frequently, used by processor 1402. The processor 1402 is connected to a north bridge 1406 by a processor bus 1408. The north bridge 1406 is connected to random access memory (RAM) 1410 by a memory bus 1412 and manages access to the RAM 1410 by the processor 1402. The north bridge 1406 is also connected to a south bridge 1414 by a chipset bus 1416. The south bridge 1414 is, in turn, connected to a peripheral bus 1418. The peripheral bus can be, for example, PCI, PCI-X, PCI Express, or other peripheral bus. The north bridge and south bridge are often referred to as a processor chipset and manage data transfer between the processor, RAM, and peripheral components on the peripheral bus 1418. In some alternative architectures, the functionality of the north bridge can be incorporated into the processor instead of using a separate north bridge chip. In some instances, system 1400 can include an accelerator card 1422 attached to the peripheral bus 1418. The accelerator can include field programmable gate arrays (FPGAs) or other hardware for accelerating certain processing. For example, an accelerator can be used for adaptive data restructuring or to evaluate algebraic expressions used in extended set processing.

Software and data are stored in external storage 1424 and can be loaded into RAM 1410 and/or cache 1404 for use by the processor. The system 1400 includes an operating system for managing system resources; non-limiting examples of operating systems include: Linux, Windows™, MACOS™, BlackBerry OS™, iOS™, and other functionally-equivalent operating systems, as well as application software running on top of the operating system for managing data storage and optimization in accordance with example instances of the present invention. In this example, system 1400 also includes network interface cards (NICs) 1420 and 1421 connected to the peripheral bus for providing network interfaces to external storage, such as Network Attached Storage (NAS) and other computer systems that can be used for distributed parallel processing.

Figure 15:
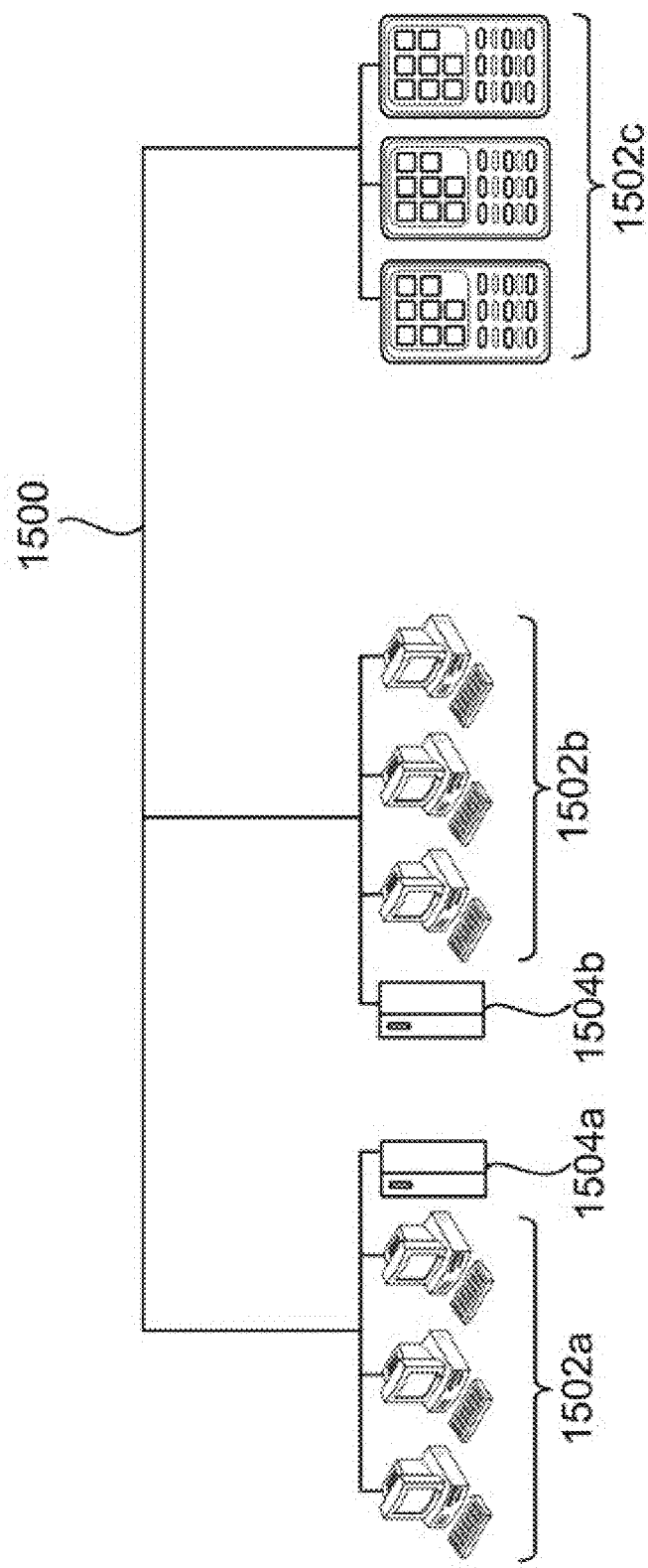
FIG. 15 is a diagram demonstrating a network configured to incorporate a plurality of computer systems, a plurality of cell phones and personal data assistants, and Network Attached Storage (NAS).

FIG. 15 is a diagram showing a network 1500 with a plurality of computer systems 1502a, and 1502b, a plurality of cell phones and personal data assistants 1502c, and Network Attached Storage (NAS) 1504a, and 1504b. In example instances, systems 1502a, 1502b, and 1502c can manage data storage and optimize data access for data stored in Network Attached Storage (NAS) 1504a and 1504b. A mathematical model can be used for the data and be evaluated using distributed parallel processing across computer systems 1502a, and 1502b, and cell phone and personal data assistant systems 1502c. Computer systems 1502a, and 1502b, and cell phone and personal data assistant systems 1502c can also provide parallel processing for adaptive data restructuring of the data stored in Network Attached Storage (NAS) 1504a and 1504b. FIG. 15 illustrates an example only, and a wide variety of other computer architectures and systems can be used in conjunction with the various instances of the present invention. For example, a blade server can be used to provide parallel processing. Processor blades can be connected through a back plane to provide parallel processing. Storage can also be connected to the back plane or as Network Attached Storage (NAS) through a separate network interface.

In some example instances, processors can maintain separate memory spaces and transmit data through network interfaces, back plane or other connectors for parallel processing by other processors. In other instances, some or all of the processors can use a shared virtual address memory space.

Figure 16:
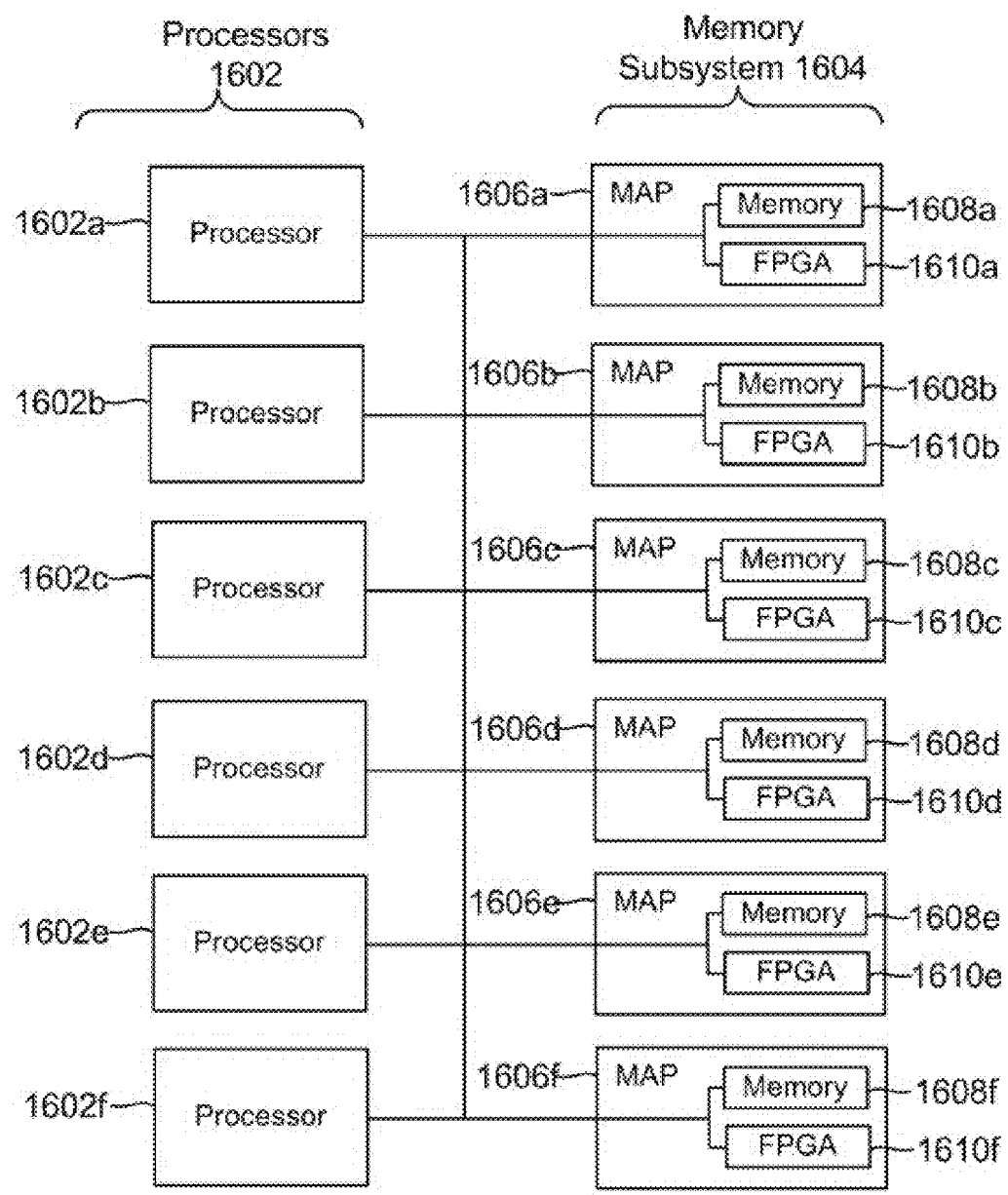
FIG. 16 is a block diagram of a multiprocessor computer system using a shared virtual address memory space.

FIG. 16 is a block diagram of a multiprocessor computer system 1600 using a shared virtual address memory space in accordance with an example embodiment. The system includes a plurality of processors 1602a-f that can access a shared memory subsystem 1604. The system incorporates a plurality of programmable hardware memory algorithm processors (MAPs) 1606a-f in the memory subsystem 1604. Each MAP 1606a-f can comprise a memory 1608a-f and one or more field programmable gate arrays (FPGAs) 1610a-f. The MAP provides a configurable functional unit and particular algorithms or portions of algorithms can be provided to the FPGAs 1610a-f for processing in close coordination with a respective processor. For example, the MAPs can be used to evaluate algebraic expressions regarding the data model and to perform adaptive data restructuring in example instances. In this example, each MAP is globally accessible by all of the processors for these purposes. In one configuration, each MAP can use Direct Memory Access (DMA) to access an associated memory 1608a-f, allowing it to execute tasks independently of, and asynchronously from the respective microprocessor 1602a-f. In this configuration, a MAP can feed results directly to another MAP for pipelining and parallel execution of algorithms.

The above computer architectures and systems are examples only, and a wide variety of other computer, cell phone, and personal data assistant architectures and systems can be used in connection with example instances, including systems using any combination of general processors, co-processors, FPGAs and other programmable logic devices, system on chips (SOCs), application specific integrated circuits (ASICs), and other processing and logic elements. In some instances, all or part of the computer system can be implemented in software or hardware. Any variety of data storage media can be used in connection with example instances, including random access memory, hard drives, flash memory, tape drives, disk arrays, Network Attached Storage (NAS) and other local or distributed data storage devices and systems.

In example instances, the computer system can be implemented using software modules executing on any of the above or other computer architectures and systems. In other instances, the functions of the system can be implemented partially or completely in firmware, programmable logic devices such as field programmable gate arrays (FPGAs) as referenced in FIG. 16, system on chips (SOCs), application specific integrated circuits (ASICs), or other processing and logic elements. For example, the Set Processor and Optimizer can be implemented with hardware acceleration through the use of a hardware accelerator card, such as accelerator card 1322 illustrated in FIG. 13.

The following examples are set forth to illustrate more clearly the principle and practice of instances disclosed herein to those skilled in the art and are not to be construed as limiting the scope of any claimed instances. Unless otherwise stated, all parts and percentages are on a weight basis.

EXAMPLES

Example 1: Functionalization of a Substrate Surface

A substrate was functionalized to support the attachment and synthesis of a library of oligonucleic acids. The substrate surface was first wet cleaned using a piranha solution comprising 90% $H_2SO_4$ and 10% $H_2O_2$ for 20 minutes. The substrate was rinsed in several beakers with DI water, held under a DI water gooseneck faucet for 5 min, and dried with $N_2$. The substrate was subsequently soaked in $NH_4OH$ (1:100; 3 mL:300 mL) for 5 min, rinsed with DI water using a handgun, soaked in three successive beakers with DI water for 1 min each, and then rinsed again with DI water using the handgun. The substrate was then plasma cleaned by exposing the substrate surface to $O_2$. A SAMCO PC-300 instrument was used to plasma etch $O_2$ at 250 watts for 1 min in downstream mode.

The cleaned substrate surface was actively functionalized with a solution comprising N-(3-triethoxysilylpropyl)-4-hydroxybutyramide using a YES-1224P vapor deposition oven system with the following parameters: 0.5 to 1 Torr, 60 min, 70° C., 135° C. vaporizer.

The substrate surface was resist coated using a Brewer Science 200× spin coater. SPR™ 3612 photoresist was spin coated on the substrate at 2500 rpm for 40 sec. The substrate was pre-baked for 30 min at 90° C. on a Brewer hot plate. The substrate was subjected to photolithography using a Karl Suss MA6 mask aligner instrument. The substrate was exposed for 2.2 sec and developed for 1 min in MSF 26A. Remaining developer was rinsed with the handgun and the substrate soaked in water for 5 min. The substrate was baked for 30 min at 100° C. in the oven, followed by visual inspection for lithography defects using a Nikon L200. A plasma cleaning process was used to remove residual resist using the SAMCO PC-300 instrument to $O_2$ plasma etch at 250 watts for 1 min.

The substrate surface was passively functionalized with a 100 μL solution of perfluorooctyltrichlorosilane mixed with 10 μL light mineral oil. The substrate was placed in a chamber, pumped for 10 min, and then the valve was closed to the pump and left to stand for 10 min. The chamber was vented to air. The substrate was resist stripped by performing two soaks for 5 min in 500 mL NMP at 70° C. with ultrasonication at maximum power (9 on Crest system). The substrate was then soaked for 5 min in 500 mL isopropanol at room temperature with ultrasonication at maximum power. The substrate was dipped in 300 mL of 200 proof ethanol and blown dry with $N_2$. The functionalized surface was activated to serve as a support for oligonucleic acid synthesis.

Example 2: Preparation of Substrates Having Distinct Loci Configurations

Substrates were manufactured to comprise a plurality of clusters each comprising a plurality of distinct loci configured to provide structural support for oligonucleic acid synthesis. Substrate starting material was a 200 mm standard, double-sided polished silicon wafer having a 725 um thickness. Substrates were processed by a method comprising thermal oxidation at 1000 Å, photolithography using a Karl Suss MA6 mask aligner to generate fiducial structures; oxide etching down to the silicon; and resist stripping. Prepared substrates have 6,144 clusters, with each cluster having 121 reaction sites or loci for oligonucleic acid synthesis. The clusters are organized into 24 sub-fields, which each comprise a 16×16 array of clusters. A schematic of a substrate produced is shown in FIGS. 1-3. As shown in FIG. 1, the substrate has a dimension of 140.000 mm by 90.000 mm. As shown in FIG. 2, the vertical distance between the centers of two adjacent clusters in one substrate is 1079.210 um and in another substrate 1142.694 um. The horizontal distance between the centers of two adjacent clusters in the substrate is 1125.0 um. An expanded view of a cluster of the substrate is shown in FIG. 3. Each cluster has 121 loci, which are separated so that the horizontal distance between two adjacent loci is 75.000 um and the vertical distance between two loci is 63.483 um. The horizontal distance between the edges of two adjacent loci is 24.0 um.

Example 3: Maximization of Microchannel Surface Area

Substrates manufactured in this example were processed to generate three-dimensional loci having shapes configured to increase surface area to volume. Examples of locus shapes prepared using the methods described in this example are shown in FIG. 5. A Silicon on Insulator (SOI) silicon wafer (sub-field size of 32.00×32.00 mm) was oxidized, and the device side processed by photolithography, deep RIE and photoresist stripping. The handle side of the substrate was processed by photolithography, deep RIE, photoresist stripping, and etching by removal of oxide layer (BOX etch). The processed substrate has a plurality of wells or holes within the handle layer, each having a width of 1.150 mm, wherein each channel has a plurality of microchannels having shapes that allow for an increase in surface area to volume. The smallest etch size for a feature of a shape of a microchannel within a substrate prepared in this example was 5 um. The distance between the centers of two adjacent clusters (wells)

is 1.693 mm in all directions. The distance between the centers of two adjacent loci (microchannels) is 97.765 in a horizontal direction and 84.667 um in a vertical direction. The prepared substrate has a set of markings or fiducials of 0.5 mm diameter. The width of the main channel is 1.150 mm and the width of the microchannel is 5 um. Detailed features of substrates prepared using these methods are shown in FIGS. 5-8.

A cluster of a processed substrate having double comb shaped loci is shown in a bird's eye view in FIG. 6. The combined height of the two longest teeth is 57 um. The distance between two teeth of the comb is 14.0 um. The width of the comb handle is 5 um. The combined height of the two shortest teeth is 38.0 um. The width of the comb in the horizontal direction is 47.0 um.

A cluster of a processed substrate having single comb shaped loci is shown in a bird's eye view in FIG. 7. The height of the longest tooth is 49.0 um. The distance between two teeth of the comb is 14.0 um. The width of the comb handle is 5 um. The height of the shortest tooth is 39.0 um. The width of the comb in the horizontal direction is 47.0 um.

Figure 8:
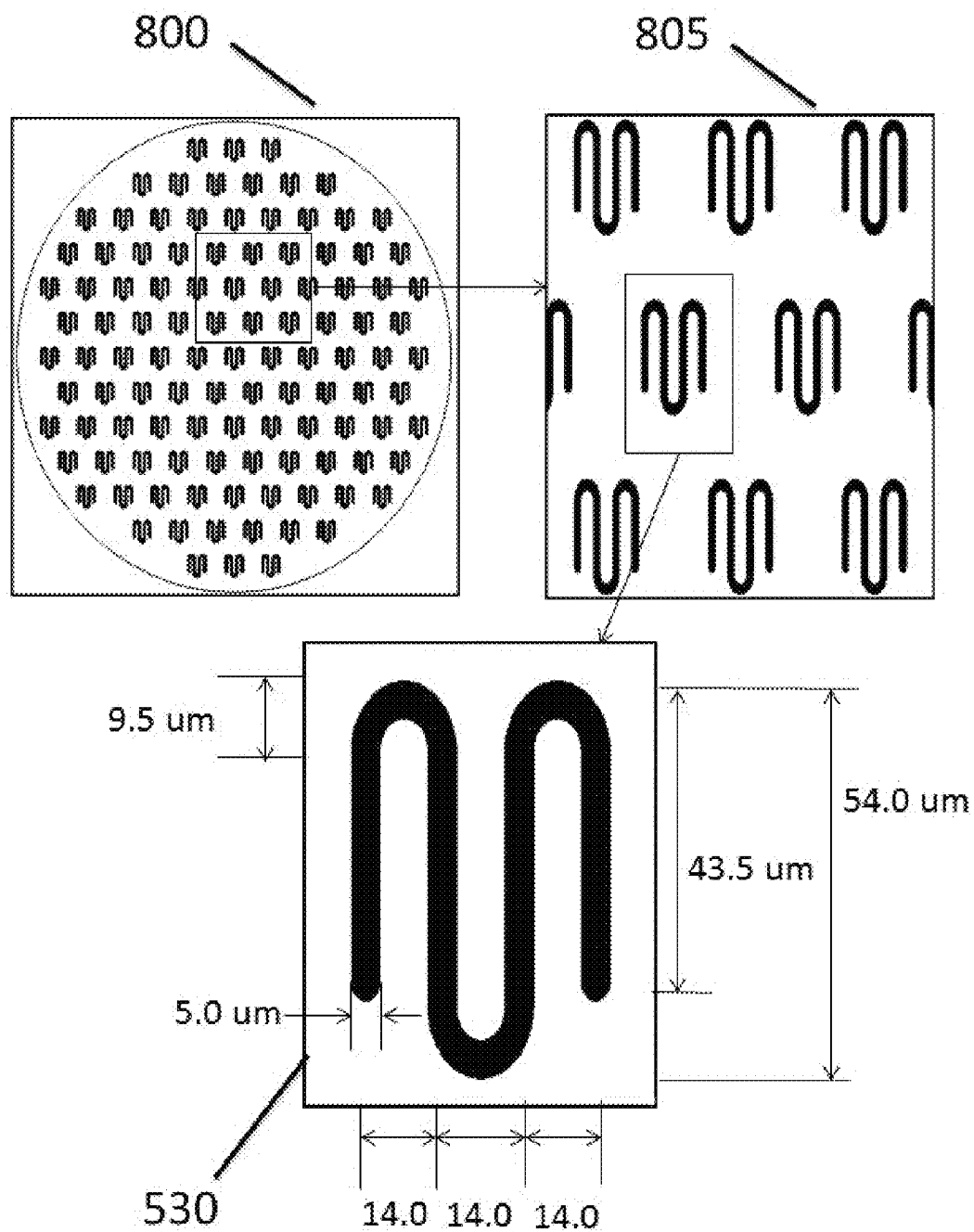
FIG. 8 illustrates a cluster having a plurality of loci with single serpentine shapes.

A cluster of a processed substrate having serpentine shaped loci is shown in a bird's eye view in FIG. 8. The height of the loci shape is 54 um. The distance between two lines of the shape is 14 urn. The width of a line of the shape is 5 urn.

Detailed measurements for prepared substrates are shown in Table 3.

TABLE 3

| | | | | | | |
|---|---|---|---|---|---|---|
| | Device depth (um) | | | 30 | | |
| | Width of segments (um) | | | 5 | | |

| Segments | No. | Internal area (um$^2$) | Top surface growth area (um$^2$) | Volume (um$^3$) | Total projected area (um$^2$) | Total Area (um$^2$) | Total Volume (um$^3$) |
|---|---|---|---|---|---|---|---|
| Double comb | | | | | | | |
| Lateral segments | 3 | 540 | 45 | 1350 | 135 | 1620 | 4050 |
| End segments | 2 | 1890 | 170 | 5100 | 340 | 3780 | 10200 |
| Middle segments | 2 | 2850 | 263 | 7875 | 525 | 5700 | 15750 |
| Rounded ends | 4 | 471 | 20 | 589 | 79 | 1885 | 2356 |
| | | | | Total | 1079 | 12985 | 32356 |
| Total growth area including top surface (um$^2$) | | | | | | 15225 | |
| Single comb | | | | | | | |
| Lateral segments | 1 | 2456 | 210 | 7050 | 210 | 2456 | 7050 |
| End segments | 2 | 2070 | 173 | 5175 | 345 | 4140 | 10350 |
| Middle segments | 2 | 2490 | 208 | 6225 | 415 | 4980 | 12450 |
| Rounded ends | 2 | 471 | 20 | 589 | 39 | 942 | 1178 |
| | | | | Total | 1009 | 12518 | 31028 |
| Total growth area including top surface (um$^2$) | | | | | | 14827 | |
| Serpentine | | | | | | | |
| Vertical segments | 4 | 2100 | 175 | 5250 | 700 | 8400 | 21000 |
| Annulus segments (whole) | 1.5 | 2639 | 220 | 6597 | 330 | 3958 | 9896 |
| Rounded ends | 1 | 471 | 20 | 589 | 20 | 471 | 589 |
| | | | | Total | 1050 | 12830 | 31485 |
| Total growth area including top surface (um$^2$) | | | | | | 15098 | |

The surface and volume parameters of loci having high surface area shapes (double comb, single comb, and serpentine) prepared using these methods were compared with the parameters of a locus having a revolver shape (barrel comprising 5 channels). The comparison is shown in Table 4. The loci having a comb or serpentine shape had a lower substrate volume than a substrate having revolver loci. The loci having a comb or serpentine shape had a greater surface area than a substrate having revolver loci. The loci having a comb or serpentine shape had a greater surface area to volume ratio than a substrate having revolver loci.

TABLE 4

|  | Revolver | Double comb | Single come | Serpentine |
|---|---|---|---|---|
| Total volume (pL) | 47 | 32 | 31 | 31 |
| Total surface area (um) | 9425 | 12985 | 12518 | 12830 |
| Surface area to volume ratio (1/um) | 0.20 | 0.40 | 0.40 | 0.41 |
| Total volume relative to revolver | 1.00 | 0.69 | 0.66 | 0.67 |
| Total surface area relative to revolver | 1.00 | 1.38 | 1.33 | 1.36 |
| Surface area to volume ratio relative revolver | 1.00 | 2.01 | 2.02 | 2.04 |

Example 4: Synthesis of a 100-Mer Oligonucleic Acid on a Substantially Planar Substrate A substantially planar substrate functionalized for oligonucleic acid synthesis was assembled into a flow cell and connected to an Applied Biosystems ABI394 DNA Synthesizer. In one experiment, the substrate was uniformly functionalized with N-(3-triethoxysilylpropyl)-4-hydroxybutyramide. In another experiment, the substrate was functionalized with a 5/95 mix of 11-acetoxyundecyltriethoxysilane and N-decyltriethoxysilane. Synthesis of 100-mer oligonucleic acids ("100-mer oligonucleotide"; 5': CGGGATCCTTATCGTCATCGTCGTACAGATC-CCGACCCATTTGCTGTCCACCAGT CATGCTAGC-CATACCATGATGATGATGATG ATGAGAACCCCGCAT##TTTTTTTTT T 3' (SEQ ID NO: 1), where # denotes Thymidine-succinyl hexamide CED phosphoramidite (CLP-2244 from ChemGenes)) were performed using the methods of Table 5.

TABLE 5

| General DNA Synthesis Process Name | Process Step | Time (sec) |
|---|---|---|
| WASH (Acetonitrile Wash Flow) | Acetonitrile System Flush | 4 |
| | Acetonitrile to Flowcell | 23 |
| | N2 System Flush | 4 |
| | Acetonitrile System Flush | 4 |
| DNA BASE ADDITION (Phosphoramidite + Activator Flow) | Activator Manifold Flush | 2 |
| | Activator to Flowcell | 6 |
| | Activator + Phosphoramidite to Flowcell | 6 |
| | Activator to Flowcell | 0.5 |
| | Activator + Phosphoramidite to Flowcell | 5 |
| | Activator to Flowcell | 0.5 |
| | Activator + Phosphoramidite to Flowcell | 5 |

TABLE 5-continued

| General DNA Synthesis Process Name | Process Step | Time (sec) |
|---|---|---|
| | Activator to Flowcell | 0.5 |
| | Activator + Phosphoramidite to Flowcell | 5 |
| | Incubate for 25 sec | 25 |
| WASH (Acetonitrile Wash Flow) | Acetonitrile System Flush | 4 |
| | Acetonitrile to Flowcell | 15 |
| | N2 System Flush | 4 |
| | Acetonitrile System Flush | 4 |
| DNA BASE ADDITION (Phosphoramidite + Activator Flow) | Activator Manifold Flush | 2 |
| | Activator to Flowcell | 5 |
| | Activator + Phosphoramidite to Flowcell | 18 |
| | Incubate for 25 sec | 25 |
| WASH (Acetonitrile Wash Flow) | Acetonitrile System Flush | 4 |
| | Acetonitrile to Flowcell | 15 |
| | N2 System Flush | 4 |
| | Acetonitrile System Flush | 4 |
| CAPPING (CapA + B, 1:1, Flow) | CapA + B to Flowcell | 15 |
| WASH (Acetonitrile Wash Flow) | Acetonitrile System Flush | 4 |
| | Acetonitrile to Flowcell | 15 |
| | Acetonitrile System Flush | 4 |
| OXIDATION (Oxidizer Flow) | Oxidizer to Flowcell | 18 |
| WASH (Acetonitrile Wash Flow) | Acetonitrile System Flush | 4 |
| | N2 System Flush | 4 |
| | Acetonitrile System Flush | 4 |
| | Acetonitrile to Flowcell | 15 |
| | Acetonitrile System Flush | 4 |
| | Acetonitrile to Flowcell | 15 |
| | N2 System Flush | 4 |
| | Acetonitrile System Flush | 4 |
| | Acetonitrile to Flowcell | 23 |
| | N2 System Flush | 4 |
| | Acetonitrile System Flush | 4 |
| DEBLOCKING (Deblock Flow) | Deblock to Flowcell | 36 |
| WASH (Acetonitrile Wash Flow) | Acetonitrile System Flush | 4 |
| | N2 System Flush | 4 |
| | Acetonitrile System Flush | 4 |
| | Acetonitrile to Flowcell | 18 |
| | N2 System Flush | 4.13 |
| | Acetonitrile System Flush | 4.13 |
| | Acetonitrile to Flowcell | 15 |

Synthesized oligonucleic acids were extracted from the substrate surface and analyzed on a BioAnalyzer chip. Oligonucleic acid products were PCR amplified, cloned and Sanger sequenced. Table 6 summarizes the Sanger sequencing results for samples taken from spots 1-5 from one chip and spots 6-10 from a second chip.

TABLE 6

| Spot | Error rate | Cycle efficiency |
|---|---|---|
| 1 | 1/763 bp | 99.87% |
| 2 | 1/824 bp | 99.88% |
| 3 | 1/780 bp | 99.87% |
| 4 | 1/429 bp | 99.77% |
| 5 | 1/1525 bp | 99.93% |
| 6 | 1/1615 bp | 99.94% |
| 7 | 1/531 bp | 99.81% |
| 8 | 1/1769 bp | 99.94% |
| 9 | 1/854 bp | 99.88% |
| 10 | 1/1451 bp | 99.93% |

Overall, 89% (233/262) of the 100-mers that were sequenced had sequences without errors. Table 7 summarizes key error characteristics for the sequences obtained from the oligonucleic acid samples from spots 1-10.

TABLE 7

| Sample ID/Spot No. | OSA_0046/1 | OSA_0047/2 | OSA_0048/3 | OSA_0049/4 | OSA_0050/5 | OSA_0051/6 |
|---|---|---|---|---|---|---|
| Total Sequences | 32 | 32 | 32 | 32 | 32 | 32 |
| Sequencing Quality | 25 of 28 | 27 of 27 | 26 of 30 | 21 of 23 | 25 of 26 | 29 of 30 |
| Oligo Quality | 23 of 25 | 25 of 27 | 22 of 26 | 18 of 21 | 24 of 25 | 25 of 29 |
| ROI Match Count | 2500 | 2698 | 2561 | 2122 | 2499 | 2666 |
| ROI Mutation | 2 | 2 | 1 | 3 | 1 | 0 |
| ROI Multi Base Deletion | 0 | 0 | 0 | 0 | 0 | 0 |
| ROI Small Insertion | 1 | 0 | 0 | 0 | 0 | 0 |
| ROI Single Base Deletion | 0 | 0 | 0 | 0 | 0 | 0 |
| Large Deletion Count | 0 | 0 | 1 | 0 | 0 | 1 |
| Mutation: G > A | 2 | 2 | 1 | 2 | 1 | 0 |
| Mutation: T > C | 0 | 0 | 0 | 1 | 0 | 0 |
| ROI Error Count | 3 | 2 | 2 | 3 | 1 | 1 |
| ROI Error Rate | Err: ~1 in 834 | Err: ~1 in 1350 | Err: ~1 in 1282 | Err: ~1 in 708 | Err: ~1 in 2500 | Err: ~1 in 2667 |
| ROI Minus Primer Error Rate | MP Err: ~1 in 763 | MP Err: ~1 in 824 | MP Err: ~1 in 780 | MP Err: ~1 in 429 | MP Err: ~1 in 1525 | MP Err: ~1 in 1615 |

| Sample ID/Spot No. | OSA_0052/7 | OSA_0053/8 | OSA_0054/9 | OSA_0055/10 |
|---|---|---|---|---|
| Total Sequences | 32 | 32 | 32 | 32 |
| Sequencing Quality | 27 of 31 | 29 of 31 | 28 of 29 | 25 of 28 |
| Oligo Quality | 22 of 27 | 28 of 29 | 26 of 28 | 20 of 25 |
| ROI Match Count | 2625 | 2899 | 2798 | 2348 |
| ROI Mutation | 2 | 1 | 2 | 1 |
| ROI Multi Base Deletion | 0 | 0 | 0 | 0 |
| ROI Small Insertion | 0 | 0 | 0 | 0 |
| ROI Single Base Deletion | 0 | 0 | 0 | 0 |
| Large Deletion Count | 1 | 0 | 0 | 0 |
| Mutation: G > A | 2 | 1 | 2 | 1 |
| Mutation: T > C | 0 | 0 | 0 | 0 |
| ROI Error Count | 3 | 1 | 2 | 1 |
| ROI Error Rate | Err: ~1 in 876 | Err: ~1 in 2900 | Err: ~1 in 1400 | Err: ~1 in 2349 |
| ROI Minus Primer Error Rate | MP Err: ~1 in 531 | MP Err: ~1 in 1769 | MP Err: ~1 in 854 | MP Err: ~1 in 1451 |

Example 5: Gene Assembly in Reactors Using PCA

Gene assembly within nanoreactors created using a three-dimensional substrate was performed. PCA reactions were performed using oligonucleic acids described in Table 8 (SEQ ID NOS: 2-61) to assemble the 3075 base LacZ gene (SEQ ID NO.: 62) using the reaction mixture of Table 9 within individual nanoreactors.

TABLE 8

| Sequence Name | Sequence |
| --- | --- |
| Oligo_1, SEQ ID NO.: 2 | 5'ATGACCATGATTACGGATTCACTGGCCGTCGTTTTACAACGTCGTGACTGGGAAAACCCTGG3' |
| Oligo_2, SEQ ID NO.: 3 | 5'GCCAGCTGGCGAAAGGGGGATGTGCTGCAAGGCGATTAAGTTGGGTAACGCCAGGGTTTTCCCAGTCACGAC3' |
| Oligo_3, SEQ ID NO.: 4 | 5'CCCCCTTTCGCCAGCTGGCGTAATAGCGAAGAGGCCCGCACCGATCGCCCTTCCCAACAGTTGCGCAGCC3' |
| Oligo_4, SEQ ID NO.: 5 | 5'CGGCACCGCTTCTGGTGCCGGAAACCAGGCAAAGCGCCATTCGCCATTCAGGCTGCGCAACTGTTGGGA3' |
| Oligo_5, SEQ ID NO.: 6 | 5'CACCAGAAGCGGTGCCGGAAAGCTGGCTGGAGTGCGATCTTCCTGAGGCCGATACTGTCGTCGTCCCCTC3' |
| Oligo_6, SEQ ID NO.: 7 | 5'GATAGGTCACGTTGGTGTAGATGGGCGCATCGTAACCGTGCATCTGCCAGTTTGAGGGGACGACGACAGTATCGG3' |
| Oligo_7, SEQ ID NO.: 8 | 5'CCCATCTACACCAACGTGACCTATCCCATTACGGTCAATCCGCCGTTTGTTCCCACGGAGAATCCGACGGGTTG3' |
| Oligo_8, SEQ ID NO.: 9 | 5'GTCTGGCCTTCCTGTAGCCAGCTTTCATCAACATTAAATGTGAGCGAGTAACAACCCGTCGGATTCTCCGTG3' |
| Oligo_9, SEQ ID NO.: 10 | 5'GCTGGCTACAGGAAGGCCAGACGCGAATTATTTTTGATGGCGTTAACTCGGCGTTTCATCTGTGGTGCAACGG3' |
| Oligo_10, SEQ ID NO.: 11 | 5'CAGGTCAAATTCAGACGGCAAACGACTGTCCTGGCCGTAACCGACCCAGCGCCCGTTGCACCACAGATGAAACG3' |
| Oligo_11, SEQ ID NO.: 12 | 5'CGTTTGCCGTCTGAATTTGACCTGAGCGCATTTTTACGCGCCGGAGAAAACCGCCTCGCGGTGATGGTGCTG3' |
| Oligo_12, SEQ ID NO.: 13 | 5'GCCGCTCATCCGCCACATATCCTGATCTTCCAGATAACTGCCGTCACTCCAGCGCAGCACCATCACCGCGAG3' |
| Oligo_13, SEQ ID NO.: 14 | 5'AGGATATGTGGCGGATGAGCGGCATTTTCCGTGACGTCTCGTTGCTGCATAAACCGACTACACAAATCAGCGATTTC3' |
| Oligo_14, SEQ ID NO.: 15 | 5'CTCCAGTACAGCGCGGCTGAAATCATCATTAAAGCGAGTGGCAACATGGAAATCGCTGATTTGTGTAGTCGGTTTATG3' |
| Oligo_15, SEQ ID NO.: 16 | 5'ATTTCAGCCGCGCTGTACTGGAGGCTGAAGTTCAGATGTGCGGCGAGTTGCGTGACTACCTACGGGTAACAGTTT3' |
| Oligo_16, SEQ ID NO.: 17 | 5'AAAGGCGCGGTGCCGCTGGCGACCTGCGTTTCACCCTGCCATAAAGAAACTGTTACCCGTAGGTAGTCACG3' |
| Oligo_17, SEQ ID NO.: 18 | 5'GCGGCACCGCGCCTTTCGGCGGTGAAATTATCGATGAGCGTGGTGGTTATGCCGATCGCGTCACACTACG3' |
| Oligo_18, SEQ ID NO.: 19 | 5'GATAGAGATTCGGGATTTCGGCGCTCCACAGTTTCGGGTTTTCGACGTTCAGACGTAGTGTGACGCGATCGGCA3' |
| Oligo_19, SEQ ID NO.: 20 | 5'GAGCGCCGAAATCCCGAATCTCTATCGTGCGGTGGTTGAACTGCACACCGCCGACGGCACGCTGATTGAAGCAG3' |
| Oligo_20, SEQ ID NO.: 21 | 5'CAGCAGCAGACCATTTTCAATCCGCACCTCGCGGAAACCGACATCGCAGGCTTCTGCTTCAATCAGCGTGCCG3' |
| Oligo_21, SEQ ID NO.: 22 | 5'CGGATTGAAAATGGTCTGCTGCTGCTGAACGGCAAGCCGTTGCTGATTCGAGGCGTTAACCGTCACGAGCATCA3' |
| Oligo_22, SEQ ID NO.: 23 | 5'GCAGGATATCCTGCACCATCGTCTGCTCATCCATGACCTGACCATGCAGAGGATGATGCTCGTGACGGTTAACGC3' |
| Oligo_23, SEQ ID NO.: 24 | 5'CAGACGATGGTGCAGGATATCCTGCTGATGAAGCAGAACAACTTTAACGCCGTGCGCTGTTCGCATTATCCGAAC3' |
| Oligo_24, SEQ ID NO.: 25 | 5'TCCACCACATACAGGCCGTAGCGGTCGCACAGCGTGTACCACAGCGGATGGTTCGGATAATGCGAACAGCGCAC3' |
| Oligo_25, SEQ ID NO.: 26 | 5'GCTACGGCCTGTATGTGGTGGATGAAGCCAATATTGAAACCCACGGCATGGTGCCAATGAATCGTCTGACCGATG3' |
| Oligo_26, SEQ ID NO.: 27 | 5'GCACCATTCGCGTTACGCGTTCGCTCATCGCCGGTAGCCAGCGCGGATCATCGGTCAGACGATTCATTGGCAC3' |
| Oligo_27, SEQ ID NO.: 28 | 5'CGCGTAACGCGAATGGTGCAGCGCGATCGTAATCACCCGAGTGTGATCATCTGGTCGCTGGGGAATGAATCAG3' |
| Oligo_28, SEQ ID NO.: 29 | 5'GGATCGACAGATTTGATCCAGCGATACAGCGCGTCGTGATTAGCGCCGTGGCCTGATTCATTCCCCAGCGACCAGATG3' |
| Oligo_29, SEQ ID NO.: 30 | 5'GTATCGCTGGATCAAATCTGTCGATCCTTCCCGCCCGGTGCAGTATGAAGGCGGCGGAGCCGACACCACGGC3' |
| Oligo_30, SEQ ID NO.: 31 | 5'CGGGAAGGGCTGGTCTTCATCCACGCGCGCGTACATCGGGCAAATAATATCGGTGGCCGTGGTGTCGGCTC3' |
| Oligo_31, SEQ ID NO.: 32 | 5'TGGATGAAGACCAGCCCTTCCCGGCTGTGCCGAAATGGTCCATCAAAAAATGGCTTTCGCTACCTGGAGAGAC3' |
| Oligo_32, SEQ ID NO.: 33 | 5'CCAAGACTGTTACCCATCGCGTGGGCGTATTCGCAAAGGATCAGCGGGCGCGTCTCTCCAGGTAGCGAAAGCC3' |
| Oligo_33, SEQ ID NO.: 34 | 5'CGCGATGGGTAACAGTCTTGGCGGTTTCGCTAAATACTGGCAGGCGTTTCGTCAGTATCCCCGTTTACAGGGC3' |
| Oligo_34, SEQ ID NO.: 35 | 5'GCCGTTTTCATCATATTTAATCAGCGACTGATCCACCCAGTCCCAGACGAAGCCGCCCTGTAAACGGGGATACTGACG3' |
| Oligo_35, SEQ ID NO.: 36 | 5'CAGTCGCTGATTAAATATGATGAAAACGGCAACCCGTGGTCGGCTTACGGCGGTGATTTTGGCGATACGCCGAACG3' |
| Oligo_36, SEQ ID NO.: 31 | 5'GCGGCGTGCGGTCGGCAAAGACCAGACCGTTCATACAGAACTGGCGATCGTTCGGCGTATCGCCAAA3' |

TABLE 8-continued

| Sequence Name | Sequence |
|---|---|
| Oligo_37, SEQ ID NO.: 38 | 5'CGACCGCACGCCGCATCCAGCGCTGACGGAAGCAAAACACCAGCAGCAGTTTTTCCAGTTCCGTTTATCCG3' |
| Oligo_38, SEQ ID NO.: 39 | 5'CTCGTTATCGCTATGACGGAACAGGTATTCGCTGGTCACTTCGATGGTTTGCCCGGATAAACGGAACTGGAAAAACTGC3' |
| Oligo_39, SEQ ID NO.: 40 | 5'AATACCTGTTCCGTCATAGCGATAACGAGCTCCTGCACTGGATGGTGGCGCTGGATGGTAAGCCGCTGGCAAGCG3' |
| Oligo_40, SEQ ID NO.: 41 | 5'GTTCAGGCAGTTCAATCAACTGTTTACCTTGTGGAGCGACATCCAGAGGCACTTCACCGCTTGCCAGCGGCTTACC3' |
| Oligo_41, SEQ ID NO.: 42 | 5'CAAGGTAAACAGTTGATTGAACTGCCTGAACTACCGCAGCCGGAGAGCGCCGGGCAACTCTGGCTCACAGTACGCGTA3' |
| Oligo_42, SEQ ID NO.: 43 | 5'GCGCTGATGTGCCCGGCTTCTGACCATGCGGTCGCGTTCGGTTGCACTACGCGTACTGTGAGCCAGAGTTG3' |
| Oligo_43, SEQ ID NO.: 44 | 5'CCGGGCACATCAGCGCCTGGCAGCAGTGGCGTCTGGCGGAAAACCTCAGTGTGACGCTCCCCGCCGC3' |
| Oligo_44, SEQ ID NO.: 45 | 5'CCAGCTCGATGCAAAAATCCATTTCGCTGGTGGTCAGATGCGGGATGGCGTGGGACGCGCGGGGAGCGTC3' |
| Oligo_45, SEQ ID NO.: 46 | 5'CGAAATGGATTTTTGCATCGAGCTGGGTAATAAGCGTTGGCAATTTAACCGCCAGTCAGGCTTTCTTTCACAGATGTG3' |
| Oligo_46, SEQ ID NO.: 47 | 5'TGAACTGATCGCGCAGCGGCGTCAGCAGTTGTTTTTTATCGCCAATCCACATCTGTGAAAGAAAGCCTGACTGG3' |
| Oligo_47, SEQ ID NO.: 48 | 5'GCCGCTGCGCGATCAGTTCACCCGTGCACCGCTGGATAACGACATTGGCGTAAGTGAAGCGACCCGCATTGAC3' |
| Oligo_48, SEQ ID NO.: 49 | 5'GGCCTGGTAATGGCCCGCCGCCTTCCAGCGTTCGACCCAGGCGTTAGGGTCAATGCGGGTCGCTTCACTTA3' |
| Oligo_49, SEQ ID NO.: 50 | 5'CGGGCCATTACCAGGCCGAAGCAGCGTTGTTGCAGTGCACGGCAGATACACTTGCTGATGCGGTGCTGAT3' |
| Oligo_50, SEQ ID NO.: 51 | 5'TCCGGCTGATAAATAAGGTTTTCCCCTGATGCTGCCACGCGTGAGCGGTCGTAATCAGCACCGCATCAGCAAGTG3' |
| Oligo_51, SEQ ID NO.: 52 | 5'GGGGAAAACCTTATTTATCAGCCGGAAAACCTACCGGATTGATGGTAGTGGTCAAATGGCGATTACCGTTGATGTTGA3' |
| Oligo_52, SEQ ID NO.: 53 | 5'GGCAGTTCAGGCCAATCCGCGCCGGATGCGGTGTATCGCTCGCCACTTCAACATCAACGGTAATCGCCATTTGAC3' |
| Oligo_53, SEQ ID NO.: 54 | 5'GCGGATTGGCCTGAACTGCCAGCTGGCGCAGGTAGCAGAGCGGGTAAACTGGCTCGGATTAGGGCCGCAAG3' |
| Oligo_54, SEQ ID NO.: 55 | 5'GGCAGATCCCAGCGGTCAAAACAGGCGGCAGTAAGGCGGTCGGGATAGTTTTCTTGCGGCCCTAATCCGAGC3' |
| Oligo_55, SEQ ID NO.: 56 | 5'GTTTTGACCGCTGGGATCTGCCATTGTCAGACATGTATACCCCGTACGTCTTCCCGAGCGAAAACGGTCTGC3' |
| Oligo_56, SEQ ID NO.: 57 | 5'GTCGCCGCGCCACTGGTGTGGGCCATAATTCAATTCGCGCGTCCCGCAGCGCAGACCGTTTTCGCTCGG3' |
| Oligo_57, SEQ ID NO.: 58 | 5'ACCAGTGGCGCGGCGACTTCCAGTTCAACATCAGCCGCTACAGTCAACAGCAACTGATGGAAACCAGCCATC3' |
| Oligo_58, SEQ ID NO.: 59 | 5'GAAACCGTCGATATTCAGCCATGTGCCTTCTTCCGCGTGCAGCAGATGGCGATGGCTGGTTTCCATCAGTTGCTG3' |
| Oligo_59, SEQ ID NO.: 60 | 5'CATGGCTGAATATCGACGGTTTCCATATGGGGATTGGTGGCGACGACTCCTGGAGCCCGTCAGTATCGGCG3' |
| Oligo_60, SEQ ID NO.: 61 | 5'TTATTTTTGACACCAGACCAACTGGTAATGGTAGCGACCGGCGCTCAGCTGGAATTCCGCCGATACTGACGGGC3' |
| LacZ gene- SEQ ID NO: 62 | 5'ATGACCATGATTACGGATTCACTGGCCGTCGTTTTACAACGTCGTGACTGGGAAAACCCTGGCGTTACCCAACTTAATCGCCTTGCAGCACATCCCCCTTTCGCCAGCTGGCGTAATAGCGAAGAGGCCCGCACCGATCGCCCTTCCCAACAGTTGCGCAGCCTGAATGGCGAATGGCGCTTTGCCTGGTTTCCGGCACCAGAAGCGGTGCCGGAAAGCTGGCTGGAGTGCGATCTTCCTGAGGCCGATACTGTCGTCGTCCCCTCAAACTGGCAGATGCACGGTTACGATGCGCCCATCTACACCAACGTGACCTATCCCATTACGGTCAATCCGCCGTTTGTTCCCACGGAGAATCCGACGGGTTGTTACTCGCTCACATTTAATGTTGATGAAAGCTGGCTACAGGAAGGCCAGACGCGAATTATTTTTGATGGCGTTAACTCGGCGTTTCATCTGTGGTGCAACGGGCGCTGGGTCGGTTACGGCCAGGACAGTCGTTTGCCGTCTGAATTTGACCTGAGCGCATTTTTACGCGCCGGAGAAAACCGCCTCGCGGTGATGGTGCTGCGCTGGAGTGACGGCAGTTATCTGGAAGATCAGGATATGTGGCGGATGAGCGGCATTTTCCGTGACGTCTCGTTGCTGCATAAACCGACTACACAAATCAGCGATTTCCATGTTGCCACTCGCTTTAATGATGATTTCAGCCGCGCTGTACTGGAGGCTGAAGTTCAGATGTGCGGCGAGTTGCGTGACTACCTACGGGTAACAGTTTCTTTATGCAGGGTGAAACGCAGGTCGCCAGCGGCACCGCGCCTTTCGGCGGTGAAATTATCGATGAGCGTGGTGGTTATGCCGATCGCGTCACACTACGTCTGAACGTCGAAAACCCGAAACTGTGGAGCGCCGAAATCCCGAATCTCTATCGTGCGGTGGTTGAACTGCACACCGCCGACGGCACGCTGATTGAAGCAGAAGCCTGCGATGTCGGTTTCCGCGAGGTGCGGATTGAAAATGGTCTGCTGCTGCTGAACGGCAAGCCGTTGCTGATTCGAGGCGTTAACCGTCACGAGCATCATCCTCTGCATGGTCAGGTCATGGATGAGCAGACGATGGTGCAGGATATCCTGCTGATGAAGCAGAACAACTTTAACGCCGTGCGCTGTTCGCATTATCCGAACCATCCGCTGTGGTACACGCTGTGCGACCGCTACGGCCTGTATGTGGTGGATGAAGCCAATATTGAAACCCACGGCATGGTGCCAATGAATCGTCTGACCGATGATCCGCGCTGGCTACCGGCGATGAGCGAACGCGTAACGCGAATGGTGCAGCGCGATCGTAATCACCCGAGTGTGATCATCTGGTCGCTGGGGAATGAATCAGGCCACGGCGCTAATCACGACGCGCTGTATCGCTGGATCAAATCTGTCGATCCTTCCCGCCCGGTGCAGTATGAAGGCGGCGGAGCCGACACCACGGCCACCGATATTATTTGCCCGATGTACGCGCGCGTGGATGAAGACCAGCCCTTCCCGGCTGTGCCGAAATGGTCCATCAAAAAATGGCTTTCGCTACCTGGAGAGACGCGCCCGCTGATCCTTTGCGAATACGCCCACGCGATGGGTAACAGTCTTGGCGGTTTCGCTAAATACTGGCAGGCGTTTCGTCAGTATCCCCGTTTACAGGGCGGCTTCGTCTGGGACTGGGTGGATCAGTCGCTGATTAAATATGATGAAAACGGCAACCCGTGGTCGGCTT |

TABLE 8-continued

| Sequence Name | Sequence |
|---|---|
| | ACGGCGGTGATTTTGGCGATACGCCGAACGA TCGCCAGTTCTGTATGAACGGTCTGGTCTTT GCCGACCGCACGCCGCATCCAGCGCTGACGG AAGCAAAACACCAGCAGCAGTTTTTCCAGTT CCGTTTATCCGGGCAAACCATCGAAGTGACC AGCGAATACCTGTTCCGTCATAGCGATAACG AGCTCCTGCACTGGATGGTGGCGCTGGATGG TAAGCCGCTGGCAAGCGGTGAAGTGCCTCTG GATGTCGCTCCACAAGGTAAACAGTTGATTG AACTGCCTGAACTACCGCAGCCGGAGAGCGC CGGGCAACTCTGGCTCACAGTACGCGTAGTG CAACCGAACGCGACCGCATGGTCAGAAGCCG GGCACATCAGCGCCTGGCAGCAGTGGCGTCT GGCGGAAAACCTCAGTGTGACGCTCCCCGCC GCGTCCCACGCCATCCCGCATCTGACCACCA GCGAAATGGATTTTTGCATCGAGCTGGGTAA TAAGCGTTGGCAATTTAACCGCCAGTCAGGC TTTCTTTCACAGATGTGGATTGGCGATAAAA AACAACTGCTGACGCCGCTGCGCGATCAGTT CACCCGTGCACCGCTGGATAACGACATTGGC GTAAGTGAAGCGACCCGCATTGACCCTAACG CCTGGGTCGAACGCTGGAAGGCGGCGGGCCA TTACCAGGCCGAAGCAGCGTTGTTGCAGTGC ACGGCAGATACACTTGCTGATGCGGTGCTGA TTACGACCGCTCACGCGTGGCAGCATCAGGG GAAAACCTTATTTATCAGCCGGAAAACCTAC CGGATTGATGGTAGTGGTCAAATGGCGATTA CCGTTGATGTTGAAGTGGCGAGCGATACACC GCATCCGGCGCGGATTGGCCTGAACTGCCAG CTGGCGCAGGTAGCAGAGCGGGTAAACTGGC TCGGATTAGGGCCGCAAGAAAACTATCCCGA CCGCCTTACTGCCGCCTGTTTTGACCGCTGG GATCTGCCATTGTCAGACATGTATACCCCGT ACGTCTTCCCGAGCGAAAACGGTCTGCGCTG CGGGACGCGCGAATTGAATTATGGCCCACAC CAGTGGCGCGGCGACTTCCAGTTCAACATCA GCCGCTACAGTCAACAGCAACTGATGGAAAC CAGCCATCGCCATCTGCTGCACGCGGAAGAA GGCACATGGCTGAATATCGACGGTTTCCATA TGGGGATTGGTGGCGACGACTCCTGGAGCCC GTCAGTATCGGCGGAATTCCAGCTGAGCGCC GGTCGCTACCATTACCAGTTGGTCTGGTGTC AAAAATAA3' |

TABLE 9

| PCA reaction mixture | 1 (x100 ul) | Final conc. |
|---|---|---|
| H₂O | 62.00 | |
| 5x Q5 buffer | 20.00 | 1x |
| 10 mM dNTP | 1.00 | 100 uM |
| BSA 20 mg/ml | 5.00 | 1 mg/ml |
| Oligonucleic acid mix (50 nM each) | 10.00 | 5 nM |
| Q5 polymerase 2 U/ul | 2.00 | 2 U/50 ul |

PCA reaction mixture drops of about 400 nL were dispensed using a Mantis dispenser (Formulatrix, Mass.) on the top of channels of a device side of a three-dimensional substrate having a plurality of loci microchannels in fluid communication with a single main channel of a cluster. A nanoreactor chip was manually mated with the substrate to pick up the droplets having the PCA reaction mixture and oligonucleic acids from each channel. The droplets were picked up into individual nanoreactors in the nanoreactor chip by releasing the nanoreactor from the substrate immediately after pick up. The nanoreactors were sealed with a heat sealing film, placed in a thermocycler for PCA. PCA thermocycling conditions are shown in Table 10. An aliquot of 0.5 ul was collected from 1-10 individual wells and the aliquots were amplified in plastic PCR tubes using forward primer (5'ATGACCATGATTACGGATTCACTGGCC3' SEQ ID NO.: 63) and reverse primer (5'TTATTTTT-GA-CACCAGACCAACTGGTAATGG3' SEQ ID NO.: 64). Thermocycling conditions for PCR are shown in Table 11 and PCR reaction components are shown in Table 12. The amplification products were ran on a BioAnalyzer instrument and on a gel. The gel showed products 1-10 having a size slightly larger than 3000 bp (data not shown). A PCA reaction performed in plastic tube was also ran on the gel as a positive control (panel 11), which shows a product having a similar size to the products from wells 1-10. A negative control (panel 12) was also run on the gel, which corresponds to a PCR reaction ran without a PCA template. The BioAnalyzer data is not shown.

TABLE 10

| No. of cycles | Temperature (° C.) | Time |
|---|---|---|
| 1 | 98 | 45 seconds |
| 40 | 98 | 15 seconds |
| | 63 | 45 seconds |
| | 72 | 60 seconds |
| 1 | 72 | 5 minutes |
| 1 | 4 | Hold |

TABLE 11

| No. of cycles | Temperature (° C.) | Time |
|---|---|---|
| 1 | 98 | 30 seconds |
| 30 | 98 | 7 seconds |
| | 63 | 30 seconds |
| | 72 | 90 seconds |
| 1 | 72 | 5 minutes |
| 1 | 4 | Hold |

TABLE 12

| PCR | 1 (x25 ul) | Final conc. |
|---|---|---|
| H2O | 17.50 | |
| 5x Q5 buffer | 5.00 | 1x |
| 10 mM dNTP | 0.50 | 200 uM |
| F-primer 20 uM | 0.63 | 0.5 uM |
| R-primer 20 uM | 0.63 | 0.5 uM |
| BSA 20 mg/ml | 0.00 | |
| Q5 pol 2 U/ul | 0.25 | 1 U/50 ul |
| Template (PCA assembly) | 0.50 | 1 ul/50 ul rxn |

Example 6: Error Correction of Assembled Nucleic Acids

A gene of about 1 kbp (SEQ ID.: 67; Table 13) was assembled using 6 purchased Ultramer oligonucleotides (SEQ ID NO.: 68-73; Table 13) and assembled in a PCA reaction. Ultramer oligonucleotides are expected to have error rates of at least 1 in 500 to 1 in 200 nucleotides. The assembled gene was amplified by PCR using a forward primer (5' ATGACCATGATTACGGATTCACTGGCC3' SEQ ID NO.: 65) and a reverse primer (5'GATAGAGAT-TCGGGATTTCGGCGCTCC3' SEQ ID NO.: 66). The amplified assembled gene was analyzed in a BioAnalyzer and cloned. DNA preparations from 24 colonies were Sanger sequenced. The BioAnalyzer analysis provided a broad peak and a tail for the uncorrected gene, indicating a high error rate. The sequencing indicated an error rate of 1/789 bases. Two rounds of error correction were followed using CorectASE (Life Technologies) according to the manufacturer's instructions. The resulting gene samples were analyzed in a BioAnalyzer after round one and round two and cloned. Twenty-four colonies were picked for sequencing. The sequencing results indicated an error rate of 1/5190 bases and 1/6315 bases after the first and second rounds of error correction, respectively.

TABLE 13

| Nucleic Acid | Sequence |
| --- | --- |
| Assembled Gene, SEQ ID NO.: 67 | 5'ATGACCATGATTACGGATTCACTGGCCGT CGTTTTACAACGTCGTGACTGGGAAAACCCT GGCGTTACCCAACTTAATCGCCTTGCAGCAC ATCCCCCTTTCGCCAGCTGGCGTAATAGCGA AGAGGCCCGCACCGATCGCCCTTCCCAACAG TTGCGCAGCCTGAATGGCGAATGGCGCTTTG CCTGGTTTCCGGCACCAGAAGCGGTGCCGGA AAGCTGGCTGGAGTGCGATCTTCCTGAGGCC GATACTGTCGTCGTCCCCTCAAACTGGCAGA TGCACGGTTACGATGCGCCCATCTACACCAA CGTGACCTATCCCATTACGGTCAATCCGCCG TTTGTTCCCACGGAGAATCCGACGGGTTGTT ACTCGCTCACATTTAATGTTGATGAAAGCTG GCTACAGGAAGGCCAGACGCGAATTATTTTT GATGGCGTTAACTCGGCGTTTCATCTGTGGT GCAACGGGCGCTGGGTCGGTTACGGCCAGGA CAGTCGTTTGCCGTCTGAATTTGACCTGAGC GCATTTTTACGCGCCGGAGAAAACCGCCTCG CGGTGATGGTGCTGCGCTGGAGTGACGGCAG TTATCTGGAAGATCAGGATATGTGGCGGATG AGCGGCATTTTCCGTGACGTCTCGTTGCTGC ATAAACCGACTACACAAATCAGCGATTTCCA TGTTGCCACTCGCTTTAATGATGATTTCAGC CGCGCTGTACTGGAGGCTGAAGTTCAGATGT GCGGCGAGTTGCGTGACTACCTACGGGTAAC AGTTTCTTTATGGCAGGGTGAAACGCAGGTC GCCAGCGGCACCGCGCCTTTCGGCGGTGAAA TTATCGATGAGCGTGGTGGTTATGCCGATCG CGTCACACTACGTCTGAACGTCGAAAACCCG AAACTGTGGAGCGCCGAAATCCCGAATCTCT ATC3' |
| Assembly Oligo- nucleotide 1, SEQ ID NO.: 68 | 5'ATGACCATGATTACGGATTCACTGGCCGT CGTTTTACAACGTCGTGACTGGGAAAACCCT GGCGTTACCCAACTTAATCGCCTTGCAGCAC ATCCCCCTTTCGCCAGCTGGCGTAATAGCGA AGAGGCCCGCACCGATCGCCCTTCCCAACAG TTGCGCAGCC3' |
| Assembly Oligo- nucleotide 2, SEQ ID NO.: 69 | 5'GATAGGTCACGTTGGTGTAGATGGGCGCA TCGTAACCGTGCATCTGCCAGTTTGAGGGGA CGACGACAGTATCGGCCTCAGGAAGATCGCA CTCCAGCCAGCTTTCCGGCACCGCTTCTGGT GCCGGAAACCAGGCAAAGCGCCATTCGCCAT TCAGGCTGCGCAACTGTTGGGA3' |
| Assembly Oligo- nucleotide 3, SEQ ID NO.: 70 | 5'CCCATCTACACCAACGTGACCTATCCCAT TACGGTCAATCCGCCGTTTGTTCCCACGGAG AATCCGACGGGTTGTTACTCGCTCACATTTA ATGTTGATGAAAGCTGGCTACAGGAAGGCCA GACGCGAATTATTTTTGATGGCGTTAACTCG GCGTTTCATCTGTGGTGCAACGG3' |
| Assembly Oligo- nucleotide 4, SEQ ID NO.: 71 | 5'GCCGCTCATCCGCCACATATCCTGATCTT CCAGATAACTGCCGTCACTCCAGCGCAGCAC CATCACCGCGAGGCGGTTTTCTCCGGCGCGT AAAAATGCGCTCAGGTCAAATTCAGACGGCA AACGACTGTCCTGGCCGTAACCGACCCAGCG CCCGTTGCACCACAGATGAAACG3' |
| Assembly Oligo- nucleotide 5, SEQ ID NO.: 72 | 5'AGGATATGTGGCGGATGAGCGGCATTTTC CGTGACGTCTCGTTGCTGCATAAACCGACTA CACAAATCAGCGATTTCCATGTTGCCACTCG CTTTAATGATGATTTCAGCCGCGCTGTACTG GAGGCTGAAGTTCAGATGTGCGGCGAGTTGC GTGACTACCTACGGGTAACAGTTT3' |
| Assembly Oligo- nucleotide 6, SEQ ID NO.: 73 | 5'GATAGAGATTCGGGATTTCGGCGCTCCAC AGTTTCGGGTTTTCGACGTTCAGACGTAGTG TGACGCGATCGGCATAACCACCACGCTCATC GATAATTTCACCGCCGAAAGGCGCGGTGCCG CTGGCGACCTGCGTTTCACCCTGCCATAAAG AAACTGTTACCCGTAGGTAGTCACG3' |

Example 7: Parallel Assembly of 240 Genes on Flat Plate

Figure 17:
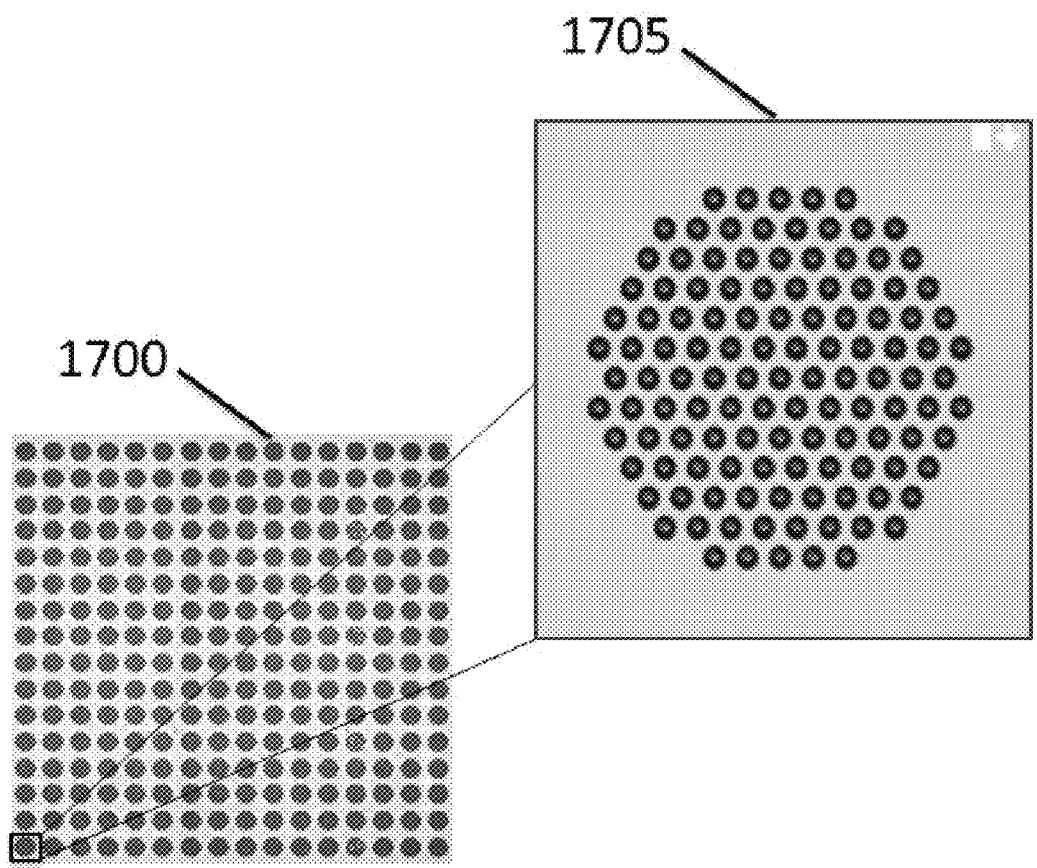
FIG. 17 depicts read counts from a sub-array having 256 clusters (left), and an image of a cluster having 121 loci (right).
Figure 18:
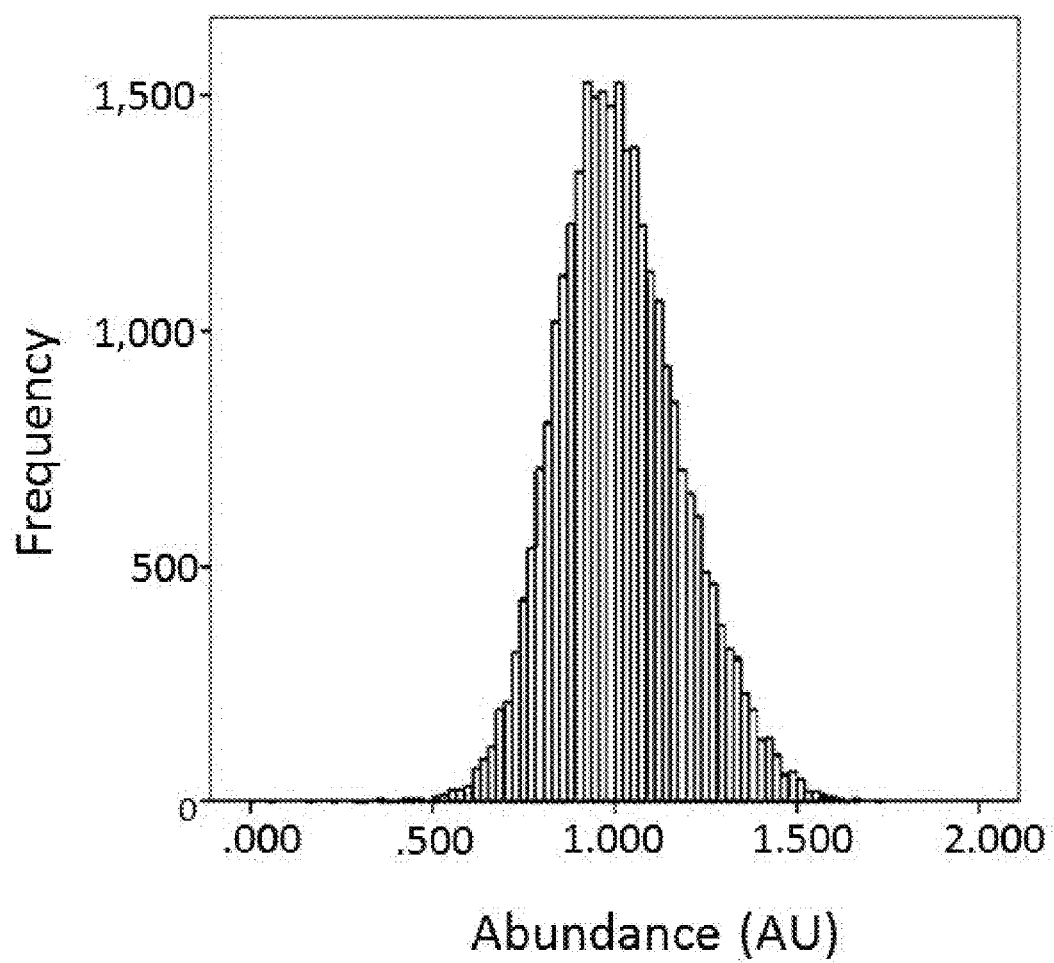
FIG. 18 is a graphical representation of oligonucleic acid frequency versus abundance from an experiment where oligonucleic acids were synthesized on the substrate of FIG. 17.
Figure 19:
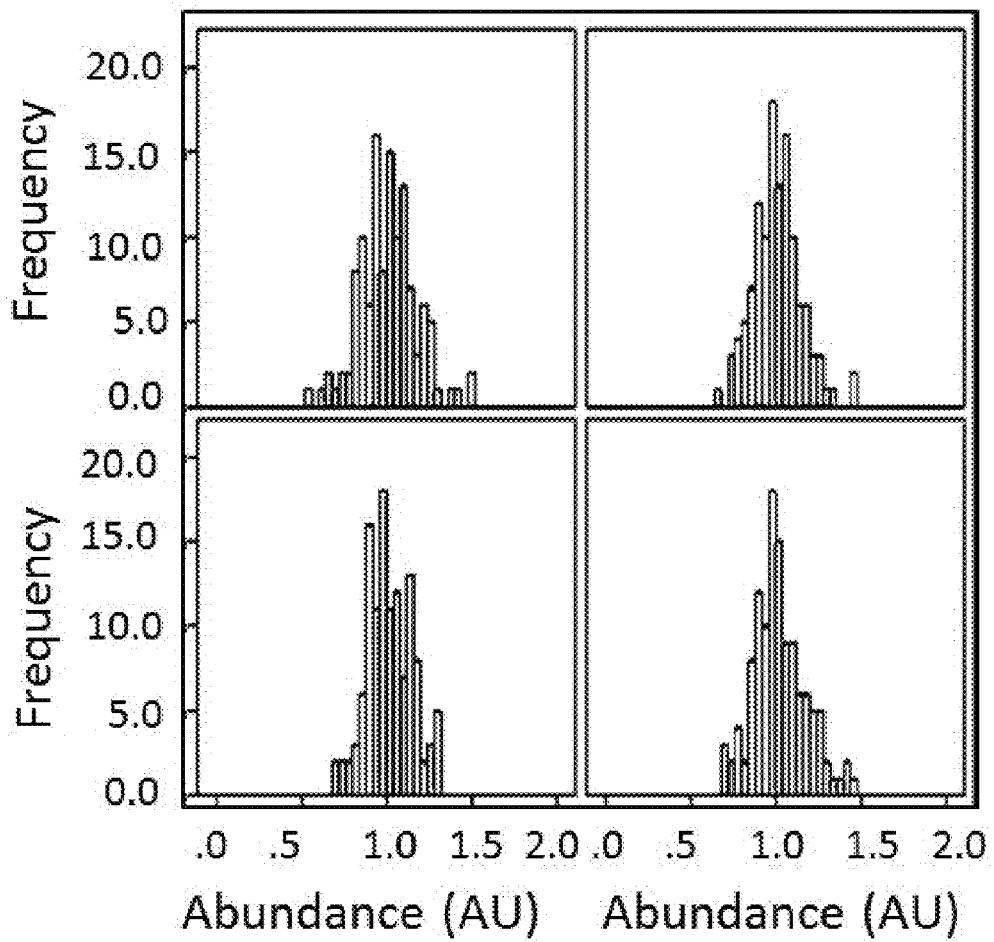
FIG. 19 is a graphical representation of oligonucleic acid frequency versus abundance for four representative clusters of the substrate of FIG. 17.
Figure 20:
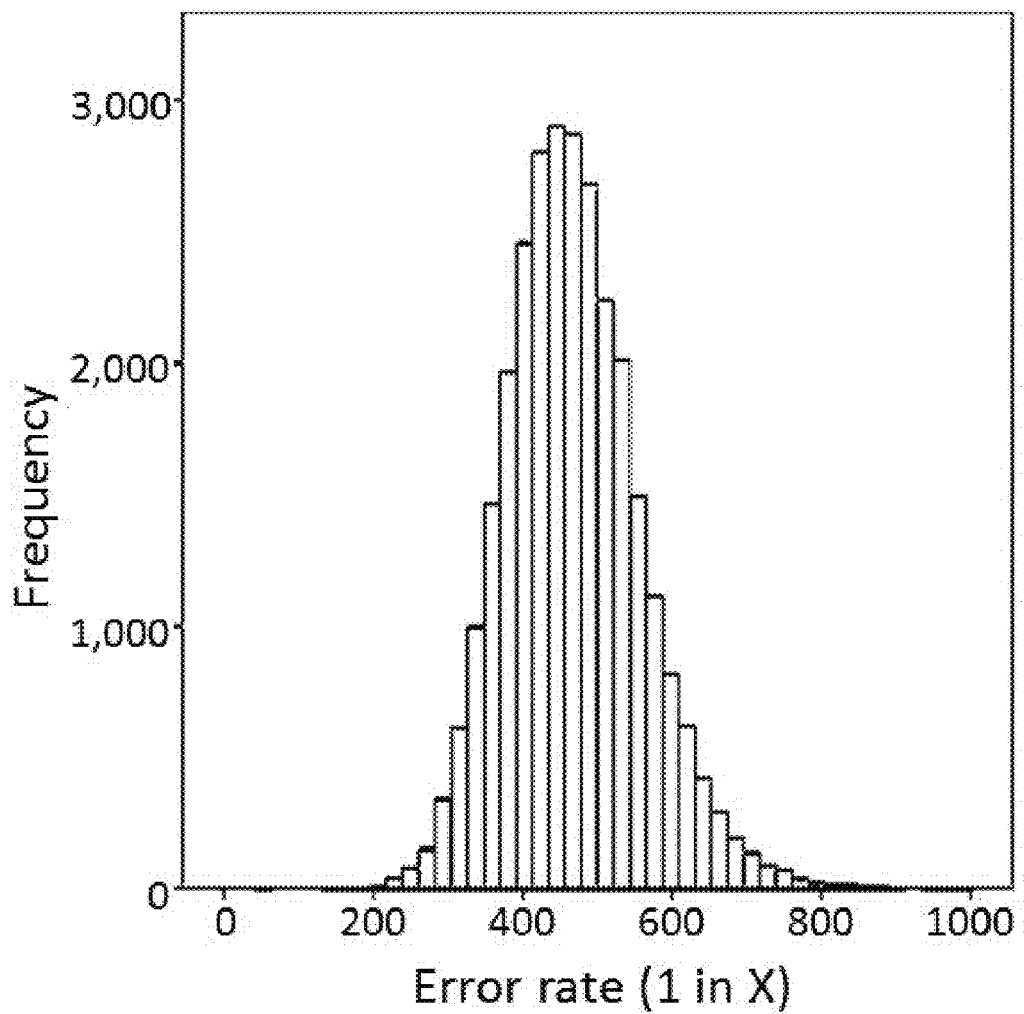
FIG. 20 is a graphical representation of oligonucleic acid frequency versus error rate for oligonucleic acids synthesized on the substrate of FIG. 17.
Figure 21:
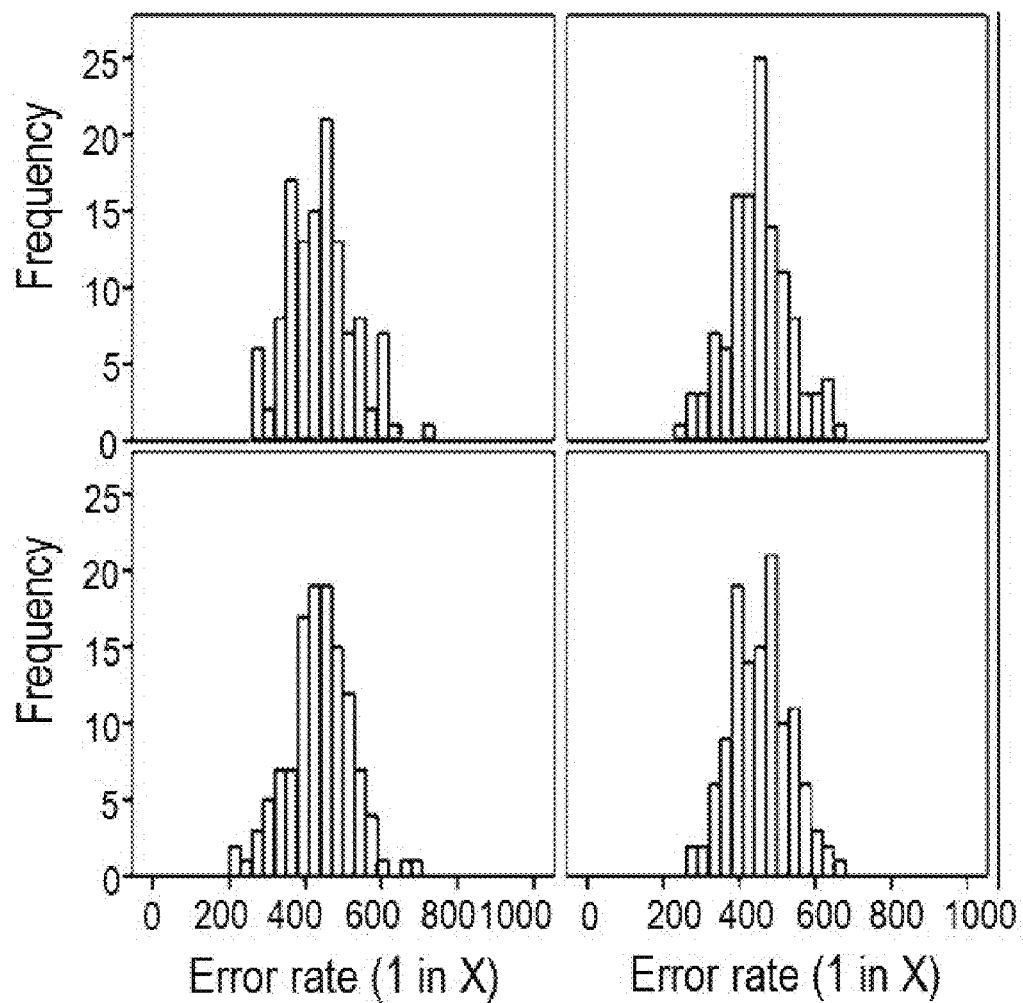
FIG. 21 is a graphical representation of oligonucleic acid frequency versus error rate for oligonucleic acids synthesized on four representative clusters of the substrate of FIG. 17.

A substrate 1700 comprising 256 clusters each comprising 121 loci on a flat silicon plate was manufactured as shown in FIG. 17. An expanded view of a cluster is shown in 1705 with 121 loci. Loci from 240 of the 256 clusters provided an attachment and support for the synthesis of oligonucleic acids having distinct sequences. Oligonucleic acid synthesis was performed by phosphoramidite chemistry using general methods from Table 5 in Example 4. Loci from 16 of the 256 clusters were control clusters. The distribution of the 29,040 unique oligonucleic acids synthesized (240×121) is shown in FIG. 18. The distribution of unique oligonucleic acids synthesized in 4 representative clusters is shown in FIG. 19. The error rate for each oligonucleic acid was determined using an Illumina MiSeq gene sequencer. The error rate distribution for the 29,040 unique oligonucleic acids is shown in FIG. 20 and averages around 1 in 500 bases, with some error rates as low as 1 in 800 bases. The error rate distribution for unique oligonucleic acids in four representative clusters is shown in FIG. 21. The library of 29,040 unique oligonucleic acids was synthesized in less than 20 hours.

Figure 22:
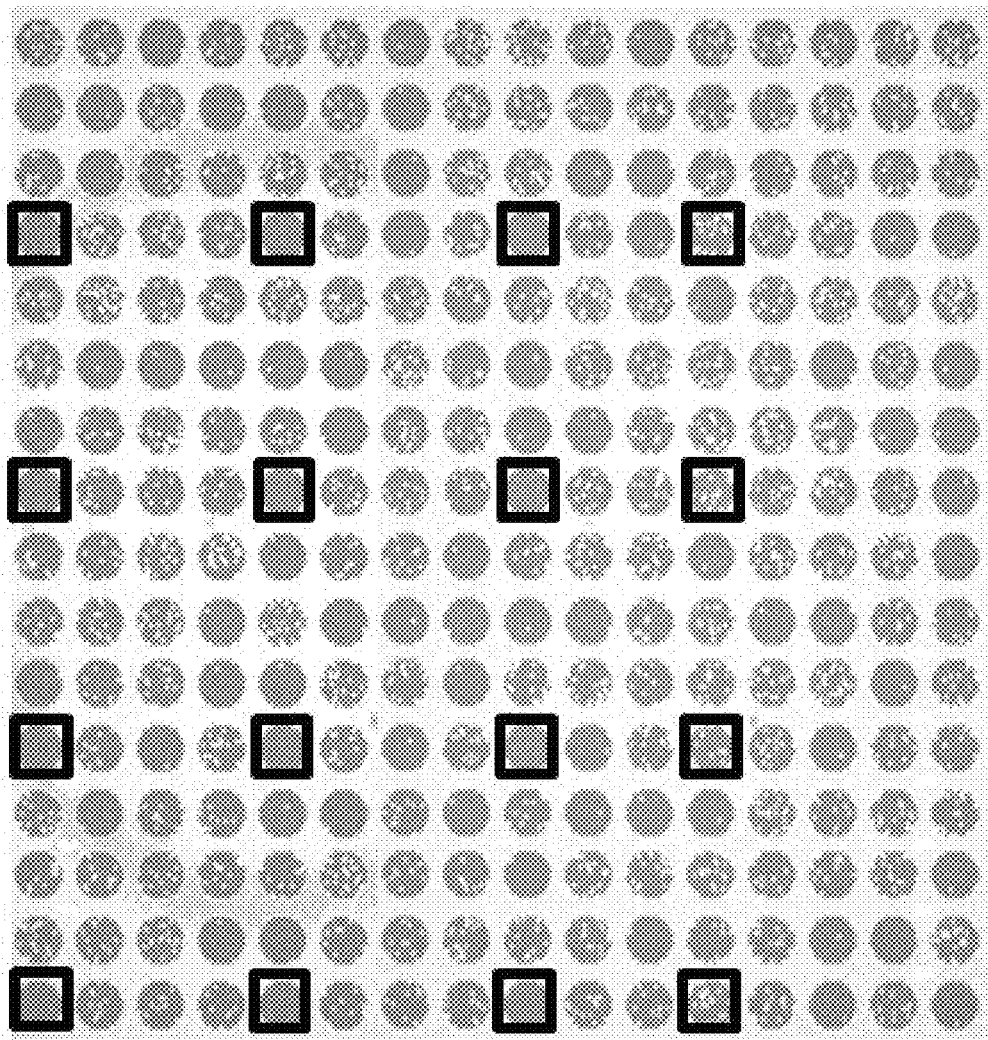
FIG. 22 is a representation of read counts from 240 assembled genes from a library of oligonucleic acids synthesized on a substrate.
Figure 23:
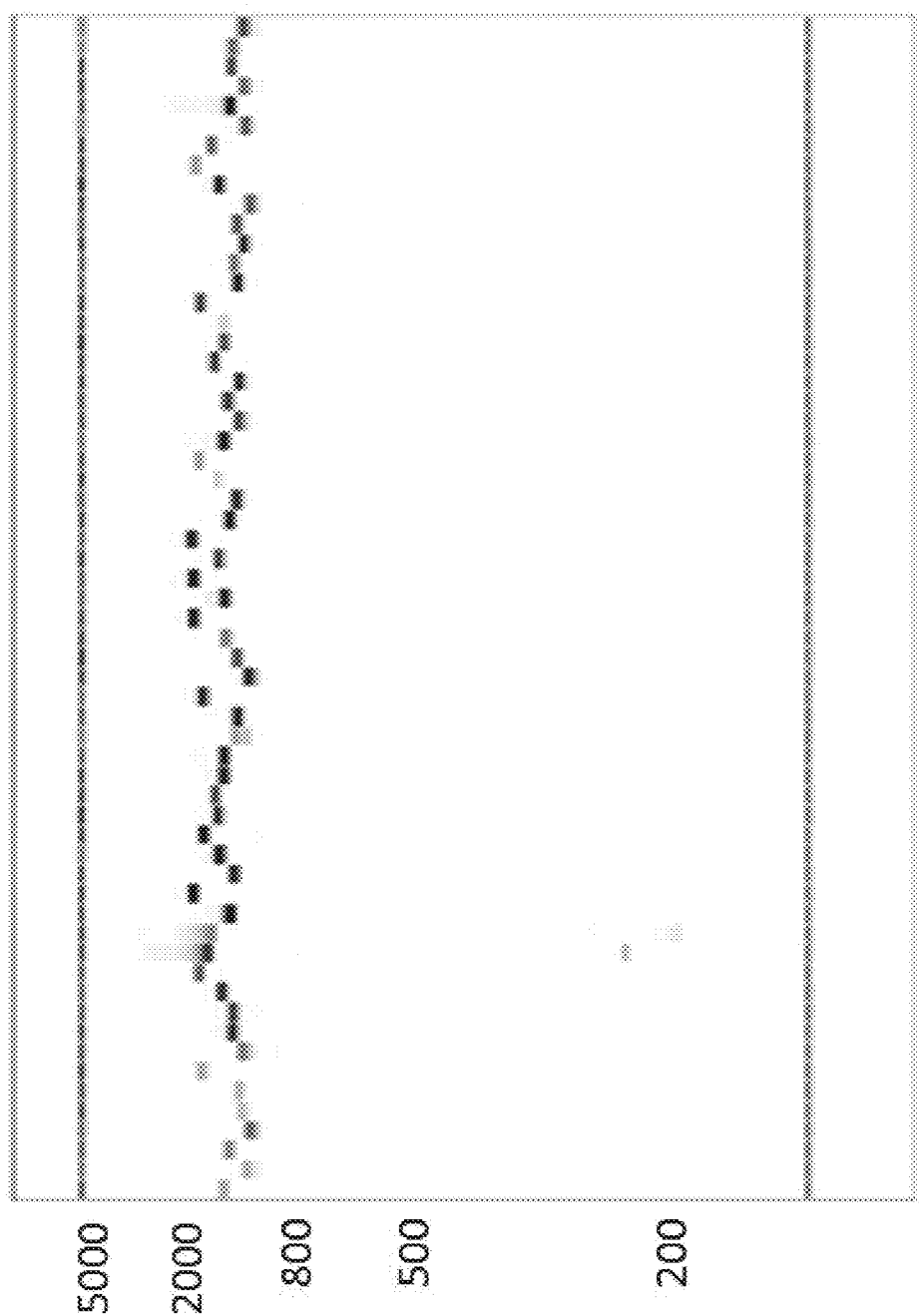
FIGS. 23, 24, 25 and 26 provide digital images from gel electrophoresis of 240 assembled genes from a library of oligonucleic acids synthesized on the substrate of FIG. 17.
Figure 24:
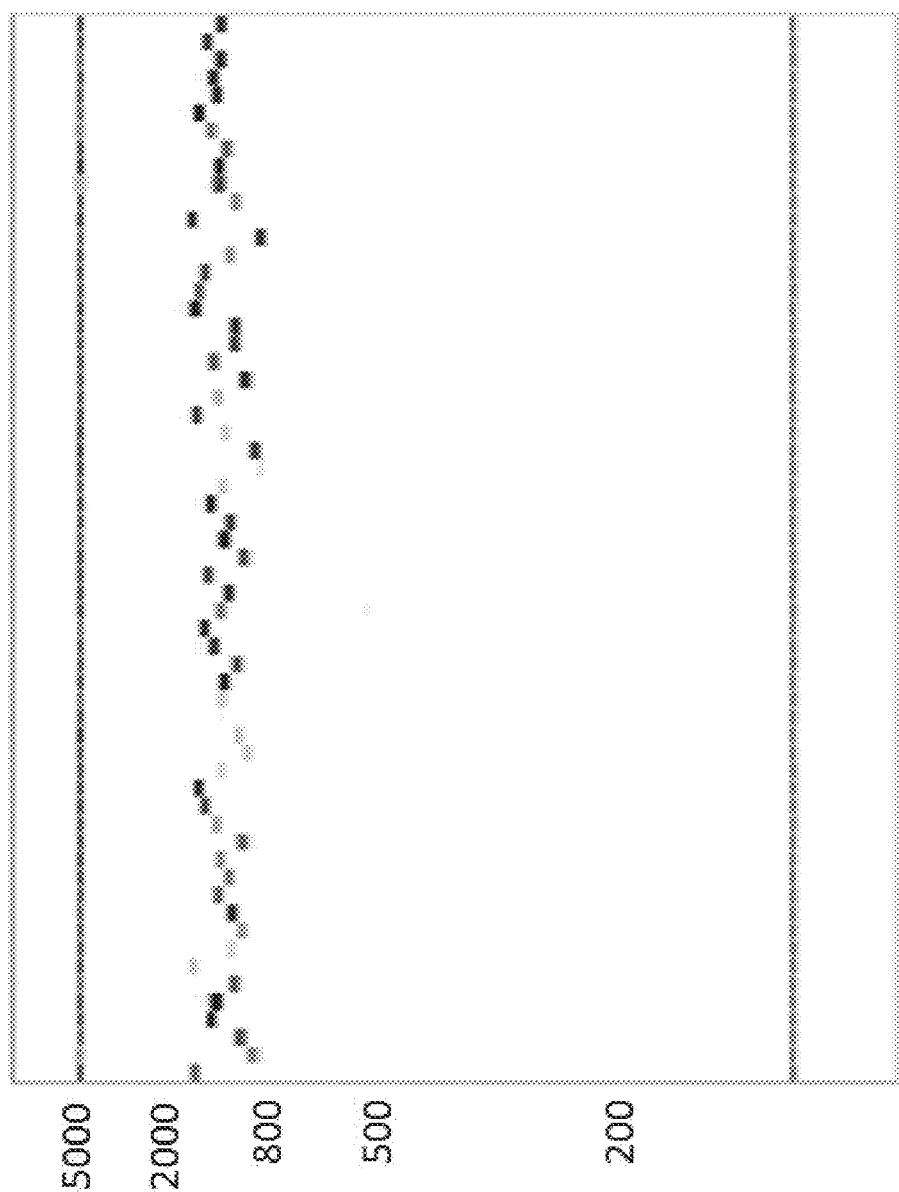
Figure 25:
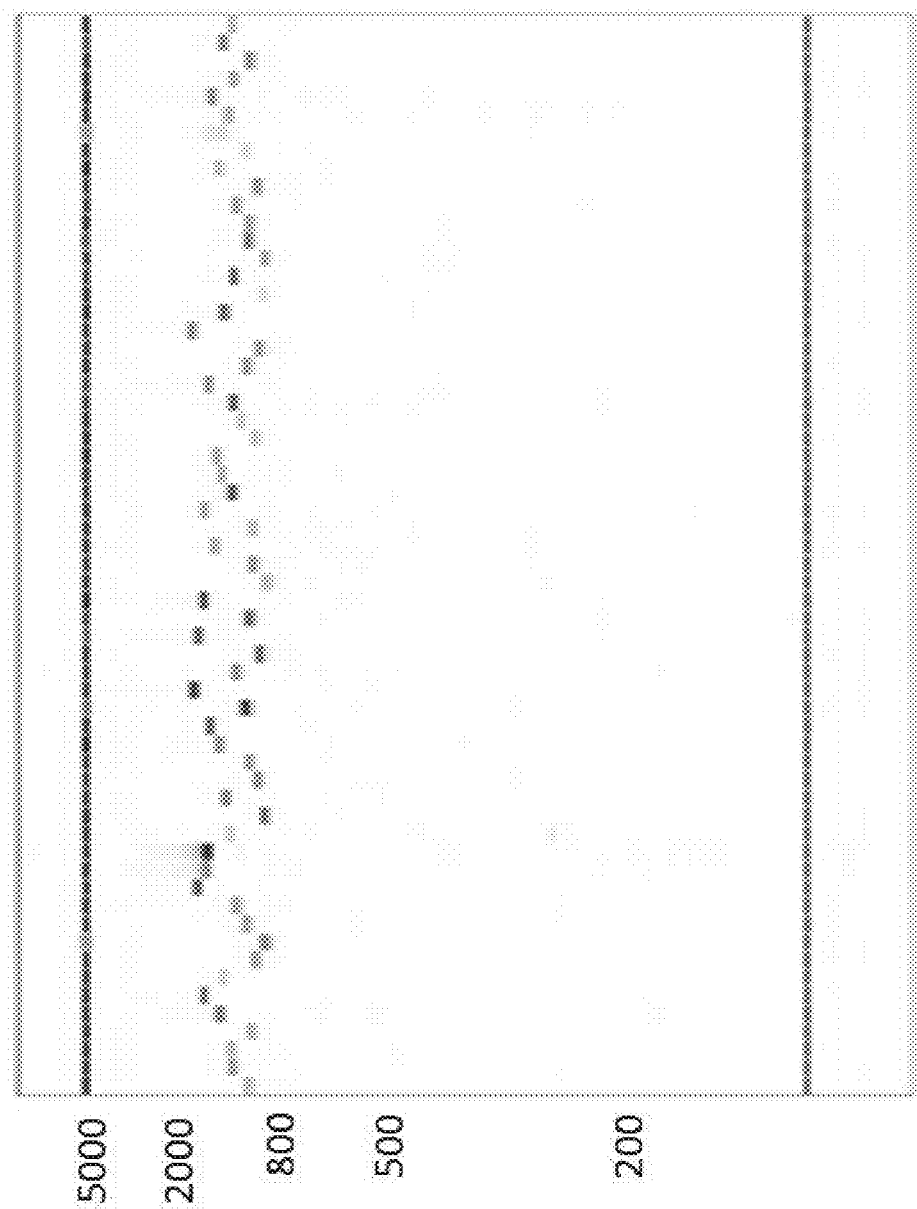
Figure 26:
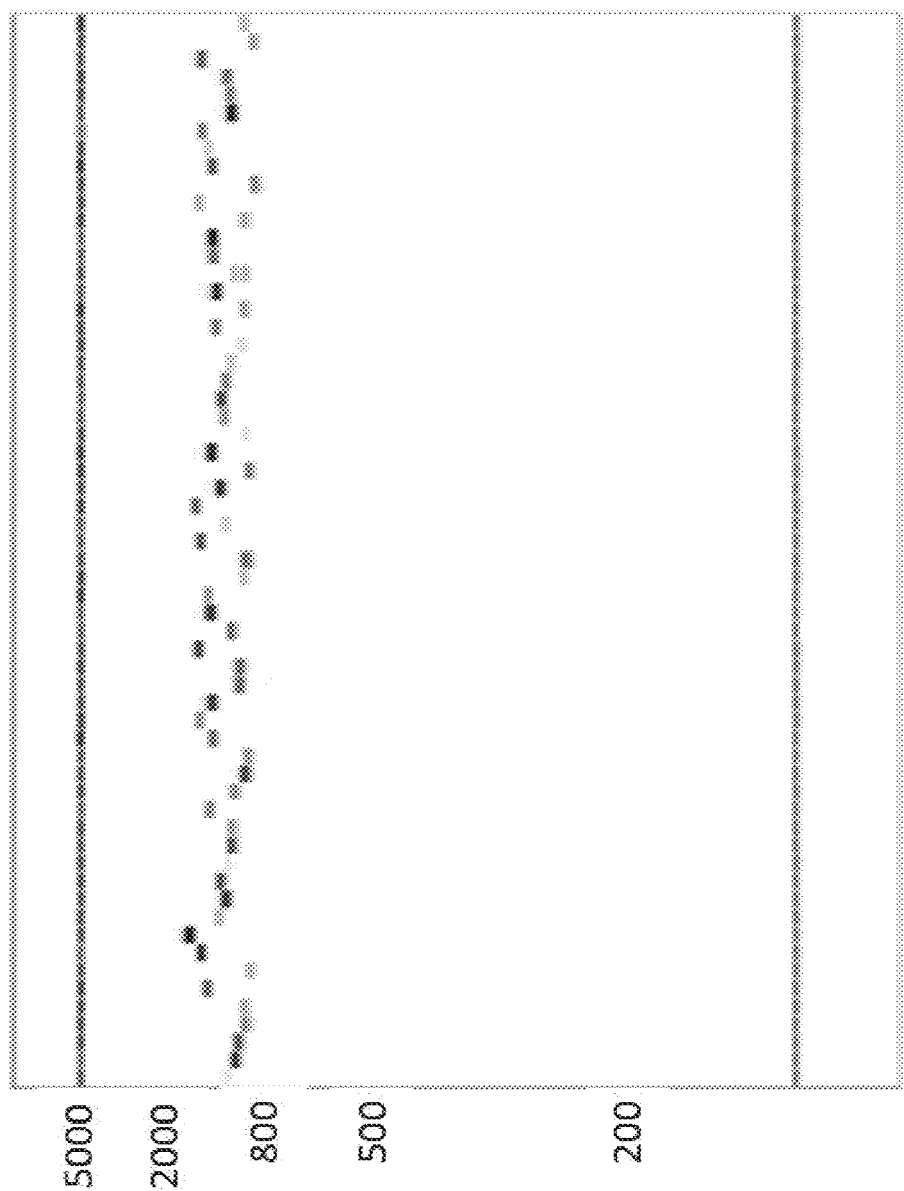
Figure 27:
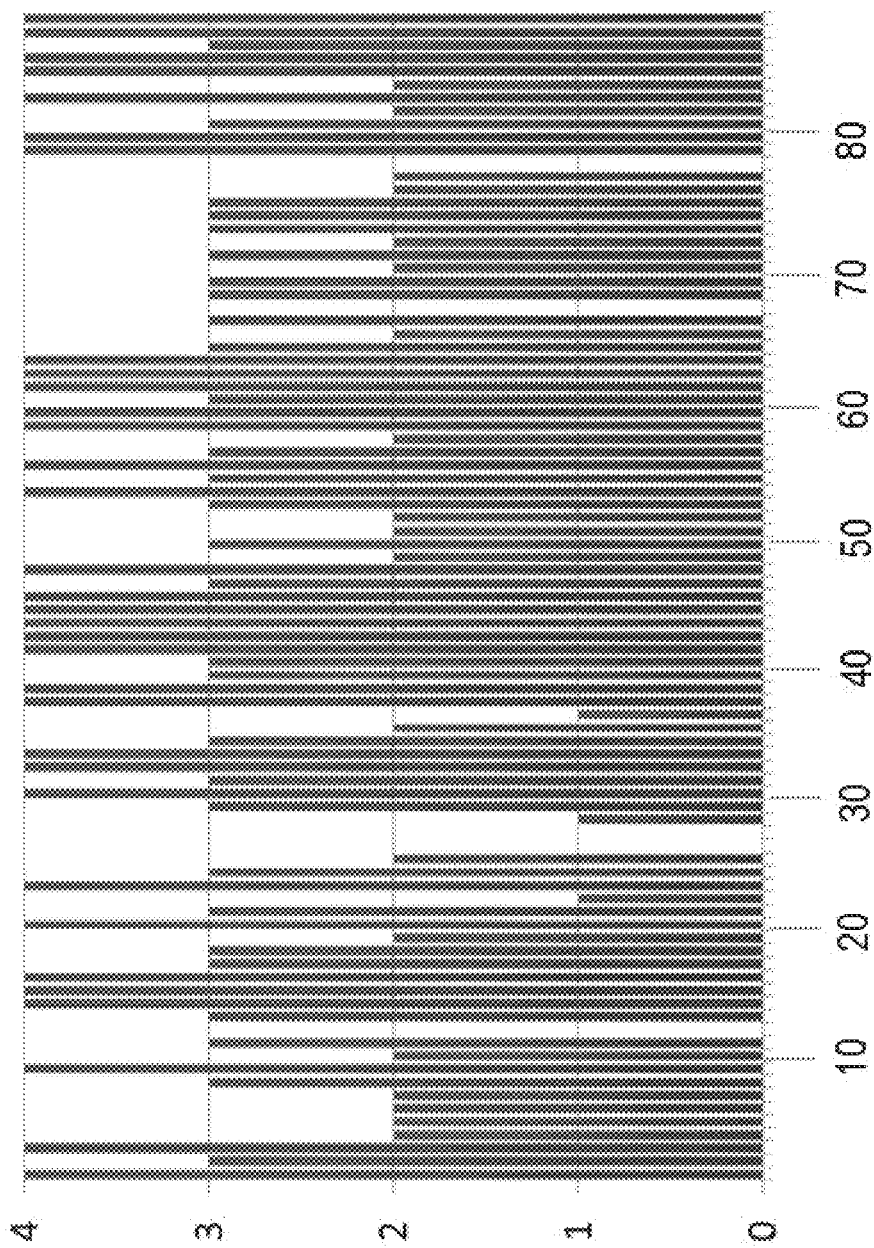
FIG. 27 provides an output reading from next generation sequencing of 240 assembled genes from a library of oligonucleic acids synthesized on the substrate of FIG. 17.

Oligonucleic acids synthesized within the loci of a cluster had overlapping sequences with one another so that when all oligonucleic acids synthesized within one cluster are pooled, they are ready for assembly into a larger nucleic acid or gene using PCA. Oligonucleic acids within a cluster were pooled and assembled using PCA reaction conditions similar to those described in Example 5. The 240 unique genes were synthesized in 3 business days, however, with 24 hour a day operation, the 240 unique genes could be synthesized in less time. The assembled genes from each of the 240 clusters were sequenced using an Illumina MiSeq gene sequencer. The read counts for the assembled genes are represented in FIG. 22. The assembled gene products were visualized on a DNA gel as shown in FIGS. 23-26. The genes synthesized ranged in size from 838 base pairs to 1470 base pairs. All 240 gene products were generated with their expected size. An output from the sequencing run is shown in FIG. 27.

Example 8: Oligonucleic Acid Library Synthesis with Low Error Rate

A substrate comprising three-dimensional features with high surface area loci was manufactured according to the methods similar to that of Example 3. Each locus was manufactured to have a single comb shape. The substrate has a plurality of clusters corresponding to a plurality of wells, wherein each channel is 1.150 mm in diameter and includes 109 loci in the form of microchannels. FIG. 10C provides a depiction for a collection of microchannels/loci extending from a main channel. Microchannels of the substrate were functionalized and used as an attachment and support for the synthesis of distinct oligonucleic acids. A library of oligonucleic acids was synthesized on the substrate and subsequently gas cleaved from the surface for sequence analysis using an Illumina MiSeq.

Error mismatch rates for oligonucleic acids synthesized within each cluster were calculated (data not shown). Error rates were from 1 in 7,000 bases to as high as 1 in 100 bases. The average mismatch error rate was 1 in 586.82 bases.

Error deletion rates for oligonucleic acids synthesized within each cluster were calculated (data not shown). Error rates were from around 1 in 1,000 bases to around 1 in 2,000 bases. The average deletion error rate was 1 in 1,966.86 bases.

Insertion rates for oligonucleic acids synthesized within each cluster were calculated (data not shown). Error rates were from 1 in 2,700 bases to around 1 in 10,000 bases. The average insertion error rate was 1 in 4,740.03 bases.

The percentage of perfect oligonucleic acids synthesized (a perfect sequence being 100% identical to a preselected nucleic acid sequence) within each cluster were calculated (data not shown). The percentage of perfect sequences ranged from about 70% to about 93.54% perfect sequences. Overall more than 90% of the oligonucleic acids had perfect sequences.

Example 9: Linker Length Analysis

Figure 28:
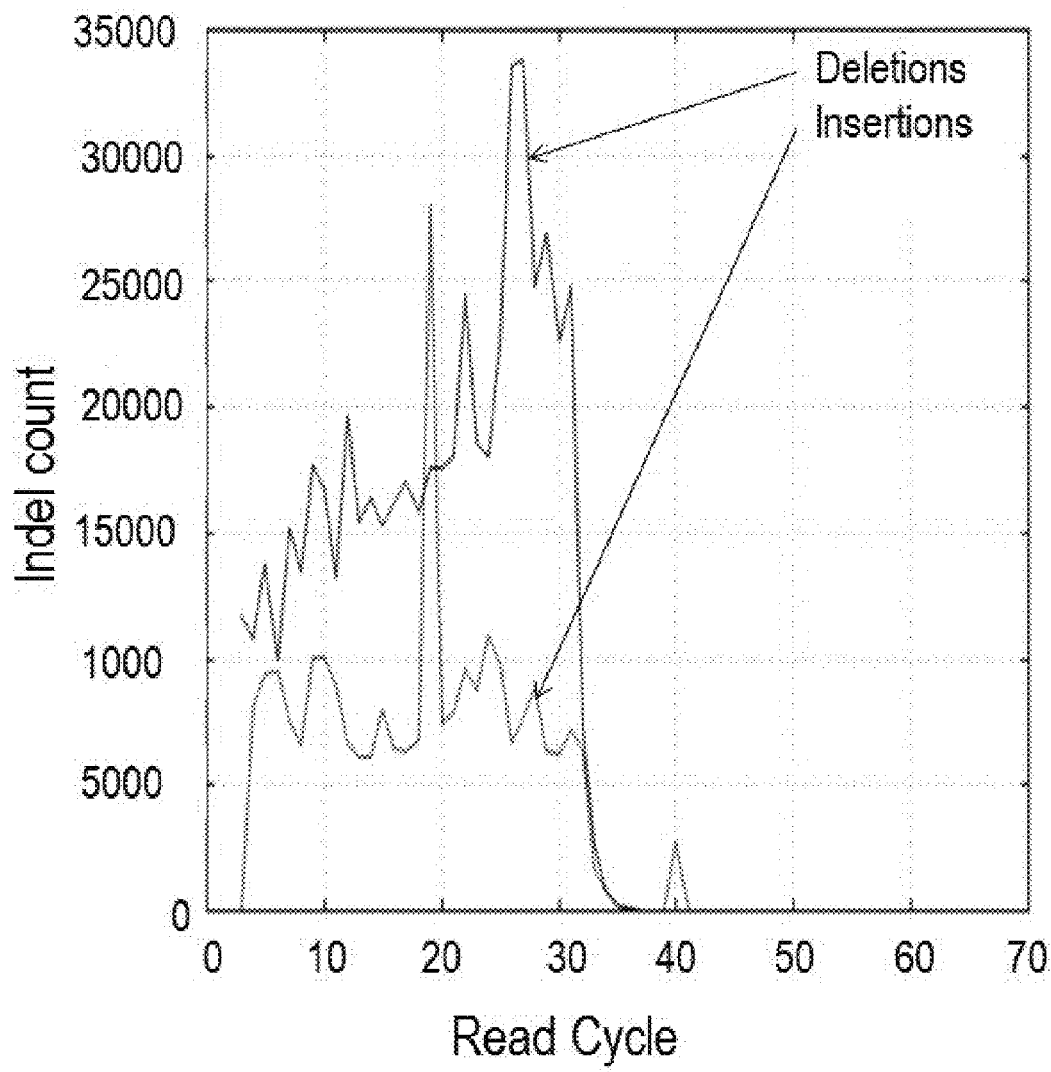
FIG. 28 provides a graphical representation of insertion/deletion ("indel") error count as a function of read cycle for a synthesized library of oligonucleic acids.

An oligonucleic acid library was synthesized as described in Example 8. Each oligonucleic acid synthesized on a locus of a cluster was tethered to the locus by a linker. Error rate as a function of base distance from substrate surface was analyzed and graphed as depicted in FIG. 28. The lowest error rates correspond to oligonucleic acids with tether between about 12 and 25 bases from the surface.

Example 10: Parallel Synthesis of Distinct Oligonucleic Acids

Figure 29:
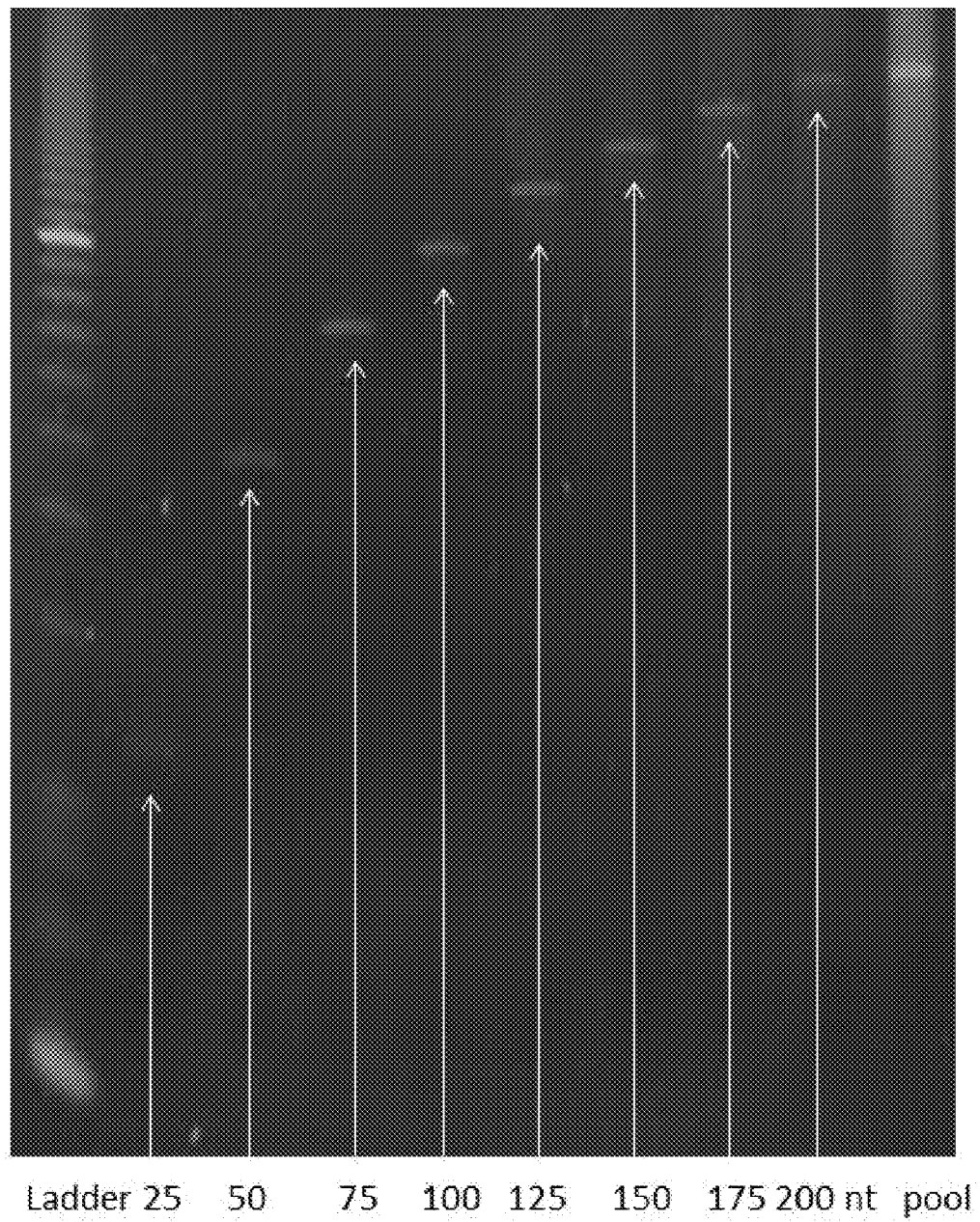
FIG. 29 provides a digital image of an electrophoresis gel showing 25mer to 200 mer oligonucleic acids synthesized using a substrate and methods provided herein.

Oligonucleic acids of various sequences and lengths were synthesized by phosphoramidite chemistry using methods as generally described in Table 5 of Example 4. Oligonucleic acids having lengths from 25 bases to 200 bases were synthesized within different clusters of a substrate. The synthesized oligonucleic acids were released from the surface, collected, and visualized by gel electrophoresis. FIG. 29 provides a captured image of the electrophoresis gel loaded with representative synthesized oligonucleic acids having lengths of 25, 50, 75, 100, 125, 150, 175 and 200 nucleotides.

As exemplified in FIG. 29, the methods and substrates described herein allow for the simultaneous synthesis of a plurality of oligonucleic acids each having different sequences and, in some cases, different sequence lengths. In particular, oligonucleic acids having 200 bases were synthesized on, and removed from a substrate. These synthesized oligonucleic acids were released from the substrate and used in downstream processes, such as visualization by gel electrophoresis. Representative quantities of synthesized oligonucleic acids extracted from each cluster in this example ranged from 113 fmol to 344 fmol. Representative yields from each cluster ranged from 48 pmol/cm$^2$ to 145 pmol/cm$^2$.

While specific instances have been shown and described herein, it will be apparent to those skilled in the art that such instances are provided by way of example only. Numerous variations, changes, and substitutions will now occur to those skilled in the art without departing from the disclosed instances. It should be understood that various alternatives to the instances described herein may be employed in practicing the invention.

---

What is claimed is:

1. A device for synthesizing oligonucleotides, comprising:
    a plate;
    a plurality of main channels, wherein each main channel extends vertically into the plate from an opening on a top side of the plate, and wherein the plurality of main channels comprises more than 250 main channels; and
    for each main channel, a plurality of microchannels connected thereto, wherein each microchannel of the plurality of microchannels extends vertically from an opening on a bottom side of the plate to said main channel, and wherein each microchannel of the plurality of microchannels has a surface area to volume ratio of greater than 0.2 $um^{-1}$.

2. The device of claim 1, wherein the surface area to volume ratio provides for rapid exchange of chemical exposure during de novo synthesis of oligonucleotides.

3. The device of claim 1, wherein the surface area to volume ratio is about 0.4 $um^{-1}$.

4. The device of claim 1, wherein each microchannel of the plurality of microchannels has a surface area greater than 10,000 $um^2$.

5. The device of claim 4, wherein each microchannel of the plurality of microchannels has a surface area of about 13,000 $um^2$.

6. The device of claim 1, wherein the plurality of microchannels comprises 50 to 500 microchannels.

7. The device of claim 1, wherein a ratio of width to depth of a narrowest segment of each microchannel is from 0.5 to 0.01.

8. The device of claim 1, wherein each microchannel of the plurality of microchannels has a total width of 30 um to 100 um.

9. The device of claim 1, wherein each microchannel of the plurality of microchannels has a depth of 10 um to 500 um.

10. The device of claim 1, wherein each main channel has a width from 0.5 mm to 2 mm.

11. The device of claim 1, wherein the plurality of main channels comprises about 10,000 main channels.

12. The device of claim 1, further comprising a plurality of first molecules, wherein each first molecule is bound to an interior surface of the plurality of microchannels and comprises a reactive group capable of binding to a nucleoside phosphoramidite.

13. The device of claim 12, wherein each first molecule is a silane or a siloxane.

14. The device of claim 13, wherein each first molecule is an aminosilane.

15. The device of claim 12, wherein each first molecule is selected from the group consisting of 11-acetoxyundecyltriethoxysilane, n-decyltriethoxysilane, (3-aminopropyl) trimethoxysilane, (3-aminopropyl)triethoxysilane, glycidyloxypropyl/trimethoxysilane, and N-(3-triethoxysilylpropyl)-4-hydroxybutyramide.

16. The device of claim 12, further comprising a plurality of second molecules, wherein each second molecule is bound to an interior surface of the main channel and lacks the reactive group capable of binding to the nucleoside phosphoramidite.

17. The device of claim 16, wherein each second molecule is a fluorosilane.

18. The device of claim 17, wherein the fluorosilane is (tridecafluorotetrahydrooctyl)-triethoxysilane.

19. The device of claim 16, wherein the first molecule has a higher surface energy than the second molecule.

20. The device of claim 1, wherein the plate is a silicon plate.

21. A device for synthesizing oligonucleotides, comprising:
    a silicon plate;
    a plurality of main channels, wherein the plurality of main channels comprises more than 250 main channels, wherein each main channel extends vertically into the silicon plate from an opening on a top side of the silicon plate, and wherein each main channel has a width of 0.5 mm to 2 mm; and
    for each main channel, a plurality of microchannels connected thereto, wherein each microchannel of the plurality of microchannels extends vertically from an opening on a bottom side of the silicon plate to said main channel, and wherein each microchannel of the plurality of microchannels comprises a total width that is less than 100 um, a microchannel surface area greater than 10,000 $um^2$, and a maximum width for a narrowest segment of the microchannel of 10 um.

22. A method for de novo oligonucleotide synthesis, comprising:
    (a) providing predetermined sequences for a plurality of non-identical oligonucleotides;
    (b) providing the device of claim 1;
    (c) adding a droplet of fluid comprising an extension reaction reagent specific to a microchannel;
    (d) allowing sufficient time for an extension reaction step to occur; and
    (e) repeating steps (c) and (d) until the plurality of non-identical oligonucleotides are synthesized, wherein each oligonucleotide comprises at least 10 bases in length and is attached to an inside region of the microchannel.

23. The method of claim 22, wherein the synthesized non-identical oligonucleotides encode sequences with an aggregate error rate of less than 1 in 2000 bases compared to the predetermined sequences.

24. The method of claim 22, further comprising washing the plate with a washing reagent, and wherein washing removes greater than 95% of unincorporated extension reaction reagent.

25. The method of claim 24, wherein washing removes greater than 99% of unincorporated extension reaction reagent.

26. The method of claim 22, wherein the synthesized plurality of non-identical oligonucleotides collectively encode for at least 200 genes at least 1 kb in length.

27. The method of claim 22, further comprising:
   releasing the plurality of non-identical oligonucleotides from the plate; and
   subjecting the plurality of non-identical oligonucleotides to a polymerase chain assembly reaction to assemble at least 200 genes.

28. The method of claim 27, wherein the at least 200 genes have an aggregate error rate of less than 1 in 2000 bases compared to the predetermined sequences without correcting errors.

* * * * *